US012291555B2

(12) United States Patent
Jang

(10) Patent No.: US 12,291,555 B2

(45) Date of Patent: May 6, 2025

(54) FUSION PROTEIN COMPRISING IL-2 PROTEIN AND CD80 PROTEIN, AND USE THEREOF

(71) Applicant: GI INNOVATION, INC., Seoul (KR)

(72) Inventor: Myung Ho Jang, Seoul (KR)

(73) Assignee: GI INNOVATION, INC., Seoul (KR)

( * ) Notice: Subject to any disclaimer, the term of this patent is extended or adjusted under 35 U.S.C. 154(b) by 463 days.

(21) Appl. No.: 17/878,664

(22) Filed: Aug. 1, 2022

(65) Prior Publication Data

US 2022/0380781 A1 Dec. 1, 2022

Related U.S. Application Data

(62) Division of application No. 16/959,312, filed as application No. PCT/KR2019/011928 on Sep. 16, 2019, now Pat. No. 11,492,384.

(60) Provisional application No. 62/832,013, filed on Apr. 10, 2019.

(30) Foreign Application Priority Data

Sep. 17, 2018 (KR) ........................ 10-2018-0110698
Jan. 7, 2019 (KR) ........................ 10-2019-0001867
May 8, 2019 (KR) ........................ 10-2019-0053436

(51) Int. Cl.

*C12N 15/62* (2006.01)
*A61P 31/12* (2006.01)
*A61P 35/00* (2006.01)
*C07K 14/55* (2006.01)
*C07K 14/705* (2006.01)
*A61K 38/00* (2006.01)

(52) U.S. Cl.

CPC .............. *C07K 14/55* (2013.01); *A61P 31/12* (2018.01); *A61P 35/00* (2018.01); *C07K 14/705* (2013.01); *C07K 14/70532* (2013.01); *C12N 15/62* (2013.01); *A61K 38/00* (2013.01); *C07K 2319/31* (2013.01)

(58) Field of Classification Search

CPC ..................................................... C12N 15/62
See application file for complete search history.

(56) References Cited

U.S. PATENT DOCUMENTS

| | | | |
|---|---|---|---|
| 6,955,807 | B1 | 10/2005 | Shanafelt et al. |
| 9,567,399 | B1 | 2/2017 | Campbell et al. |
| 2013/0149305 | A1 | 6/2013 | Ostrand-Rosenberg |
| 2016/0175397 | A1 | 6/2016 | Umana et al. |
| 2017/0145071 | A1 | 5/2017 | Brennan et al. |

FOREIGN PATENT DOCUMENTS

| | | | |
|---|---|---|---|
| CN | 86104525 | A | 2/1987 |
| CN | 1309705 | A | 8/2001 |
| CN | 103298935 | A | 9/2013 |
| CN | 103360471 | A | 10/2013 |
| JP | 2002-515251 | A | 5/2002 |
| JP | 2014-500868 | A | 1/2014 |
| JP | 2014-506793 | A | 3/2014 |
| KR | 10-2018-0069903 | A | 6/2018 |
| RU | 2 312 677 | C2 | 12/2007 |
| RU | 2 322 455 | C2 | 4/2008 |
| WO | 99/60135 | A1 | 11/1999 |
| WO | 03/048334 | A2 | 6/2003 |
| WO | 03/095488 | A1 | 11/2003 |
| WO | 2005/017148 | A1 | 2/2005 |
| WO | 2012/062228 | A2 | 5/2012 |
| WO | 2016/164937 | A2 | 10/2016 |
| WO | 2017/220989 | A1 | 12/2017 |
| WO | 2018184964 | A1 | 10/2018 |

OTHER PUBLICATIONS

Russian Office Action issued Jul. 27, 2023 in Application No. 2020122291.

Roland Kontermann et al., "Bispecific antibodies," Drug Discovery Today, Mar. 2015, vol. 7, No. 20, pp. 838-847 (10 pages total), Figure 1.

Yumi Maeda et al., "Engineering of functional chimeric protein G-Vargula Luciferase," Analytical Biochemistry, 1997, vol. 249, No. 2, pp. 147-152 (6 pages total).

Wolfgang Glaesner et al., "Engineering and characterization of the long-acting glucagon-like peptide-1 analogue LY2189265, an Fc fusion protein," Diabetes/Metabolism Research and Reviews, 2010, vol. 26, No. 4, pp. 287-296 (10 pages total), Figure 1.

Sylviane Muller et al., "Spliceosomal peptide P140 for immunotherapy of systemic lupus erythematosus," Results of an Early Phase II Clinical Trial, Arthritis & Rheumatism: Official Journal of the American College of Rheumatology, Dec. 2008, vol. 58, No. 12, pp. 3873-3883 (11 pages total).

Marla J. Berry et al., "Substitution of Cysteine for Selenocysteine in Type I Iodothyronine Deiodinase Reduces the Catalytic Efficiency of the Protein but Enhances its Translation," Endocrinology, 1992, vol. 131, No. 4, pp. 1848-1852 (5 pages total).

Brigitte Gasser et al., "Antibody production with yeasts and filamentous fungi: on the road to large scale?," Biotechnology Letters, 2007, vol. 29, No. 2, p. 201-212 (12 pages total).

Extended European Search Report dated Aug. 20, 2024 in Application No. 24175556.0.

Paul M. Sondel et al., "Current and Potential Uses of Immunocytokines as Cancer Immunotherapy", Antibodies, Jul. 4, 2012, pp. 149-171, vol. 1.

(Continued)

*Primary Examiner* — Prema M Mertz

(74) *Attorney, Agent, or Firm* — Sughrue Mion, PLLC

(57) ABSTRACT

Provided is a fusion protein comprising IL-2 protein and CD80 protein. A fusion protein containing CD80 fragment, immunoglobulin Fc, and an IL-2 variant can activate immune cells, such as natural killer cells, and at the same time, can control immune cell regulatory activity of regulatory T cells. Therefore, a pharmaceutical composition containing the fusion protein as an active ingredient is very industrially useful in that such pharmaceutical composition can increase immune activity in the body, and thus can be effectively used against infectious diseases as well as cancer.

20 Claims, 63 Drawing Sheets

Specification includes a Sequence Listing.

(56) References Cited

OTHER PUBLICATIONS

Susannah D. Barbee et al., "Abstract BOOS: FPT155, a novel therapeutic CD80-Fc fusion protein with potent antitumor activity in preclinical models", Molecular Cancer Therapeutics, Oct. 26-30, 2017, 2 pages.
International Search Report for PCT/KR2019/0011928, dated Dec. 30, 2019.
Chan et al., "IL-2/B7.1 (CD80) Fusagene Transduction of AML Blasts by a Self-Inactivating Lentiviral Vector Stimulates T Cell Responses in Vitro: a Strategy to Generate Whole Cell Vaccines for AML" Molecular Therapy, vol. 11, No. 1, Jan. 2005, pp. 120-131.
Kong et al., "Expression of fusion IL2-B7.1(IgV+C) and effects on T lymphocytes", Biochem. Cell Biol., 2007, vol. 85, pp. 685-695 (11 pages total).
Chan et al., "1131. Generation of Whole Cell Vaccines for Acute Myeloid Leukaemia by Lentivirus Mediated IL-2/CD80 Transduction", Molecular Therapy, 2005, vol. 11, Supplement 1, p. S436 (1 page total).
Tania Carmenate et al., "Human IL-2 Mutein with Higher Antitumor Efficacy Than Wild Type IL-2", The Journal of Immunology, 2013, vol. 190, No. 12, pp. 6230-6238 (9 pages total).
International Searching Authority, International Preliminary Report on Patentability issued Mar. 9, 2021 in Application No. PCT/KR2019/011928 with English translation.
International Searching Authority, Written Opinion mailed Dec. 30, 2019 in Application No. PCT/KR2019/011928 with English translation.
Xiaoying Chen et al., "Fusion protein linkers: Property, design, and functionality", Advanced Drug Delivery Reviews, 2013, vol. 65, pp. 1357-1369 (13 pages total).

[Fig. 1]
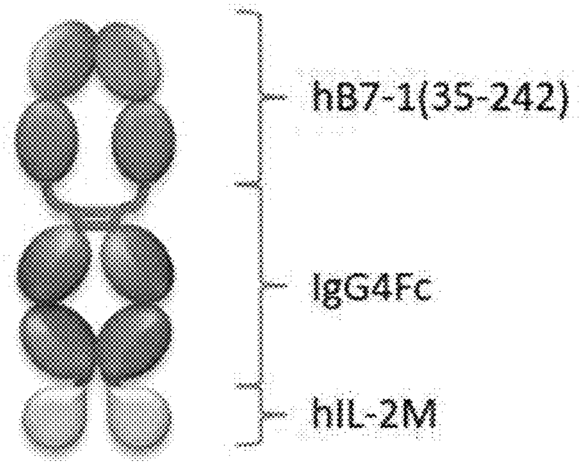
[Fig. 2]
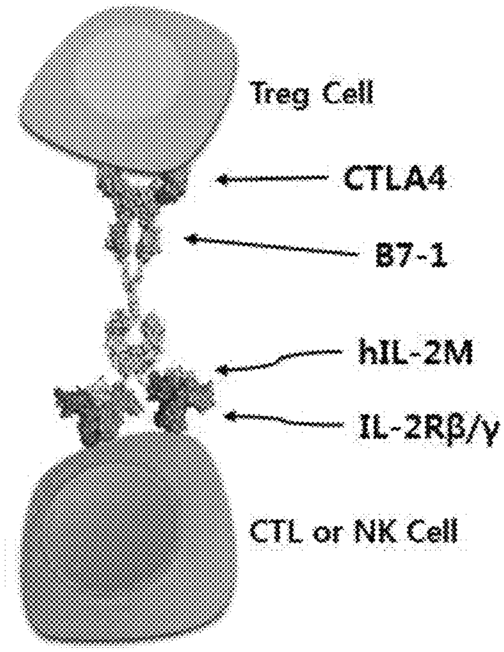

[Fig. 3]
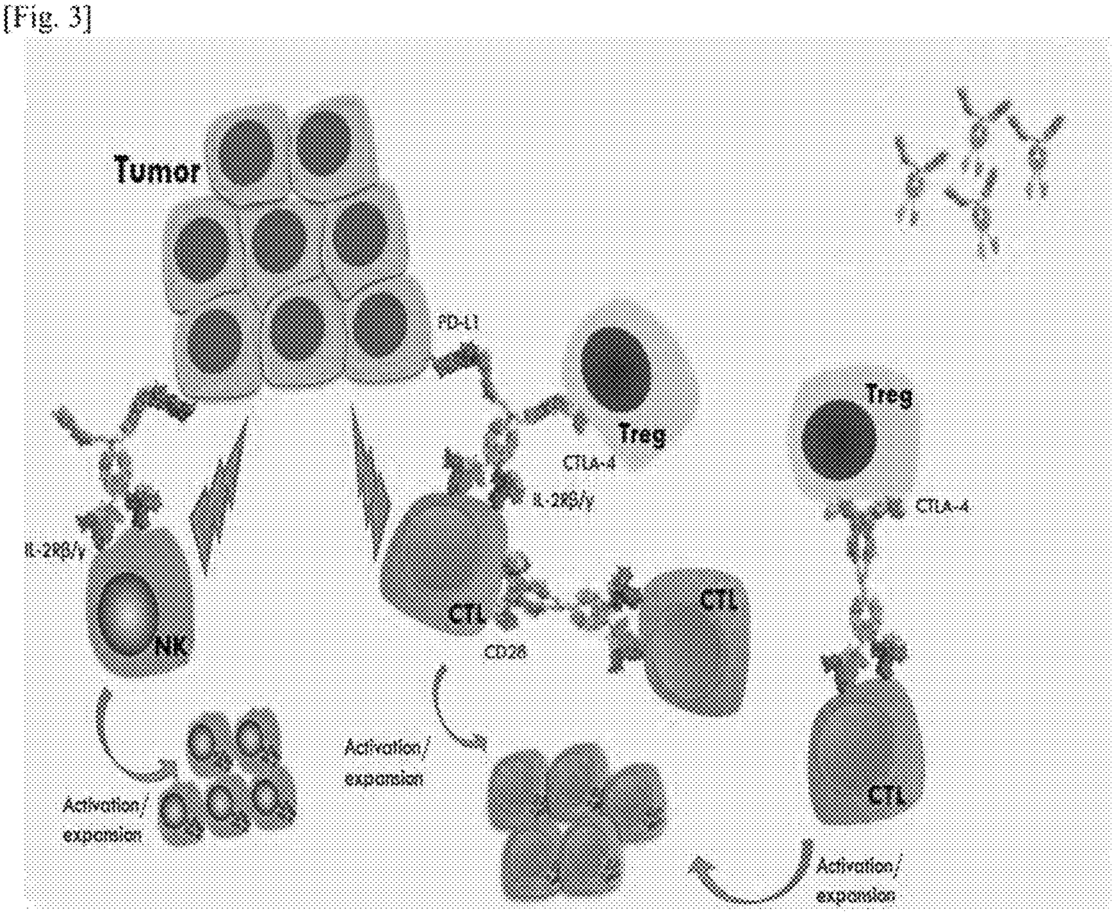
[Fig. 4]
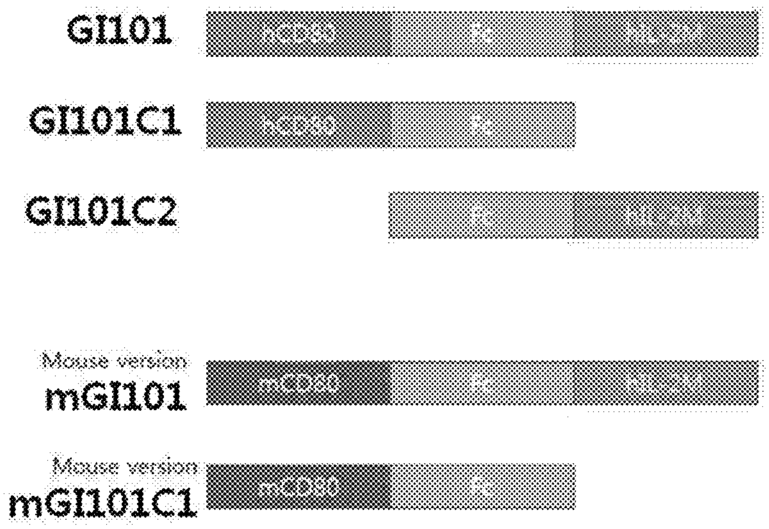

[Fig. 5]
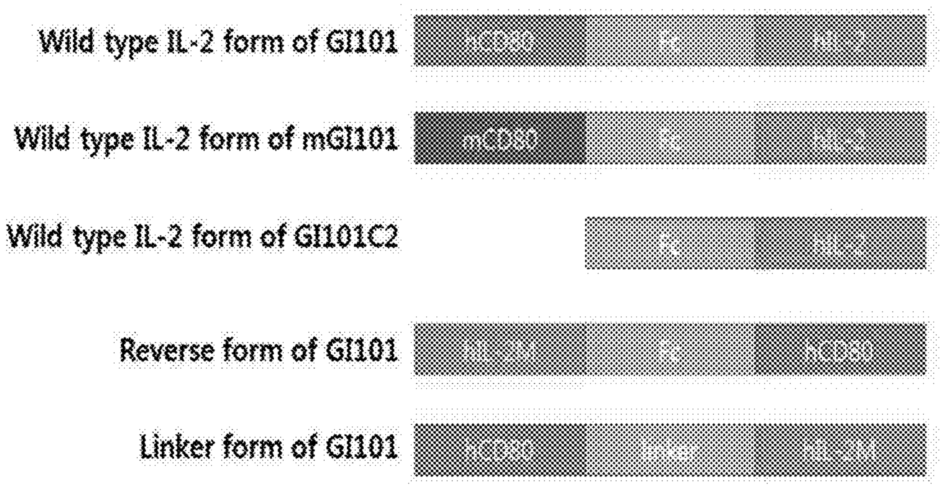
[Fig. 6]
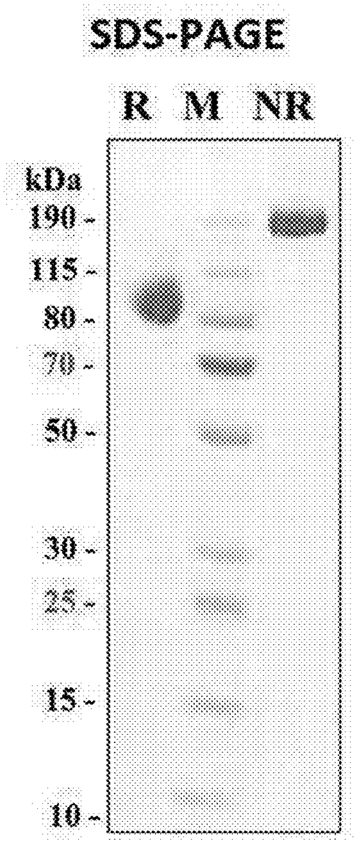

[Fig. 7]
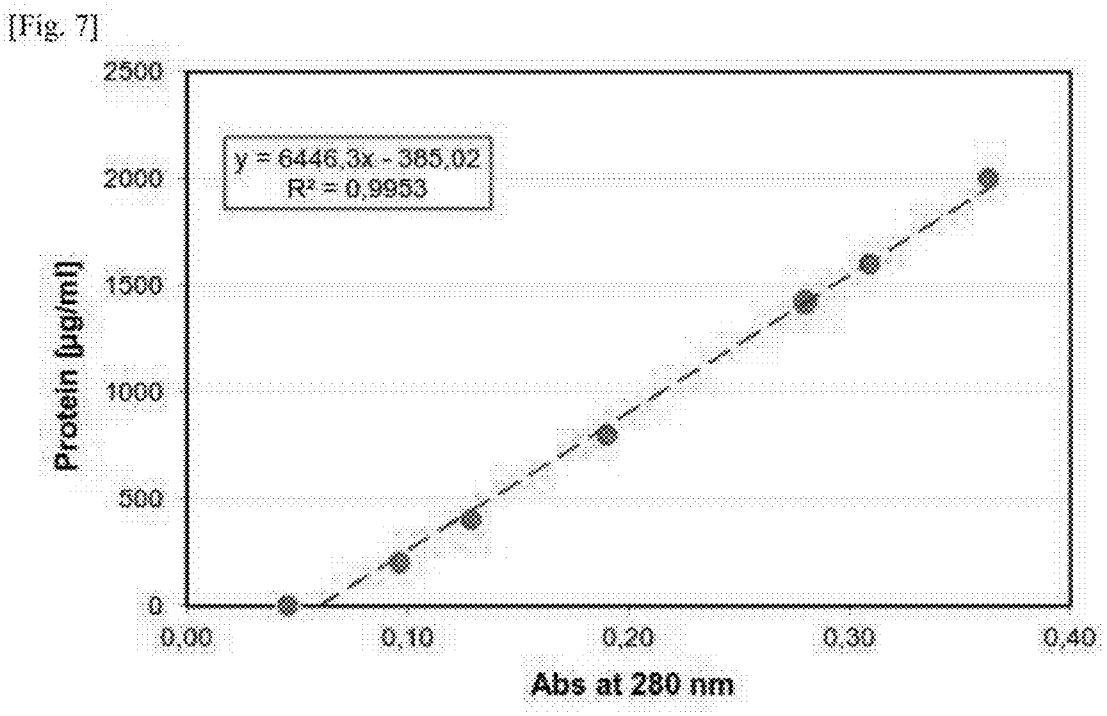

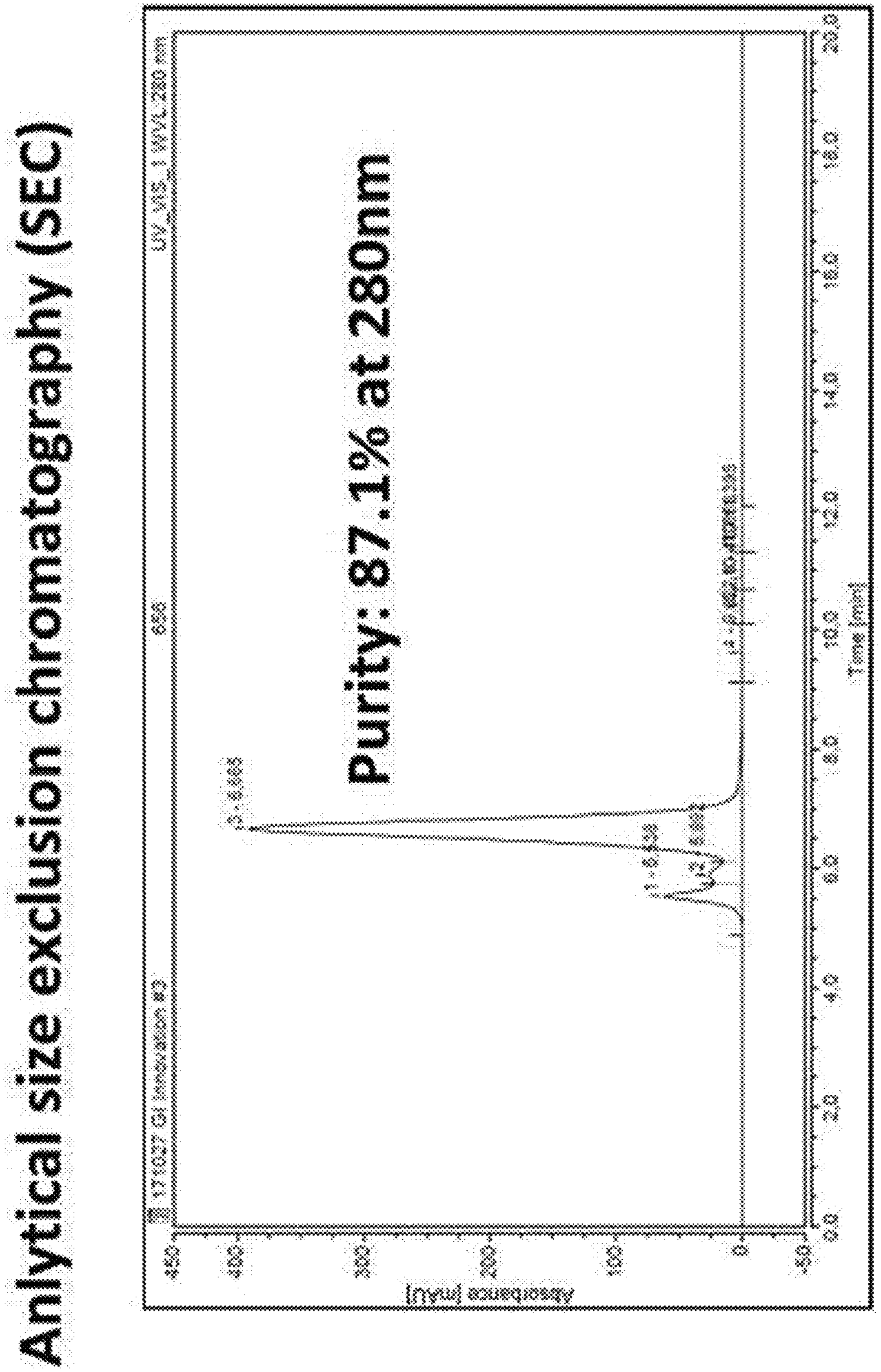
[Fig. 8]

[Fig. 9]
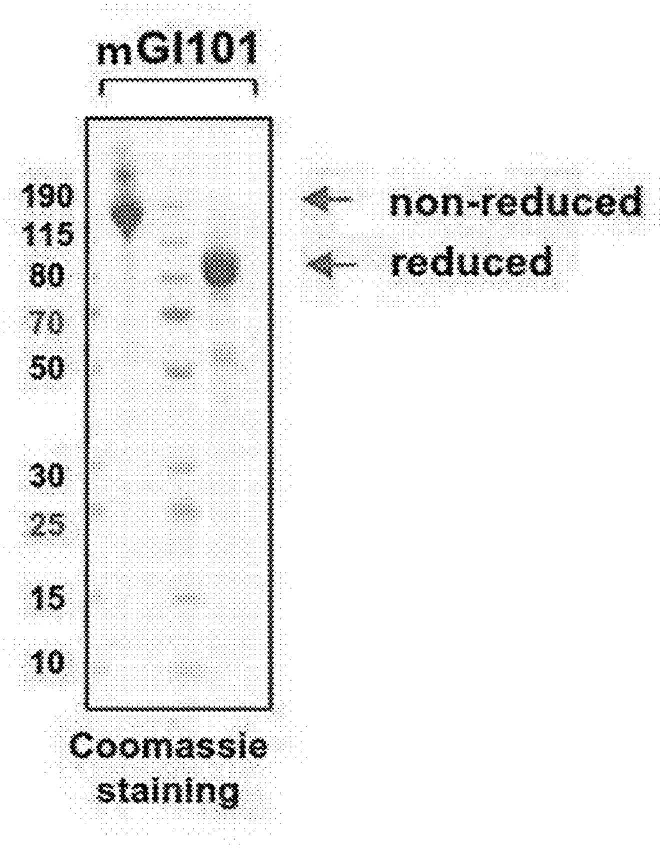
[Fig. 10]
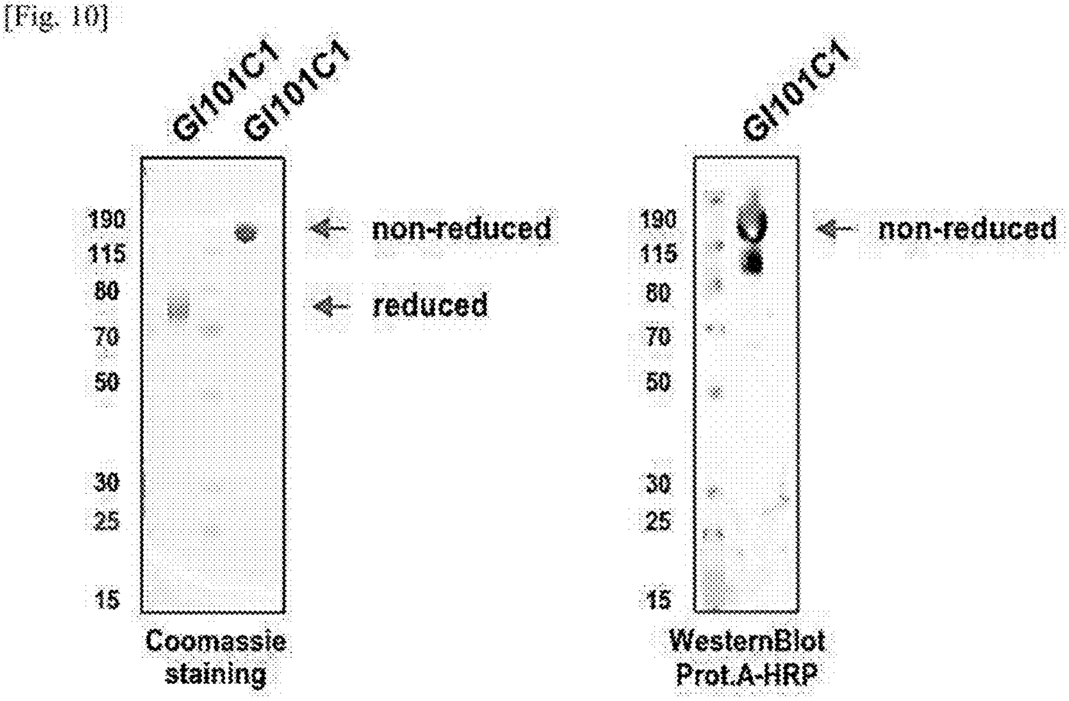

[Fig. 11]
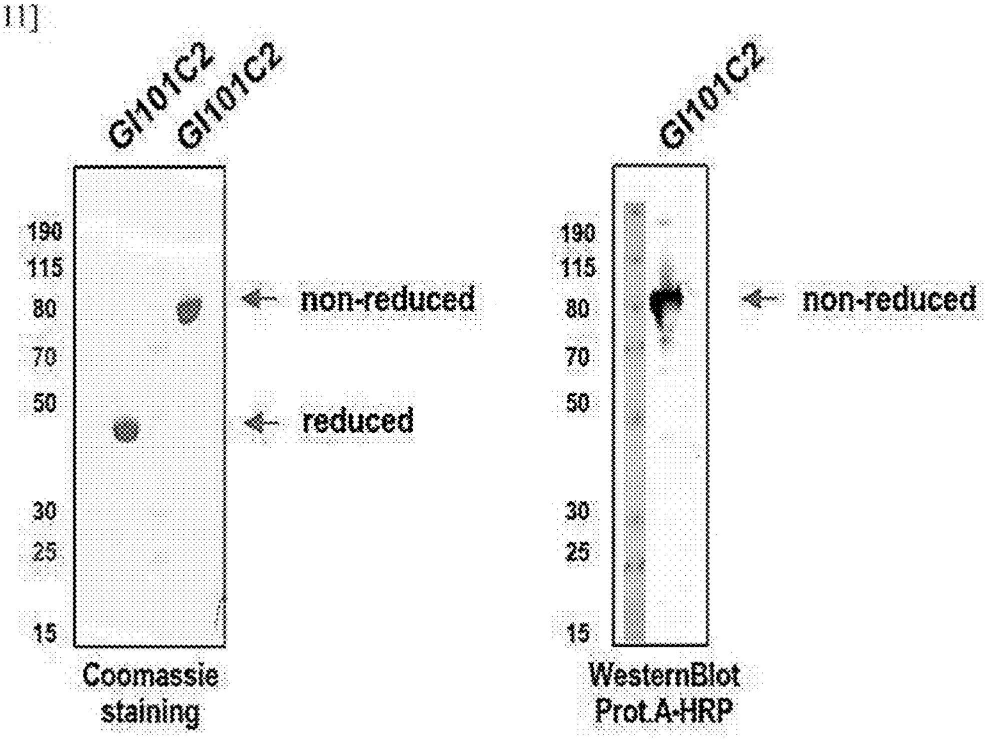
[Fig. 12]
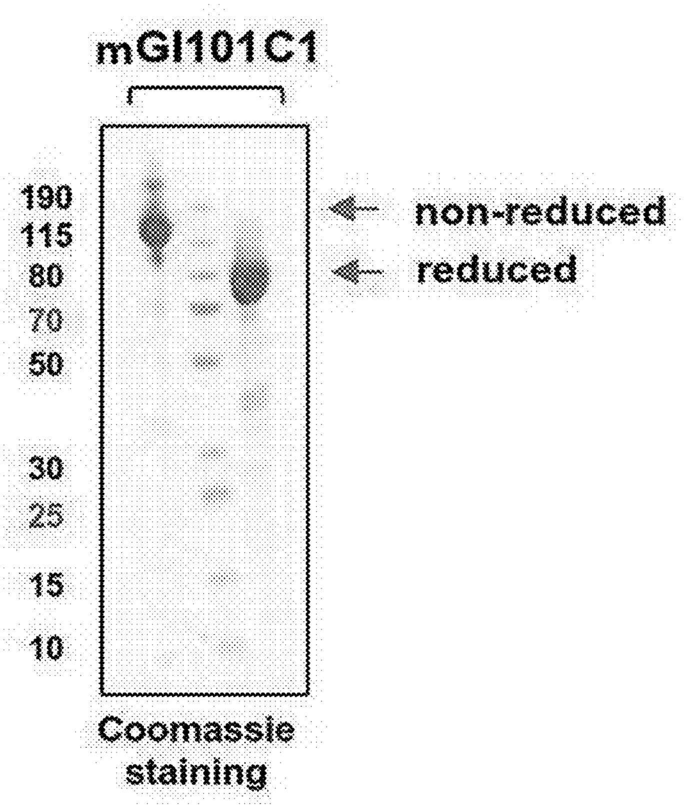

[Fig. 13]
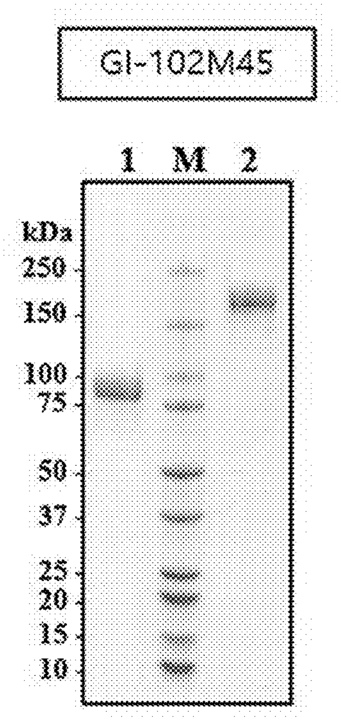
| Lane | Sample name | Loading amount |
|---|---|---|
| M | Size Marker | 5 uL |
| 1 | Reduced | 3 ug |
| 2 | Non-reduced | 3 ug |
[Fig. 14]
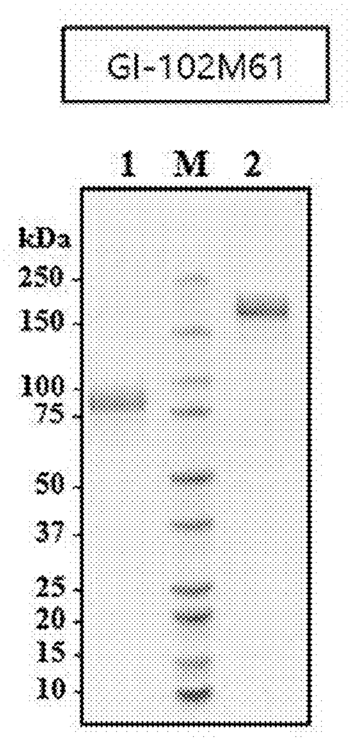
| Lane | Sample name | Loading amount |
|---|---|---|
| M | Size Marker | 5 uL |
| 1 | Reduced | 3 ug |
| 2 | Non-reduced | 3 ug |

[Fig. 15]
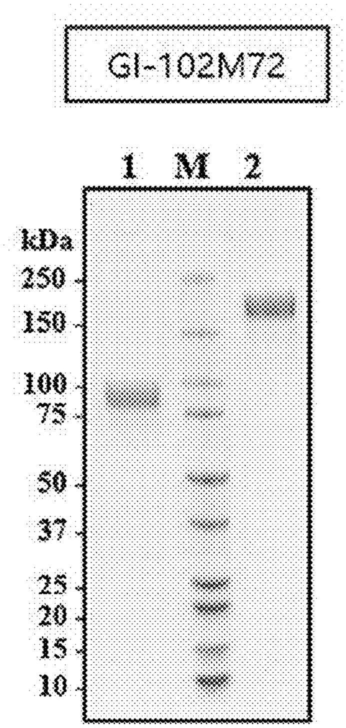
| Lane | Sample name | Loading amount |
|---|---|---|
| M | Size Marker | 5 uL |
| 1 | Reduced | 3 ug |
| 2 | Non-reduced | 3 ug |
BIO-RAD 4-15% TGX$^{TM}$ gel
200 V, 30 min running, 1X TGS buffer
[Fig. 16]
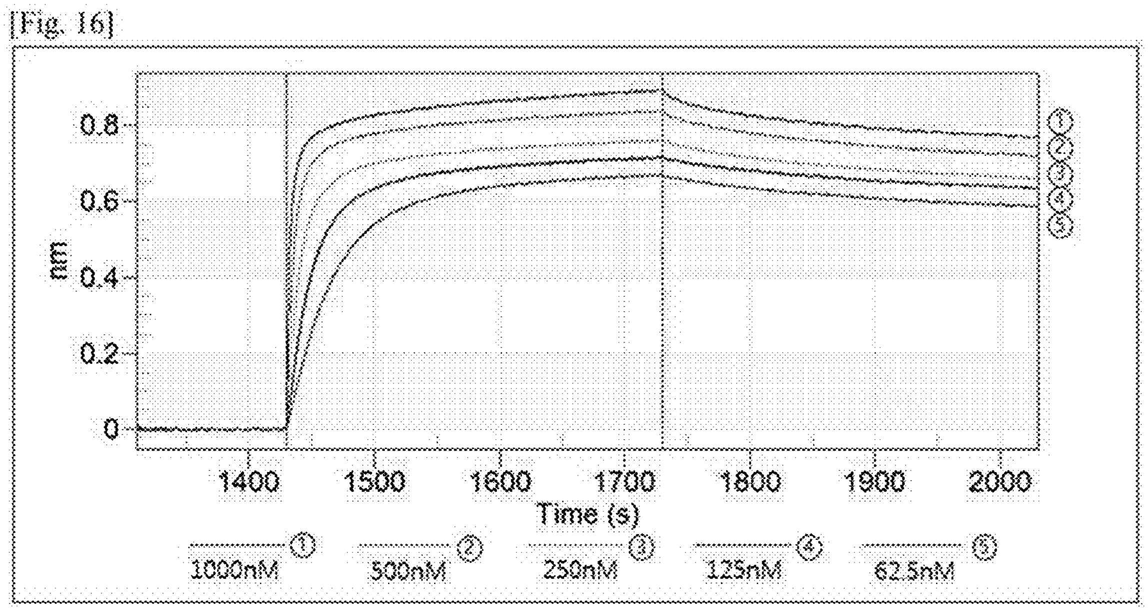
| Analyte | $K_D$ (M) | $K_{on}$ (1/Ms) | $K_{dis}$ (1/s) |
|---|---|---|---|
| GI101 | 1.07E-09 | 3.86E+05 | 4.14E-04 |

[Fig. 17]
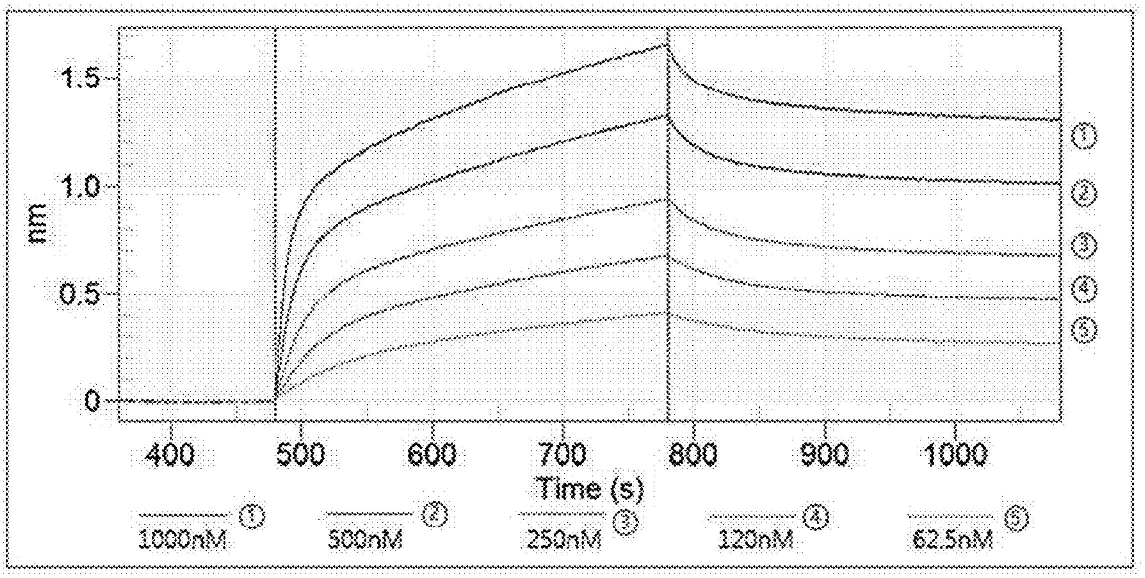
| Analyte | $K_D$ (M) | $K_{on}$ (1/Ms) | $K_{dis}$ (1/s) |
|---|---|---|---|
| GI101 | 3.46E-08 | 7.0E+04 | 2.42E-03 |
[Fig. 18]
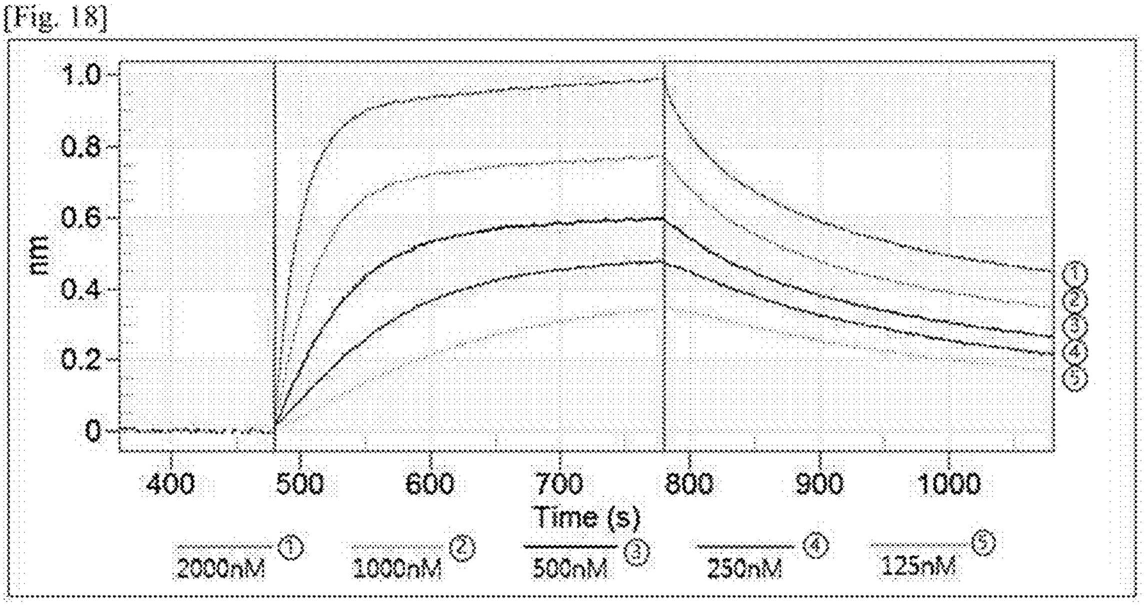
| Analyte | $K_D$ (M) | $K_{on}$ (1/Ms) | $K_{dis}$ (1/s) |
|---|---|---|---|
| PD-1 | 1.13E-07 | 2.72E+04 | 3.07E-03 |

[Fig. 19]
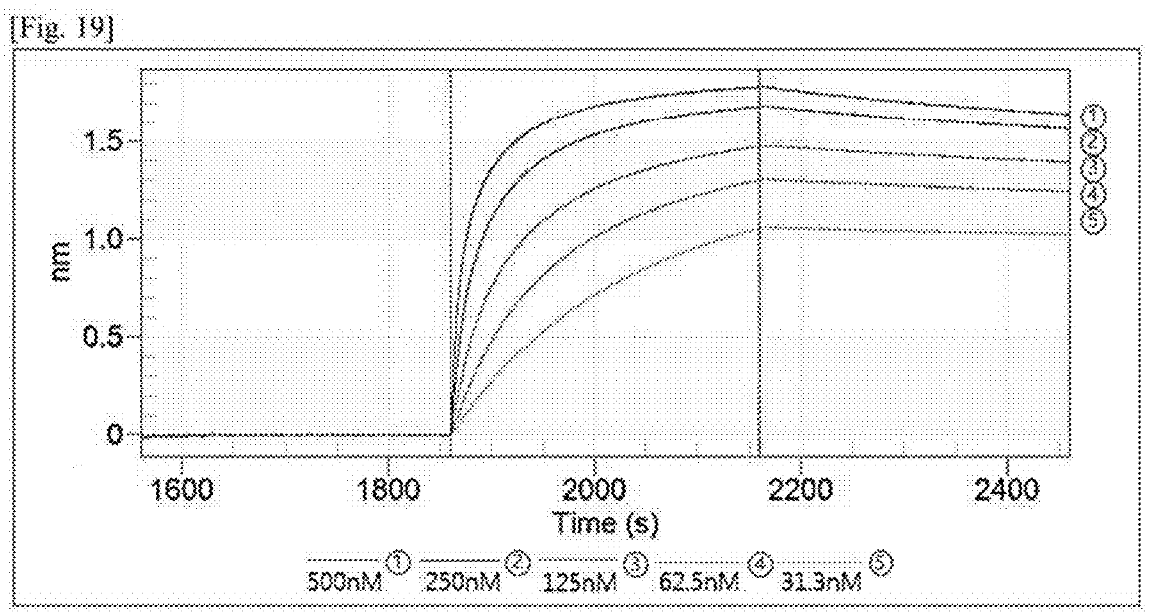
| Analyte | $K_D$ (M) | $K_{on}$ (1/Ms) | $K_{dis}$ (1/s) |
|---|---|---|---|
| mGI101 | 2.58E-08 | 3.05E+05 | 7.88E-04 |
[Fig. 20]
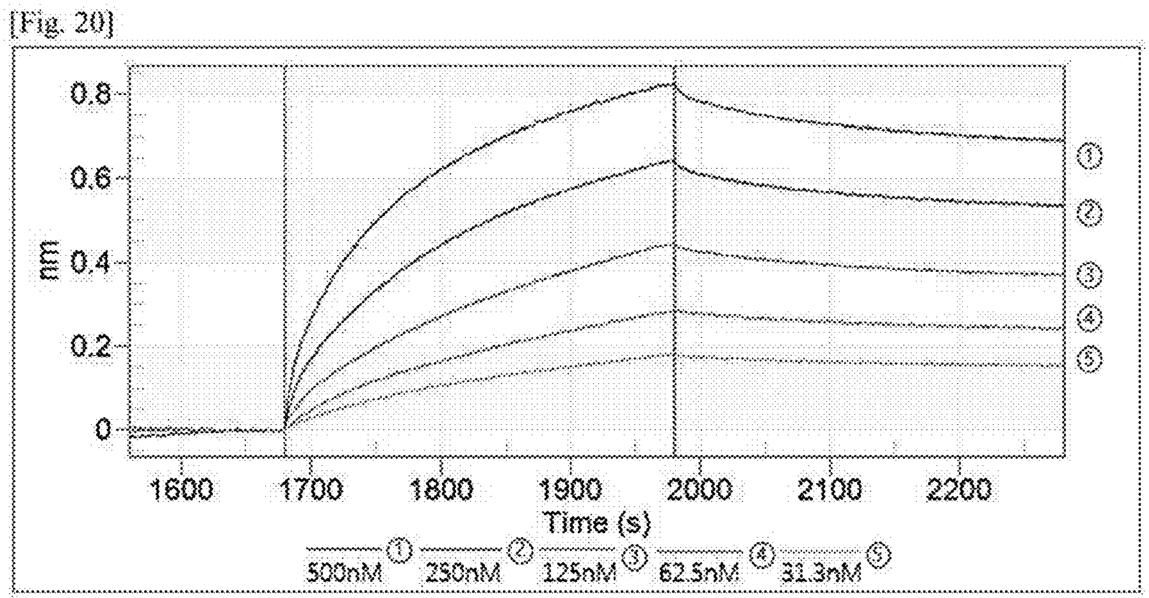
| Analyte | $K_D$ (M) | $K_{on}$ (1/Ms) | $K_{dis}$ (1/s) |
|---|---|---|---|
| mGI101 | 9.91E-09 | 8.12E+05 | 8.04E-03 |

[Fig. 21]
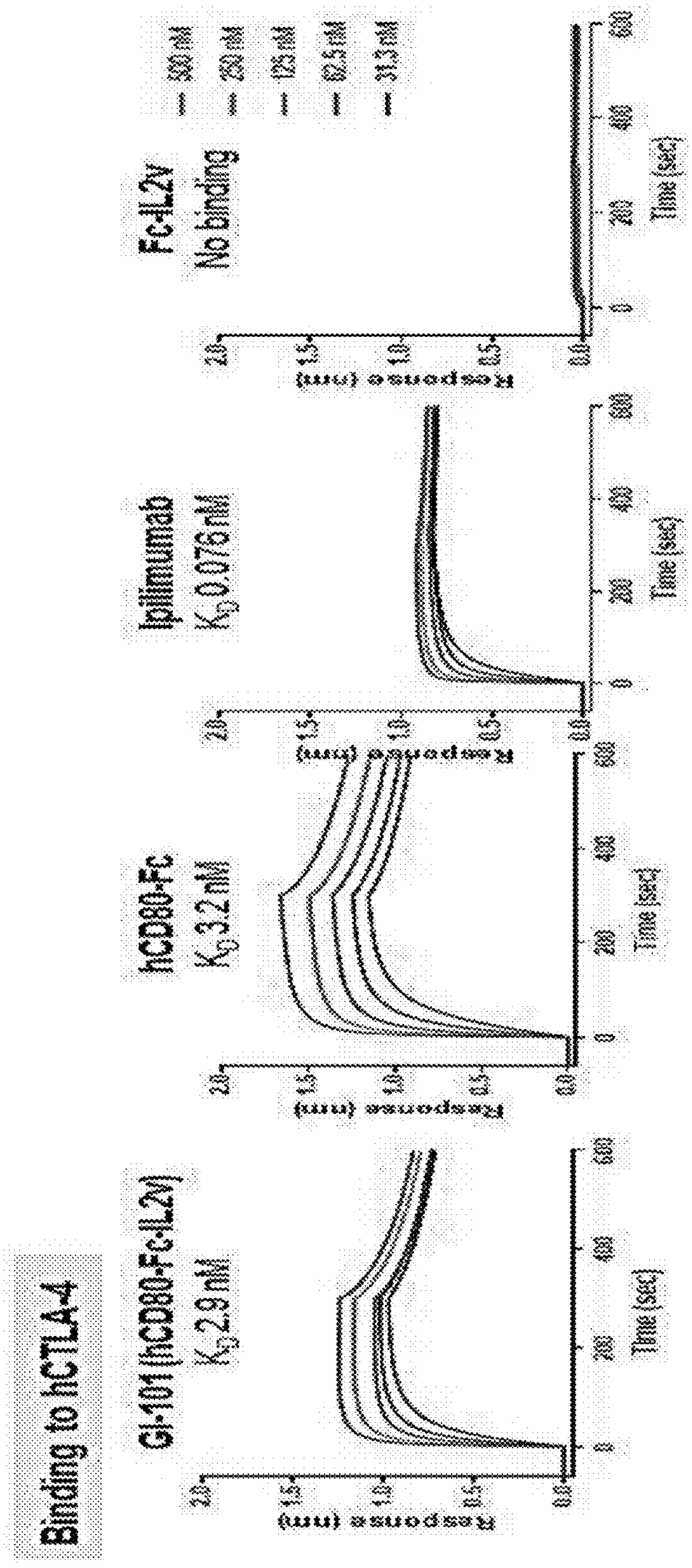

[Fig. 22]
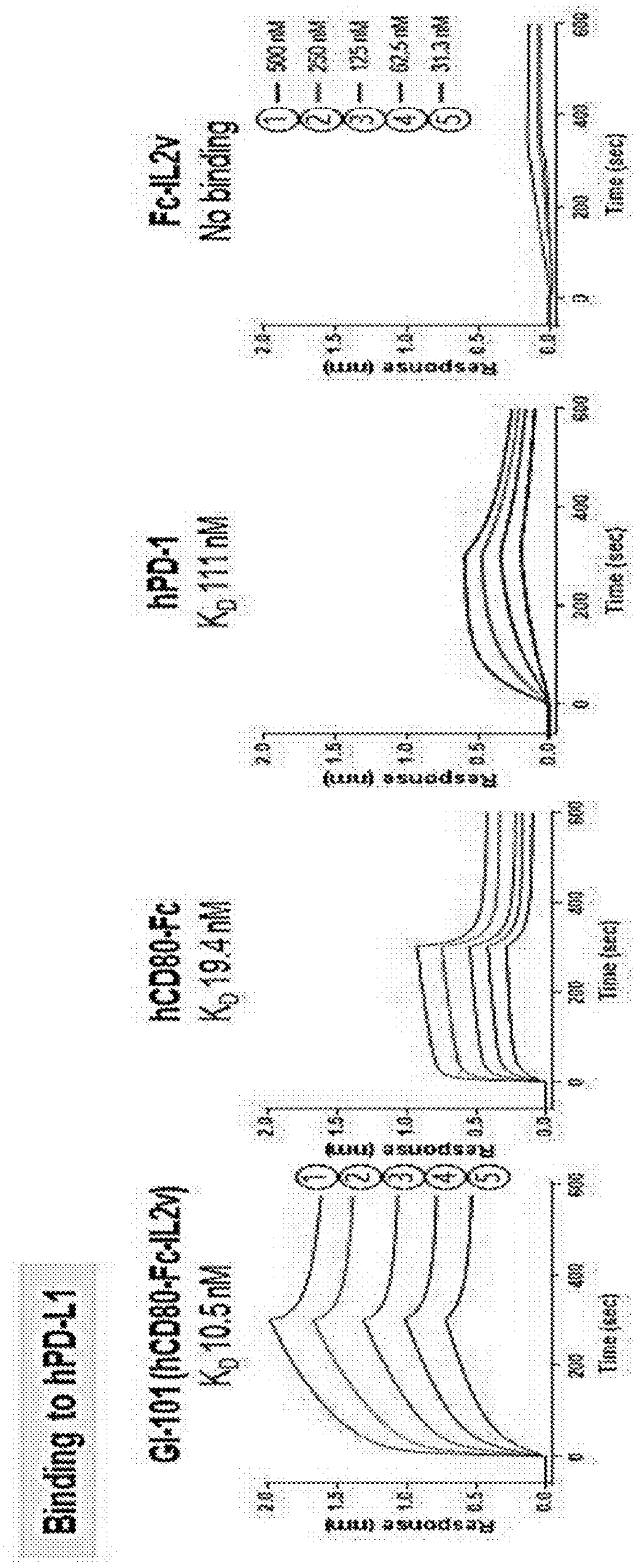

[Fig. 23]
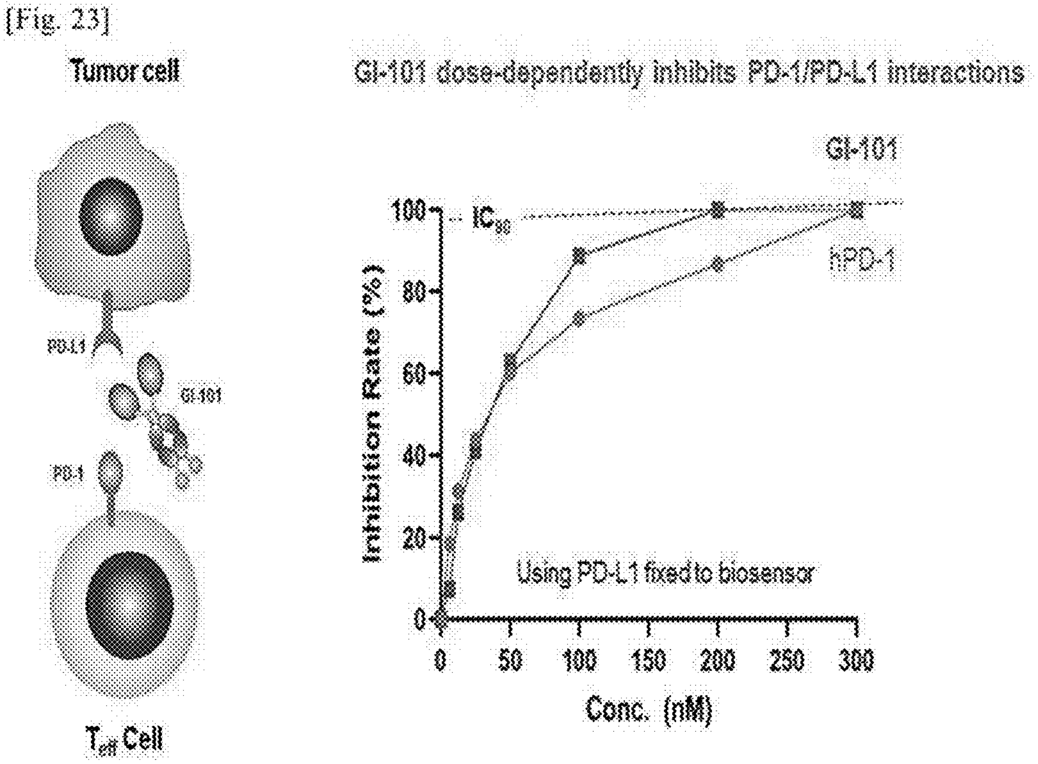

[Fig. 24]
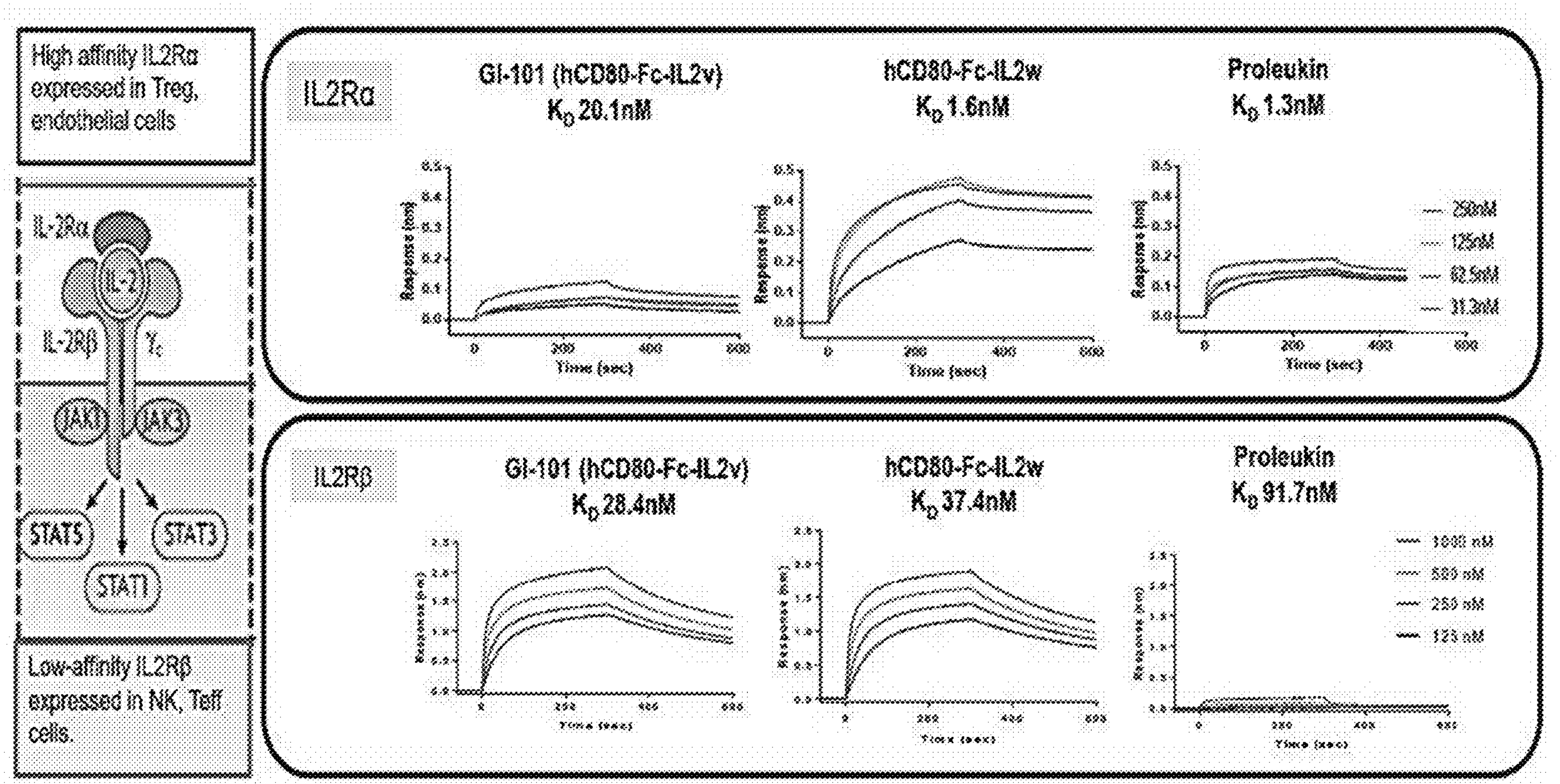
| References | Kd (nM) | | | |
|---|---|---|---|---|
| Receptor | *hIL2w | **NKTR-214 (IL2) | **NKTR-214 (1-PEG-IL2) | **NKTR-214 (2-PEG-IL2) |
| hIL2Rα | 10 (x14) | 8.6 (x28) | 189.7 (x9) | 486.6 (x8) |
| hIL2Rβ | 144 | 238.9 | 1769.5 | 3951.8 |

[Fig. 25]
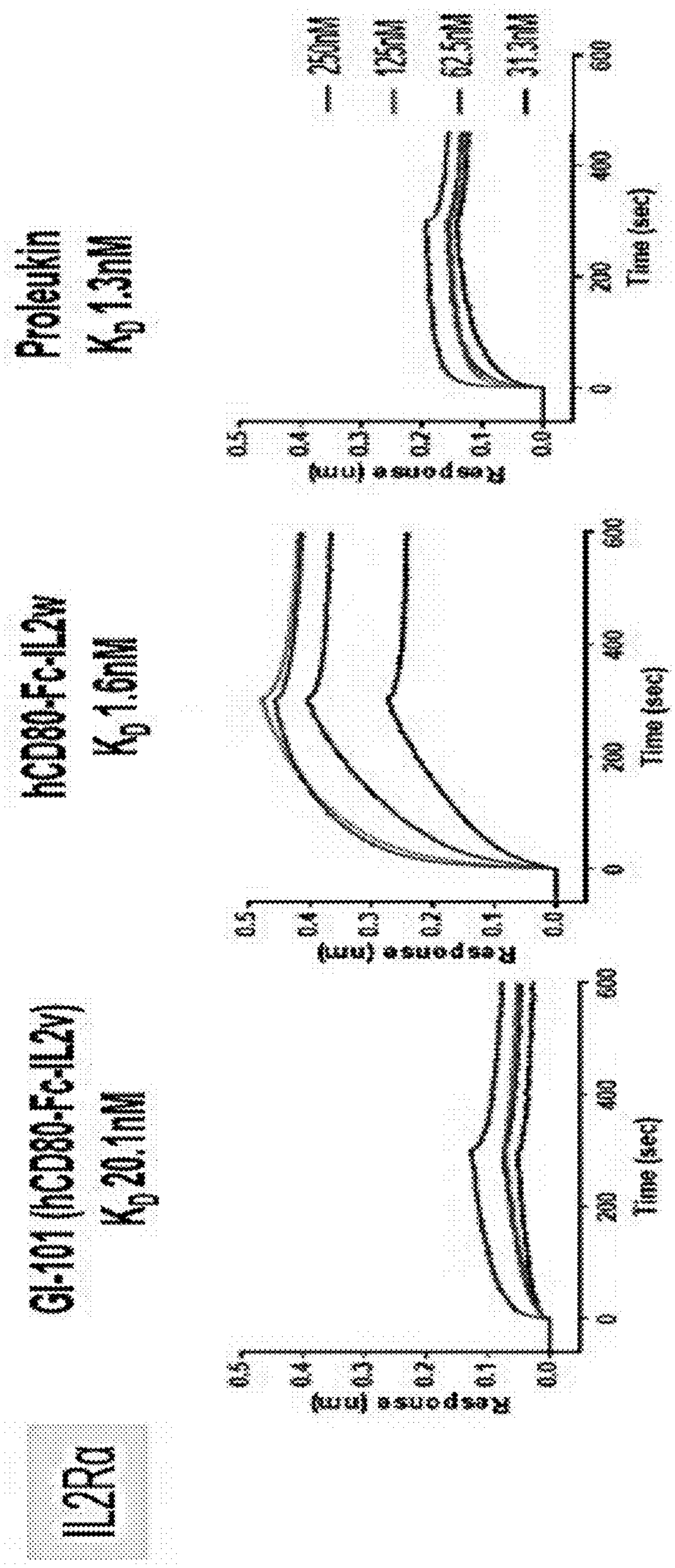

[Fig. 26]
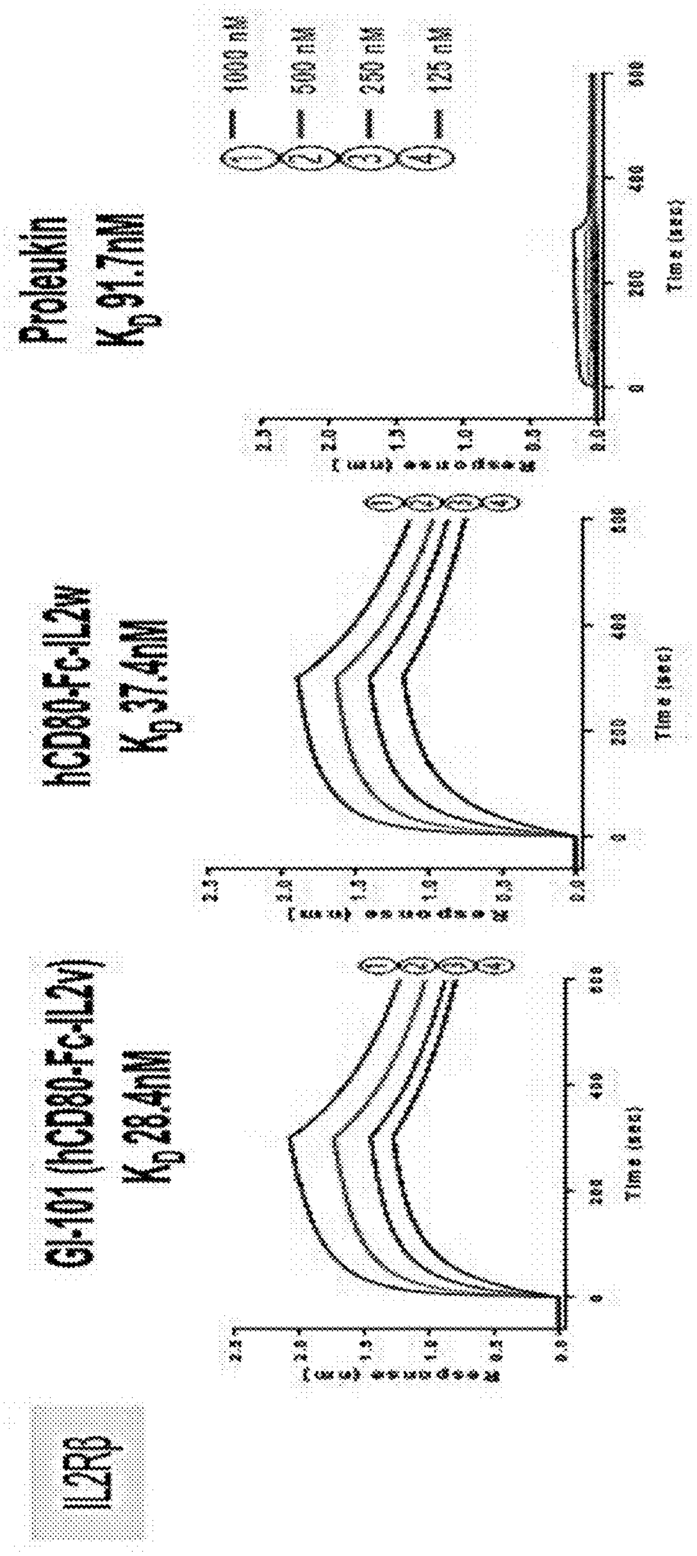

[Fig. 27]
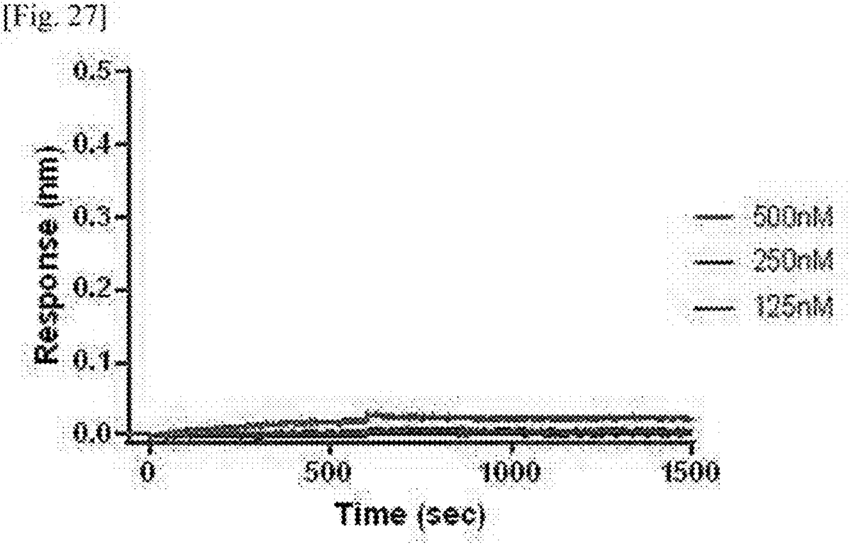
[Fig. 28]
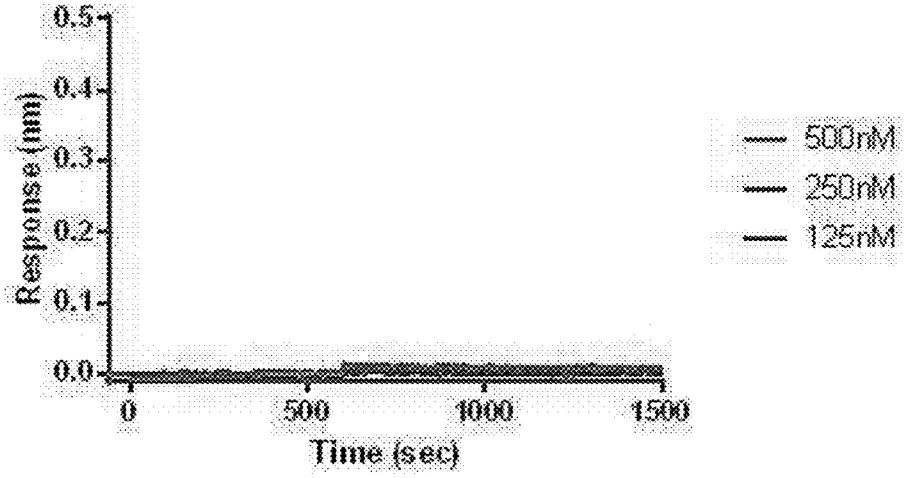

[Fig. 29]
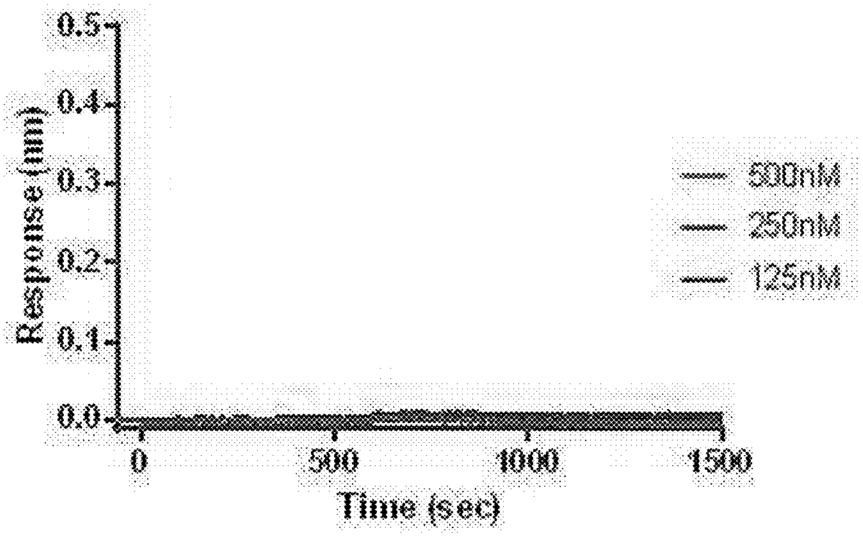
[Fig. 30]
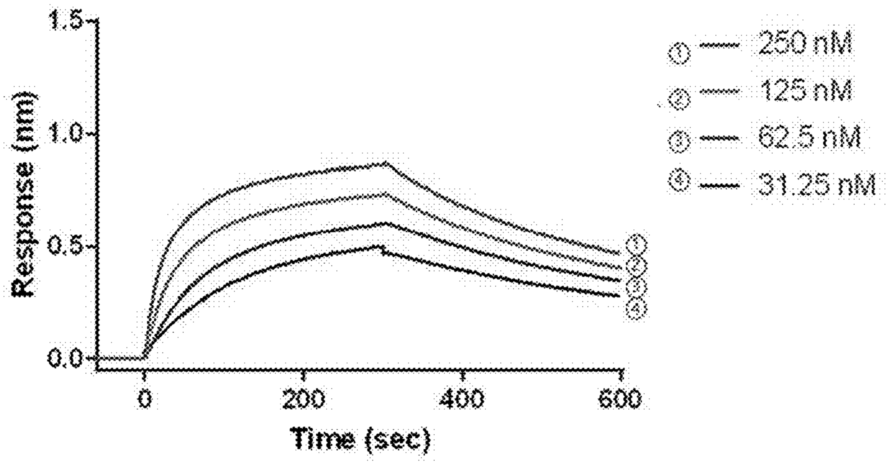
| Kon | Koff | Kd |
|---|---|---|
| 1.30X105 | 2.01X10-3 | 1.55X10-8 |

[Fig. 31]
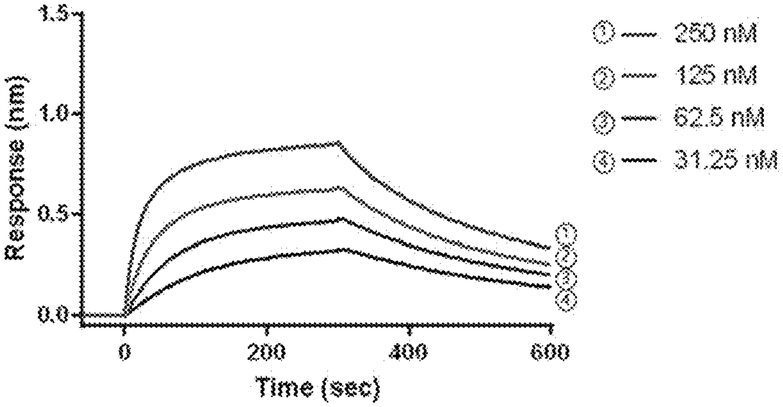
| Kon | Koff | Kd |
|---|---|---|
| 1.32X105 | 3.11X10-3 | 2.36X10-8 |
[Fig. 32]
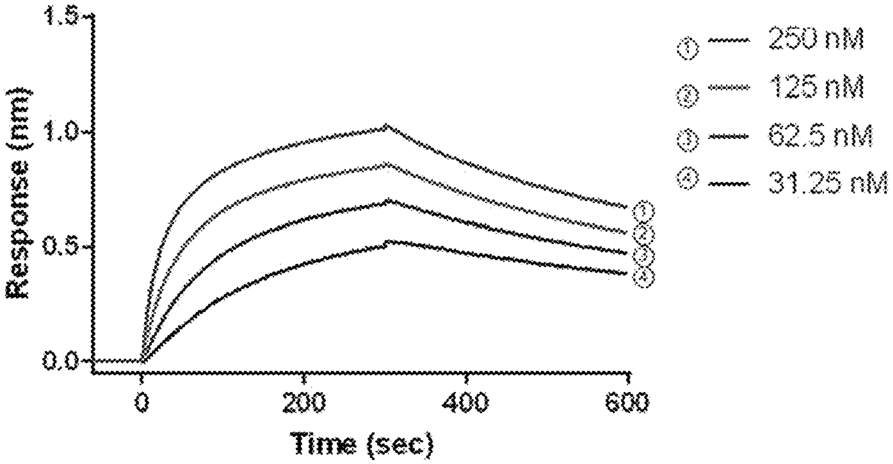
| Kon | Koff | Kd |
|---|---|---|
| 1.10X105 | 1.27X10-3 | 1.15X10-8 |

[Fig. 33]
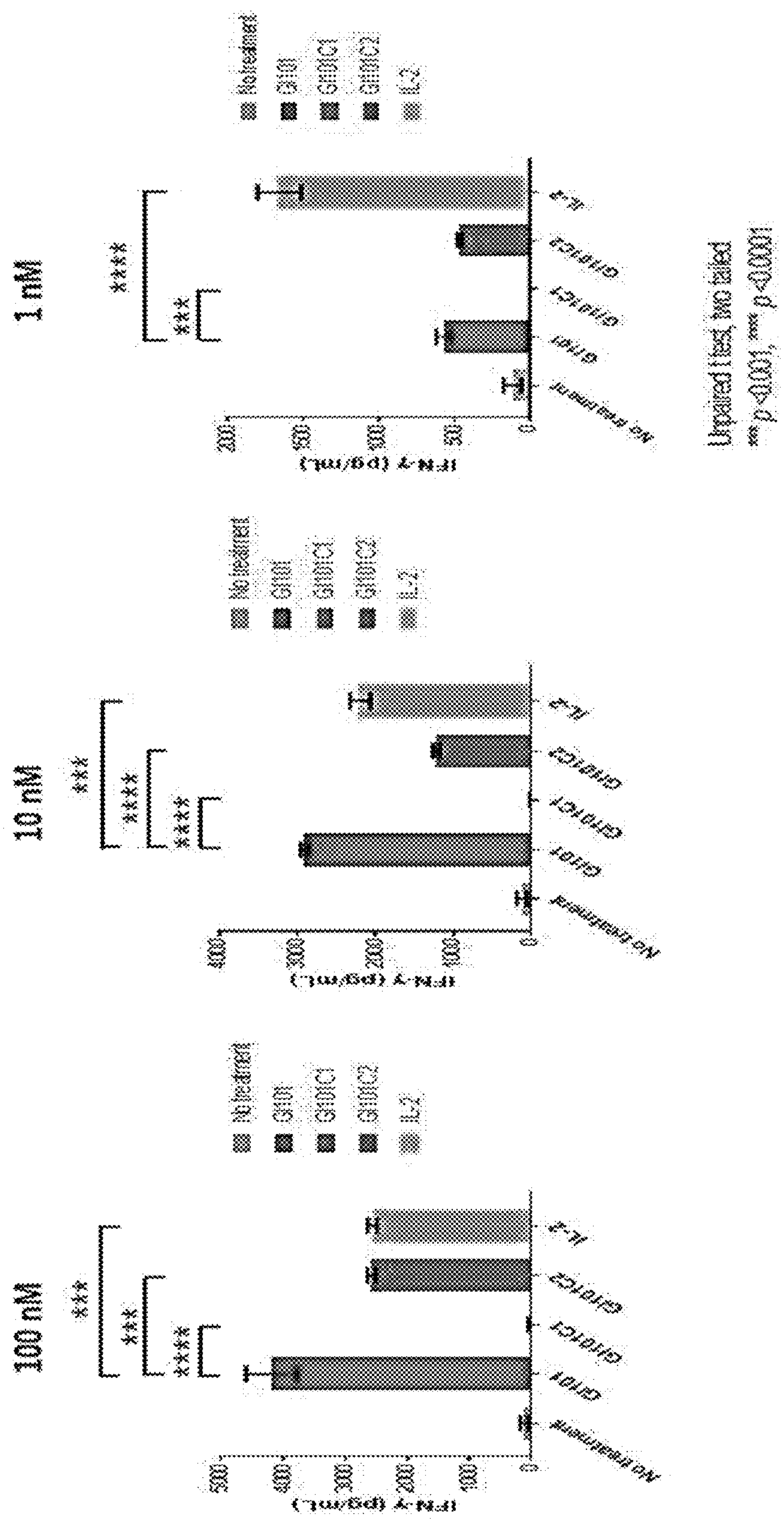

[Fig. 34]
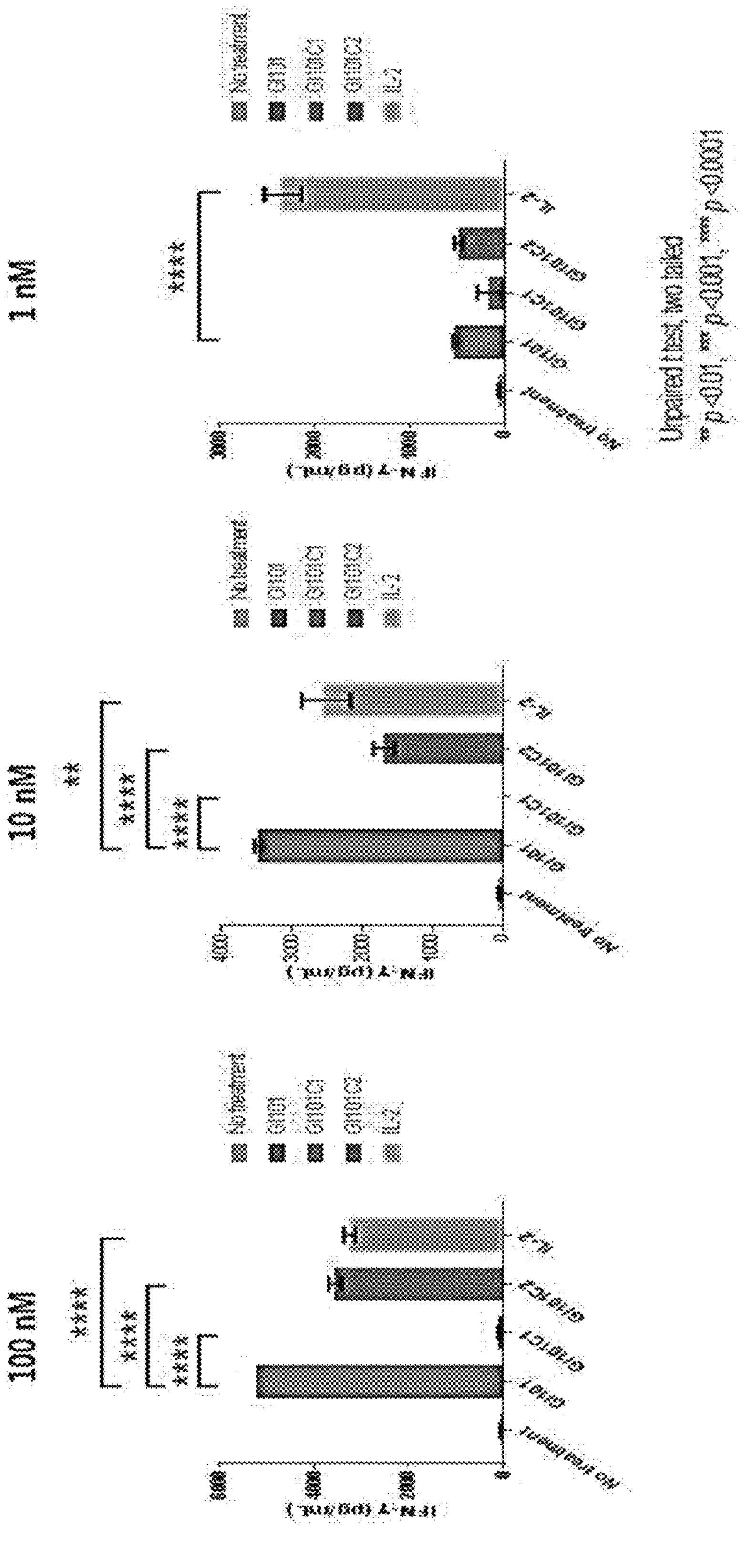

[Fig. 35]
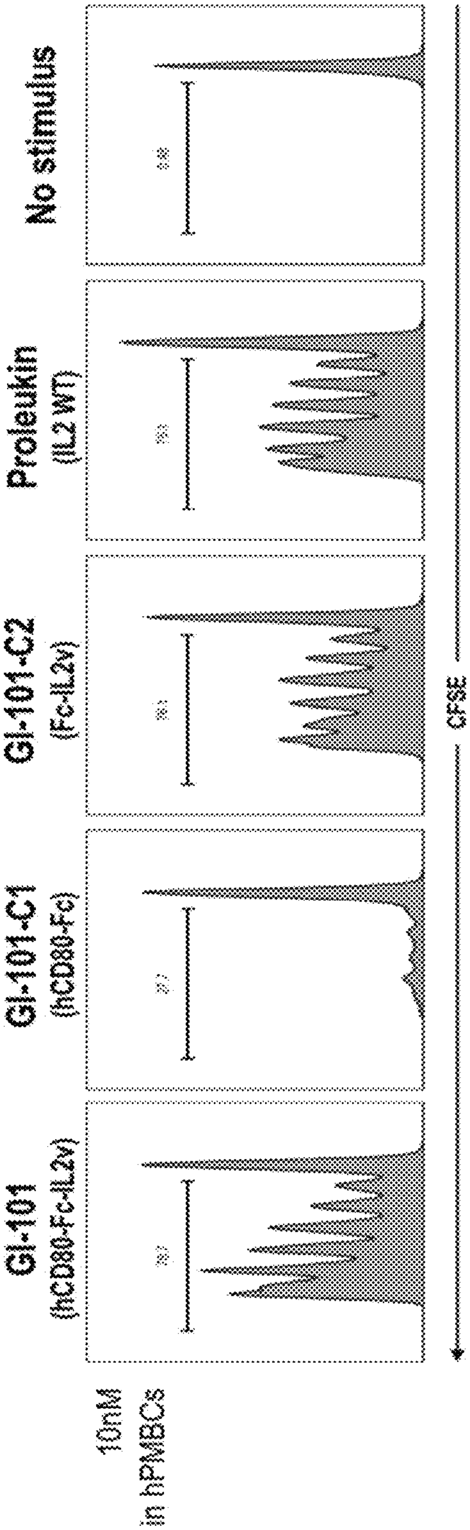

[Fig. 36]
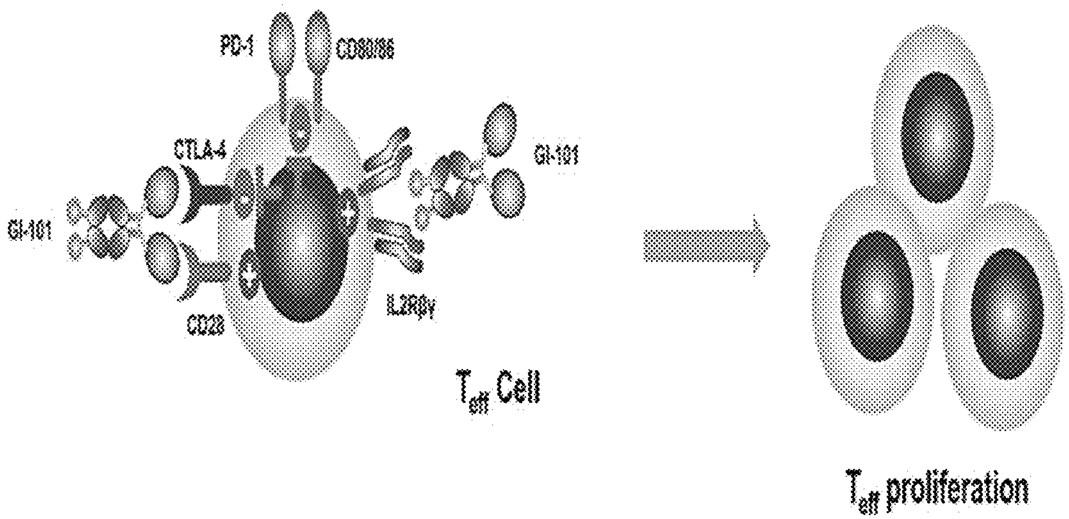

[Fig. 37]
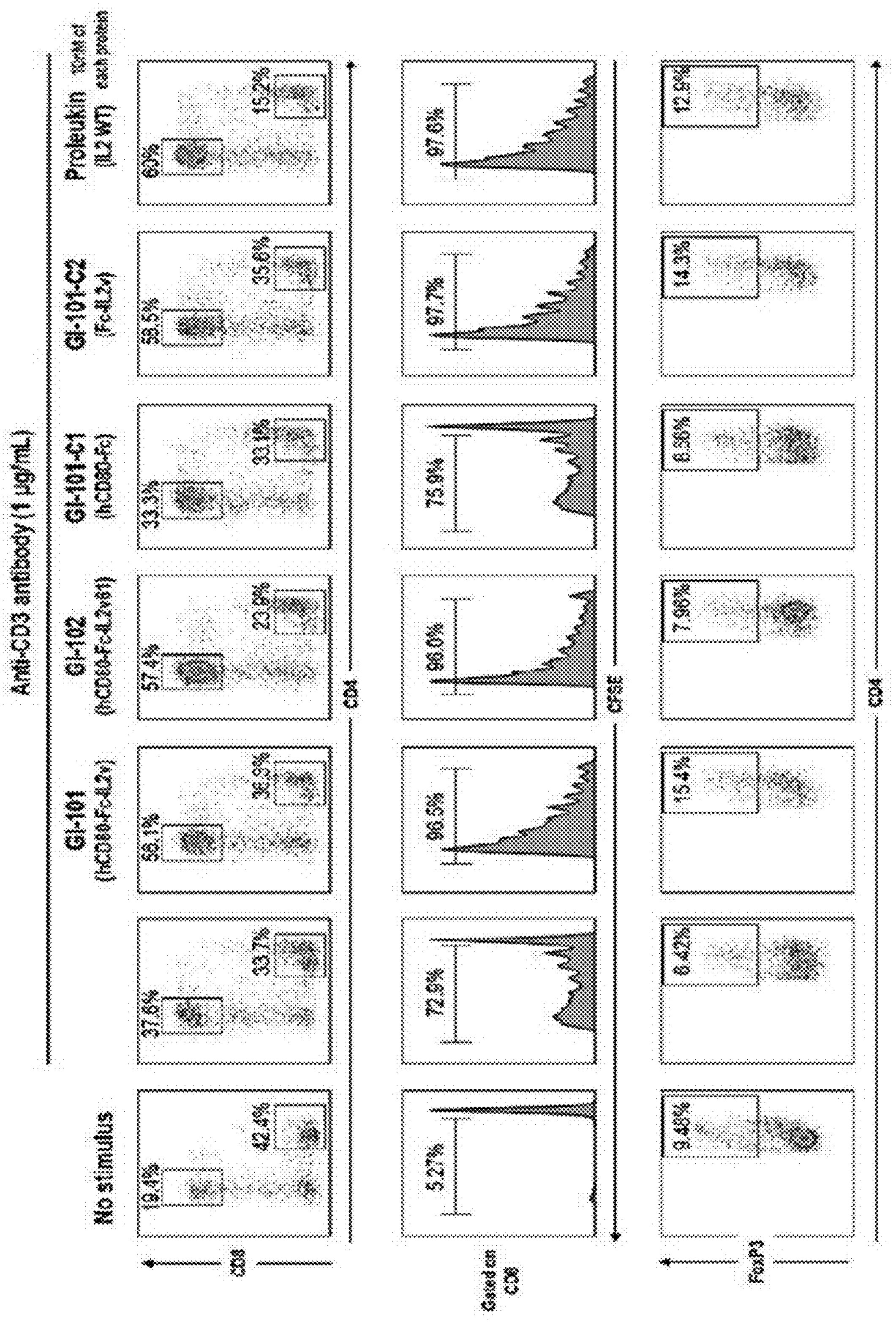

[Fig. 38]
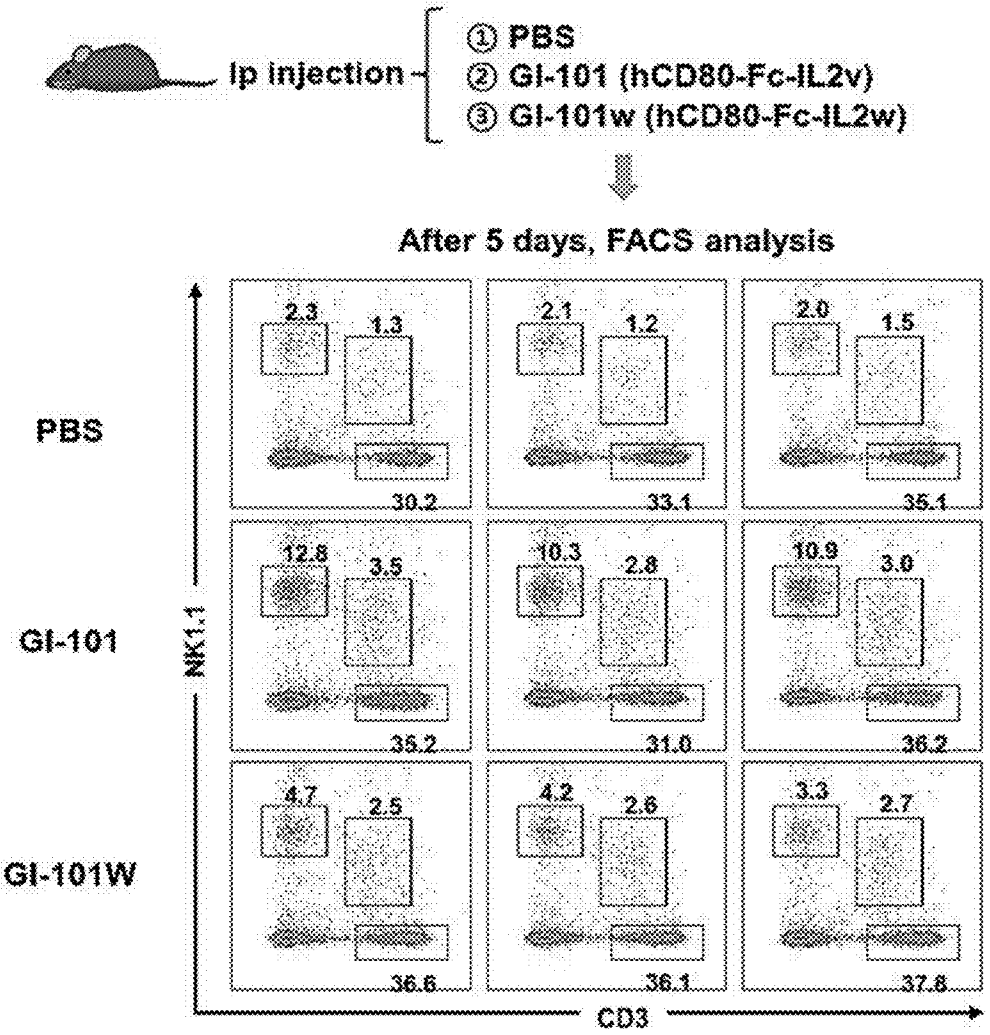

[Fig. 39]
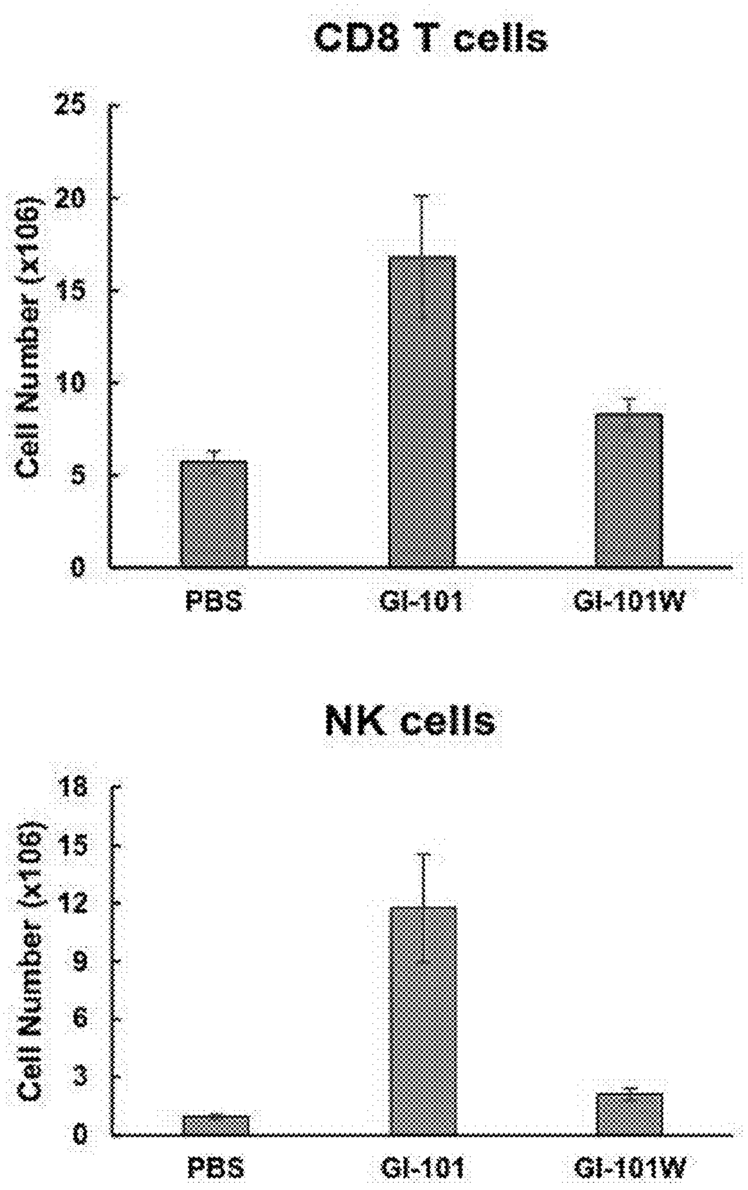

[Fig. 40]
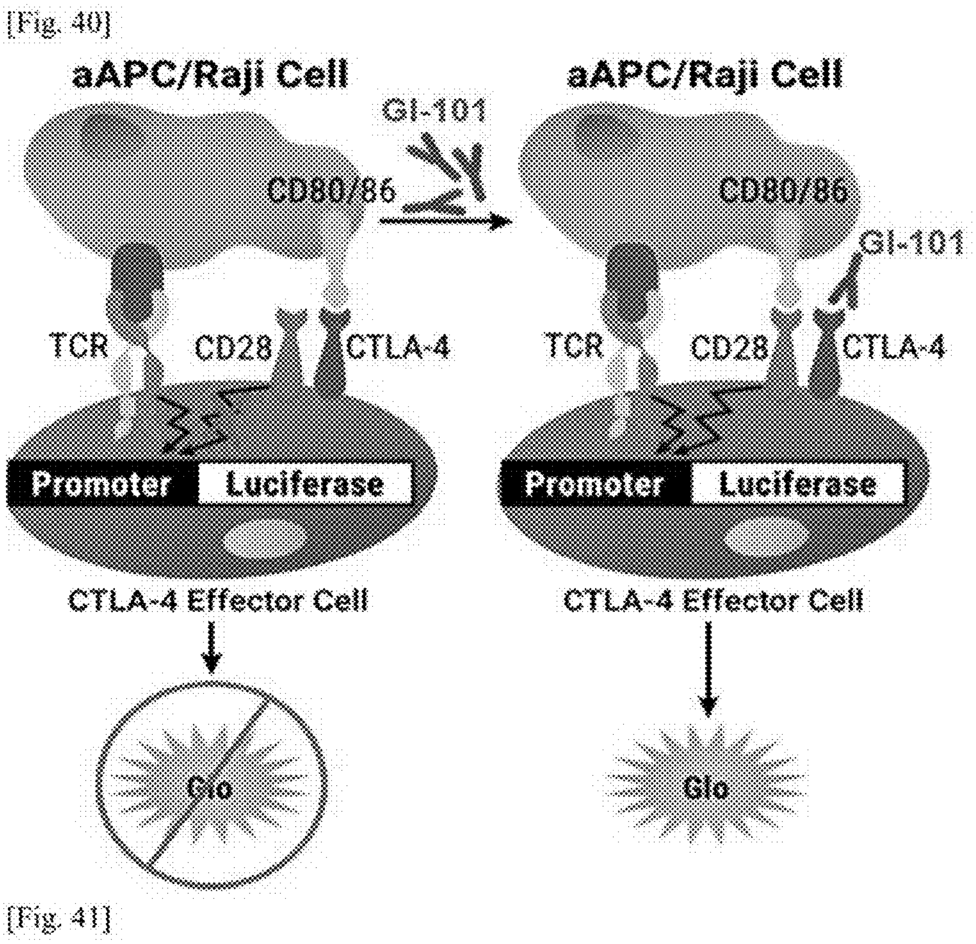
[Fig. 41]
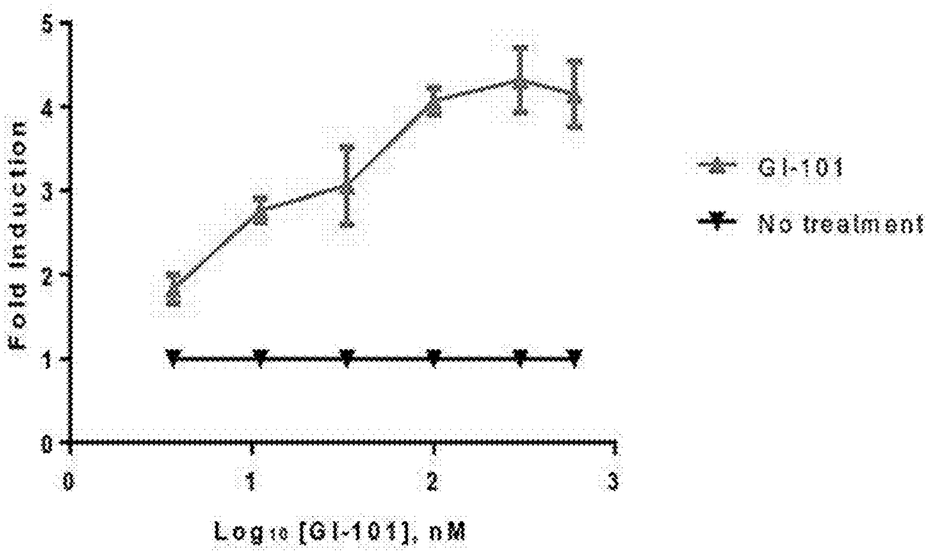

[Fig. 42]
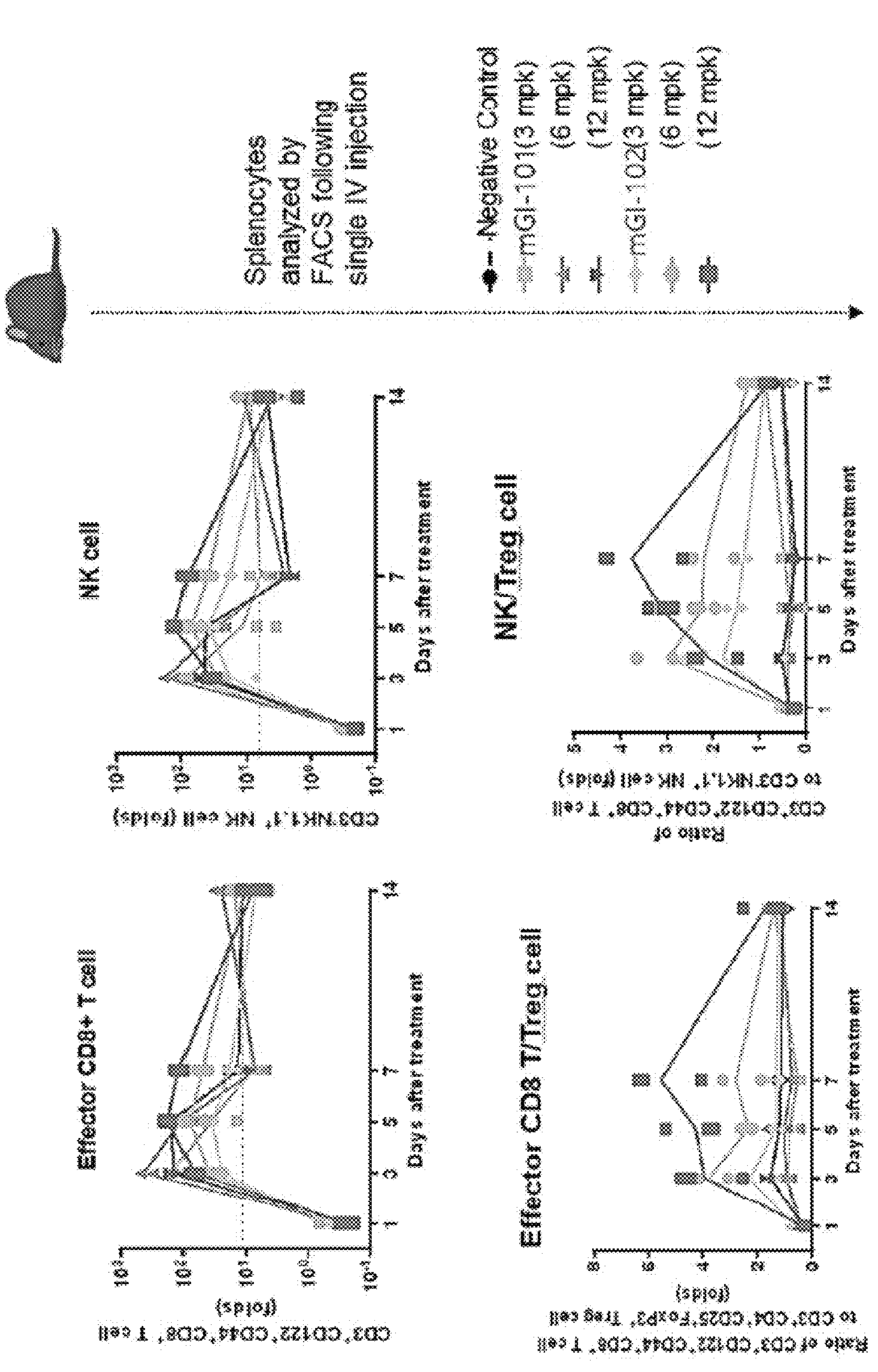

[Fig. 43]
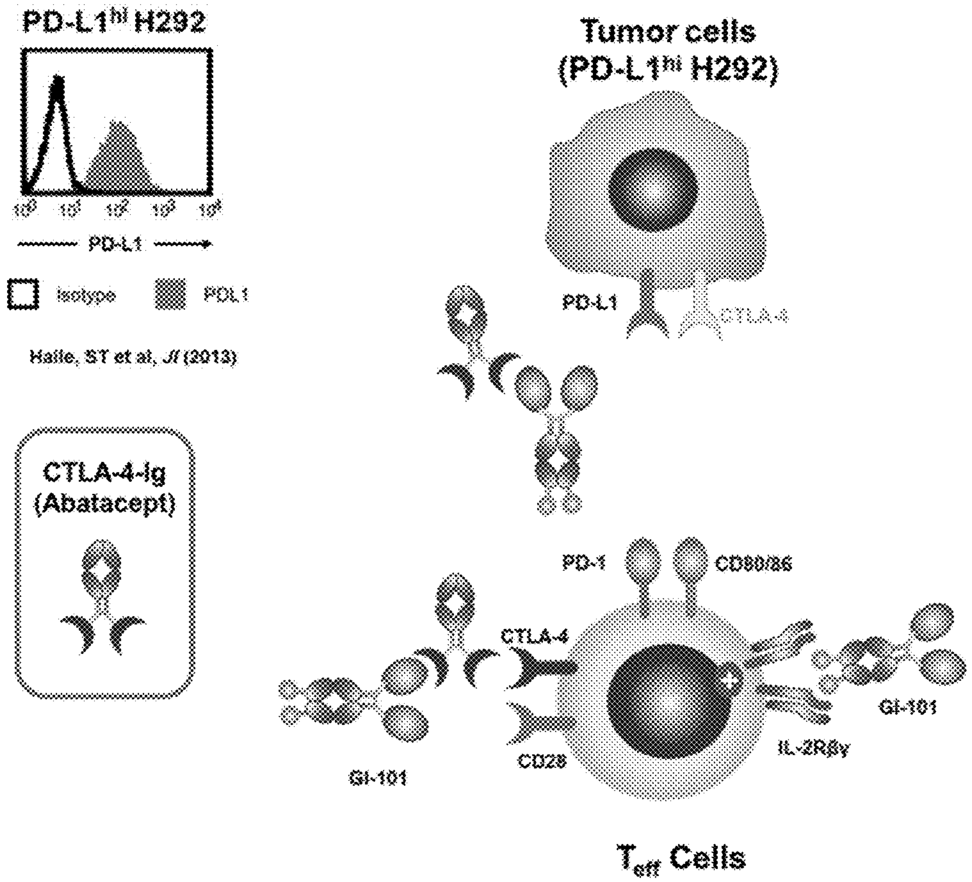
[Fig. 44]
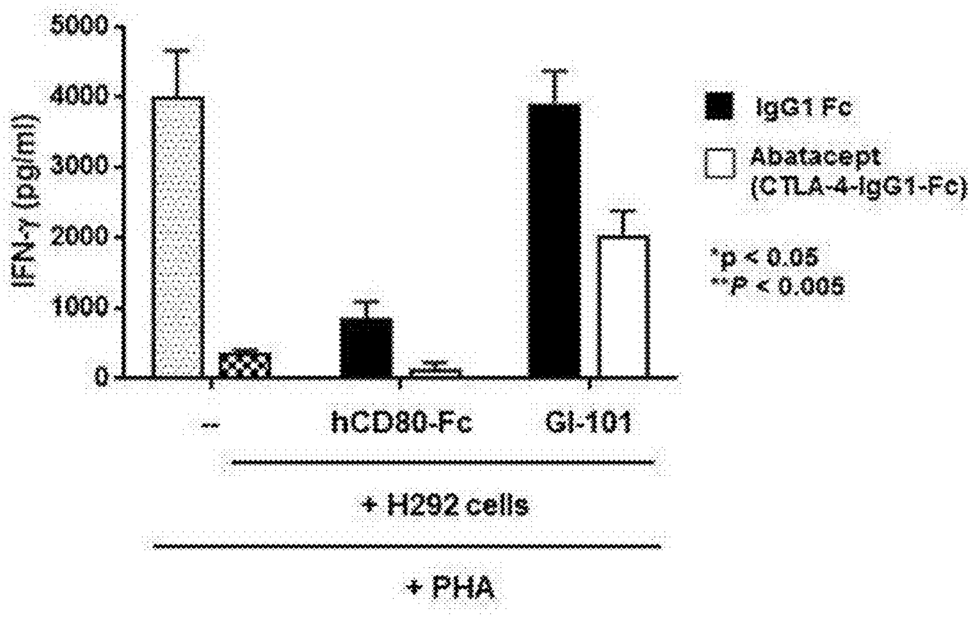

[Fig. 45]
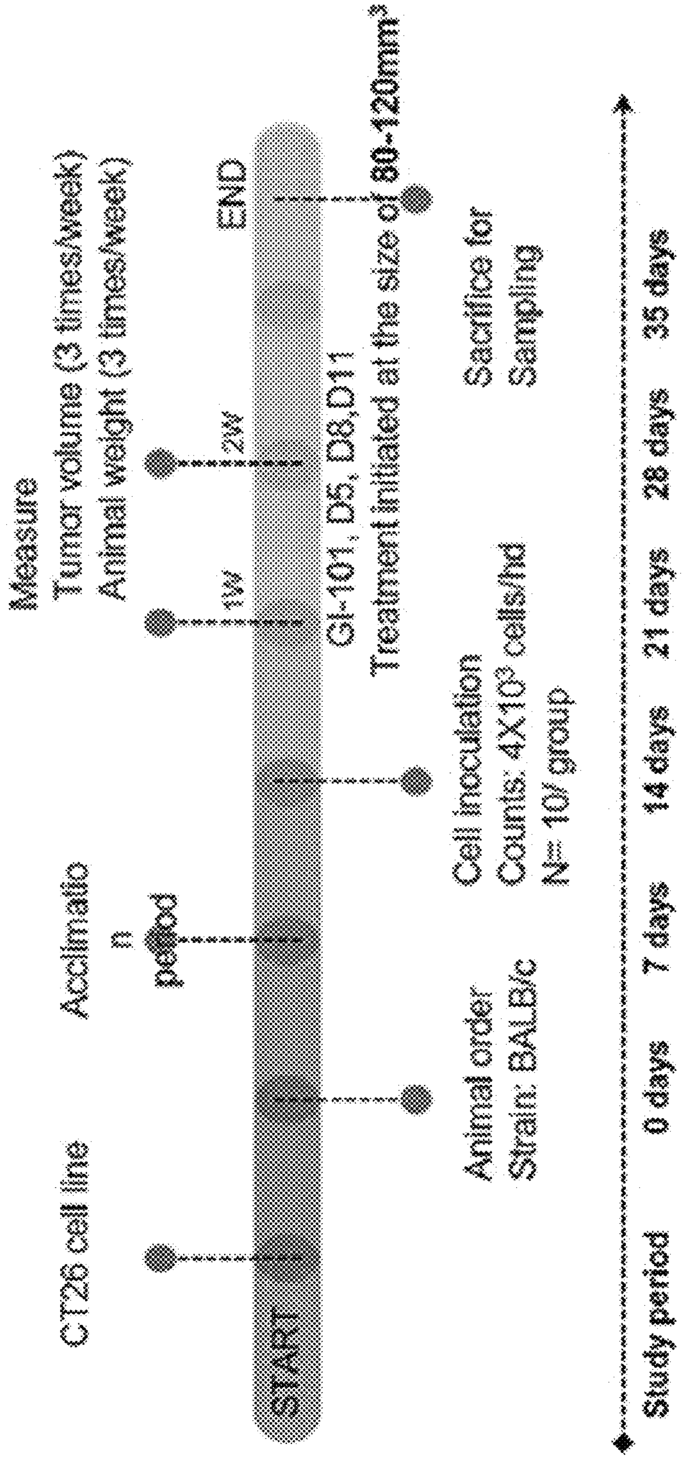

[Fig. 46]
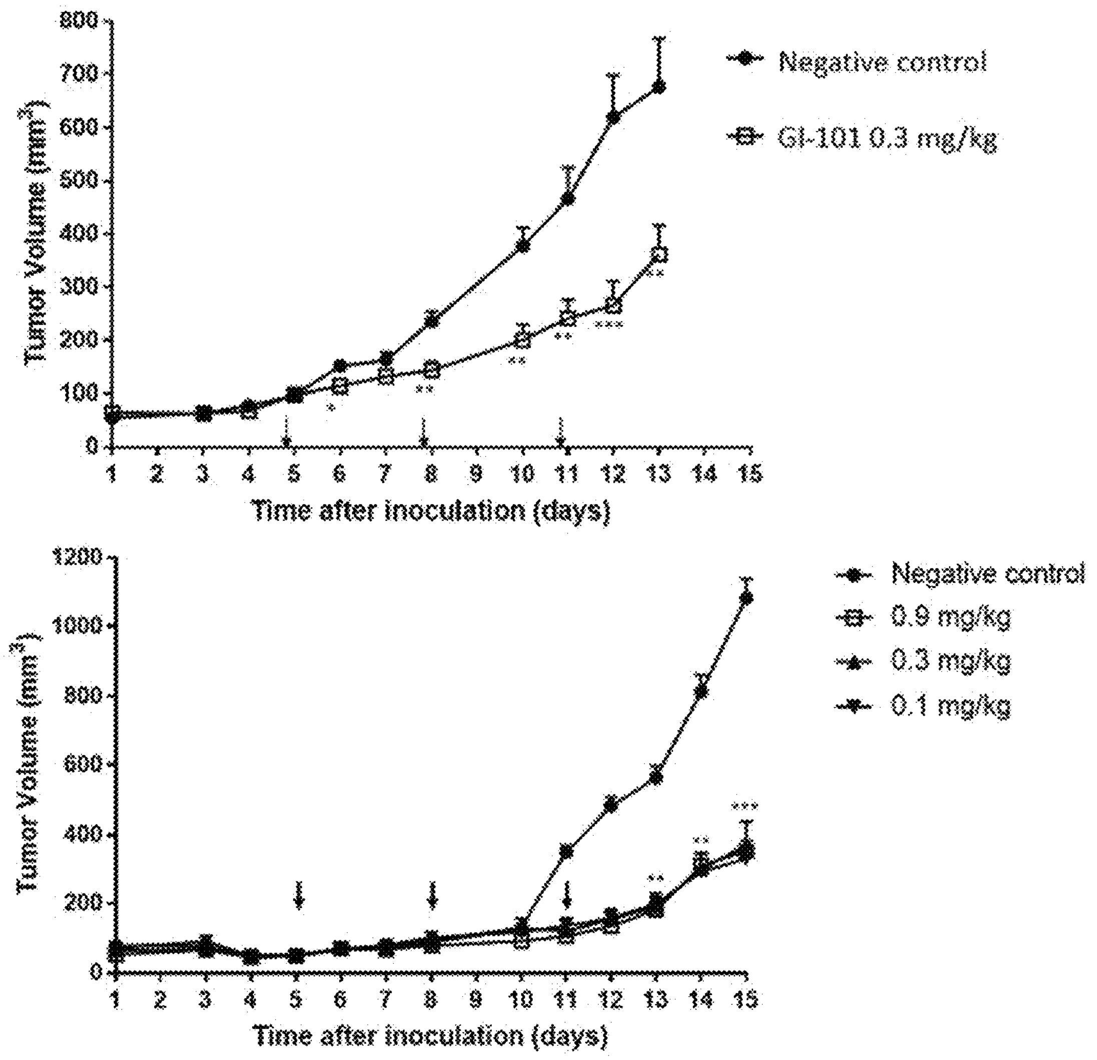
* p<0.05,  p<0.005, * p<0.001
Each point represents mean + SE (n=10)

[Fig. 47]
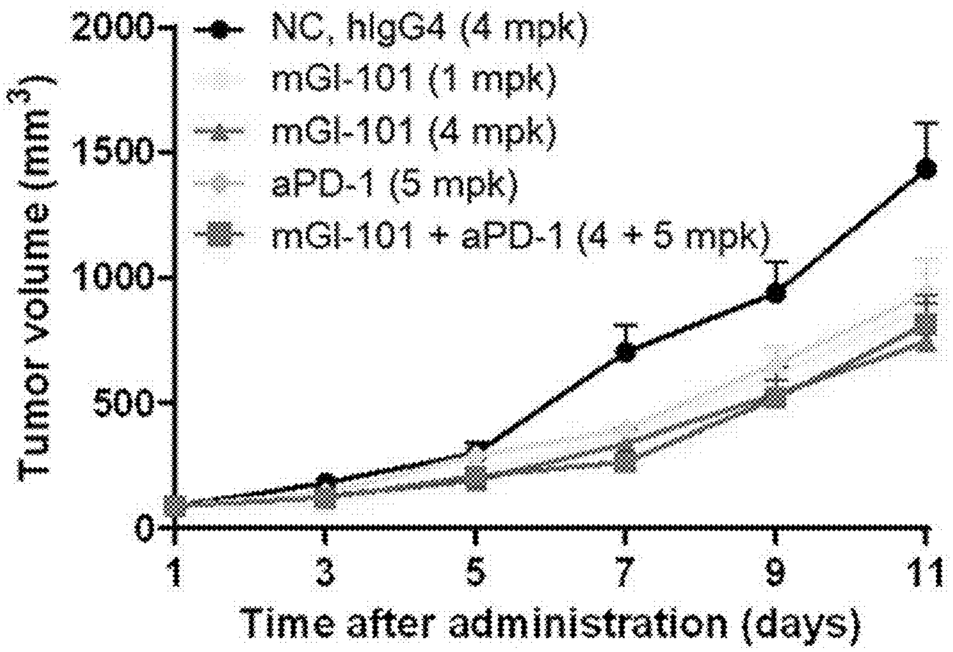
[Fig. 48]
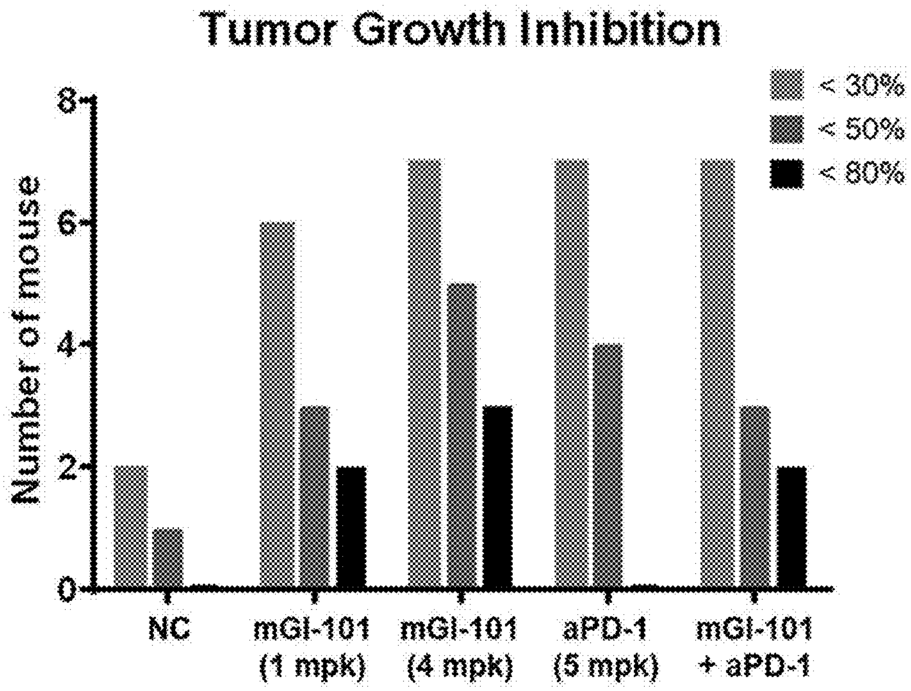

[Fig. 49]
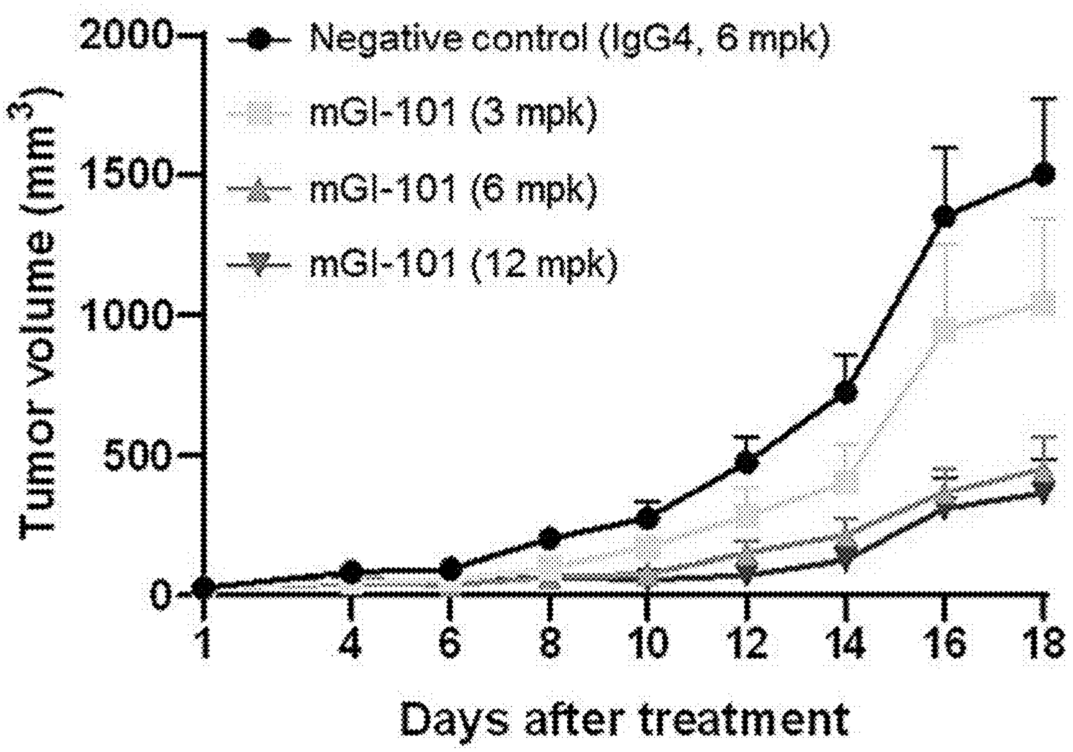
[Fig. 50]
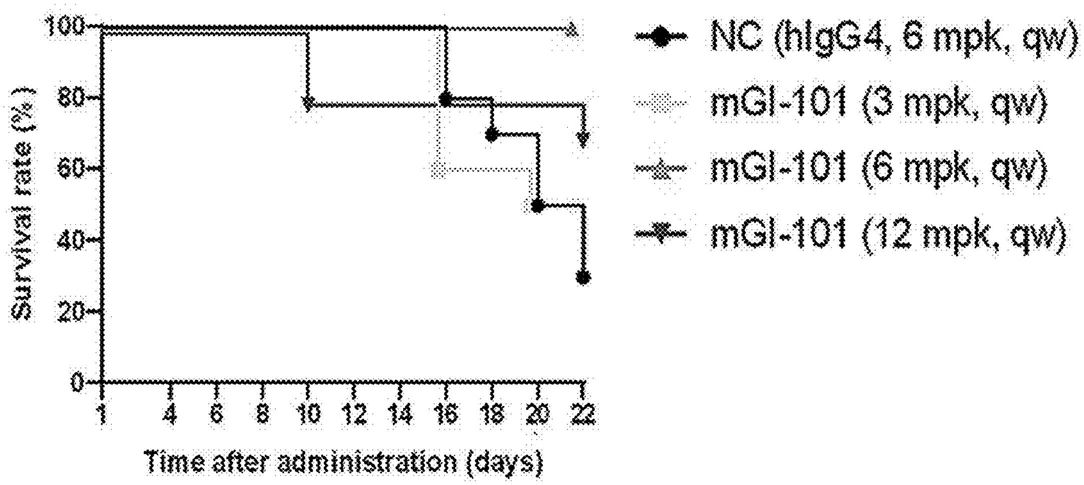

[Fig. 51]
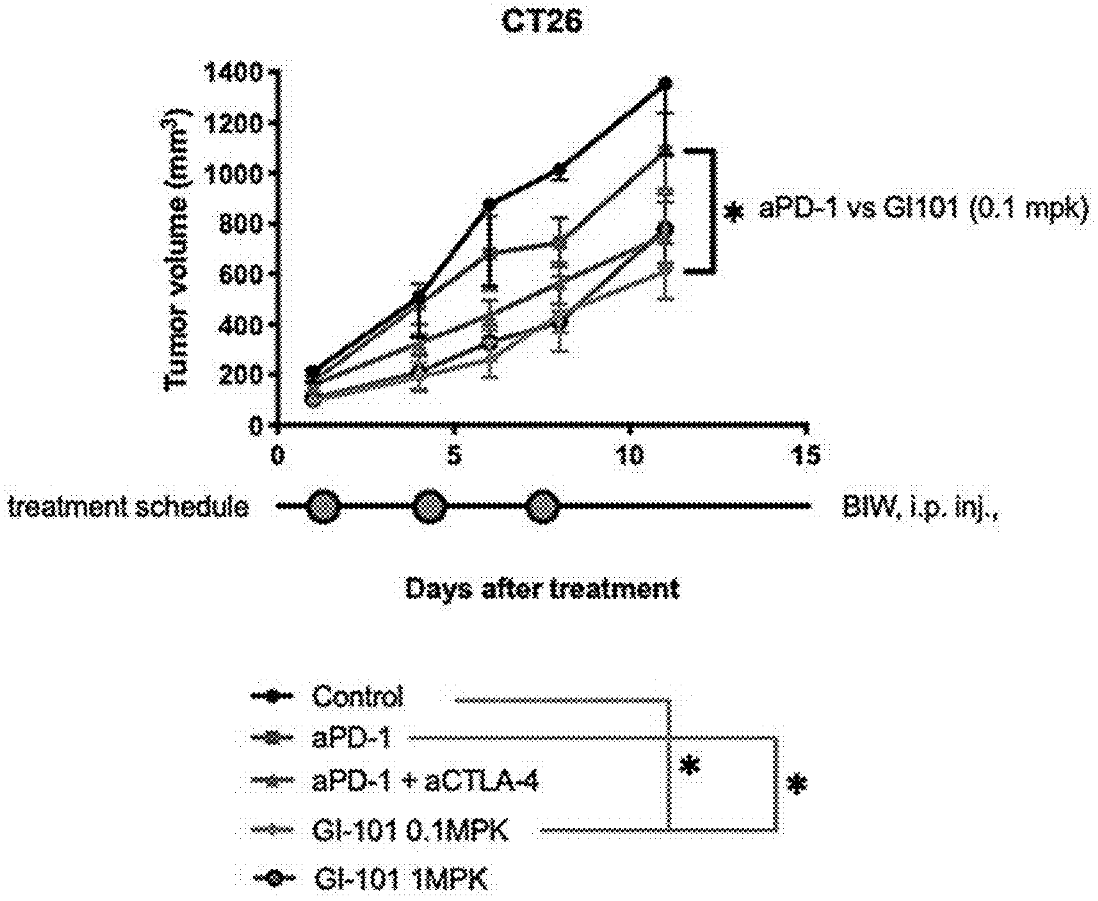

[Fig. 52]
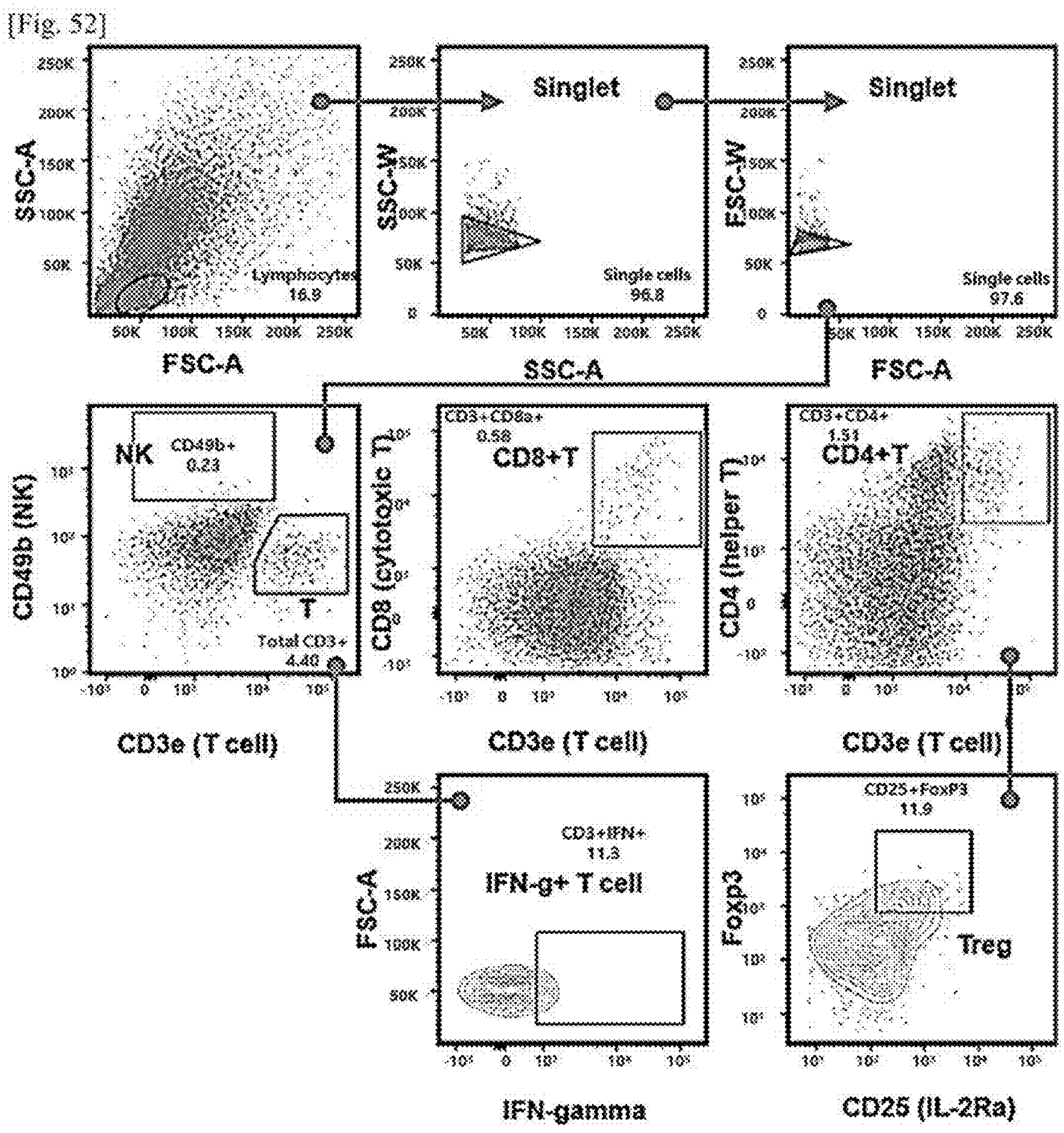

[Fig. 53]
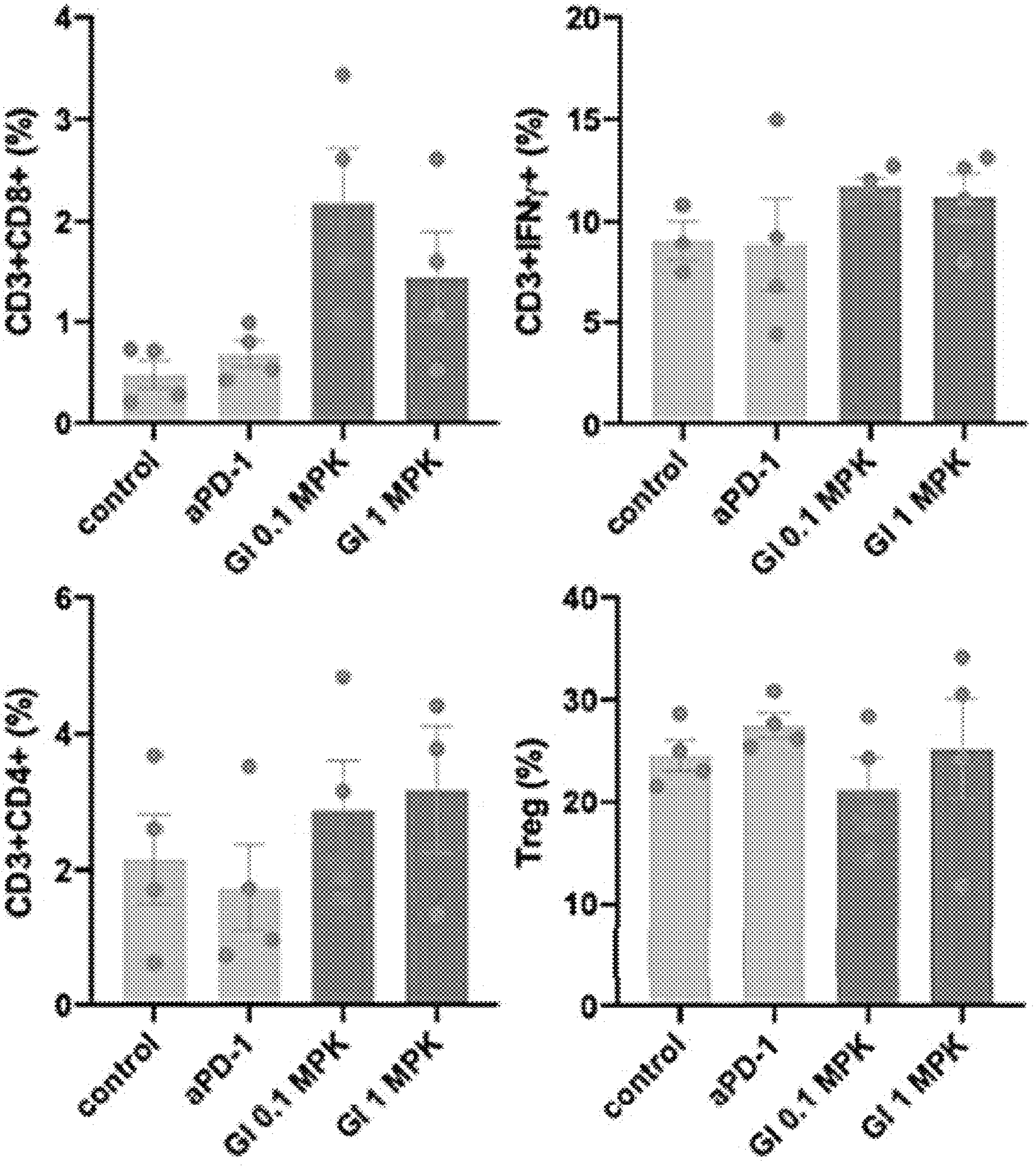

[Fig. 54]
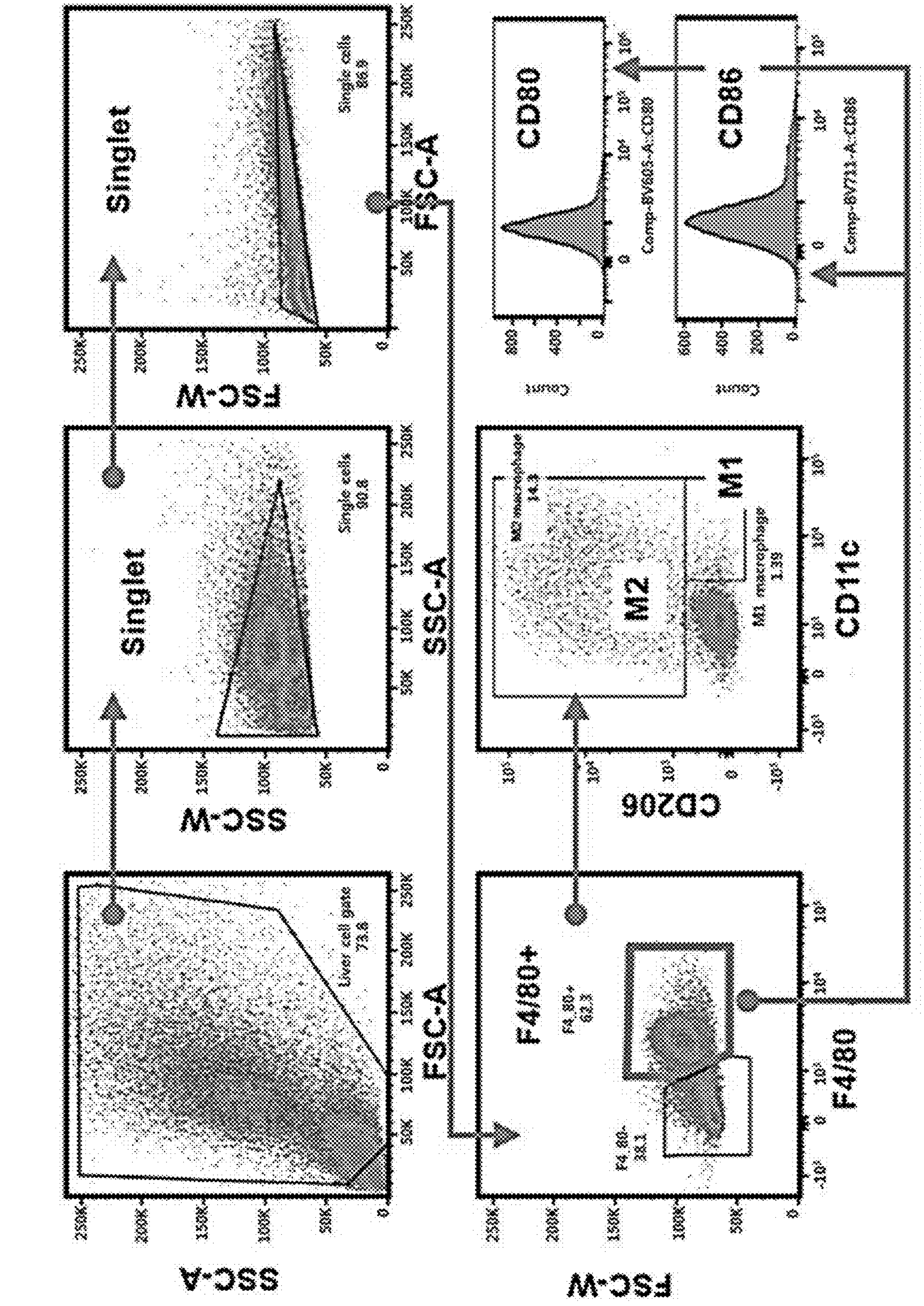

[Fig. 55]
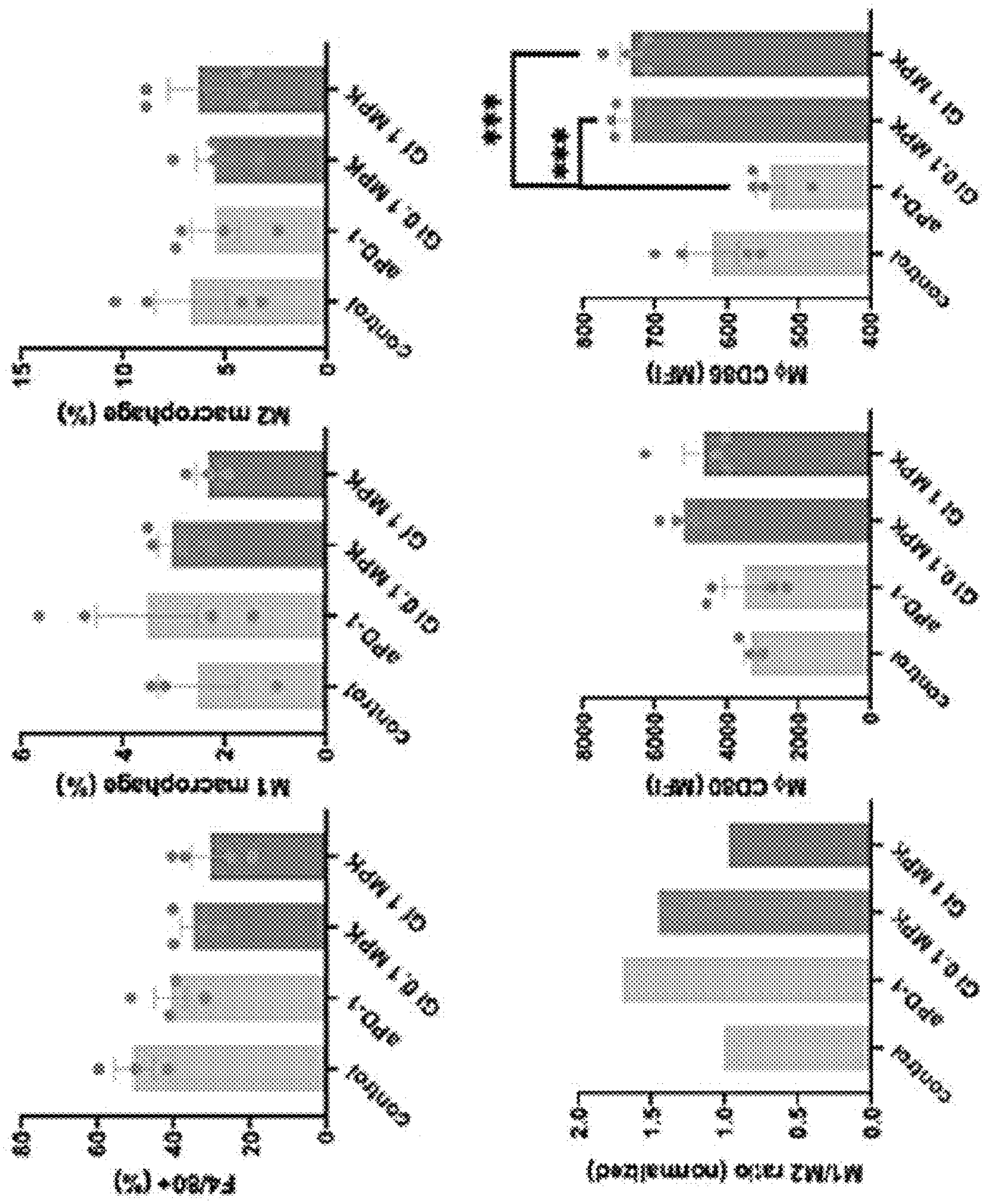

[Fig. 56]
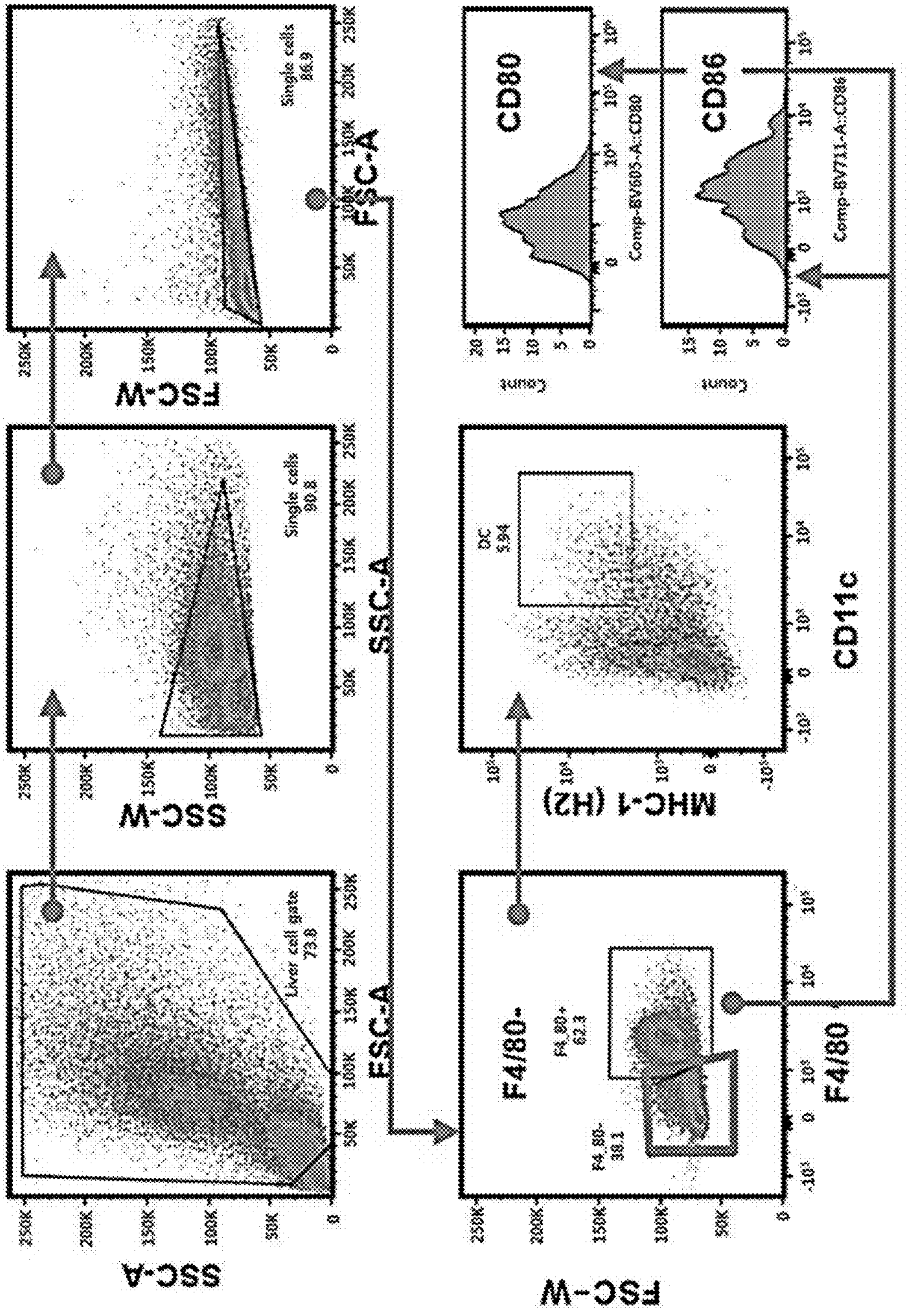

[Fig. 57]
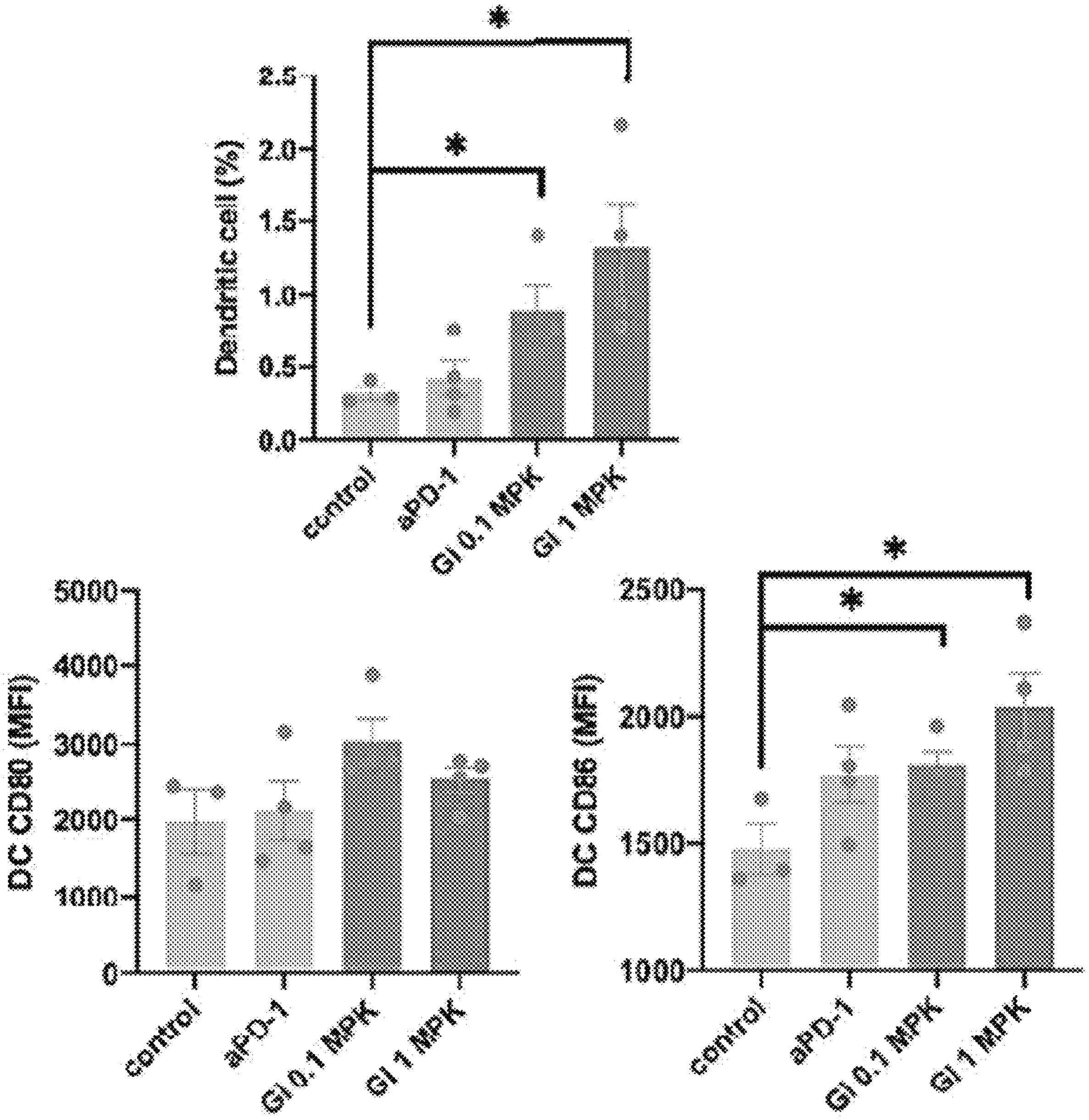

[Fig. 58]
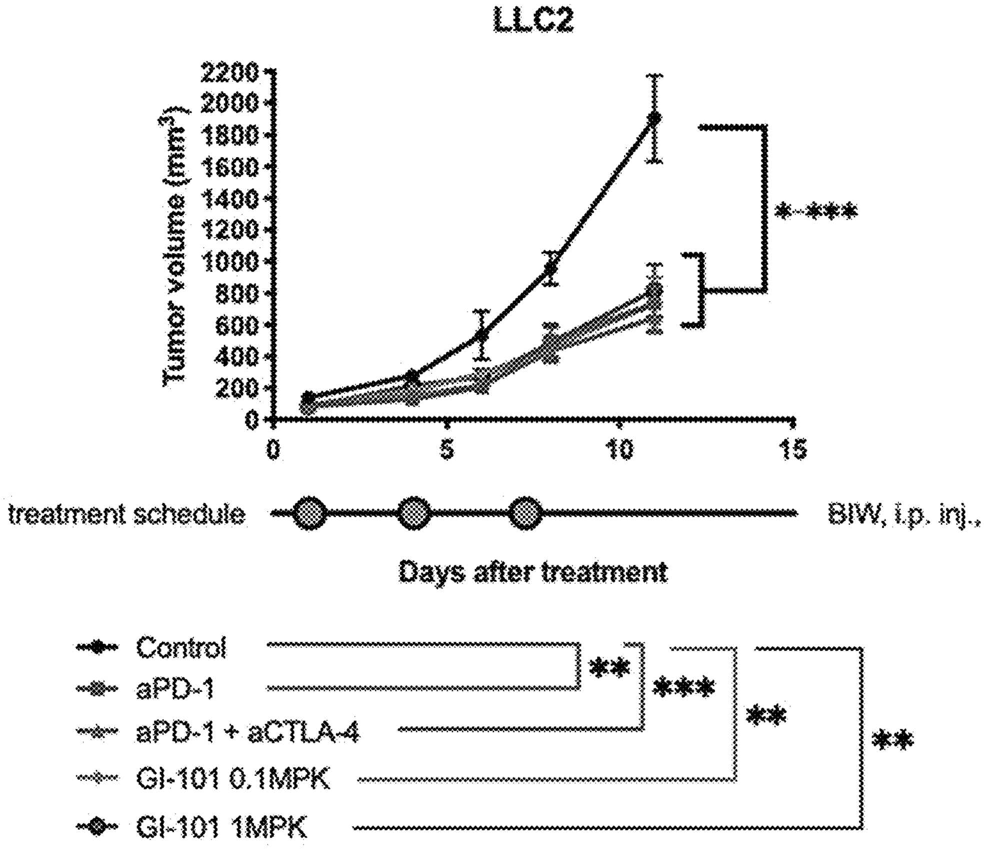

[Fig. 59]
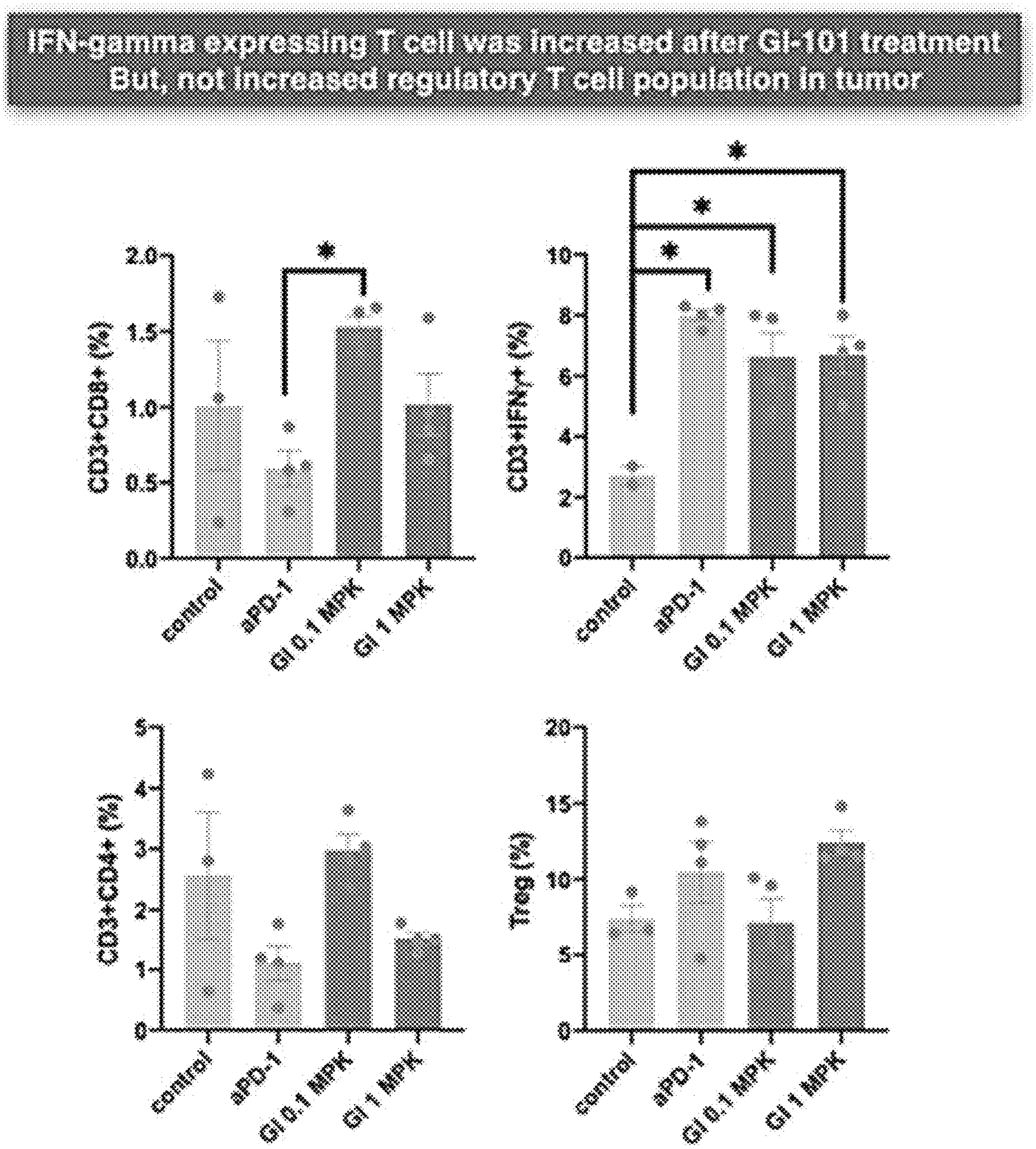

[Fig. 60]
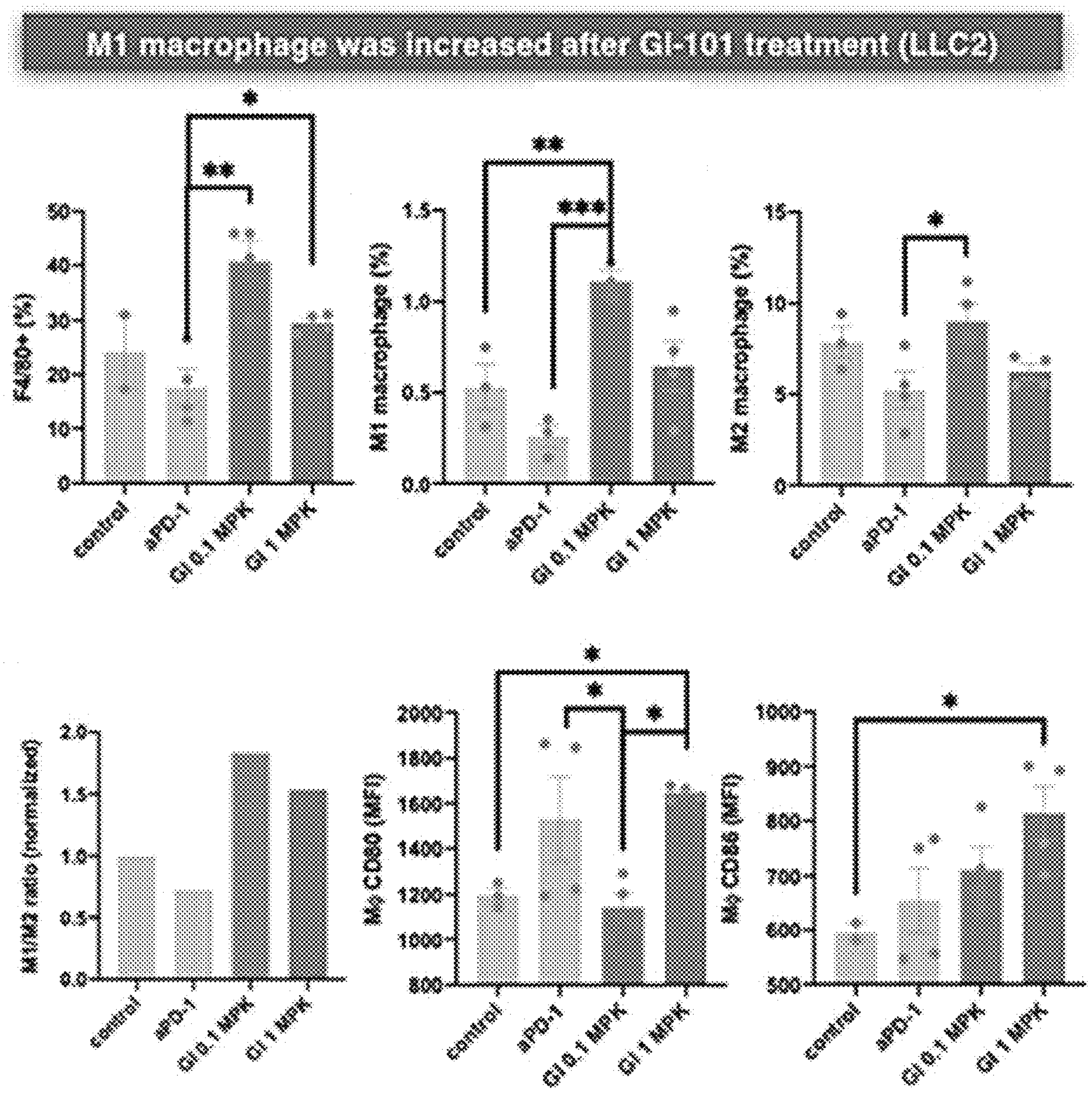

[Fig. 61]
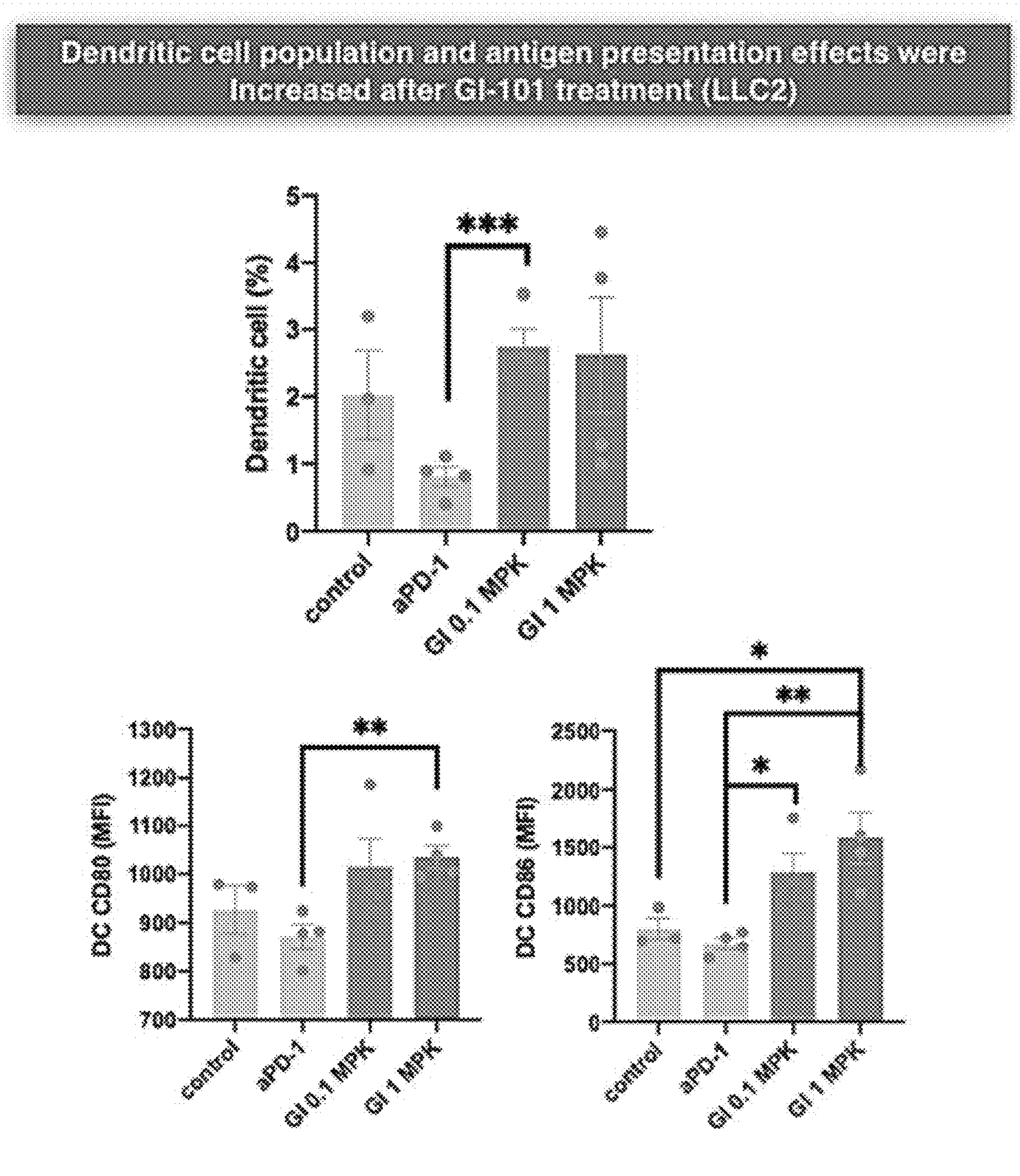

[Fig. 62]
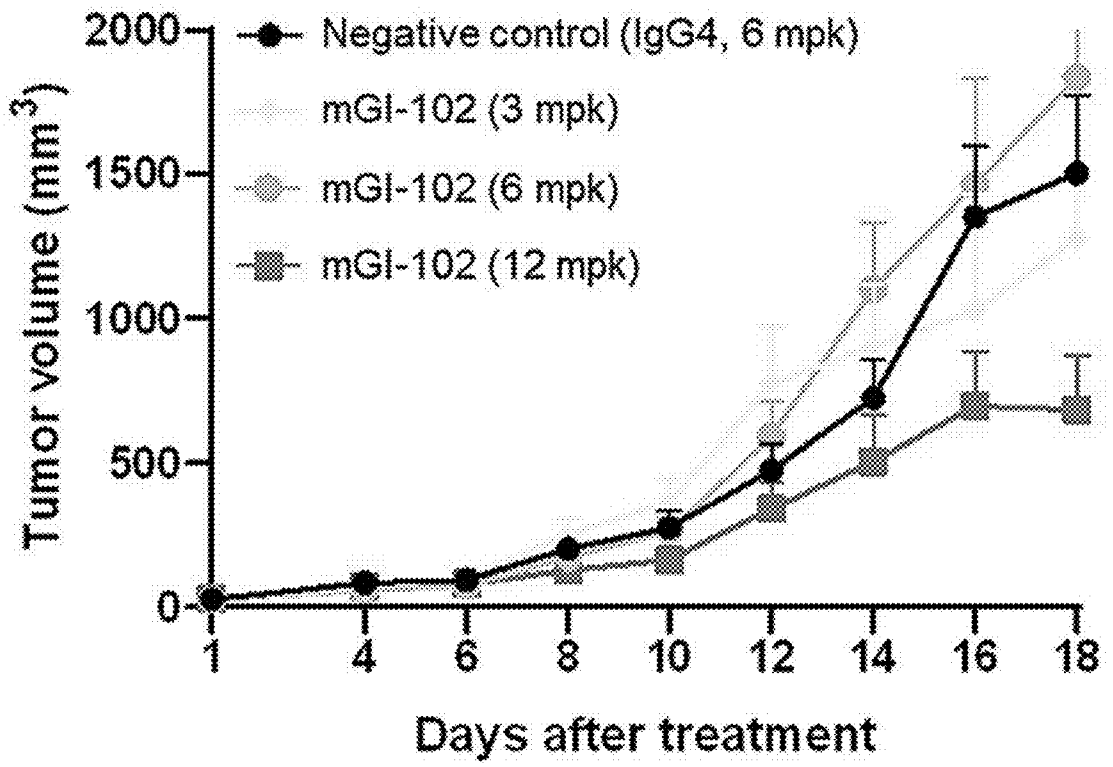
[Fig. 63]
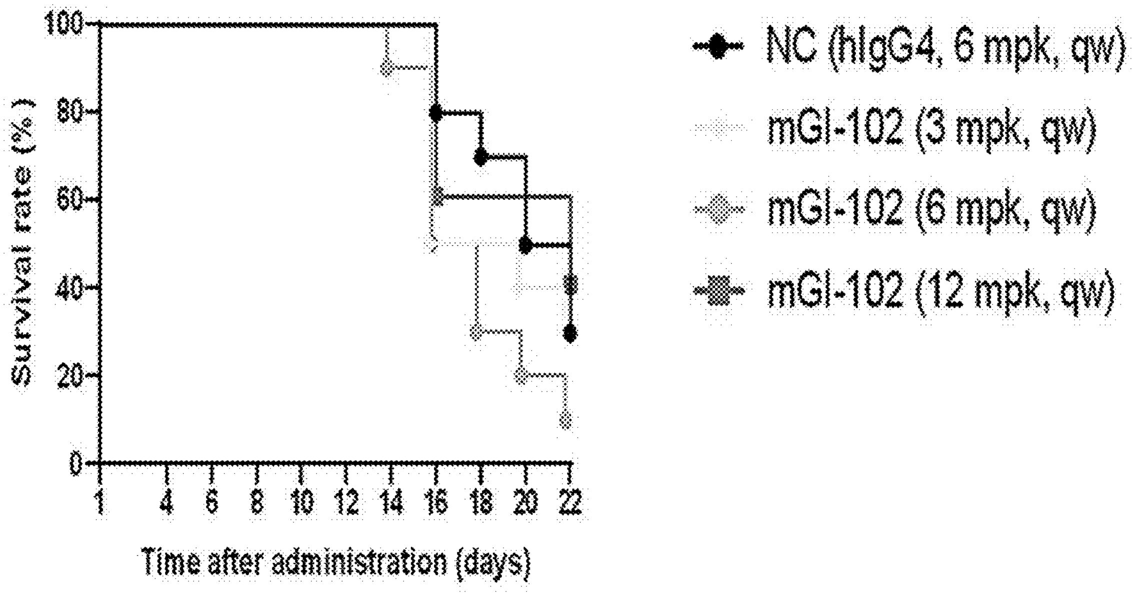

[Fig. 64]
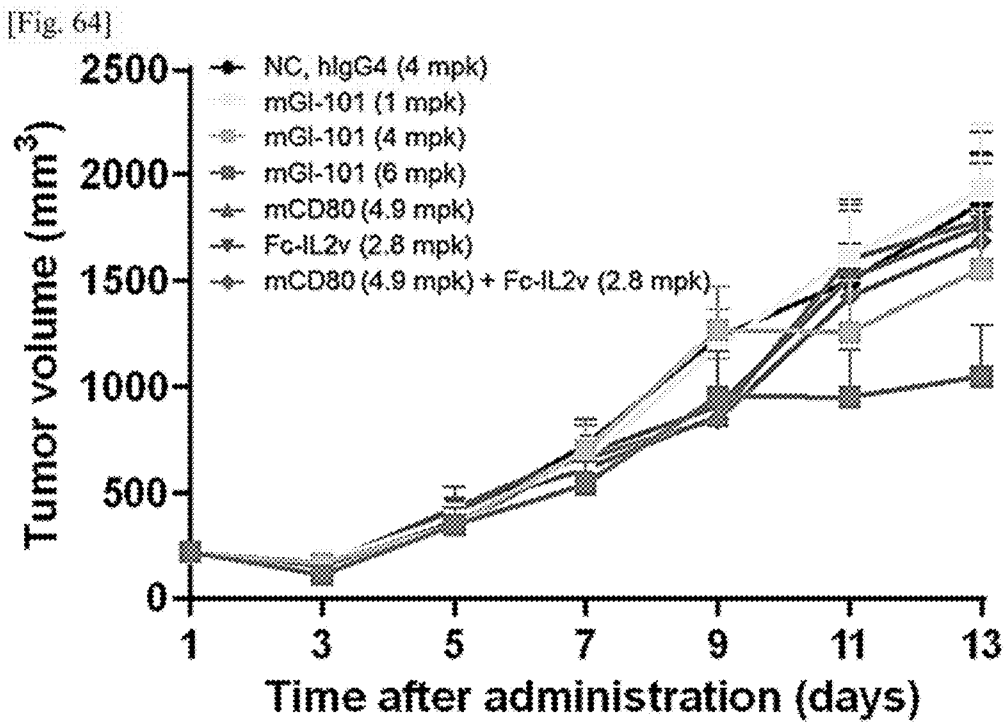
[Fig. 65]
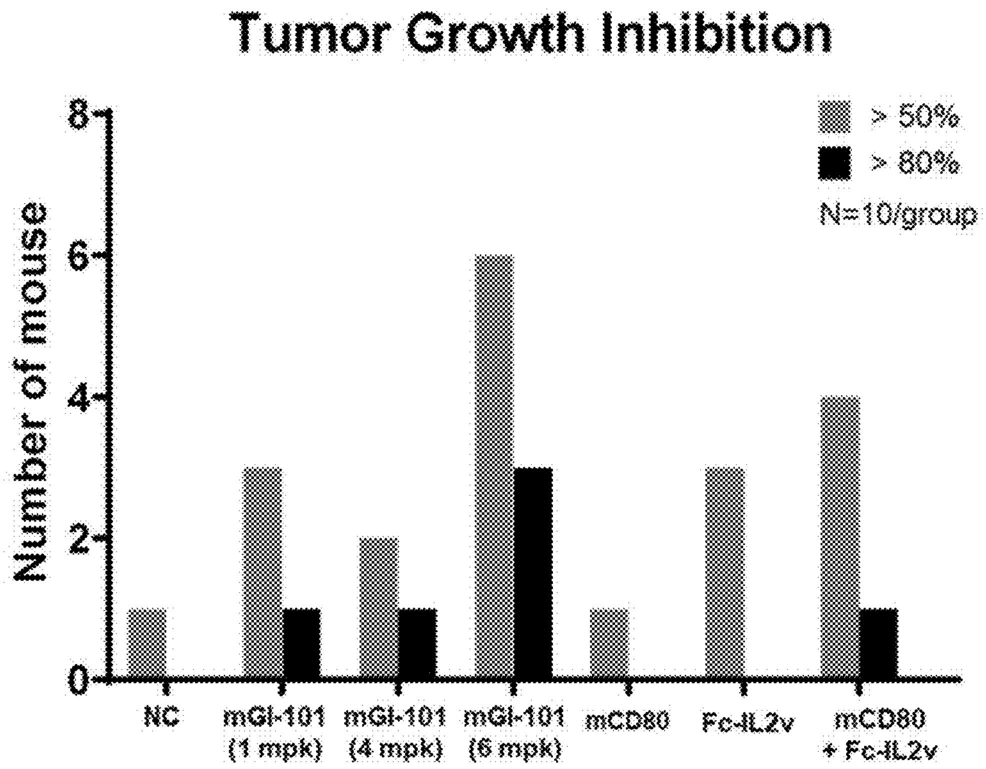

[Fig. 66]

A 2-Week Intravenous Dose Toxicity Study of GI-101 in Cynomolgus Monkeys

Table 1 Clinical observations

Sex: Male

| Group | Animal No. | Day -1 | Day 1 | | Day 2 | Day 3 | Day 4 | Day 5 | Day 6 | Day 7 | Day 8 | | Day 9 | Day 10 | Day 11 | Day 12 | Day 13 | Day 14 | Day of necropsy |
|---|---|---|---|---|---|---|---|---|---|---|---|---|---|---|---|---|---|---|---|
| | | am | Pre | 0.5 h | am | am | am | am | am | am | Pre | 0.5 h | am | am | am | am | am | am | am |
| 0 mg/kg/day | CJ1M01 | NA | NA | NA | NA | NA | NA | NA | NA | NA | NA | NA | NA | NA | NA | NA | NA | NA | NA |
| | CJ1M02 | NA | NA | NA | NA | NA | NA | NA | NA | NA | NA | NA | NA | NA | NA | NA | NA | NA | NA |
| | CJ1M03 | NA | NA | NA | NA | NA | NA | NA | NA | NA | NA | NA | NA | NA | NA | NA | NA | NA | NA |
| 5 mg/kg/day | CJ2M01 | NA | NA | NA | NA | NA | NA | NA | NA | NA | NA | NA | NA | NA | NA | NA | NA | NA | NA |
| | CJ2M02 | NA | NA | NA | NA | NA | NA | NA | NA | NA | NA | NA | NA | NA | NA | NA | NA | NA | NA |
| | CJ2M03 | NA | NA | NA | NA | NA | NA | NA | NA | NA | NA | NA | NA | NA | NA | NA | NA | NA | NA |
| 10 mg/kg/day | CJ3M01 | NA | NA | NA | NA | NA | NA | NA | NA | NA | NA | NA | NA | NA | NA | NA | NA | NA | NA |
| | CJ3M02 | NA | NA | NA | NA | NA | NA | NA | NA | NA | NA | NA | NA | NA | NA | NA | NA | NA | NA |
| | CJ3M03 | NA | NA | NA | NA | NA | NA | NA | NA | NA | NA | NA | NA | NA | NA | NA | NA | NA | NA |

General Footnote: Pre: Pre-dosing 0.5 h: 0.5 hours post-dosing
NA: No clinical or fecal abnormalities

[Fig. 67]
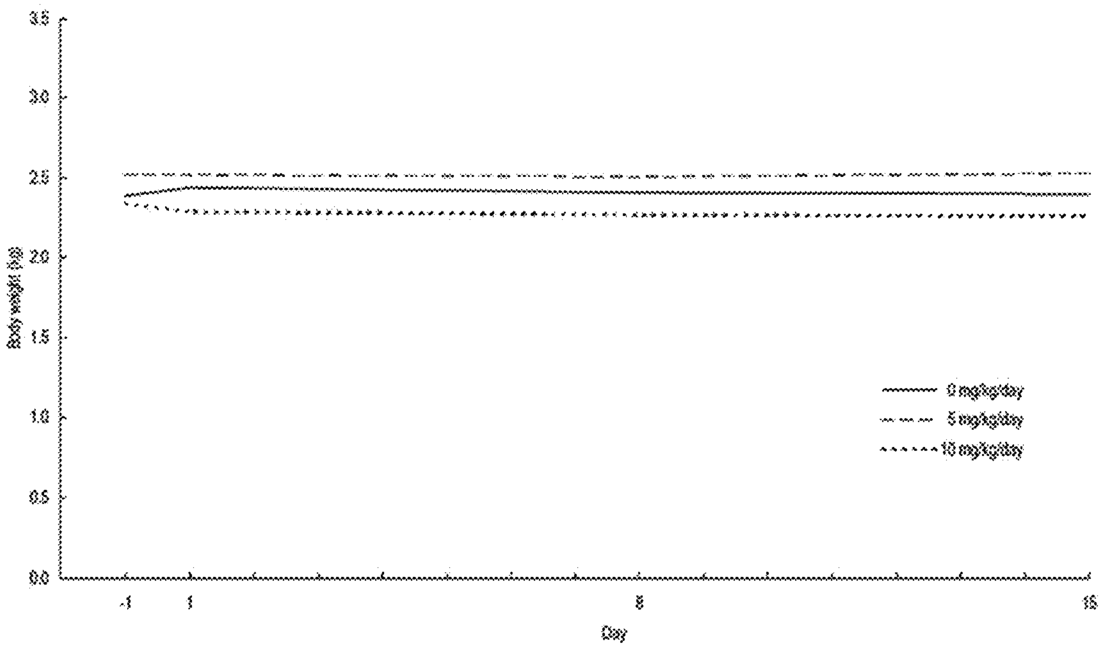
[Fig. 68]
Body weight (kg)
| Sex: Male<br>Day(s) Relative to Start Date | | 0 mg/kg/day | 5 mg/kg/day | 10 mg/kg/day |
|---|---|---|---|---|
| -1 | Mean | 2.39 | 2.52 | 2.34 |
| | S.D. | 0.10 | 0.31 | 0.16 |
| | N | 3 | 3 | 3 |
| 1 | Mean | 2.44 | 2.52 | 2.29 |
| | S.D. | 0.07 | 0.31 | 0.16 |
| | N | 3 | 3 | 3 |
| 8 | Mean | 2.41 | 2.51 | 2.27 |
| | S.D. | 0.12 | 0.34 | 0.08 |
| | N | 3 | 3 | 3 |
| 15 | Mean | 2.40 | 2.53 | 2.26 |
| | S.D. | 0.12 | 0.34 | 0.11 |
| | N | 3 | 3 | 3 |
Statistical Test: Generalised Anova/Ancova Test Transformation: Identity (No Transformation)

[Fig. 69]

A 2-Week Intravenous Dose Toxicity Study of GI-101 in Cynomolgus Monkeys

Table 3 Food consumption

Sex: Male

Unit: (g/day)

| Group | Animal No. | Day -1 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| 0 | CJ1M01 | 100 | 100 | 100 | 100 | 100 | 100 | 100 | 100 | 100 | 100 | 100 | 100 | 100 | 100 | 100 |
| mg/kg/day | CJ1M02 | 100 | 100 | 100 | 100 | 100 | 100 | 100 | 100 | 100 | 100 | 100 | 100 | 100 | 100 | 100 |
| | CJ1M03 | 100 | 100 | 100 | 100 | 100 | 100 | 100 | 100 | 100 | 100 | 100 | 100 | 100 | 100 | 100 |
| | Mean | 100 | 100 | 100 | 100 | 100 | 100 | 100 | 100 | 100 | 100 | 100 | 100 | 100 | 100 | 100 |
| | S.D. | 0 | 0 | 0 | 0 | 0 | 0 | 0 | 0 | 0 | 0 | 0 | 0 | 0 | 0 | 0 |
| | N | 3 | 3 | 3 | 3 | 3 | 3 | 3 | 3 | 3 | 3 | 3 | 3 | 3 | 3 | 3 |
| 5 | CJ2M01 | 100 | 100 | 100 | 100 | 100 | 100 | 100 | 100 | 100 | 100 | 100 | 100 | 100 | 100 | 100 |
| mg/kg/day | CJ2M02 | 100 | 100 | 100 | 100 | 100 | 100 | 100 | 100 | 100 | 100 | 100 | 100 | 100 | 100 | 100 |
| | CJ2M03 | 100 | 100 | 100 | 100 | 100 | 100 | 100 | 100 | 100 | 100 | 100 | 100 | 100 | 100 | 100 |
| | Mean | 100 | 100 | 100 | 100 | 100 | 100 | 100 | 100 | 100 | 100 | 100 | 100 | 100 | 100 | 100 |
| | S.D. | 0 | 0 | 0 | 0 | 0 | 0 | 0 | 0 | 0 | 0 | 0 | 0 | 0 | 0 | 0 |
| | N | 3 | 3 | 3 | 3 | 3 | 3 | 3 | 3 | 3 | 3 | 3 | 3 | 3 | 3 | 3 |
| 10 | CJ3M01 | 100 | 100 | 100 | 100 | 100 | 100 | 100 | 100 | 100 | 100 | 100 | 100 | 100 | 100 | 100 |
| mg/kg/day | CJ3M02 | 100 | 100 | 100 | 100 | 100 | 100 | 100 | 100 | 100 | 100 | 100 | 100 | 100 | 100 | 100 |
| | CJ3M03 | 100 | 100 | 100 | 100 | 100 | 100 | 100 | 100 | 100 | 100 | 100 | 100 | 100 | 100 | 100 |
| | Mean | 100 | 100 | 100 | 100 | 100 | 100 | 100 | 100 | 100 | 100 | 100 | 100 | 100 | 100 | 100 |
| | S.D. | 0 | 0 | 0 | 0 | 0 | 0 | 0 | 0 | 0 | 0 | 0 | 0 | 0 | 0 | 0 |
| | N | 3 | 3 | 3 | 3 | 3 | 3 | 3 | 3 | 3 | 3 | 3 | 3 | 3 | 3 | 3 |

[Fig. 70]

| Sex: Male | Day(s) Relative to Start Date | | 0 mg/kg/day | 5 mg/kg/day | 10 mg/kg/day |
|---|---|---|---|---|---|
| %Retic. (%) | -2 | Mean | 0.75 | 1.40 | 0.53 |
| | | S.D. | 0.07 | 0.52 | 0.30 |
| | | N | 3 | 3 | 3 |
| | 15 | Mean | 1.67 | 3.10 d¹ | 3.14 d¹ |
| | | S.D. | 0.61 | 0.55 | 0.32 |
| | | N | 3 | 3 | 3 |
| #Retic (10^9/L) | -2 | Mean | 44.0 | 81.9 | 55.1 |
| | | S.D. | 7.0 | 26.4 | 19.7 |
| | | N | 3 | 3 | 3 |
| | 15 | Mean | 91.5 | 171.6 d¹ | 161.5 d¹ |
| | | S.D. | 33.6 | 32.3 | 17.2 |
| | | N | 3 | 3 | 3 |
| PLT (10^3/μL) | -2 | Mean | 404 | 380 | 380 |
| | | S.D. | 25 | 90 | 28 |
| | | N | 3 | 3 | 3 |
| | 15 | Mean | 501 | 522 | 601 |
| | | S.D. | 29 | 135 | 85 |
| | | N | 3 | 3 | 3 |

[Fig. 71]

| Sex: Male | Day(s) Relative to Start Date | | 0 mg/kg/day | 5 mg/kg/day | 10 mg/kg/day |
|---|---|---|---|---|---|
| WBC (10^3/μL) | -2 | Mean | 10.59 | 8.18 | 8.29 |
| | | S.D. | 1.63 | 1.43 | 2.11 |
| | | N | 3 | 3 | 3 |
| | 15 | Mean | 8.09 | 12.08 | 16.52 |
| | | S.D. | 0.25 | 0.74 | 6.81 |
| | | N | 3 | 3 | 3 |
| %Neut (%) | -2 | Mean | 38.1 | 23.1 | 23.6 |
| | | S.D. | 23.2 | 3.2 | 13.1 |
| | | N | 3 | 3 | 3 |
| | 15 | Mean | 35.9 | 14.5 | 22.4 |
| | | S.D. | 14.3 | 2.1 | 14.2 |
| | | N | 3 | 3 | 3 |
| %Lymph (%) | -2 | Mean | 57.7 | 71.6 | 69.8 |
| | | S.D. | 21.7 | 2.8 | 13.7 |
| | | N | 3 | 3 | 3 |
| | 15 | Mean | 59.6 | 81.2 | 69.5 |
| | | S.D. | 13.1 | 1.4 | 15.0 |
| | | N | 3 | 3 | 3 |

[Fig. 72]

| Sex: Male<br>Day(s) Relative to Start Date | | | 0<br>mg/kg/day | 5<br>mg/kg/day | 10<br>mg/kg/day |
|---|---|---|---|---|---|
| #Neut<br>(10^3/μL) | -2 | Mean | 4.24 | 1.86 | 1.77 |
| | | S.D. | 3.09 | 0.22 | 0.52 |
| | | N | 3 | 3 | 3 |
| | 15 | Mean | 2.93 | 1.76 | 3.11 |
| | | S.D. | 1.26 | 0.35 | 0.63 |
| | | N | 3 | 3 | 3 |
| #Lymph<br>(10^3/μL) | -2 | Mean | 5.92 | 5.87 | 5.98 |
| | | S.D. | 1.78 | 1.24 | 2.54 |
| | | N | 3 | 3 | 3 |
| | 15 | Mean | 4.80 | 9.80 | 12.05 |
| | | S.D. | 0.94 | 0.48 | 6.47 |
| | | N | 3 | 3 | 3 |
| #Mono<br>(10^3/μL) | -2 | Mean | 0.36 | 0.37 | 0.45 |
| | | S.D. | 0.10 | 0.09 | 0.08 |
| | | N | 3 | 3 | 3 |
| | 15 | Mean | 0.32 | 0.33 | 0.77 d) |
| | | S.D. | 0.11 | 0.05 | 0.26 |
| | | N | 3 | 3 | 3 |

[Fig. 73]

| Sex: Male<br>Day(s) Relative to Start Date | | | 0<br>mg/kg/day | 5<br>mg/kg/day | 10<br>mg/kg/day |
|---|---|---|---|---|---|
| AST<br>(U/L) | -2 | Mean | 36 | 45 | 30 |
| | | S.D. | 19 | 21 | 7 |
| | | N | 3 | 3 | 3 |
| | 15 | Mean | 24 | 34 | 33 |
| | | S.D. | 5 | 5 | 6 |
| | | N | 3 | 3 | 3 |
| ALT<br>(U/L) | -2 | Mean | 58 | 72 | 34 |
| | | S.D. | 51 | 71 | 8 |
| | | N | 3 | 3 | 3 |
| | 15 | Mean | 34 | 52 | 36 |
| | | S.D. | 6 | 44 | 5 |
| | | N | 3 | 3 | 3 |
| ALP<br>(U/L) | -2 | Mean | 1511 | 1658 | 1972 |
| | | S.D. | 542 | 258 | 357 |
| | | N | 3 | 3 | 3 |
| | 15 | Mean | 1395 | 1444 | 1565 |
| | | S.D. | 365 | 346 | 235 |
| | | N | 3 | 3 | 3 |

[Fig. 74]

| Sex: Male | Day(s) Relative to Start Date | | 0 mg/kg/day | 5 mg/kg/day | 10 mg/kg/day |
|---|---|---|---|---|---|
| LD (U/L) | -2 | Mean | 255 | 289 | 292 |
| | | S.D. | 6 | 57 | 47 |
| | | N | 3 | 3 | 3 |
| | 15 | Mean | 236 | 304 | 351 dd' |
| | | S.D. | 15 | 47 | 38 |
| | | N | 3 | 3 | 3 |
| CK (U/L) | -2 | Mean | 132 | 140 | 182 |
| | | S.D. | 23 | 4 | 61 |
| | | N | 3 | 3 | 3 |
| | 15 | Mean | 120 | 128 | 140 |
| | | S.D. | 31 | 19 | 23 |
| | | N | 3 | 3 | 3 |
| GLU (mg/dL) | -2 | Mean | 98 | 91 | 112 |
| | | S.D. | 17 | 4 | 15 |
| | | N | 3 | 3 | 3 |
| | 15 | Mean | 87 | 88 | 104 |
| | | S.D. | 9 | 17 | 5 |
| | | N | 3 | 3 | 3 |

[Fig. 75]

| Sex: Male | Day(s) Relative to Start Date | | 0 mg/kg/day | 5 mg/kg/day | 10 mg/kg/day |
|---|---|---|---|---|---|
| BIL (mg/dL) | -2 | Mean | 0.10 | 0.15 d' | 0.10 |
| | | S.D. | 0.02 | 0.03 | 0.01 |
| | | N | 3 | 3 | 3 |
| | 15 | Mean | 0.11 | 0.15 | 0.10 |
| | | S.D. | 0.04 | 0.03 | 0.03 |
| | | N | 3 | 3 | 3 |
| UN (mg/dL) | -2 | Mean | 19.1 | 15.4 | 18.8 |
| | | S.D. | 7.2 | 2.3 | 4.5 |
| | | N | 3 | 3 | 3 |
| | 15 | Mean | 16.2 | 13.9 | 14.2 |
| | | S.D. | 5.6 | 0.7 | 2.4 |
| | | N | 3 | 3 | 3 |
| CRE (mg/dL) | -2 | Mean | 0.73 | 0.69 | 0.73 |
| | | S.D. | 0.07 | 0.17 | 0.10 |
| | | N | 3 | 3 | 3 |
| | 15 | Mean | 0.72 | 0.66 | 0.65 |
| | | S.D. | 0.06 | 0.13 | 0.11 |
| | | N | 3 | 3 | 3 |

[Fig. 76]

| Sex: Male | | | 0 mg/kg/day | 5 mg/kg/day | 10 mg/kg/day |
|---|---|---|---|---|---|
| Day(s) Relative to Start Date | | | | | |
| CHO (mg/dL) | -2 | Mean | 109 | 162 | 147 |
| | | S.D. | 23 | 59 | 47 |
| | | N | 3 | 3 | 3 |
| | 15 | Mean | 108 | 159 | 143 |
| | | S.D. | 24 | 46 | 34 |
| | | N | 3 | 3 | 3 |
| TG (mg/dL) | -2 | Mean | 44 | 27 | 40 |
| | | S.D. | 24 | 12 | 2 |
| | | N | 3 | 3 | 3 |
| | 15 | Mean | 35 | 29 | 34 |
| | | S.D. | 2 | 14 | 14 |
| | | N | 3 | 3 | 3 |
| PL (mg/dL) | -2 | Mean | 180 | 236 | 220 |
| | | S.D. | 48 | 43 | 65 |
| | | N | 3 | 3 | 3 |
| | 15 | Mean | 164 | 216 | 195 |
| | | S.D. | 31 | 52 | 40 |
| | | N | 3 | 3 | 3 |

[Fig. 77]

| Sex: Male | | | 0 mg/kg/day | 5 mg/kg/day | 10 mg/kg/day |
|---|---|---|---|---|---|
| Day(s) Relative to Start Date | | | | | |
| IP (mg/dL) | -2 | Mean | 5.16 | 5.14 | 5.00 |
| | | S.D. | 1.16 | 0.91 | 0.90 |
| | | N | 3 | 3 | 3 |
| | 15 | Mean | 5.52 | 5.94 | 5.66 |
| | | S.D. | 0.61 | 0.61 | 0.94 |
| | | N | 3 | 3 | 3 |
| CA (mg/dL) | -2 | Mean | 9.63 | 9.82 | 9.79 |
| | | S.D. | 0.59 | 0.55 | 0.19 |
| | | N | 3 | 3 | 3 |
| | 15 | Mean | 9.45 | 9.48 | 9.31 |
| | | S.D. | 0.57 | 0.25 | 0.03 |
| | | N | 3 | 3 | 3 |
| NA (mEq/L) | -2 | Mean | 152.8 | 154.5 | 153.9 |
| | | S.D. | 2.4 | 4.2 | 2.5 |
| | | N | 3 | 3 | 3 |
| | 15 | Mean | 151.8 | 153.5 | 153.4 |
| | | S.D. | 3.3 | 2.0 | 3.3 |
| | | N | 3 | 3 | 3 |

[Fig. 78]

| Sex: Male | Day(s) Relative to Start Date | | 0 mg/kg/day | 5 mg/kg/day | 10 mg/kg/day |
|---|---|---|---|---|---|
| K (mEq/L) | -2 | Mean | 4.28 | 4.17 | 3.90 |
| | | S.D. | 0.69 | 0.29 | 0.40 |
| | | N | 3 | 3 | 3 |
| | 15 | Mean | 3.99 | 4.09 | 3.85 |
| | | S.D. | 0.50 | 0.18 | 0.14 |
| | | N | 3 | 3 | 3 |
| CL (mEq/L) | -2 | Mean | 112.3 | 111.1 | 110.7 |
| | | S.D. | 2.2 | 3.9 | 2.6 |
| | | N | 3 | 3 | 3 |
| | 15 | Mean | 111.5 | 109.6 | 110.2 |
| | | S.D. | 0.7 | 3.7 | 2.8 |
| | | N | 3 | 3 | 3 |
| TP (g/dL) | -2 | Mean | 7.20 | 7.36 | 7.53 |
| | | S.D. | 0.59 | 0.42 | 0.22 |
| | | N | 3 | 3 | 3 |
| | 15 | Mean | 6.99 | 7.22 | 7.30 |
| | | S.D. | 0.62 | 0.37 | 0.11 |
| | | N | 3 | 3 | 3 |

[Fig. 79]

| Sex: Male | Day(s) Relative to Start Date | | 0 mg/kg/day | 5 mg/kg/day | 10 mg/kg/day |
|---|---|---|---|---|---|
| ALB (g/dL) | -2 | Mean | 4.18 | 4.11 | 4.14 |
| | | S.D. | 0.34 | 0.46 | 0.19 |
| | | N | 3 | 3 | 3 |
| | 15 | Mean | 4.09 | 3.98 | 3.88 |
| | | S.D. | 0.36 | 0.47 | 0.17 |
| | | N | 3 | 3 | 3 |
| A/G | -2 | Mean | 1.39 | 1.27 | 1.22 |
| | | S.D. | 0.06 | 0.19 | 0.04 |
| | | N | 3 | 3 | 3 |
| | 15 | Mean | 1.41 | 1.24 | 1.13 |
| | | S.D. | 0.04 | 0.22 | 0.07 |
| | | N | 3 | 3 | 3 |

[Fig. 80]

Sex: Male

| Group | Animal No. | Tumor necrosis factor-α (pg/mL) | | | | Interferon-γ (pg/mL) | | | | Interleukin-1β (pg/mL) | | | | Interleukin-2 (pg/mL) | | | | Interleukin-4 (pg/mL) | | | |
|---|---|---|---|---|---|---|---|---|---|---|---|---|---|---|---|---|---|---|---|---|---|
| | | Pretest | Day 3 | Day 8 | Day 15 | Pretest | Day 3 | Day 8 | Day 15 | Pretest | Day 3 | Day 8 | Day 15 | Pretest | Day 3 | Day 8 | Day 15 | Pretest | Day 3 | Day 8 | Day 15 |
| 0 | CJ1M01 | BLQ | BLQ | BLQ | BLQ | BLQ | BLQ | BLQ | BLQ | BLQ | BLQ | BLQ | BLQ | BLQ | BLQ | BLQ | BLQ | BLQ | BLQ | BLQ | BLQ |
| mg/kg/day | CJ1M02 | BLQ | BLQ | BLQ | BLQ | BLQ | BLQ | BLQ | BLQ | BLQ | BLQ | BLQ | BLQ | BLQ | BLQ | BLQ | BLQ | BLQ | BLQ | BLQ | BLQ |
| | CJ1M03 | BLQ | BLQ | BLQ | BLQ | BLQ | BLQ | BLQ | BLQ | BLQ | BLQ | BLQ | BLQ | BLQ | BLQ | BLQ | BLQ | BLQ | BLQ | BLQ | BLQ |
| | Mean | N.C. | N.C. | N.C. | N.C. | N.C. | N.C. | N.C. | N.C. | N.C. | N.C. | N.C. | N.C. | N.C. | N.C. | N.C. | N.C. | N.C. | N.C. | N.C. | N.C. |
| | S.D. | N.C. | N.C. | N.C. | N.C. | N.C. | N.C. | N.C. | N.C. | N.C. | N.C. | N.C. | N.C. | N.C. | N.C. | N.C. | N.C. | N.C. | N.C. | N.C. | N.C. |
| | N | 0 | 0 | 0 | 0 | 0 | 0 | 0 | 0 | 0 | 0 | 0 | 0 | 0 | 0 | 0 | 0 | 0 | 0 | 0 | 0 |
| 5 | CJ2M01 | BLQ | BLQ | BLQ | BLQ | BLQ | BLQ | BLQ | BLQ | BLQ | BLQ | BLQ | BLQ | BLQ | BLQ | BLQ | BLQ | BLQ | BLQ | BLQ | BLQ |
| mg/kg/day | CJ2M02 | BLQ | BLQ | BLQ | BLQ | BLQ | BLQ | BLQ | BLQ | BLQ | BLQ | BLQ | BLQ | BLQ | BLQ | BLQ | BLQ | BLQ | BLQ | BLQ | BLQ |
| | CJ2M03 | BLQ | BLQ | BLQ | BLQ | BLQ | BLQ | BLQ | BLQ | BLQ | BLQ | BLQ | BLQ | BLQ | BLQ | BLQ | BLQ | BLQ | BLQ | BLQ | BLQ |
| | Mean | N.C. | N.C. | N.C. | N.C. | N.C. | N.C. | N.C. | N.C. | N.C. | N.C. | N.C. | N.C. | N.C. | N.C. | N.C. | N.C. | N.C. | N.C. | N.C. | N.C. |
| | S.D. | N.C. | N.C. | N.C. | N.C. | N.C. | N.C. | N.C. | N.C. | N.C. | N.C. | N.C. | N.C. | N.C. | N.C. | N.C. | N.C. | N.C. | N.C. | N.C. | N.C. |
| | N | 0 | 0 | 0 | 0 | 0 | 0 | 0 | 0 | 0 | 0 | 0 | 0 | 0 | 0 | 0 | 0 | 0 | 0 | 0 | 0 |
| 10 | CJ3M01 | BLQ | BLQ | BLQ | BLQ | BLQ | 5.51 | 4.60 | BLQ | BLQ | BLQ | BLQ | BLQ | BLQ | BLQ | BLQ | BLQ | BLQ | BLQ | BLQ | BLQ |
| mg/kg/day | CJ3M02 | BLQ | BLQ | BLQ | BLQ | BLQ | 12.74 | BLQ | BLQ | BLQ | BLQ | BLQ | BLQ | BLQ | BLQ | BLQ | BLQ | BLQ | BLQ | BLQ | BLQ |
| | CJ3M03 | BLQ | BLQ | BLQ | BLQ | BLQ | BLQ | BLQ | BLQ | BLQ | BLQ | BLQ | BLQ | BLQ | BLQ | BLQ | BLQ | BLQ | BLQ | BLQ | BLQ |
| | Mean | N.C. | N.C. | N.C. | N.C. | N.C. | 9.13 | N.C. | N.C. | N.C. | N.C. | N.C. | N.C. | N.C. | N.C. | N.C. | N.C. | N.C. | N.C. | N.C. | N.C. |
| | S.D. | N.C. | N.C. | N.C. | N.C. | N.C. | N.C. | N.C. | N.C. | N.C. | N.C. | N.C. | N.C. | N.C. | N.C. | N.C. | N.C. | N.C. | N.C. | N.C. | N.C. |
| | N | 0 | 0 | 0 | 0 | 0 | 0 | 0 | 0 | 0 | 0 | 0 | 0 | 0 | 0 | 0 | 0 | 0 | 0 | 0 | 0 |

General Footnote: Day 8: Prior to dosing

BLQ: Below the lower limit of quantification (4.9 pg/mL for Interleukin-4, 2.4 pg/mL for the others)

When plasma concentrations were BLQ in 1 of the 3 animals, the mean of the 2 remaining animals was calculated.

The mean was regarded as N.C. when plasma concentrations in 2 of the 3 animals were BLQ.

N.C.: Not calculated

[Fig. 81]

Sex: Male

| Group | Animal No. | Interleukin-6 (pg/mL) Pretest | Day 3 | Day 8 | Day 15 | Interleukin-8 (pg/mL) Pretest | Day 3 | Day 8 | Day 15 | Interleukin-10 (pg/mL) Pretest | Day 3 | Day 8 | Day 15 | Interleukin-12 (pg/mL) Pretest | Day 3 | Day 8 | Day 15 |
|---|---|---|---|---|---|---|---|---|---|---|---|---|---|---|---|---|---|
| 0 | CJ1M01 | BLQ | 2.95 | BLQ | 3.34 | 4047.41 | 4861.65 | 7894.37 | 6783.89 | BLQ | BLQ | BLQ | BLQ | BLQ | BLQ | BLQ | BLQ |
| mg/kg/day | CJ1M02 | BLQ | BLQ | BLQ | BLQ | 3418.18 | 1382.07 | 6035.41 | 4096.95 | BLQ | BLQ | BLQ | BLQ | BLQ | BLQ | BLQ | BLQ |
| | CJ1M03 | BLQ | 2.78 | BLQ | BLQ | 809.60 | 905.96 | 972.78 | 981.31 | BLQ | BLQ | BLQ | BLQ | BLQ | BLQ | BLQ | BLQ |
| | Mean | N.C. | 2.87 | N.C. | N.C. | 2758.40 | 2383.23 | 4967.52 | 3954.05 | N.C. | N.C. | N.C. | N.C. | N.C. | N.C. | N.C. | N.C. |
| | S.D. | N.C. | N.C. | N.C. | N.C. | 1716.78 | 2159.54 | 3582.23 | 2903.93 | N.C. | N.C. | N.C. | N.C. | N.C. | N.C. | N.C. | N.C. |
| | N | 0 | 2 | 0 | 1 | 3 | 3 | 3 | 3 | 0 | 0 | 0 | 0 | 0 | 0 | 0 | 0 |
| 5 | CJ2M01 | BLQ | BLQ | BLQ | BLQ | 4800.40 | 3355.74 | 5986.48 | 5511.93 | BLQ | BLQ | BLQ | BLQ | BLQ | BLQ | BLQ | BLQ |
| mg/kg/day | CJ2M02 | BLQ | BLQ | BLQ | BLQ | 2633.61 | 2388.95 | 4778.15 | 5266.00 | BLQ | BLQ | BLQ | BLQ | BLQ | BLQ | BLQ | BLQ |
| | CJ2M03 | BLQ | 2.91 | BLQ | BLQ | 7482.97 | 6571.61 | 9663.74 | 8892.13 | BLQ | BLQ | BLQ | BLQ | 7.07 | 6.31 | BLQ | BLQ |
| | Mean | N.C. | N.C. | N.C. | N.C. | 4972.33 | 4105.43 | 6809.46 | 6556.69 | N.C. | N.C. | N.C. | N.C. | N.C. | N.C. | N.C. | N.C. |
| | S.D. | N.C. | N.C. | N.C. | N.C. | 2429.25 | 2189.79 | 2544.64 | 2026.29 | N.C. | N.C. | N.C. | N.C. | N.C. | N.C. | N.C. | N.C. |
| | N | 0 | 1 | 0 | 0 | 3 | 3 | 3 | 3 | 0 | 0 | 0 | 0 | 1 | 1 | 0 | 0 |
| 10 | CJ3M01 | BLQ | 5.26 | BLQ | BLQ | 8312.98 | 2753.66 | 7101.75 | 8973.45 | BLQ | 19.41 | BLQ | BLQ | 3.41 | BLQ | BLQ | 2.96 |
| mg/kg/day | CJ3M02 | BLQ | BLQ | BLQ | BLQ | 7136.73 | 2722.78 | 9985.51 | 9298.79 | BLQ | 108.34 | BLQ | BLQ | BLQ | BLQ | BLQ | BLQ |
| | CJ3M03 | BLQ | 2.41 | BLQ | BLQ | 5832.12 | 4900.91 | 8873.95 | 9812.62 | BLQ | 39.40 | BLQ | BLQ | BLQ | BLQ | BLQ | BLQ |
| | Mean | N.C. | 3.84 | N.C. | N.C. | 7093.94 | 3459.12 | 8653.74 | d* 9361.62 | N.C. | 55.72 | N.C. | N.C. | N.C. | N.C. | N.C. | N.C. |
| | S.D. | N.C. | N.C. | N.C. | N.C. | 1240.98 | 1248.73 | 1454.44 | 423.10 | N.C. | 46.66 | N.C. | N.C. | N.C. | N.C. | N.C. | N.C. |
| | N | 0 | 2 | 0 | 0 | 3 | 3 | 3 | 3 | 0 | 3 | 0 | 0 | 1 | 0 | 0 | 1 |

General Footnote: Day 8: Prior to dosing

BLQ: Below the lower limit of quantification (12.2 pg/mL for Interleukin-10, 2.4 pg/mL for the others)

When plasma concentrations were BLQ in 1 of the 3 animals, the mean of the 2 remaining animals was calculated.

The mean was regarded as N.C. when plasma concentrations in 2 of the 3 animals were BLQ.

N.C.: Not calculated

1 [d - Test: Dunnett 2 Sided $p < 0.05$]

[Fig. 82]

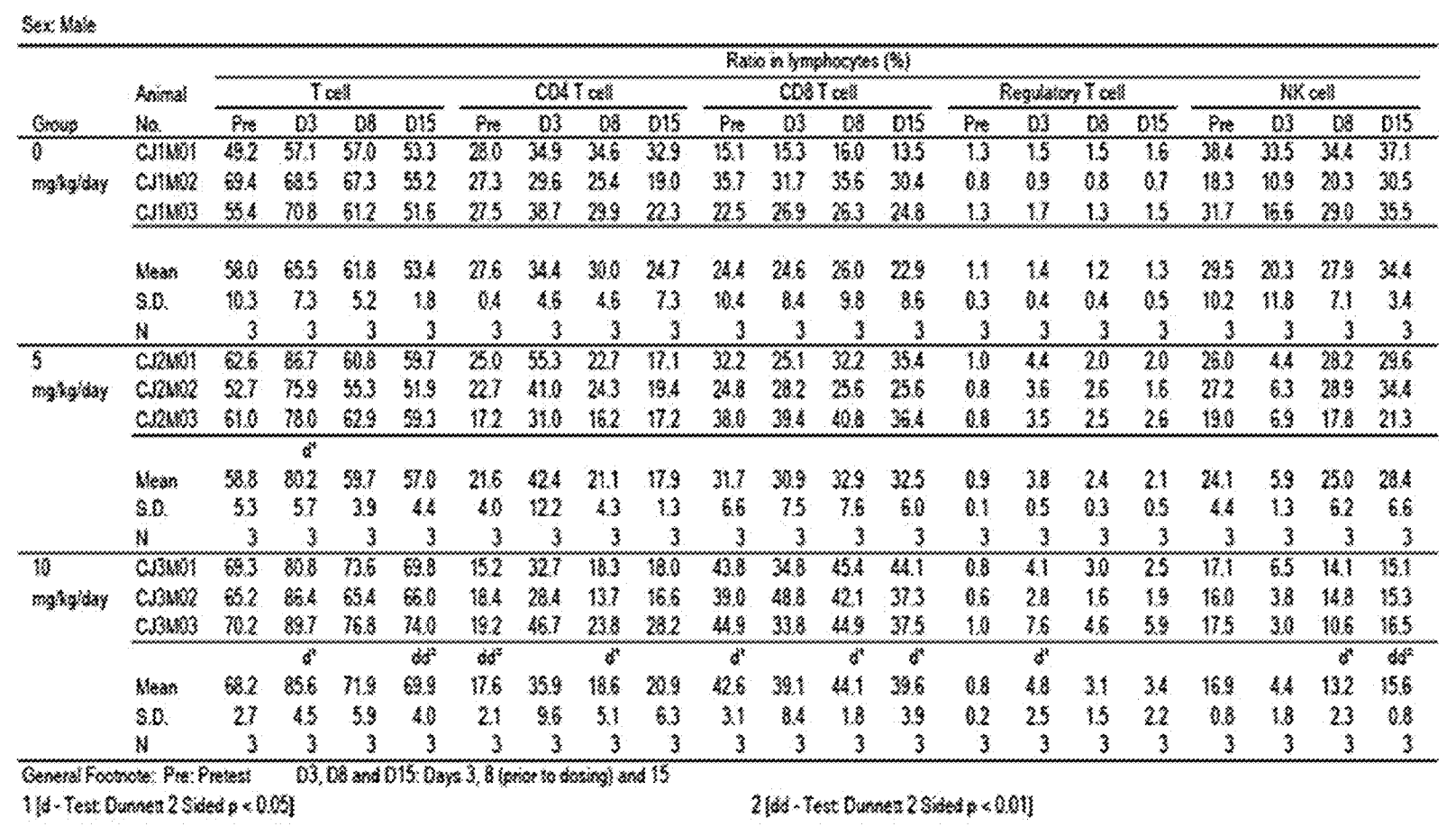

Sex: Male

| Group | Animal No. | T cell Pre | T cell D3 | T cell D8 | T cell D15 | CD4 T cell Pre | CD4 T cell D3 | CD4 T cell D8 | CD4 T cell D15 | CD8 T cell Pre | CD8 T cell D3 | CD8 T cell D8 | CD8 T cell D15 | Regulatory T cell Pre | Regulatory T cell D3 | Regulatory T cell D8 | Regulatory T cell D15 | NK cell Pre | NK cell D3 | NK cell D8 | NK cell D15 |
|---|---|---|---|---|---|---|---|---|---|---|---|---|---|---|---|---|---|---|---|---|---|
| | | Ratio in lymphocytes (%) | | | | | | | | | | | | | | | | | | | |
| 0 | CJ1M01 | 49.2 | 57.1 | 57.0 | 53.3 | 28.0 | 34.9 | 34.6 | 32.9 | 15.1 | 15.3 | 16.0 | 13.5 | 1.3 | 1.5 | 1.5 | 1.6 | 38.4 | 33.5 | 34.4 | 37.1 |
| mg/kg/day | CJ1M02 | 69.4 | 68.5 | 67.3 | 55.2 | 27.3 | 29.6 | 25.4 | 19.0 | 35.7 | 31.7 | 35.6 | 30.4 | 0.8 | 0.9 | 0.8 | 0.7 | 18.3 | 10.9 | 20.3 | 30.5 |
| | CJ1M03 | 55.4 | 70.8 | 61.2 | 51.6 | 27.5 | 38.7 | 29.9 | 22.3 | 22.5 | 26.9 | 26.3 | 24.8 | 1.3 | 1.7 | 1.3 | 1.5 | 31.7 | 16.6 | 29.0 | 35.5 |
| | Mean | 58.0 | 65.5 | 61.8 | 53.4 | 27.6 | 34.4 | 30.0 | 24.7 | 24.4 | 24.6 | 26.0 | 22.9 | 1.1 | 1.4 | 1.2 | 1.3 | 29.5 | 20.3 | 27.9 | 34.4 |
| | S.D. | 10.3 | 7.3 | 5.2 | 1.8 | 0.4 | 4.6 | 4.6 | 7.3 | 10.4 | 8.4 | 9.8 | 8.6 | 0.3 | 0.4 | 0.4 | 0.5 | 10.2 | 11.8 | 7.1 | 3.4 |
| | N | 3 | 3 | 3 | 3 | 3 | 3 | 3 | 3 | 3 | 3 | 3 | 3 | 3 | 3 | 3 | 3 | 3 | 3 | 3 | 3 |
| 5 | CJ2M01 | 62.6 | 86.7 | 60.8 | 59.7 | 25.0 | 55.3 | 22.7 | 17.1 | 32.2 | 25.1 | 32.2 | 35.4 | 1.0 | 4.4 | 2.0 | 2.0 | 26.0 | 4.4 | 28.2 | 29.6 |
| mg/kg/day | CJ2M02 | 52.7 | 75.9 | 55.3 | 51.9 | 22.7 | 41.0 | 24.3 | 19.4 | 24.8 | 28.2 | 25.6 | 25.6 | 0.8 | 3.6 | 2.6 | 1.6 | 27.2 | 6.3 | 28.9 | 34.4 |
| | CJ2M03 | 61.0 | 78.0 | 62.9 | 59.3 | 17.2 | 31.0 | 16.2 | 17.2 | 38.0 | 39.4 | 40.8 | 36.4 | 0.8 | 3.5 | 2.5 | 2.6 | 19.0 | 6.9 | 17.8 | 21.3 |
| | | | d[1] | | | | | | | | | | | | | | | | | | |
| | Mean | 58.8 | 80.2 | 59.7 | 57.0 | 21.6 | 42.4 | 21.1 | 17.9 | 31.7 | 30.9 | 32.9 | 32.5 | 0.9 | 3.8 | 2.4 | 2.1 | 24.1 | 5.9 | 25.0 | 28.4 |
| | S.D. | 5.3 | 5.7 | 3.9 | 4.4 | 4.0 | 12.2 | 4.3 | 1.3 | 6.6 | 7.5 | 7.6 | 6.0 | 0.1 | 0.5 | 0.3 | 0.5 | 4.4 | 1.3 | 6.2 | 6.6 |
| | N | 3 | 3 | 3 | 3 | 3 | 3 | 3 | 3 | 3 | 3 | 3 | 3 | 3 | 3 | 3 | 3 | 3 | 3 | 3 | 3 |
| 10 | CJ3M01 | 69.3 | 80.8 | 73.6 | 69.8 | 15.2 | 32.7 | 18.3 | 18.0 | 43.8 | 34.8 | 45.4 | 44.1 | 0.8 | 4.1 | 3.0 | 2.5 | 17.1 | 6.5 | 14.1 | 15.1 |
| mg/kg/day | CJ3M02 | 65.2 | 86.4 | 65.4 | 66.0 | 18.4 | 28.4 | 13.7 | 16.6 | 39.0 | 48.8 | 42.1 | 37.3 | 0.6 | 2.8 | 1.6 | 1.9 | 16.0 | 3.8 | 14.8 | 15.3 |
| | CJ3M03 | 70.2 | 89.7 | 76.8 | 74.0 | 19.2 | 46.7 | 23.8 | 28.2 | 44.9 | 33.8 | 44.9 | 37.5 | 1.0 | 7.6 | 4.6 | 5.9 | 17.5 | 3.0 | 10.6 | 16.5 |
| | | | d[1] | | dd[2] | dd[2] | | d[1] | | d[1] | | d[1] | d[1] | | d[1] | | | | | d[1] | dd[2] |
| | Mean | 68.2 | 85.6 | 71.9 | 69.9 | 17.6 | 35.9 | 18.6 | 20.9 | 42.6 | 39.1 | 44.1 | 39.6 | 0.8 | 4.8 | 3.1 | 3.4 | 16.9 | 4.4 | 13.2 | 15.6 |
| | S.D. | 2.7 | 4.5 | 5.9 | 4.0 | 2.1 | 9.6 | 5.1 | 6.3 | 3.1 | 8.4 | 1.8 | 3.9 | 0.2 | 2.5 | 1.5 | 2.2 | 0.8 | 1.8 | 2.3 | 0.8 |
| | N | 3 | 3 | 3 | 3 | 3 | 3 | 3 | 3 | 3 | 3 | 3 | 3 | 3 | 3 | 3 | 3 | 3 | 3 | 3 | 3 |

General Footnote: Pre: Pretest D3, D8 and D15: Days 3, 8 (prior to dosing) and 15

1 [d - Test: Dunnett 2 Sided $p < 0.05$] 2 [dd - Test: Dunnett 2 Sided $p < 0.01$]

[Fig. 83]

Sex: Male

| Group | Animal No. | Lymphocytes (10^3/μL) Pre | Lymphocytes (10^3/μL) D15 | Absolute count (10^3/μL) T cell Pre | T cell D15 | CD4 T cell Pre | CD4 T cell D15 | CD8 T cell Pre | CD8 T cell D15 | Regulatory T cell Pre | Regulatory T cell D15 | NK cell Pre | NK cell D15 |
|---|---|---|---|---|---|---|---|---|---|---|---|---|---|
| 0 | CJ1M01 | 7.40 | 5.60 | 3.64 | 2.98 | 2.07 | 1.84 | 1.12 | 0.76 | 0.10 | 0.09 | 2.84 | 2.08 |
| mg/kg/day | CJ1M02 | 6.42 | 5.03 | 4.46 | 2.78 | 1.75 | 0.96 | 2.29 | 1.53 | 0.05 | 0.04 | 1.17 | 1.53 |
| | CJ1M03 | 3.94 | 3.77 | 2.18 | 1.95 | 1.08 | 0.84 | 0.89 | 0.93 | 0.05 | 0.06 | 1.25 | 1.34 |
| | Mean | 5.92 | 4.80 | 3.43 | 2.57 | 1.63 | 1.21 | 1.43 | 1.07 | 0.07 | 0.06 | 1.75 | 1.65 |
| | S.D. | 1.78 | 0.94 | 1.15 | 0.55 | 0.51 | 0.55 | 0.75 | 0.40 | 0.03 | 0.03 | 0.94 | 0.38 |
| | N | 3 | 3 | 3 | 3 | 3 | 3 | 3 | 3 | 3 | 3 | 3 | 3 |
| 5 | CJ2M01 | 5.01 | 9.42 | 3.14 | 5.62 | 1.25 | 1.61 | 1.61 | 3.33 | 0.05 | 0.19 | 1.30 | 2.79 |
| mg/kg/day | CJ2M02 | 7.29 | 10.34 | 3.84 | 5.37 | 1.65 | 2.01 | 1.81 | 2.65 | 0.06 | 0.17 | 1.98 | 3.56 |
| | CJ2M03 | 5.32 | 9.63 | 3.25 | 5.71 | 0.92 | 1.66 | 2.02 | 3.51 | 0.04 | 0.25 | 1.01 | 2.05 |
| | | | | | | | | | | | dd[2] | | |
| | Mean | 5.87 | 9.80 | 3.41 | 5.57 | 1.27 | 1.76 | 1.81 | 3.16 | 0.05 | 0.20 | 1.43 | 2.80 |
| | S.D. | 1.24 | 0.48 | 0.36 | 0.18 | 0.37 | 0.22 | 0.21 | 0.45 | 0.01 | 0.04 | 0.50 | 0.76 |
| | N | 3 | 3 | 3 | 3 | 3 | 3 | 3 | 3 | 3 | 3 | 3 | 3 |
| 10 | CJ3M01 | 8.36 | 13.41 | 5.81 | 9.36 | 1.27 | 2.41 | 3.67 | 5.91 | 0.07 | 0.34 | 1.43 | 2.02 |
| mg/kg/day | CJ3M02 | 6.25 | 17.73 | 4.08 | 11.70 | 1.15 | 2.94 | 2.44 | 6.61 | 0.04 | 0.34 | 1.00 | 2.71 |
| | CJ3M03 | 3.32 | 5.01 | 2.33 | 3.71 | 0.64 | 1.41 | 1.49 | 1.88 | 0.03 | 0.30 | 0.58 | 0.83 |
| | | | | | d[1] | | | | d[1] | | dd[2] | | |
| | Mean | 5.98 | 12.05 | 4.07 | 8.26 | 1.02 | 2.25 | 2.53 | 4.80 | 0.05 | 0.33 | 1.00 | 1.85 |
| | S.D. | 2.54 | 6.47 | 1.74 | 4.11 | 0.33 | 0.78 | 1.09 | 2.55 | 0.02 | 0.02 | 0.43 | 0.95 |
| | N | 3 | 3 | 3 | 3 | 3 | 3 | 3 | 3 | 3 | 3 | 3 | 3 |

General Footnote: Pre: Pretest D15: Day 15

1 [d - Test: Dunnett 2 Sided p < 0.05] 2 [dd - Test: Dunnett 2 Sided p < 0.01]

[Fig. 84]

Sex: Male

| Group | Animal No. | Ratio to baseline (pretest, %) T cell Pre | T cell D3 | T cell D8 | T cell D15 | CD4 T cell Pre | CD4 T cell D3 | CD4 T cell D8 | CD4 T cell D15 | CD8 T cell Pre | CD8 T cell D3 | CD8 T cell D8 | CD8 T cell D15 | Regulatory T cell Pre | Regulatory T cell D3 | Regulatory T cell D8 | Regulatory T cell D15 | NK cell Pre | NK cell D3 | NK cell D8 | NK cell D15 |
|---|---|---|---|---|---|---|---|---|---|---|---|---|---|---|---|---|---|---|---|---|---|
| 0 | CJ1M01 | 1.00 | 1.16 | 1.16 | 1.06 | 1.00 | 1.25 | 1.24 | 1.18 | 1.00 | 1.01 | 1.06 | 0.69 | 1.00 | 1.15 | 1.15 | 1.23 | 1.00 | 0.87 | 0.90 | 0.97 |
| mg/kg/day | CJ1M02 | 1.00 | 0.99 | 0.97 | 0.80 | 1.00 | 1.08 | 0.93 | 0.70 | 1.00 | 0.89 | 1.00 | 0.65 | 1.00 | 1.13 | 1.00 | 0.88 | 1.00 | 0.60 | 1.11 | 1.67 |
| | CJ1M03 | 1.00 | 1.28 | 1.10 | 0.93 | 1.00 | 1.41 | 1.09 | 0.81 | 1.00 | 1.20 | 1.17 | 1.10 | 1.00 | 1.31 | 1.00 | 1.15 | 1.00 | 0.52 | 0.91 | 1.12 |
| | Mean | 1.00 | 1.14 | 1.08 | 0.94 | 1.00 | 1.25 | 1.09 | 0.90 | 1.00 | 1.03 | 1.08 | 0.95 | 1.00 | 1.20 | 1.05 | 1.09 | 1.00 | 0.66 | 0.97 | 1.25 |
| | S.D. | 0.00 | 0.15 | 0.10 | 0.14 | 0.00 | 0.17 | 0.16 | 0.25 | 0.00 | 0.16 | 0.09 | 0.13 | 0.00 | 0.10 | 0.09 | 0.18 | 0.00 | 0.18 | 0.12 | 0.37 |
| | N | 3 | 3 | 3 | 3 | 3 | 3 | 3 | 3 | 3 | 3 | 3 | 3 | 3 | 3 | 3 | 3 | 3 | 3 | 3 | 3 |
| 5 | CJ2M01 | 1.00 | 1.38 | 0.97 | 0.95 | 1.00 | 2.21 | 0.91 | 0.68 | 1.00 | 0.78 | 1.00 | 1.10 | 1.00 | 4.40 | 2.00 | 2.00 | 1.00 | 0.17 | 1.08 | 1.14 |
| mg/kg/day | CJ2M02 | 1.00 | 1.44 | 1.05 | 0.98 | 1.00 | 1.81 | 1.07 | 0.85 | 1.00 | 1.14 | 1.03 | 1.03 | 1.00 | 4.50 | 3.25 | 2.00 | 1.00 | 0.23 | 1.06 | 1.26 |
| | CJ2M03 | 1.00 | 1.28 | 1.03 | 0.97 | 1.00 | 1.80 | 0.94 | 1.00 | 1.00 | 1.04 | 1.07 | 0.96 | 1.00 | 4.38 | 3.13 | 3.25 | 1.00 | 0.36 | 0.94 | 1.12 |
| | | | | | | | | | | | | | | | dd[2] | d[1] | | | d[1] | | |
| | Mean | 1.00 | 1.37 | 1.02 | 0.97 | 1.00 | 1.94 | 0.97 | 0.84 | 1.00 | 0.99 | 1.03 | 1.03 | 1.00 | 4.43 | 2.79 | 2.42 | 1.00 | 0.25 | 1.03 | 1.17 |
| | S.D. | 0.00 | 0.08 | 0.04 | 0.02 | 0.00 | 0.23 | 0.09 | 0.16 | 0.00 | 0.19 | 0.04 | 0.07 | 0.00 | 0.06 | 0.69 | 0.72 | 0.00 | 0.10 | 0.08 | 0.08 |
| | N | 3 | 3 | 3 | 3 | 3 | 3 | 3 | 3 | 3 | 3 | 3 | 3 | 3 | 3 | 3 | 3 | 3 | 3 | 3 | 3 |
| 10 | CJ3M01 | 1.00 | 1.17 | 1.06 | 1.01 | 1.00 | 2.15 | 1.20 | 1.18 | 1.00 | 0.79 | 1.04 | 1.01 | 1.00 | 5.13 | 3.75 | 3.13 | 1.00 | 0.38 | 0.82 | 0.88 |
| mg/kg/day | CJ3M02 | 1.00 | 1.33 | 1.00 | 1.01 | 1.00 | 1.54 | 0.74 | 0.90 | 1.00 | 1.25 | 1.08 | 0.96 | 1.00 | 4.67 | 2.67 | 3.17 | 1.00 | 0.24 | 0.93 | 0.96 |
| | CJ3M03 | 1.00 | 1.28 | 1.09 | 1.05 | 1.00 | 2.43 | 1.24 | 1.47 | 1.00 | 0.75 | 1.00 | 0.84 | 1.00 | 7.60 | 4.60 | 5.90 | 1.00 | 0.17 | 0.61 | 0.94 |
| | | | | | | | d[1] | | | | | | | | dd[2] | dd[2] | d[1] | | d[1] | | |
| | Mean | 1.00 | 1.26 | 1.05 | 1.02 | 1.00 | 2.04 | 1.06 | 1.18 | 1.00 | 0.93 | 1.04 | 0.94 | 1.00 | 5.80 | 3.67 | 4.07 | 1.00 | 0.26 | 0.79 | 0.93 |
| | S.D. | 0.00 | 0.08 | 0.05 | 0.02 | 0.00 | 0.46 | 0.28 | 0.29 | 0.00 | 0.28 | 0.04 | 0.09 | 0.00 | 1.58 | 0.97 | 1.59 | 0.00 | 0.11 | 0.16 | 0.04 |
| | N | 3 | 3 | 3 | 3 | 3 | 3 | 3 | 3 | 3 | 3 | 3 | 3 | 3 | 3 | 3 | 3 | 3 | 3 | 3 | 3 |

General Footnote: Pre: Pretest D3, D8 and D15: Days 3, 8 (prior to dosing) and 15

1 [d - Test: Dunnett 2 Sided p < 0.05] 2 [dd - Test: Dunnett 2 Sided p < 0.01]

[Fig. 85]

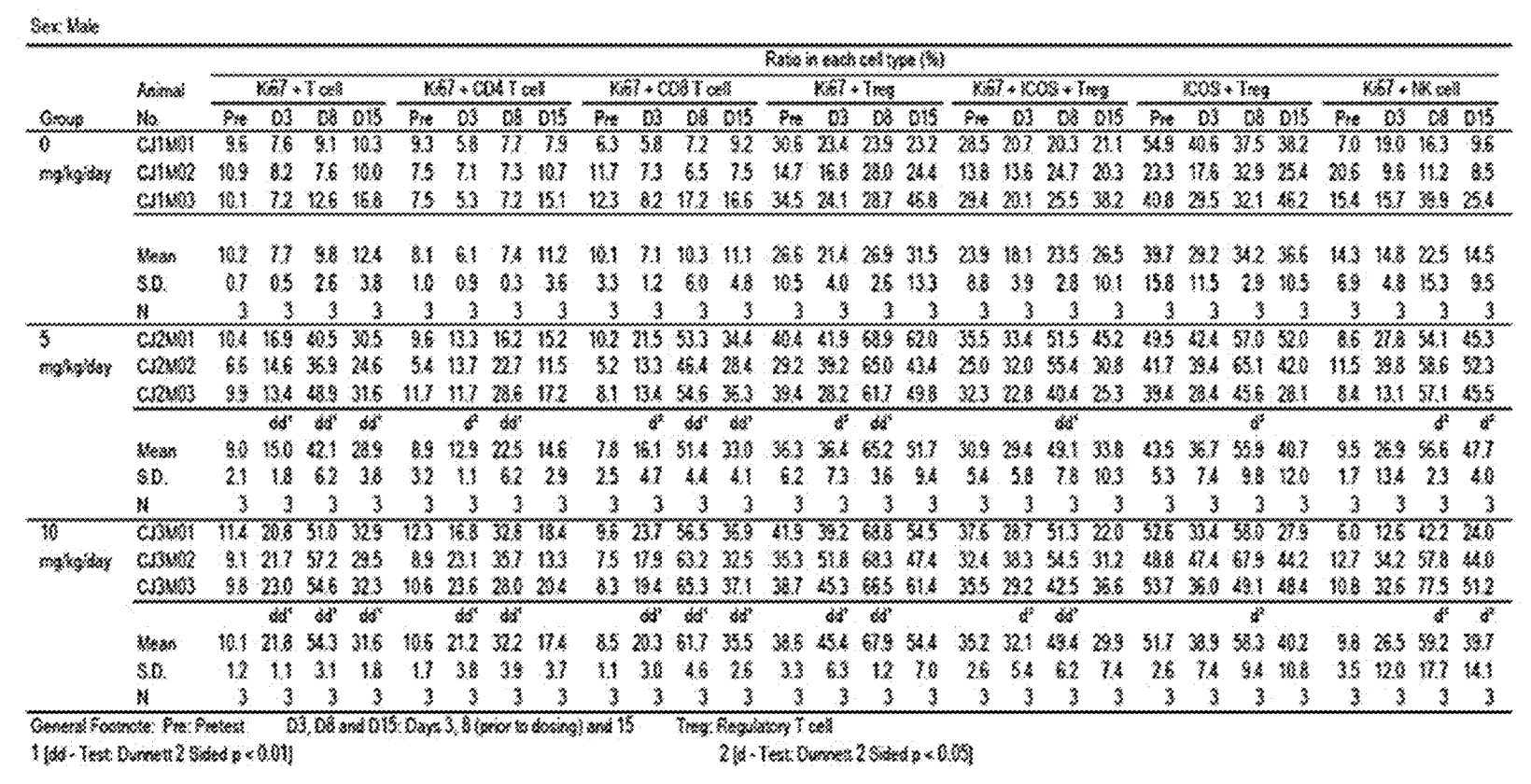

Sex: Male

| Group | Animal No. | Ki67 + T cell Pre | Ki67 + T cell D3 | Ki67 + T cell D8 | Ki67 + T cell D15 | Ki67 + CD4 T cell Pre | Ki67 + CD4 T cell D3 | Ki67 + CD4 T cell D8 | Ki67 + CD4 T cell D15 | Ki67 + CD8 T cell Pre | Ki67 + CD8 T cell D3 | Ki67 + CD8 T cell D8 | Ki67 + CD8 T cell D15 | Ki67 + Treg Pre | Ki67 + Treg D3 | Ki67 + Treg D8 | Ki67 + Treg D15 | Ki67 + ICOS + Treg Pre | Ki67 + ICOS + Treg D3 | Ki67 + ICOS + Treg D8 | Ki67 + ICOS + Treg D15 | ICOS + Treg Pre | ICOS + Treg D3 | ICOS + Treg D8 | ICOS + Treg D15 | Ki67 + NK cell Pre | Ki67 + NK cell D3 | Ki67 + NK cell D8 | Ki67 + NK cell D15 |
|---|---|---|---|---|---|---|---|---|---|---|---|---|---|---|---|---|---|---|---|---|---|---|---|---|---|---|---|---|---|
| | | Ratio in each cell type (%) | | | | | | | | | | | | | | | | | | | | | | | | | | | |
| 0 mg/kg/day | CJ1M01 | 9.6 | 7.6 | 9.1 | 10.3 | 9.3 | 5.8 | 7.7 | 7.9 | 6.3 | 5.8 | 7.2 | 9.2 | 30.6 | 23.4 | 23.9 | 23.2 | 28.5 | 20.7 | 20.3 | 21.1 | 54.9 | 40.6 | 37.5 | 38.2 | 7.0 | 19.0 | 16.3 | 9.6 |
| | CJ1M02 | 10.9 | 8.2 | 7.6 | 10.0 | 7.5 | 7.1 | 7.3 | 10.7 | 11.7 | 7.3 | 6.5 | 7.5 | 14.7 | 16.8 | 28.0 | 24.4 | 13.8 | 13.6 | 24.7 | 20.3 | 23.3 | 17.6 | 32.9 | 25.4 | 20.6 | 9.6 | 11.2 | 8.5 |
| | CJ1M03 | 10.1 | 7.2 | 12.6 | 16.8 | 7.5 | 5.3 | 7.2 | 15.1 | 12.3 | 8.2 | 17.2 | 16.6 | 34.5 | 24.1 | 28.7 | 46.8 | 29.4 | 20.1 | 25.5 | 38.2 | 40.8 | 29.5 | 32.1 | 46.2 | 15.4 | 15.7 | 39.9 | 25.4 |
| | Mean | 10.2 | 7.7 | 9.8 | 12.4 | 8.1 | 6.1 | 7.4 | 11.2 | 10.1 | 7.1 | 10.3 | 11.1 | 26.6 | 21.4 | 26.9 | 31.5 | 23.9 | 18.1 | 23.5 | 26.5 | 39.7 | 29.2 | 34.2 | 36.6 | 14.3 | 14.8 | 22.5 | 14.5 |
| | S.D. | 0.7 | 0.5 | 2.6 | 3.8 | 1.0 | 0.9 | 0.3 | 3.6 | 3.3 | 1.2 | 6.0 | 4.8 | 10.5 | 4.0 | 2.6 | 13.3 | 8.8 | 3.9 | 2.8 | 10.1 | 15.8 | 11.5 | 2.9 | 10.5 | 6.9 | 4.8 | 15.3 | 9.5 |
| | N | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 |
| 5 mg/kg/day | CJ2M01 | 10.4 | 16.9 | 40.5 | 30.5 | 9.6 | 13.3 | 16.2 | 15.2 | 10.2 | 21.5 | 53.3 | 34.4 | 40.4 | 41.9 | 68.9 | 62.0 | 35.5 | 33.4 | 51.5 | 45.2 | 49.5 | 42.4 | 57.0 | 52.0 | 8.6 | 27.8 | 54.1 | 45.3 |
| | CJ2M02 | 6.6 | 14.6 | 36.9 | 24.6 | 5.4 | 13.7 | 22.7 | 11.5 | 5.2 | 13.3 | 46.4 | 28.4 | 29.2 | 39.2 | 65.0 | 43.4 | 25.0 | 32.0 | 55.4 | 30.8 | 41.7 | 39.4 | 65.1 | 42.0 | 11.5 | 39.8 | 58.6 | 52.3 |
| | CJ2M03 | 9.9 | 13.4 | 48.9 | 31.6 | 11.7 | 11.7 | 28.6 | 17.2 | 8.1 | 13.4 | 54.6 | 36.3 | 39.4 | 28.2 | 61.7 | 49.8 | 32.3 | 22.8 | 40.4 | 25.3 | 39.4 | 28.4 | 45.6 | 28.1 | 8.4 | 13.1 | 57.1 | 45.5 |
| | | | dd[1] | dd[1] | dd[1] | | d[2] | dd[1] | | | d[2] | dd[1] | dd[1] | | d[2] | dd[1] | | | | dd[1] | | | | d[2] | | | | d[2] | d[2] |
| | Mean | 9.0 | 15.0 | 42.1 | 28.9 | 8.9 | 12.9 | 22.5 | 14.6 | 7.8 | 16.1 | 51.4 | 33.0 | 36.3 | 36.4 | 65.2 | 51.7 | 30.9 | 29.4 | 49.1 | 33.8 | 43.5 | 36.7 | 55.9 | 40.7 | 9.5 | 26.9 | 56.6 | 47.7 |
| | S.D. | 2.1 | 1.8 | 6.2 | 3.8 | 3.2 | 1.1 | 6.2 | 2.9 | 2.5 | 4.7 | 4.4 | 4.1 | 6.2 | 7.3 | 3.6 | 9.4 | 5.4 | 5.8 | 7.8 | 10.3 | 5.3 | 7.4 | 9.8 | 12.0 | 1.7 | 13.4 | 2.3 | 4.0 |
| | N | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 |
| 10 mg/kg/day | CJ3M01 | 11.4 | 20.8 | 51.0 | 32.9 | 12.3 | 16.8 | 32.8 | 18.4 | 9.6 | 23.7 | 56.5 | 36.9 | 41.9 | 39.2 | 68.8 | 54.5 | 37.6 | 28.7 | 51.3 | 22.0 | 52.6 | 33.4 | 58.0 | 27.9 | 6.0 | 12.6 | 42.2 | 24.0 |
| | CJ3M02 | 9.1 | 21.7 | 57.2 | 29.5 | 8.9 | 23.1 | 35.7 | 13.3 | 7.5 | 17.9 | 63.2 | 32.5 | 35.3 | 51.8 | 68.3 | 47.4 | 32.4 | 38.3 | 54.5 | 31.2 | 48.8 | 47.4 | 67.9 | 44.2 | 12.7 | 34.2 | 57.8 | 44.0 |
| | CJ3M03 | 9.8 | 23.0 | 54.6 | 32.3 | 10.6 | 23.6 | 28.0 | 20.4 | 8.3 | 19.4 | 65.3 | 37.1 | 38.7 | 45.3 | 66.5 | 61.4 | 35.5 | 29.2 | 42.5 | 36.6 | 53.7 | 36.0 | 49.1 | 48.4 | 10.8 | 32.6 | 77.5 | 51.2 |
| | | | dd[1] | dd[1] | dd[1] | | dd[1] | dd[1] | | | dd[1] | dd[1] | dd[1] | | dd[1] | dd[1] | | | d[2] | dd[1] | | | | d[2] | | | | d[2] | d[2] |
| | Mean | 10.1 | 21.8 | 54.3 | 31.6 | 10.6 | 21.2 | 32.2 | 17.4 | 8.5 | 20.3 | 61.7 | 35.5 | 38.6 | 45.4 | 67.9 | 54.4 | 35.2 | 32.1 | 49.4 | 29.9 | 51.7 | 38.9 | 58.3 | 40.2 | 9.8 | 26.5 | 59.2 | 39.7 |
| | S.D. | 1.2 | 1.1 | 3.1 | 1.8 | 1.7 | 3.8 | 3.9 | 3.7 | 1.1 | 3.0 | 4.6 | 2.6 | 3.3 | 6.3 | 1.2 | 7.0 | 2.6 | 5.4 | 6.2 | 7.4 | 2.6 | 7.4 | 9.4 | 10.8 | 3.5 | 12.0 | 17.7 | 14.1 |
| | N | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 |

General Footnote: Pre: Pretest D3, D8 and D15: Days 3, 8 (prior to dosing) and 15 Treg: Regulatory T cell 1 [dd - Test: Dunnett 2 Sided p < 0.01] 2 [d - Test: Dunnett 2 Sided p < 0.05]

[Fig. 86]

Sex: Male

| Group | Animal No. | Absolute count in each cell type (10^3/μL) Ki67 + T cell Pre | Ki67 + T cell D15 | Ki67 + CD4 T cell Pre | Ki67 + CD4 T cell D15 | Ki67 + CD8 T cell Pre | Ki67 + CD8 T cell D15 | Ki67 + Treg Pre | Ki67 + Treg D15 | Ki67 + ICOS + Treg Pre | Ki67 + ICOS + Treg D15 | ICOS + Treg Pre | ICOS + Treg D15 | Ki67 + NK cell Pre | Ki67 + NK cell D15 |
|---|---|---|---|---|---|---|---|---|---|---|---|---|---|---|---|
| 0 | CJ1M01 | 0.35 | 0.31 | 0.19 | 0.15 | 0.07 | 0.07 | 0.03 | 0.02 | 0.03 | 0.02 | 0.05 | 0.03 | 0.20 | 0.20 |
| mg/kg/day | CJ1M02 | 0.49 | 0.28 | 0.13 | 0.10 | 0.27 | 0.11 | 0.01 | 0.01 | 0.01 | 0.01 | 0.01 | 0.01 | 0.24 | 0.13 |
| | CJ1M03 | 0.22 | 0.33 | 0.08 | 0.13 | 0.11 | 0.15 | 0.02 | 0.03 | 0.01 | 0.02 | 0.02 | 0.03 | 0.19 | 0.34 |
| | Mean | 0.35 | 0.31 | 0.13 | 0.13 | 0.15 | 0.11 | 0.02 | 0.02 | 0.02 | 0.02 | 0.03 | 0.02 | 0.21 | 0.22 |
| | S.D. | 0.14 | 0.03 | 0.06 | 0.03 | 0.11 | 0.04 | 0.01 | 0.01 | 0.01 | 0.01 | 0.02 | 0.01 | 0.03 | 0.11 |
| | N | 3 | 3 | 3 | 3 | 3 | 3 | 3 | 3 | 3 | 3 | 3 | 3 | 3 | 3 |
| 5 | CJ2M01 | 0.33 | 1.71 | 0.12 | 0.24 | 0.16 | 1.15 | 0.02 | 0.12 | 0.02 | 0.09 | 0.02 | 0.10 | 0.11 | 1.26 |
| mg/kg/day | CJ2M02 | 0.25 | 1.32 | 0.09 | 0.23 | 0.09 | 0.75 | 0.02 | 0.07 | 0.02 | 0.05 | 0.03 | 0.07 | 0.23 | 1.86 |
| | CJ2M03 | 0.32 | 1.80 | 0.11 | 0.29 | 0.16 | 1.27 | 0.02 | 0.12 | 0.01 | 0.06 | 0.02 | 0.07 | 0.08 | 0.93 |
| | | | | | d[1] | | | | dd[2] | | d[1] | | d[1] | | d[1] |
| | Mean | 0.30 | 1.61 | 0.11 | 0.25 | 0.14 | 1.06 | 0.02 | 0.10 | 0.02 | 0.07 | 0.02 | 0.08 | 0.14 | 1.35 |
| | S.D. | 0.04 | 0.26 | 0.02 | 0.03 | 0.04 | 0.27 | 0.00 | 0.03 | 0.01 | 0.02 | 0.01 | 0.02 | 0.08 | 0.47 |
| | N | 3 | 3 | 3 | 3 | 3 | 3 | 3 | 3 | 3 | 3 | 3 | 3 | 3 | 3 |
| 10 | CJ3M01 | 0.66 | 3.08 | 0.16 | 0.44 | 0.35 | 2.18 | 0.03 | 0.19 | 0.03 | 0.07 | 0.04 | 0.09 | 0.09 | 0.48 |
| mg/kg/day | CJ3M02 | 0.37 | 3.45 | 0.10 | 0.39 | 0.18 | 2.15 | 0.01 | 0.16 | 0.01 | 0.11 | 0.02 | 0.15 | 0.13 | 1.19 |
| | CJ3M03 | 0.23 | 1.20 | 0.07 | 0.29 | 0.12 | 0.70 | 0.01 | 0.18 | 0.01 | 0.11 | 0.02 | 0.15 | 0.06 | 0.42 |
| | | | d[1] | | dd[2] | | d[1] | | dd[2] | | dd[2] | | dd[2] | | |
| | Mean | 0.42 | 2.58 | 0.11 | 0.37 | 0.22 | 1.68 | 0.02 | 0.18 | 0.02 | 0.10 | 0.03 | 0.13 | 0.09 | 0.70 |
| | S.D. | 0.22 | 1.21 | 0.05 | 0.08 | 0.12 | 0.85 | 0.01 | 0.02 | 0.01 | 0.02 | 0.01 | 0.03 | 0.04 | 0.43 |
| | N | 3 | 3 | 3 | 3 | 3 | 3 | 3 | 3 | 3 | 3 | 3 | 3 | 3 | 3 |

General Footnote: Pre: Pretest D15: Day 15 Treg: Regulatory T cell

1 [d - Test: Dunnett 2 Sided $p < 0.05$] 2 [dd - Test: Dunnett 2 Sided $p < 0.01$]

[Fig. 87]

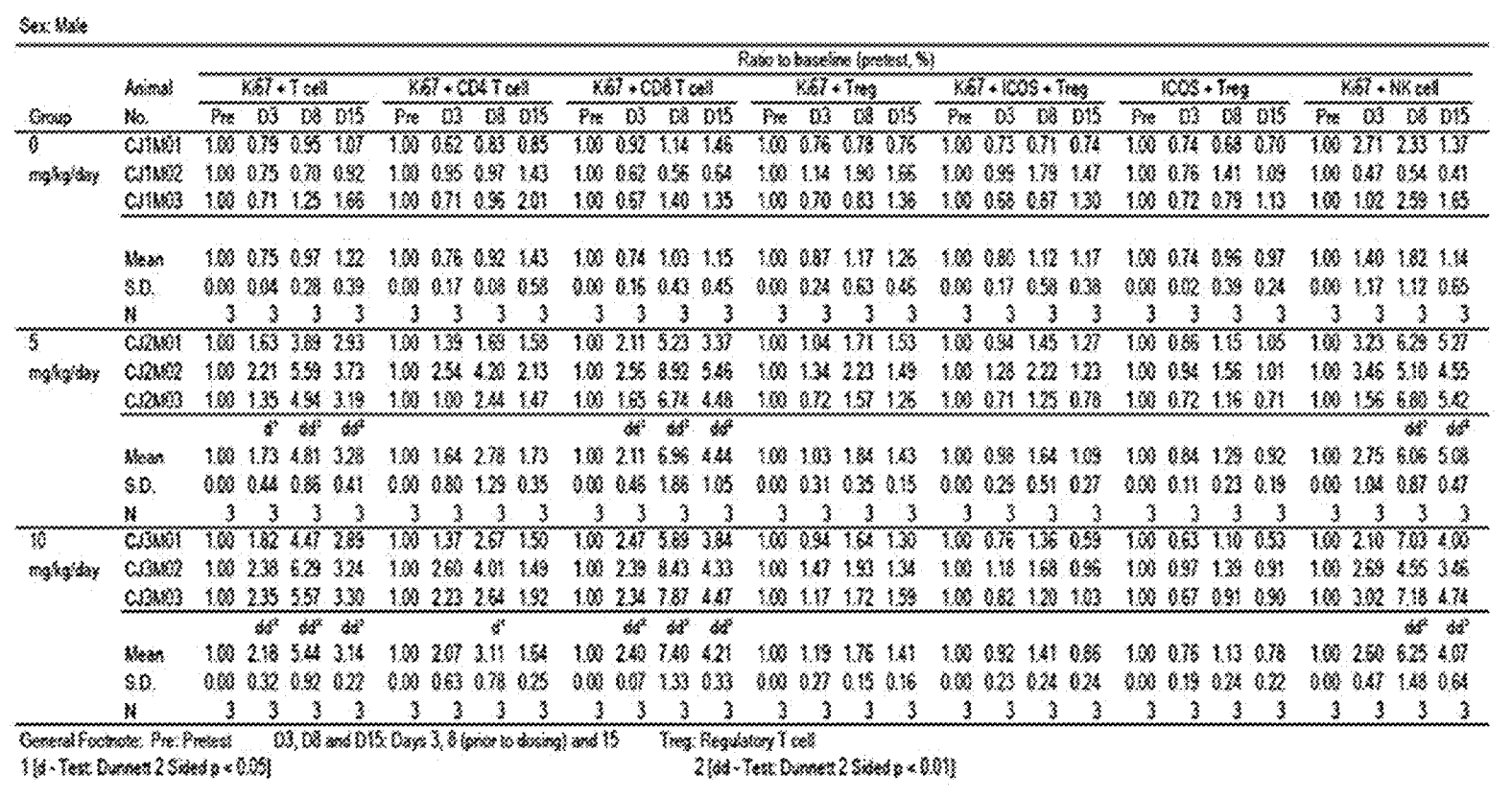

Sex: Male

| Group | Animal | Ratio to baseline (pretest, %) | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| | | Ki67 + T cell | | | | Ki67 + CD4 T cell | | | | Ki67 + CD8 T cell | | | | Ki67 + Treg | | | | Ki67 + ICOS + Treg | | | | ICOS + Treg | | | | Ki67 + NK cell | | | |
| Group | No. | Pre | D3 | D8 | D15 | Pre | D3 | D8 | D15 | Pre | D3 | D8 | D15 | Pre | D3 | D8 | D15 | Pre | D3 | D8 | D15 | Pre | D3 | D8 | D15 | Pre | D3 | D8 | D15 |
| 0 | CJ1M01 | 1.00 | 0.79 | 0.95 | 1.07 | 1.00 | 0.62 | 0.83 | 0.85 | 1.00 | 0.92 | 1.14 | 1.46 | 1.00 | 0.76 | 0.78 | 0.76 | 1.00 | 0.73 | 0.71 | 0.74 | 1.00 | 0.74 | 0.68 | 0.70 | 1.00 | 2.71 | 2.33 | 1.37 |
| mg/kg/day | CJ1M02 | 1.00 | 0.75 | 0.70 | 0.92 | 1.00 | 0.95 | 0.97 | 1.43 | 1.00 | 0.62 | 0.56 | 0.64 | 1.00 | 1.14 | 1.90 | 1.66 | 1.00 | 0.99 | 1.79 | 1.47 | 1.00 | 0.76 | 1.41 | 1.09 | 1.00 | 0.47 | 0.54 | 0.41 |
| | CJ1M03 | 1.00 | 0.71 | 1.25 | 1.66 | 1.00 | 0.71 | 0.96 | 2.01 | 1.00 | 0.67 | 1.40 | 1.35 | 1.00 | 0.70 | 0.83 | 1.36 | 1.00 | 0.58 | 0.87 | 1.30 | 1.00 | 0.72 | 0.79 | 1.13 | 1.00 | 1.02 | 2.59 | 1.65 |
| | Mean | 1.00 | 0.75 | 0.97 | 1.22 | 1.00 | 0.76 | 0.92 | 1.43 | 1.00 | 0.74 | 1.03 | 1.15 | 1.00 | 0.87 | 1.17 | 1.26 | 1.00 | 0.80 | 1.12 | 1.17 | 1.00 | 0.74 | 0.96 | 0.97 | 1.00 | 1.40 | 1.82 | 1.14 |
| | S.D. | 0.00 | 0.04 | 0.28 | 0.39 | 0.00 | 0.17 | 0.08 | 0.58 | 0.00 | 0.15 | 0.43 | 0.45 | 0.00 | 0.24 | 0.63 | 0.46 | 0.00 | 0.17 | 0.58 | 0.38 | 0.00 | 0.02 | 0.39 | 0.24 | 0.00 | 1.17 | 1.12 | 0.65 |
| | N | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 |
| 5 | CJ2M01 | 1.00 | 1.63 | 3.89 | 2.93 | 1.00 | 1.39 | 1.69 | 1.58 | 1.00 | 2.11 | 5.23 | 3.37 | 1.00 | 1.04 | 1.71 | 1.53 | 1.00 | 0.94 | 1.45 | 1.27 | 1.00 | 0.86 | 1.15 | 1.05 | 1.00 | 3.23 | 6.29 | 5.27 |
| mg/kg/day | CJ2M02 | 1.00 | 2.21 | 5.59 | 3.73 | 1.00 | 2.54 | 4.20 | 2.13 | 1.00 | 2.56 | 8.92 | 5.46 | 1.00 | 1.34 | 2.23 | 1.49 | 1.00 | 1.28 | 2.22 | 1.23 | 1.00 | 0.94 | 1.56 | 1.01 | 1.00 | 3.46 | 5.10 | 4.55 |
| | CJ2M03 | 1.00 | 1.35 | 4.94 | 3.19 | 1.00 | 1.00 | 2.44 | 1.47 | 1.00 | 1.65 | 6.74 | 4.48 | 1.00 | 0.72 | 1.57 | 1.26 | 1.00 | 0.71 | 1.25 | 0.78 | 1.00 | 0.72 | 1.16 | 0.71 | 1.00 | 1.56 | 6.80 | 5.42 |
| | | | d[1] | dd[2] | dd[2] | | | | | | dd[2] | dd[2] | dd[2] | | | | | | | | | | | | | | | dd[2] | dd[2] |
| | Mean | 1.00 | 1.73 | 4.81 | 3.28 | 1.00 | 1.64 | 2.78 | 1.73 | 1.00 | 2.11 | 6.96 | 4.44 | 1.00 | 1.03 | 1.84 | 1.43 | 1.00 | 0.98 | 1.64 | 1.09 | 1.00 | 0.84 | 1.29 | 0.92 | 1.00 | 2.75 | 6.06 | 5.08 |
| | S.D. | 0.00 | 0.44 | 0.86 | 0.41 | 0.00 | 0.80 | 1.29 | 0.35 | 0.00 | 0.46 | 1.86 | 1.05 | 0.00 | 0.31 | 0.35 | 0.15 | 0.00 | 0.29 | 0.51 | 0.27 | 0.00 | 0.11 | 0.23 | 0.19 | 0.00 | 1.04 | 0.87 | 0.47 |
| | N | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 |
| 10 | CJ3M01 | 1.00 | 1.82 | 4.47 | 2.89 | 1.00 | 1.37 | 2.67 | 1.50 | 1.00 | 2.47 | 5.89 | 3.84 | 1.00 | 0.94 | 1.64 | 1.30 | 1.00 | 0.76 | 1.36 | 0.59 | 1.00 | 0.63 | 1.10 | 0.53 | 1.00 | 2.10 | 7.03 | 4.00 |
| mg/kg/day | CJ3M02 | 1.00 | 2.38 | 6.29 | 3.24 | 1.00 | 2.60 | 4.01 | 1.49 | 1.00 | 2.39 | 8.43 | 4.33 | 1.00 | 1.47 | 1.93 | 1.34 | 1.00 | 1.18 | 1.68 | 0.96 | 1.00 | 0.97 | 1.39 | 0.91 | 1.00 | 2.69 | 4.55 | 3.46 |
| | CJ3M03 | 1.00 | 2.35 | 5.57 | 3.30 | 1.00 | 2.23 | 2.64 | 1.92 | 1.00 | 2.34 | 7.87 | 4.47 | 1.00 | 1.17 | 1.72 | 1.59 | 1.00 | 0.82 | 1.20 | 1.03 | 1.00 | 0.67 | 0.91 | 0.90 | 1.00 | 3.02 | 7.18 | 4.74 |
| | | | dd[2] | dd[2] | dd[2] | | | d[1] | | | dd[2] | dd[2] | dd[2] | | | | | | | | | | | | | | | dd[2] | dd[2] |
| | Mean | 1.00 | 2.18 | 5.44 | 3.14 | 1.00 | 2.07 | 3.11 | 1.64 | 1.00 | 2.40 | 7.40 | 4.21 | 1.00 | 1.19 | 1.76 | 1.41 | 1.00 | 0.92 | 1.41 | 0.86 | 1.00 | 0.76 | 1.13 | 0.78 | 1.00 | 2.60 | 6.25 | 4.07 |
| | S.D. | 0.00 | 0.32 | 0.92 | 0.22 | 0.00 | 0.63 | 0.78 | 0.25 | 0.00 | 0.07 | 1.33 | 0.33 | 0.00 | 0.27 | 0.15 | 0.16 | 0.00 | 0.23 | 0.24 | 0.24 | 0.00 | 0.19 | 0.24 | 0.22 | 0.00 | 0.47 | 1.48 | 0.64 |
| | N | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 | 3 |

General Footnote: Pre: Pretest D3, D8 and D15: Days 3, 8 (prior to dosing) and 15 Treg: Regulatory T cell 1 [d - Test: Dunnett 2 Sided $p < 0.05$] 2 [dd - Test: Dunnett 2 Sided $p < 0.01$]

[Fig. 88]
Day(s): 15 Relative to Start Date
| Sex: Male | | 0 mg/kg/day | 5 mg/kg/day | 10 mg/kg/day |
|---|---|---|---|---|
| Liver (g) | Mean | 41.5 | 42.7 | 42.1 |
| | S.D. | 0.9 | 7.1 | 5.6 |
| | N | 3 | 3 | 3 |
| Liver (%) | Mean | 1.73 | 1.68 | 1.86 |
| | S.D. | 0.09 | 0.10 | 0.10 |
| | N | 3 | 3 | 3 |
| Spleen (g) | Mean | 1.727 | 3.358 | 3.886 d* |
| | S.D. | 0.520 | 0.758 | 1.087 |
| | N | 3 | 3 | 3 |
| Spleen (%) | Mean | 0.072 | 0.132 | 0.171 d* |
| | S.D. | 0.023 | 0.025 | 0.040 |
| | N | 3 | 3 | 3 |
| Pancreas (g) | Mean | 4.27 | 4.27 | 3.24 |
| | S.D. | 0.54 | 1.20 | 0.38 |
| | N | 3 | 3 | 3 |
[Fig. 89A]
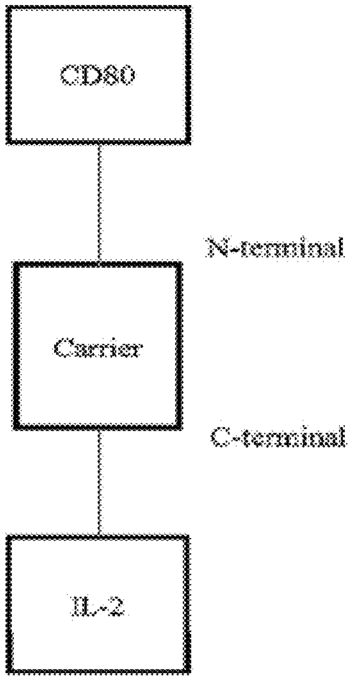
[Fig. 89B]
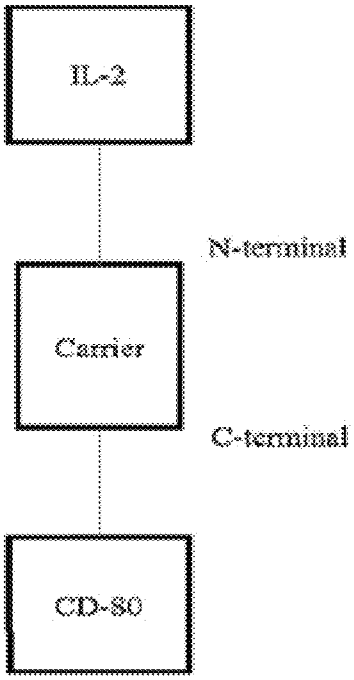

FUSION PROTEIN COMPRISING IL-2 PROTEIN AND CD80 PROTEIN, AND USE THEREOF

CROSS REFERENCE TO RELATED APPLICATIONS

This application is a Divisional of U.S. application Ser. No. 16/959,312 filed Jun. 30, 2020, which is a National Stage of International Application No. PCT/KR2019/011928 filed Sep. 16, 2019, claiming priority based on Korean Patent Application No. 10-2018-0110698 filed Sep. 17, 2018, Korean Patent Application No. 10-2019-0001867 filed Jan. 7, 2019, U.S. Provisional Patent Application No. 62/832,013 filed Apr. 10, 2019, and Korean Patent Application No. 10-2019-0053436 filed May 8, 2019.

SEQUENCE LISTING

The content of the electronically submitted sequence listing, file name: Sequence_Listing_As_Filed.xml; size: 73,090 bytes; and date of creation: Aug. 1, 2022, filed herewith, is incorporated herein by reference in its entirety.

Technical Field

The present invention relates to a fusion protein comprising an IL-2 protein and a CD80 protein, and a use thereof. Specifically, the present invention relates to a novel fusion protein having cancer therapeutic and immunopotentiating efficacy.

Background Art

Interleukin 2 (IL-2), also called T-cell growth factor (TCGF), is a globular glycoprotein that plays a central role in lymphocyte production, survival, and homeostasis. IL-2 has a protein size of 15.5 kDa to 16 kDa and consists of 133 amino acids. IL-2 mediates various immune actions by binding to an IL-2 receptor composed of three distinct subunits.

In addition, IL-2 is synthesized mainly by activated T cells, in particular by CD4+ helper T cells. IL-2 stimulates proliferation and differentiation of T cells, and induces production of cytotoxic T lymphocytes (CTLs) and differentiation of peripheral blood lymphocytes into cytotoxic cells and lymphokine-activated killer cells (LAK cells).

Furthermore, IL-2 is involved in proliferation and differentiation of B cells, promotes immunoglobulin synthesis by B cells, and stimulates production, proliferation, and activation of natural killer cells (NK cells). Therefore, IL-2 is used as an anticancer agent, because it can increase lymphocyte populations and increase the function of the immune cells in the living body. Currently, therapy with IL-2 has been approved and used for patients with metastatic renal cell carcinoma and malignant melanoma.

However, IL-2 has a dual function in immune responses in that it is important not only for mediating an increase in number of immune cells and activity thereof, but also for maintaining immune tolerance. In addition, it has been reported that IL-2 may not be optimal for inhibiting tumor growth. The reason is that in the presence of IL-2, activation-induced cell death (AICD) may occur in the resulting cytotoxic T lymphocytes and immune responses may be inhibited by IL-2-dependent regulatory T cells (Treg cells) (Imai et al., *Cancer Sci* 98, 416-423, 2007).

In addition, severe cardiovascular, pulmonary, renal, hepatic, gastrointestinal, neuronal, cutaneous, hematological, and systemic side effects occur in patients who have received immunotherapy with IL-2. Therefore, various IL-2 mutations have been studied to improve therapeutic efficacy of IL-2 and minimize side effects thereof (U.S. Pat. No. 5,229,109 B). However, there are still many problems to be solved in order to utilize IL-2 for pharmacological purposes.

Meanwhile, CD80, also known as B7-1, is a member of the B7 family of membrane-bound proteins that are involved in immune regulation by binding to its ligand by way of delivering costimulatory responses and coinhibitory responses. CD80 is a transmembrane protein expressed on the surface of T cells, B cells, dendritic cells, and monocytes. CD80 is known to bind CD28, CTLA4 (CD152), and PD-L1. CD80, CD86, CTLA4, and CD28 are involved in a costimulatory-coinhibitory system. For example, they regulate activity of T cells and are involved in proliferation, differentiation, and survival thereof.

For example, when CD80 and CD86 interact with CD28, costimulatory signals are generated to activate T cells. Eventually, CD80 binds to CTLA4 and stimulates CTLA4 to be upregulated. As a result, CD80 inhibits T cell responses prior to immune response activation caused by CD80/CD28 interaction. This feedback loop allows for fine regulation of immune responses.

In addition, CD80 is known to bind PD-L1, another B7 family member, with affinity similar to that with which CD28 binds PD-L 1. PD-L1 is known as one of two ligands for programmed death-1 (PD-1) protein, and PD-L1 is known to be involved in T cell regulation. Binding of CD80 to PD-L1 is another mechanism that can block PD-1/PD-L1 interaction, which may prevent inhibition of T cell responses in tumors. At the same time, however, an increase in CD80 levels causes CD80 to bind to CD28 so that CTLA4 is induced, thereby inducing or inhibiting T cell responses.

DISCLOSURE OF INVENTION

Technical Problem

The present inventors have studied to develop IL-2 which is safe and effective. As a result, the present inventors have discovered that a novel fusion protein comprising, in one molecule, an IL-2 protein and a CD80 protein can activate immune cells and effectively regulate Treg cells, thereby completing the present invention.

Solution to Problem

In order to achieve the above object, in an aspect of the present invention, there is provided a fusion protein comprising an IL-2 protein and a CD80 protein.

In another aspect of the present invention, there is provided a fusion protein dimer obtained by attaching the two fusion proteins to each other.

In yet another aspect of the present invention, there is provided a polynucleotide encoding the fusion protein.

In still yet another aspect of the present invention, there is provided a vector comprising the polynucleotide.

In still yet another aspect of the present invention, there is provided a transformed cell into which the vector has been introduced.

In still yet another aspect of the present invention, there is provided a pharmaceutical composition for preventing or treating cancer or an infectious disease, comprising, as an active ingredient, the fusion protein or the fusion protein dimer.

In still yet another aspect of the present invention, there is provided a use of the fusion protein for treatment of cancer or an infectious disease.

In still yet another aspect of the present invention, there is provided a use of the fusion protein for manufacture of a medicament for treating cancer or an infectious disease.

Advantageous Effects of Invention

A fusion protein comprising an IL-2 protein and a CD80 protein can not only activate immune cells owing to IL-2, but also effectively regulate Treg cells owing to CD80. Therefore, the fusion protein can attack cancer cells in an efficient manner, and thus can be usefully employed for treatment of cancer or an infectious disease.

BRIEF DESCRIPTION OF DRAWINGS

FIG. 1 illustrates a schematic embodiment of a fusion protein.

FIG. 2 illustrates a mechanism by which the fusion protein regulates two different types of immune cells; however, it should be understood that the mechanism by which the action of the fusion protein is expressed is not limited thereto.

FIG. 3 illustrates a mechanism by which the fusion protein exhibits an anticancer effect.

FIG. 4 illustrates a schematic view of the structure of the fusion protein. Here, each of GI101 and mGI101 is an embodiment of the fusion protein herein, and GI101C1, GI101C2, and mGI101C1 are comparative examples for comparison with activity of the fusion protein.

FIG. 5 illustrates various embodiments of the fusion protein herein. Human- and mouse-derived proteins may be combined to prepare a fusion protein. CD80 protein and IL-2 protein may be bound to each other via various linkers other than Fc.

FIG. 6 illustrates a result obtained by identifying the obtained fusion protein (GI101) with SDS-PAGE.

FIG. 7 illustrates amounts of the fusion protein (GI101) depending on absorbance.

FIG. 8 illustrates a result obtained by analyzing the obtained fusion protein (GI101) by size exclusion chromatography (SEC).

FIG. 9 illustrates a result obtained by identifying the obtained mGI101 fusion protein with SDS-PAGE.

FIG. 10 illustrates results obtained by identifying the obtained GI101C1 fusion protein with SDS-PAGE.

FIG. 11 illustrates results obtained by identifying the obtained GI101C2 fusion protein with SDS-PAGE.

FIG. 12 illustrates a result obtained by identifying the obtained mGI101C1 fusion protein with SDS-PAGE.

FIG. 13 illustrates results obtained by identifying the obtained GI102-M45 fusion protein with SDS-PAGE.

FIG. 14 illustrates results obtained by identifying the obtained GI102-M61 fusion protein with SDS-PAGE.

FIG. 15 illustrates results obtained by identifying the obtained GI102-M72 fusion protein with SDS-PAGE.

FIG. 16 illustrates binding affinity between hCTLA4 and GI101.

FIG. 17 illustrates binding affinity between hPD-L1 and GI101.

FIG. 18 illustrates binding affinity between hPD-L1 and hPD-1.

FIG. 19 illustrates binding affinity between mCTLA4 and mGI101.

FIG. 20 illustrates binding affinity between mPD-L1 and mGI101.

FIGS. 21 and 22 illustrate results obtained by identifying binding ability between GI-101 (hCD80-Fc-hIL-2v) and CTLA-4, and between GI-101 (hCD80-Fc-hIL-2v) and PD-L1. It was identified that GI-101 (hCD80-Fc-hIL-2v) has high binding ability for CTLA-4 and PD-L1.

FIG. 23 illustrates an effect of GI101 on PD-1/PD-L1 binding. GI101 effectively inhibited PD-1/PD-L1 binding.

FIG. 24 illustrates results obtained by identifying binding affinity between GI101 and IL-2Rα or IL-2Rβ.

FIG. 25 illustrates results obtained by identifying binding affinity between GI101 and IL-2Rα.

FIG. 26 illustrates results obtained by identifying binding affinity between GI101 and IL-2Rβ.

FIG. 27 illustrates results obtained by identifying binding affinity between IL-2Rα and GI102-M45.

FIG. 28 illustrates results obtained by identifying binding affinity between IL-2Rα and GI102-M61.

FIG. 29 illustrates results obtained by identifying binding affinity between IL-2Rα and GI102-M72.

FIG. 30 illustrates results obtained by identifying binding affinity between IL-2Rβ and GI102-M45.

FIG. 31 illustrates results obtained by identifying binding affinity between IL-2Rβ and GI102-M61.

FIG. 32 illustrates results obtained by identifying binding affinity between IL-2Rβ and GI102-M72.

FIGS. 33 and 34 illustrate results obtained by measuring amounts of IFN-γ secreted from cells when the cells are subjected to treatment with GI101, GI101C1, GI101C2, or IL-2 at respective concentrations and incubation is performed.

FIGS. 35 and 36 illustrate results obtained by identifying effects of GI101, GI101C1, GI101C2, and IL-2 (Proleukin) on proliferation of CD8+ T cells.

FIG. 37 illustrates results obtained by identifying effects of GI101 and GI102 on proliferation of CD8+ T cells and CD4+ T cells. Here, FIG. 37A illustrates proportions of CD8+ T cells and CD4+ T cells, FIG. 37B illustrates proliferation capacity of CD8+ T cells, and FIG. 37C illustrates a proportion of CD4+/FoxP3+ Treg cells.

FIGS. 38 and 39 illustrate results obtained by identifying effects of GI101 and GI101w on proliferation of CD8+ T cells and NK cells.

FIGS. 40 and 41 illustrate results obtained by identifying an effect of GI101 on effector T cells.

FIG. 42 illustrates results obtained by identifying effects of mGI101 and mGI102-M61 on mouse immune cells.

FIGS. 43 and 44 illustrate results obtained by identifying an effect of GI101 on cancer cells overexpressing PD-L1.

FIGS. 45 and 46 illustrate results obtained by identifying a tumor inhibitory effect of GI101 in mouse-derived colorectal cancer cell-transplanted mice.

FIG. 47 illustrates results obtained by identifying a tumor inhibitory effect of mGI101 in mouse-derived melanoma-transplanted mice.

FIG. 48 illustrates tumor inhibition of mGI101 in mouse-derived melanoma-transplanted mice.

FIG. 49 illustrates results obtained by identifying a tumor inhibitory effect of mGI101, depending on its dose, in mouse-derived colorectal cancer cell-transplanted mice.

FIG. 50 illustrates results obtained by analyzing survival rate of mouse-derived colorectal cancer cell-transplanted mice having received mGI101.

FIG. 51 illustrates results obtained by identifying a tumor inhibitory effect of GI101 in mouse-derived colorectal cancer cell-transplanted mice.

FIG. 52 illustrates results obtained by subjecting mouse-derived colorectal cancer cell-transplanted mice to treatment with hIgG4, anti-PD-1 antibody, or GI101, and then analyzing, with FACS, CD8+ T cells, IFN-γ T cells, CD4+ T cells, and Treg cells in cancer tissues.

FIG. 53 graphically illustrates results obtained by subjecting mouse-derived colorectal cancer cell-transplanted mice to treatment with hIgG4, anti-PD-1 antibody, or GI101, and then analyzing, with FACS, CD8+ T cells, IFN-γ T cells, CD4+ T cells, and Treg cells in cancer tissues.

FIG. 54 illustrates results obtained by subjecting mouse-derived colorectal cancer cell-transplanted mice to treatment with hIgG4, anti-PD-1 antibody, or GI101, and then analyzing, with FACS, macrophages in cancer tissues.

FIG. 55 graphically illustrates results obtained by subjecting mouse-derived colorectal cancer cell-transplanted mice to treatment with hIgG4, anti-PD-1 antibody, or GI101, and then analyzing, with FACS, macrophages in cancer tissues.

FIG. 56 illustrates results obtained by subjecting mouse-derived colorectal cancer cell-transplanted mice to treatment with hIgG4, anti-PD-1 antibody, or GI101, and then analyzing, with FACS, dendritic cells in cancer tissues.

FIG. 57 graphically illustrates results obtained by subjecting mouse-derived colorectal cancer cell-transplanted mice to treatment with hIgG4, anti-PD-1 antibody, or GI101, and then analyzing, with FACS, dendritic cells in cancer tissues.

FIG. 58 illustrates results obtained by identifying a tumor inhibitory effect of GI101 in mouse-derived lung cancer cell-transplanted mice.

FIG. 59 graphically illustrates results obtained by subjecting mouse-derived lung cancer cell-transplanted mice to treatment with hIgG4, anti-PD-1 antibody, or GI101, and then analyzing, with FACS, CD8+ T cells, IFN-γ T cells, CD4+ T cells, and Treg cells in cancer tissues.

FIG. 60 graphically illustrates results obtained by subjecting mouse-derived lung cancer cell-transplanted mice to treatment with hIgG4, anti-PD-1 antibody, or GI101, and then analyzing, with FACS, macrophages in cancer tissues.

FIG. 61 graphically illustrates results obtained by subjecting mouse-derived lung cancer cell-transplanted mice to treatment with hIgG4, anti-PD-1 antibody, or GI101, and then analyzing, with FACS, dendritic cells in cancer tissues.

FIG. 62 illustrates results obtained by identifying a tumor inhibitory effect of mGI102-M61 in mouse-derived colorectal cancer cell-transplanted mice.

FIG. 63 illustrates results obtained by analyzing survival rate of mouse-derived colorectal cancer cell-transplanted mice having received mGI102-M61.

FIG. 64 illustrates results obtained by identifying a tumor inhibitory effect of mGI101 in mouse-derived colorectal cancer cell-transplanted mice.

FIG. 65 illustrates tumor inhibition of mGI101 in mouse-derived colorectal cancer cell-transplanted mice.

FIG. 66 illustrates results obtained by making 15-day clinical observations for monkeys having received PBS or GI101.

FIGS. 67 and 68 illustrate results obtained by measuring body weights on days −1, 1, 8, and 15 for monkeys having received PBS or GI101.

FIG. 69 illustrates 15-day food consumption for monkeys having received PBS or GI101.

FIGS. 70 to 72 illustrate results obtained by analyzing the blood on days −1, 1, 8, and 15 for monkeys having received PBS or GI101.

FIGS. 73 to 79 illustrate results obtained by performing clinical and chemical analysis on days −1, 1, 8, and 15 days for monkeys having received PBS or GI101.

FIGS. 80 and 81 illustrate results obtained by analyzing cytokines on days −1, 1, 8, and 15 for monkeys having received PBS or GI101.

FIGS. 82 to 87 illustrate results obtained by analyzing immune cells on days −1, 1, 8, and 15 for monkeys having received PBS or GI101.

FIG. 88 illustrates results obtained by sacrificing, on day 16, monkeys having received PBS or GI101 to obtain spleen tissues, and pathologically analyzing the spleen tissues.

FIGS. 89A and 89B illustrate fusion proteins, in each of which CD80 protein and IL-2 protein are bound to a carrier protein. Specifically, FIG. 89A illustrates the fusion protein in which the CD80 protein and the IL-2 protein are bound to N-terminus and C-terminus of the carrier protein, respectively. In addition, FIG. 89B illustrates the fusion protein in which the CD80 protein and the IL-2 protein are bound to C-terminus and N-terminus of the carrier protein, respectively.

BEST MODE FOR CARRYING OUT THE INVENTION

Fusion Protein Comprising IL-2 Protein and CD80 Protein

In an aspect of the present invention, there is provided a fusion protein comprising an IL-2 protein and a CD80 protein.

As used herein, the term "IL-2" or "interleukin-2", unless otherwise stated, refers to any wild-type IL-2 obtained from any vertebrate source, including mammals, for example, primates (such as humans) and rodents (such as mice and rats). IL-2 may be obtained from animal cells, and also includes one obtained from recombinant cells capable of producing IL-2. In addition, IL-2 may be wild-type IL-2 or a variant thereof.

In the present specification, IL-2 or a variant thereof may be collectively expressed by the term "IL-2 protein" or "IL-2 polypeptide." IL-2, an IL-2 protein, an IL-2 polypeptide, and an IL-2 variant specifically bind to, for example, an IL-2 receptor. This specific binding may be identified by methods known to those skilled in the art.

An embodiment of IL-2 may have the amino acid sequence of SEQ ID NO: 35 or SEQ ID NO: 36. Here, IL-2 may also be in a mature form. Specifically, the mature IL-2 may not contain a signal sequence, and may have the amino acid sequence of SEQ ID NO: 10. Here, IL-2 may be used under a concept encompassing a fragment of wild-type IL-2 in which a portion of N-terminus or C-terminus of the wild-type IL-2 is truncated.

In addition, the fragment of IL-2 may be in a form in which 1, 2, 3, 4, 5, 6, 7, 8, 9, 10, 11, 12, 13, 14, 15, 16, 17, 18, 19, 20, 21, 22, 23, 24, or 25 contiguous amino acids are truncated from N-terminus of a protein having the amino acid sequence of SEQ ID NO: 35 or SEQ ID NO: 36. In addition, the fragment of IL-2 may be in a form in which 1, 2, 3, 4, 5, 6, 7, 8, 9, 10, 11, 12, 13, 14, 15, 16, 17, 18, 19, 20, 21, 22, 23, 24, or 25 contiguous amino acids are truncated from C-terminus of a protein having the amino acid sequence of SEQ ID NO: 35 or SEQ ID NO: 36.

As used herein, the term “IL-2 variant” refers to a form in which a portion of amino acids in the full-length IL-2 or the above-described fragment of IL-2 is substituted. That is, an IL-2 variant may have an amino acid sequence different from wild-type IL-2 or a fragment thereof. However, an IL-2 variant may have activity equivalent or similar to the wild-type IL-2. Here, “IL-2 activity” may, for example, refer to specific binding to an IL-2 receptor, which specific binding can be measured by methods known to those skilled in the art.

Specifically, an IL-2 variant may be obtained by substitution of a portion of amino acids in the wild-type IL-2. An embodiment of the IL-2 variant obtained by amino acid substitution may be obtained by substitution of at least one of the $38^{th}$, $42^{nd}$, $45^{th}$, $61^{st}$, and $72^{nd}$ amino acids in the amino acid sequence of SEQ ID NO: 10.

Specifically, the IL-2 variant may be obtained by substitution of at least one of the $38^{th}$, $42^{nd}$, $45^{th}$, $61^{st}$, or $72^{nd}$ amino acid in the amino acid sequence of SEQ ID NO: 10 with another amino acid. In addition, when IL-2 is in a form in which a portion of N-terminus in the amino acid sequence of SEQ ID NO: 35 is truncated, the amino acid at a position complementarily corresponding to that in the amino acid sequence of SEQ ID NO: 10 may be substituted with another amino acid. For example, when IL-2 has the amino acid sequence of SEQ ID NO: 35, its IL-2 variant may be obtained by substitution of at least one of $58^{th}$, $62^{nd}$, $65^{th}$, $81^{st}$, or $92^{nd}$ amino acid in the amino acid sequence of SEQ ID NO: 35 with another amino acid. These amino acid residues correspond to the $38^{th}$, $42^{nd}$, $45^{th}$, $61^{st}$, and $72^{nd}$ amino acid residues in the amino acid sequence of SEQ ID NO: 10, respectively. According to an embodiment, one, two, three, four, five, six, seven, eight, nine, or ten amino acids may be substituted as long as such IL-2 variant maintains IL-2 activity. According to another embodiment, one to five amino acids may be substituted.

In an embodiment, an IL-2 variant may be in a form in which two amino acids are substituted. Specifically, the IL-2 variant may be obtained by substitution of the $38^{th}$ and $42^{nd}$ amino acids in the amino acid sequence of SEQ ID NO: 10. In addition, in an embodiment, the IL-2 variant may be obtained by substitution of the $38^{th}$ and $45^{th}$ amino acids in the amino acid sequence of SEQ ID NO: 10. In addition, in an embodiment, the IL-2 variant may be obtained by substitution of the $38^{th}$ and $61^{st}$ amino acids in the amino acid sequence of SEQ ID NO: 10. In addition, in an embodiment, the IL-2 variant may be obtained by substitution of the $38^{th}$ and $72^{nd}$ amino acids in the amino acid sequence of SEQ ID NO: 10. In addition, in an embodiment, the IL-2 variant may be obtained by substitution of the $42^{nd}$ and $45^{th}$ amino acids in the amino acid sequence of SEQ ID NO: 10. In addition, in an embodiment, the IL-2 variant may be obtained by substitution of the $42^{nd}$ and $61^{st}$ amino acids in the amino acid sequence of SEQ ID NO: 10. In addition, in an embodiment, the IL-2 variant may be obtained by substitution of the $42^{nd}$ and $72^{nd}$ amino acids in the amino acid sequence of SEQ ID NO: 10. In addition, in an embodiment, the IL-2 variant may be obtained by substitution of the $45^{th}$ and $61^{st}$ amino acids in the amino acid sequence of SEQ ID NO: 10. In addition, in an embodiment, the IL-2 variant may be obtained by substitution of the $45^{th}$ and $72^{nd}$ amino acids in the amino acid sequence of SEQ ID NO: 10. In addition, in an embodiment, the IL-2 variant may be obtained by substitution of the $61^{st}$ and $72^{nd}$ amino acids in the amino acid sequence of SEQ ID NO: 10.

Furthermore, an IL-2 variant may be in a form in which three amino acids are substituted. Specifically, the IL-2 variant may be obtained by substitution of the $38^{th}$, $42^{nd}$, and $45^{th}$ amino acids in the amino acid sequence of SEQ ID NO: 10. In addition, in an embodiment, the IL-2 variant may be obtained by substitution of the $38^{th}$, $42^{nd}$, and $61^{st}$ amino acids in the amino acid sequence of SEQ ID NO: 10. In addition, in an embodiment, the IL-2 variant may be obtained by substitution of the $38^{th}$, $42^{nd}$, and $72^{nd}$ amino acids in the amino acid sequence of SEQ ID NO: 10. In addition, in an embodiment, the IL-2 variant may be obtained by substitution of the $38^{th}$, $45^{th}$, and $61^{st}$ amino acids in the amino acid sequence of SEQ ID NO: 10. In addition, in an embodiment, the IL-2 variant may be obtained by substitution of the $38^{th}$, $45^{th}$, and $72^{nd}$ amino acids in the amino acid sequence of SEQ ID NO: 10. In addition, in an embodiment, the IL-2 variant may be obtained by substitution of the $38^{th}$, $61^{st}$, and $72^{nd}$ amino acids in the amino acid sequence of SEQ ID NO: 10. In addition, in an embodiment, the IL-2 variant may be obtained by substitution of the $42^{nd}$, $45^{th}$, and $61^{st}$ amino acids in the amino acid sequence of SEQ ID NO: 10. In addition, in an embodiment, the IL-2 variant may be obtained by substitution of the $42^{nd}$, $45^{th}$, and $72^{nd}$ amino acids in the amino acid sequence of SEQ ID NO: 10. In addition, in an embodiment, the IL-2 variant may be obtained by substitution of the $45^{th}$, $61^{st}$, and $72^{nd}$ amino acids in the amino acid sequence of SEQ ID NO: 10.

In addition, an IL-2 variant may be in a form in which four amino acids are substituted. Specifically, the IL-2 variant may be obtained by substitution of the $38^{th}$, $42^{nd}$, $45^{th}$, and $61^{st}$ amino acids in the amino acid sequence of SEQ ID NO: 10. In addition, in an embodiment, the IL-2 variant may be obtained by substitution of the $38^{th}$, $42^{nd}$, $45^{th}$, and $72^{nd}$ amino acids in the amino acid sequence of SEQ ID NO: 10. In addition, in an embodiment, the IL-2 variant may be obtained by substitution of the $38^{th}$, $45^{th}$, $61^{st}$, and $72^{nd}$ amino acids in the amino acid sequence of SEQ ID NO: 10. In addition, in an embodiment, the IL-2 variant may be obtained by substitution of the $38^{th}$, $42^{nd}$, $61^{st}$, and $72^{nd}$ amino acids in the amino acid sequence of SEQ ID NO: 10. In addition, in an embodiment, the IL-2 variant may be obtained by substitution of $42^{nd}$, $45^{th}$, $61^{st}$, and $72^{nd}$ amino acids in the amino acid sequence of SEQ ID NO: 10.

Furthermore, an IL-2 variant may be in a form in which five amino acids are substituted. Specifically, the IL-2 variant may be obtained by substitution of each of the $38^{th}$, $42^{nd}$, $45^{th}$, $61^{st}$, and $72^{nd}$ amino acids in the amino acid sequence of SEQ ID NO: 10 with another amino acid.

Here, the “another amino acid” introduced by the substitution may be any one selected from the group consisting of alanine, arginine, asparagine, aspartic acid, cysteine, glutamic acid, glutamine, histidine, isoleucine, leucine, lysine, methionine, phenylalanine, proline, serine, threonine, tryptophan, tyrosine, and valine. However, regarding amino acid substitution for the IL-2 variant, in the amino acid sequence of SEQ ID NO: 10, the $38^{th}$ amino acid cannot be substituted with arginine, the $42^{nd}$ amino acid cannot be substituted with phenylalanine, the $45^{th}$ amino acid cannot be substituted with tyrosine, the $61^{st}$ amino acid cannot be substituted with glutamic acid, and the $72^{nd}$ amino acid cannot be substituted with leucine.

Regarding amino acid substitution for an IL-2 variant, in the amino acid sequence of SEQ ID NO: 10, the $38^{th}$ amino acid, arginine, may be substituted with an amino acid other than arginine. Preferably, regarding amino acid substitution for an IL-2 variant, in the amino acid sequence of SEQ ID NO: 10, the $38^{th}$ amino acid, arginine, may be substituted with alanine (R38A).

Regarding amino acid substitution for an IL-2 variant, in the amino acid sequence of SEQ ID NO: 10, the 42nd amino acid, phenylalanine, may be substituted with an amino acid other than phenylalanine. Preferably, regarding amino acid substitution for an IL-2 variant, in the amino acid sequence of SEQ ID NO: 10, the 42nd amino acid, phenylalanine, may be substituted with alanine (F42A).

Regarding amino acid substitution for an IL-2 variant, in the amino acid sequence of SEQ ID NO: 10, the 45th amino acid, tyrosine, may be substituted with an amino acid other than tyrosine. Preferably, regarding amino acid substitution for an IL-2 variant, in the amino acid sequence of SEQ ID NO: 10, the 45th amino acid, tyrosine, may be substituted with alanine (Y45A).

Regarding amino acid substitution for an IL-2 variant, in the amino acid sequence of SEQ ID NO: 10, the 61st amino acid, glutamic acid, may be substituted with an amino acid other than glutamic acid. Preferably, regarding amino acid substitution for an IL-2 variant, in the amino acid sequence of SEQ ID NO: 10, the 61st amino acid, glutamic acid, may be substituted with arginine (E61R).

Regarding amino acid substitution for an IL-2 variant, in the amino acid sequence of SEQ ID NO: 10, the 72nd amino acid, leucine, may be substituted with an amino acid other than leucine. Preferably, regarding amino acid substitution for an IL-2 variant, in the amino acid sequence of SEQ ID NO: 10, the 72nd amino acid, leucine, may be substituted with glycine (L72G).

Specifically, an IL-2 variant may be obtained by at least one substitution selected from the group consisting of R38A, F42A, Y45A, E61R, and L72G, in the amino acid sequence of SEQ ID NO: 10.

Specifically, an IL-2 variant may be obtained by amino acid substitutions at two, three, four, or five positions among the positions selected from the group consisting of R38A, F42A, Y45A, E61R, and L72G.

In addition, an IL-2 variant may be in a form in which two amino acids are substituted. Specifically, an IL-2 variant may be obtained by the substitutions, R38A and F42A. In addition, in an embodiment, an IL-2 variant may be obtained by the substitutions, R38A and Y45A. In addition, in an embodiment, an IL-2 variant may be obtained by the substitutions, R38A and E61R. In addition, in an embodiment, an IL-2 variant may be obtained by the substitutions, R38A and L72G. In addition, in an embodiment, an IL-2 variant may be obtained by the substitutions, F42A and Y45A. In addition, in an embodiment, an IL-2 variant may be obtained by the substitutions, F42A and E61R. In addition, in an embodiment, an IL-2 variant may be obtained by the substitutions, F42A and L72G. In addition, in an embodiment, an IL-2 variant may be obtained by the substitutions, E61R and L72G.

Furthermore, an IL-2 variant may be in a form in which three amino acids are substituted. Specifically, an IL-2 variant may be obtained by the substitutions, R38A, F42A, and Y45A. In addition, in an embodiment, an IL-2 variant may be obtained by the substitutions, R38A, F42A, and E61R. In addition, in an embodiment, an IL-2 variant may be obtained by the substitutions, R38A, F42A, and L72G. In addition, in an embodiment, an IL-2 variant may be obtained by the substitutions, R38A, Y45A, and E61R. In addition, in an embodiment, an IL-2 variant may be obtained by the substitutions, R38A, Y45A, and L72G. In addition, in an embodiment, an IL-2 variant may be obtained by the substitutions, F42A, Y45A, and E61R. In addition, in an embodiment, an IL-2 variant may be obtained by the substitutions, F42A, Y45A, and L72G. In addition, in an embodiment, an IL-2 variant may be obtained by the substitutions, F42A, E61R, and L72G. In addition, in an embodiment, an IL-2 variant may be obtained by the substitutions, Y45A, E61R, and L72G.

In addition, an IL-2 variant may be in a form in which four amino acids are substituted. Specifically, an IL-2 variant may be obtained by the substitutions, R38A, F42A, Y45A, and E61R. In addition, in an embodiment, an IL-2 variant may be obtained by the substitutions, R38A, F42A, Y45A, and L72G. In addition, in an embodiment, an IL-2 variant may be obtained by the substitutions, R38A, F42A, E61R, and L72G. In addition, in an embodiment, an IL-2 variant may be obtained by the substitutions, R38A, Y45A, E61R, and L72G. In addition, in an embodiment, an IL-2 variant may be obtained by the substitutions, F42A, Y45A, E61R, and L72G.

Furthermore, an IL-2 variant may be obtained by the substitutions, R38A, F42A, Y45A, E61R, and L72G.

Preferably, an embodiment of the IL-2 variant may contain which are any one selected from the following substitution combinations (a) to (d) in the amino acid sequence of SEQ ID NO: 10:

(a) R38A/F42A (b) R38A/F42A/Y45A (c) R38A/F42A/E61R (d) R38A/F42A/L72G

Here, when IL-2 has the amino acid sequence of SEQ ID NO: 35, an amino acid substitution may be present at a position complementarily corresponding to that in the amino acid sequence of SEQ ID NO: 10. In addition, even when IL-2 is a fragment of the amino acid sequence of SEQ ID NO: 35, an amino acid substitution may be present at a position complementarily corresponding to that in the amino acid sequence of SEQ ID NO: 10.

Specifically, an IL-2 variant may have the amino acid sequence of SEQ ID NO: 6, 22, 23, or 24.

In addition, an IL-2 variant may be characterized by having low in vivo toxicity. Here, the low in vivo toxicity may be a side effect caused by binding of IL-2 to the IL-2 receptor alpha chain (IL-2Rα). Various IL-2 variants have been developed to ameliorate the side effect caused by binding of IL-2 to IL-2Rα, and such IL-2 variants may be those disclosed in U.S. Pat. No. 5,229,109 and Korean Patent No. 1667096. In particular, IL-2 variants described in the present application have low binding ability for the IL-2 receptor alpha chain (IL-2Rα) and thus have lower in vivo toxicity than the wild-type IL-2.

As used herein, the term "CD80", also called "B7-1", is a membrane protein present in dendritic cells, activated B cells, and monocytes. CD80 provides co-stimulatory signals essential for activation and survival of T cells. CD80 is known as a ligand for the two different proteins, CD28 and CTLA-4, present on the surface of T cells. CD80 is composed of 288 amino acids, and may specifically have the amino acid sequence of SEQ ID NO: 11. In addition, as used herein, the term "CD80 protein" refers to the full-length CD80 or a CD80 fragment.

As used herein, the term "CD80 fragment" refers to a cleaved form of CD80. In addition, the CD80 fragment may be an extracellular domain of CD80. An embodiment of the CD80 fragment may be obtained by elimination of the 1st to 34th amino acids from N-terminus which are a signal sequence of CD80. Specifically, an embodiment of the CD80 fragment may be a protein composed of the 35th to 288th amino acids in SEQ ID NO: 11. In addition, an embodiment of the CD80 fragment may be a protein composed of the 35th to 242nd amino acids in SEQ ID NO: 11. In addition, an embodiment of the CD80 fragment may be a protein composed of the 35th to 232nd amino acids in SEQ ID NO: 11. In addition, an embodiment of the CD80 fragment may be a protein composed of the $35^{th}$ to $139^{th}$ amino acids in SEQ ID NO: 11. In addition, an embodiment of the CD80 fragment may be a protein composed of the $142^{nd}$ to $242^{nd}$ amino acids in SEQ ID NO: 11. In an embodiment, a CD80 fragment may have the amino acid sequence of SEQ ID NO: 2.

In addition, the IL-2 protein and the CD80 protein may be attached to each other via a linker or a carrier. Specifically, the IL-2 or a variant thereof and the CD80 (B7-1) or a fragment thereof may be attached to each other via a linker or a carrier. In the present description, the linker and the carrier may be used interchangeably.

The linker links two proteins. An embodiment of the linker may include 1 to 50 amino acids, albumin or a fragment thereof, an Fc domain of an immunoglobulin, or the like. Here, the Fc domain of immunoglobulin refers to a protein that contains heavy chain constant region 2 (CH2) and heavy chain constant region 3 (CH3) of an immunoglobulin, and does not contain heavy and light chain variable regions and light chain constant region 1 (CH1) of an immunoglobulin. The immunoglobulin may be IgG, IgA, IgE, IgD, or IgM, and may preferably be IgG4. Here, Fc domain of wild-type immunoglobulin G4 may have the amino acid sequence of SEQ ID NO: 4.

In addition, the Fc domain of an immunoglobulin may be an Fc domain variant as well as wild-type Fc domain. In addition, as used herein, the term "Fc domain variant" may refer to a form which is different from the wild-type Fc domain in terms of glycosylation pattern, has a high glycosylation as compared with the wild-type Fc domain, or has a low glycosylation as compared with the wild-type Fc domain, or a deglycosylated form. In addition, an aglycosylated Fc domain is included therein. The Fc domain or a variant thereof may be adapted to have an adjusted number of sialic acids, fucosylations, or glycosylations, through culture conditions or genetic manipulation of a host.

In addition, glycosylation of the Fc domain of an immunoglobulin may be modified by conventional methods such as chemical methods, enzymatic methods, and genetic engineering methods using microorganisms. In addition, the Fc domain variant may be in a mixed form of respective Fc regions of immunoglobulins, IgG, IgA, IgE, IgD, and IgM. In addition, the Fc domain variant may be in a form in which some amino acids of the Fc domain are substituted with other amino acids. An embodiment of the Fc domain variant may have the amino acid sequence of SEQ ID NO: 12.

The fusion protein may have a structure in which, using an Fc domain as a linker (or carrier), a CD80 protein and an IL-2 protein, or an IL-2 protein and a CD80 protein are linked to N-terminus and C-terminus of the linker or carrier, respectively (FIGS. 89A and 89B). Linkage between N-terminus or C-terminus of the Fc domain and CD-80 or IL-2 may optionally be achieved by a linker peptide.

Specifically, a fusion protein may consist of the following structural formula (I) or (II):

$$N'\text{-}X\text{-}[\text{linker }(1)]_n\text{-Fc domain-}[\text{linker }(2)]_m\text{-}Y\text{—}C' \quad (I)$$

$$N'\text{-}Y\text{-}[\text{linker }(1)]_n\text{-Fc domain-}[\text{linker }(2)]_m\text{-}X\text{—}C' \quad (II)$$

Here, in the structural formulas (I) and (II),
N' is the N-terminus of the fusion protein,
C' is the C-terminus of the fusion protein,
X is a CD80 protein,
Y is an IL-2 protein,
the linkers (1) and (2) are peptide linkers, and
n and m are each independently 0 or 1.

Preferably, the fusion protein may consist of the structural formula (I). The IL-2 protein is as described above. In addition, the CD80 protein is as described above. According to an embodiment, the IL-2 protein may be an IL-2 variant with one to five amino acid substitutions as compared with the wild-type IL-2. The CD80 protein may be a fragment obtained by truncation of up to about 34 contiguous amino acid residues from the N-terminus or C-terminus of the wild-type CD80. Alternatively, the CD protein may be an extracellular immunoglobulin-like domain having the activity of binding to the T cell surface receptors CTLA-4 and CD28.

Specifically, the fusion protein may have the amino acid sequence of SEQ ID NO: 9, 26, 28, or 30. According to another embodiment, the fusion protein includes a polypeptide having a sequence identity of 85%, 86%, 87%, 88%, 89%, 90%, 91%, 92%, 93%, 94%, 95%, 96%, 97%, 98%, 99%, or 100% to the amino acid sequence of SEQ ID NO: 9, 26, 28, or 30. Here, the identity is, for example, percent homology, and may be determined through homology comparison software such as BlastN software of the National Center of Biotechnology Information (NCBI).

The peptide linker (1) may be included between the CD80 protein and the Fc domain. The peptide linker (1) may consist of 5 to 80 contiguous amino acids, 20 to 60 contiguous amino acids, 25 to 50 contiguous amino acids, or 30 to 40 contiguous amino acids. In an embodiment, the peptide linker (1) may consist of 30 amino acids. In addition, the peptide linker (1) may contain at least one cysteine. Specifically, the peptide linker (1) may contain one, two, or three cysteines. In addition, the peptide linker (1) may be derived from the hinge of an immunoglobulin. In an embodiment, the peptide linker (1) may be a peptide linker consisting of the amino acid sequence of SEQ ID NO: 3.

The peptide linker (2) may consist of 1 to 50 contiguous amino acids, 3 to 30 contiguous amino acids, or 5 to 15 contiguous amino acids. In an embodiment, the peptide linker (2) may be $(G4S)_n$ (where n is an integer of 1 to 10). Here, in $(G4S)_n$, n may be 1, 2, 3, 4, 5, 6, 7, 8, 9, or 10. In an embodiment, the peptide linker (2) may be a peptide linker consisting of the amino acid sequence of SEQ ID NO: 5.

In another aspect of the present invention, there is provided a dimer obtained by binding of two fusion proteins, each of which comprises an IL-2 protein and a CD80 protein. The fusion protein comprising IL-2 or a variant thereof and CD80 or a fragment thereof is as described above.

Here, the binding between the fusion proteins constituting the dimer may be achieved by, but is not limited to, a disulfide bond formed by cysteines present in the linker. The fusion proteins constituting the dimer may be the same or different fusion proteins from each other. Preferably, the dimer may be a homodimer. An embodiment of the fusion protein constituting the dimer may be a protein having the amino acid sequence of SEQ ID NO: 9.

Polynucleotide Encoding Fusion Protein

In yet another aspect of the present invention, there is provided a polynucleotide encoding a fusion protein comprising an IL-2 protein and a CD80 protein. Specifically, the polynucleotide may contain the nucleotide sequence of SEQ ID NO: 8, 25, 27, or 29. The fusion protein comprising an IL-2 protein and a CD80 protein is as described above. In the polynucleotide, one or more nucleotides may be altered by substitution, deletion, insertion, or a combination thereof.

When a nucleotide sequence is prepared by chemical synthesis, synthetic methods well known in the art may be used, such as those described in Engels and Uhlmann (Angew Chem IntEd Eng., 37: 73-127, 1988). Such methods may include triester, phosphite, phosphoramidite and H-phosphate methods, PCR and other autoprimer methods, oligonucleotide syntheses on solid supports, and the like.

According to an embodiment, the polypeptide may contain a nucleic acid sequence having an identity, to SEQ ID NO: 8, 25, 27, or 29, of at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100%.

The polynucleotide may further contain a nucleic acid encoding a signal sequence or a leader sequence. As used herein, the term "signal sequence" refers to a signal peptide that directs secretion of a target protein. The signal peptide is translated and then cleaved in a host cell. Specifically, the signal sequence is an amino acid sequence that initiates migration of a protein across the endoplasmic reticulum (ER) membrane. In an embodiment, the signal sequence may have the amino acid sequence of SEQ ID NO: 1.

Signal sequences are well known in the art for their characteristics. Such signal sequences typically contain 16 to 30 amino acid residues, and may contain more or fewer amino acid residues than such amino acid residues. A typical signal peptide is composed of three regions, that is, a basic N-terminal region, a central hydrophobic region, and a more polar C-terminal region. The central hydrophobic region contains 4 to 12 hydrophobic residues that cause the signal sequence to be immobilized during migration of an immature polypeptide through the membrane lipid bilayer.

After initiation, signal sequences are cleaved in the lumen of ER by cellular enzymes, commonly known as signal peptidases. Here, the signal sequence may be a secretory signal sequence of tPa (tissue plasminogen activator), HSV gDs (signal sequence of Herpes simplex virus glycoprotein D), or a growth hormone. Preferably, a secretory signal sequence used in higher eukaryotic cells including mammals and the like may be used. In addition, a signal sequence included in the wild-type IL-2 and/or CD-80 may be used, or a signal sequence that has been substituted with a codon having high expression frequency in a host cell may be used.

Vector with Polynucleotide Encoding Fusion Protein

In still yet another aspect of the present invention, there is provided a vector comprising the polynucleotide.

The vector may be introduced into a host cell to be recombined with and inserted into the genome of the host cell. Or, the vector is understood as nucleic acid means containing a polynucleotide sequence which is autonomously replicable as an episome. The vectors include linear nucleic acids, plasmids, phagemids, cosmids, RNA vectors, viral vectors, and analogs thereof. Examples of the viral vector include, but are not limited to, retroviruses, adenoviruses, and adeno-associated viruses.

Specifically, the vector may include plasmid DNA, phage DNA, and the like; and commercially developed plasmids (pUC18, pBAD, pIDTSAMRT-AMP, and the like), *E. coli*-derived plasmids (pYG601BR322, pBR325, pUC118, pUC119, and the like), Bacillus subtilis-derived plasmids (pUB110, pTP5, and the like), yeast-derived plasmids (YEp13, YEp24, YCp50, and the like), phage DNA (Charon4A, Charon21A, EMBL3, EMBL4, λ gt10, λ gt11, λ ZAP, and the like), animal viral vectors (retroviruses, adenoviruses, vaccinia viruses, and the like), insect viral vectors (baculoviruses and the like). Since the vector exhibits different expression levels and modification of a protein depending on a host cell, it is preferred to select and use a host cell which is most suitable for the purpose.

As used herein, the term "gene expression" or "expression" of a target protein is understood to mean transcription of DNA sequences, translation of mRNA transcripts, and secretion of fusion protein products or fragments thereof. A useful expression vector may be RcCMV (Invitrogen, Carlsbad) or a variant thereof. Expression vectors may further contain human cytomegalovirus (CMV) promoter for promoting continuous transcription of a target gene in mammalian cells, and a bovine growth hormone polyadenylation signal sequence for increasing the stability level of RNA after transcription.

Transformed Cell Expressing Fusion Protein

In still yet another aspect of the present invention, there is provided a transformed cell into which the vector has been introduced.

Host cells for the transformed cell may include, but are not limited to, prokaryotic cells, eukaryotic cells, and cells of mammalian, vegetable, insect, fungal, or bacterial origin. As an example of the prokaryotic cells, *E. coli* may be used. In addition, as an example of the eukaryotic cells, yeast may be used. In addition, for the mammalian cells, CHO cells, F2N cells, CSO cells, BHK cells, Bowes melanoma cells, HeLa cells, 911 cells, AT1080 cells, A549 cells, HEK 293 cells, HEK293T cells, or the like may be used. However, the mammalian cells are not limited thereto, and any cells which are known to those skilled in the art to be usable as mammalian host cells may be used.

In addition, for the introduction of an expression vector into the host cell, $CaCl_2$ precipitation, Hanahan method whose efficiency has been increased efficiency by using a reducing agent such as dimethyl sulfoxide (DMSO) in $CaCl_2$ precipitation, electroporation, calcium phosphate precipitation, protoplast fusion, agitation using silicon carbide fiber, Agrobacteria-mediated transformation, transformation using PEG, dextran sulfate-, Lipofectamine-, or dry/inhibition-mediated transformation, or the like may be used.

As described above, for optimization of properties of a fusion protein as a therapeutic agent or for any other purpose, glycosylation pattern of the fusion protein (for example, sialic acids, fucosylations, glycosylations) may be adjusted by manipulating, through methods known to those skilled in the art, glycosylation-related genes possessed by host cells.

Method for Producing a Fusion Protein

In still yet another aspect of the present invention, there is provided a method for producing a fusion protein comprising an IL-2 protein and a CD80 protein, the method comprising culturing the transformed cells. Specifically, the production method may comprise i) culturing the transformed cells to obtain a culture; and ii) collecting the fusion protein from the culture.

Culturing the transformed cells may be carried out using methods well known in the art. Specifically, the culture may be carried out in a batch process, or carried out continuously in a fed batch or repeated fed batch process.

Use of Fusion Protein or Dimer Thereof

In still yet another aspect of the present invention, there is provided a pharmaceutical composition for treating or preventing cancer or an infectious disease, and/or for increasing efficacy in treating cancer or an infectious disease, the composition comprising, as an active ingredient, a fusion protein comprising an IL-2 protein and a CD80 protein or a fusion protein dimer where the two fusion proteins are attached.

The fusion protein comprising an IL-2 protein and a CD80 protein, or the fusion protein dimer where the two fusion proteins are attached is as described above.

The cancer may be selected from the group consisting of gastric cancer, liver cancer, lung cancer, colorectal cancer, breast cancer, prostate cancer, ovarian cancer, pancreatic cancer, cervical cancer, thyroid cancer, laryngeal cancer, acute myeloid leukemia, brain tumor, neuroblastoma, retinoblastoma, head and neck cancer, salivary gland cancer, and lymphoma. In addition, the infectious disease may be any one selected from the group consisting of hepatitis B, hepatitis C, human papilloma virus (HPV) infection, cytomegalovirus infection, viral respiratory disease, and influenza.

A preferred dose of the pharmaceutical composition varies depending on the patient's condition and body weight, severity of disease, form of drug, route and duration of administration and may be appropriately selected by those skilled in the art. In the pharmaceutical composition for treating or preventing cancer or an infectious disease of the present invention, the active ingredient may be contained in any amount (effective amount) depending on application, dosage form, blending purpose, and the like, as long as the active ingredient can exhibit anticancer activity or a therapeutic effect on an infectious disease. A conventional effective amount thereof will be determined within a range of 0.001% to 20.0% by weight, based on the total weight of the composition. Here, the term "effective amount" refers to an amount of an active ingredient capable of inducing an anticancer effect or an infectious disease-treating effect. Such an effective amount can be experimentally determined within the scope of common knowledge of those skilled in the art.

As used herein, the term "treatment" may be used to mean both therapeutic and prophylactic treatment. Here, prophylaxis may be used to mean that a pathological condition or disease of an individual is alleviated or mitigated. In an embodiment, the term "treatment" includes both application or any form of administration for treating a disease in a mammal, including a human. In addition, the term includes inhibiting or slowing down a disease or disease progression; and includes meanings of restoring or repairing impaired or lost function so that a disease is partially or completely alleviated; stimulating inefficient processes; or alleviating a serious disease.

As used herein, the term "efficacy" refers to capacity that can be determined by one or parameters, for example, survival or disease-free survival over a certain period of time such as one year, five years, or ten years. In addition, the parameter may include inhibition of size of at least one tumor in an individual.

Pharmacokinetic parameters such as bioavailability and underlying parameters such as clearance rate may also affect efficacy. Thus, "enhanced efficacy" (for example, improvement in efficacy) may be due to enhanced pharmacokinetic parameters and improved efficacy, which may be measured by comparing clearance rate and tumor growth in test animals or human subjects, or by comparing parameters such as survival, recurrence, or disease-free survival.

As used herein, the term "therapeutically effective amount" or "pharmaceutically effective amount" refers to an amount of a compound or composition effective to prevent or treat the disease in question, which is sufficient to treat the disease at a reasonable benefit/risk ratio applicable to medical treatment and does not cause adverse effects. A level of the effective amount may be determined depending on factors including the patient's health condition, type and severity of disease, activity of drug, the patient's sensitivity to drug, mode of administration, time of administration, route of administration and excretion rate, duration of treatment, formulation or simultaneously used drugs, and other factors well known in the medical field. In an embodiment, the therapeutically effective amount means an amount of drug effective to treat cancer.

Here, the pharmaceutical composition may further comprise a pharmaceutically acceptable carrier. The pharmaceutically acceptable carrier may be any carrier as long as the carrier is a non-toxic substance suitable for delivery to a patient. Distilled water, alcohol, fat, wax, and inert solid may be contained as the carrier. A pharmaceutically acceptable adjuvant (buffer, dispersant) may also be contained in the pharmaceutical composition.

Specifically, by including a pharmaceutically acceptable carrier in addition to the active ingredient, the pharmaceutical composition may be prepared into a parenteral formulation depending on its route of administration using conventional methods known in the art. Here, the term "pharmaceutically acceptable" means that the carrier does not have more toxicity than the subject to be applied (prescribed) can adapt while not inhibiting activity of the active ingredient.

When the pharmaceutical composition is prepared into a parenteral formulation, it may be made into preparations in the form of injections, transdermal patches, nasal inhalants, or suppositories with suitable carriers according to methods known in the art. In a case of being made into injections, sterile water, ethanol, polyol such as glycerol or propylene glycol, or a mixture thereof may be used as a suitable carrier; and an isotonic solution, such as Ringer's solution, phosphate buffered saline (PBS) containing triethanol amine or sterile water for injection, and 5% dextrose, or the like may preferably be used. Formulation of pharmaceutical compositions is known in the art, and reference may specifically be made to Remington's Pharmaceutical Sciences (19th ed., 1995) and the like. This document is considered part of the present description.

A preferred dose of the pharmaceutical composition may range from 0.01 μg/kg to 10 g/kg, or 0.01 mg/kg to 1 g/kg, per day, depending on the patient's condition, body weight, sex, age, severity of the patient, and route of administration. The dose may be administered once a day or may be divided into several times a day. Such a dose should not be construed as limiting the scope of the present invention in any aspect.

Subjects to which the pharmaceutical composition can be applied (prescribed) are mammals and humans, with humans being particularly preferred. In addition to the active ingredient, the pharmaceutical composition of the present application may further contain any compound or natural extract, which has already been validated for safety and is known to have anticancer activity or a therapeutic effect on an infectious disease, so as to boost or reinforce anticancer activity.

In still yet another aspect of the present invention, there is provided a use of a fusion protein comprising an IL-2 protein and a CD80 protein for treating cancer or an infectious disease.

In still yet another aspect of the present invention, there is provided a use of a fusion protein comprising an IL-2 protein and a CD80 protein for enhancing a therapeutic effect on cancer or an infectious disease.

In still yet another aspect of the present invention, there is provided a use of a fusion protein comprising an IL-2 protein and a CD80 protein for manufacture of a medicament for treating cancer or an infectious disease.

In still yet another aspect of the present invention, there is provided a method for treating cancer or an infectious disease, and/or a method for enhancing a therapeutic effect on cancer or an infectious disease, comprising administering, to a subject, a fusion protein comprising an IL-2 protein and a CD80 protein or a fusion protein dimer where the two fusion proteins are attached.

The subject may be an individual suffering from cancer or an infectious disease. In addition, the subject may be a mammal, preferably a human. The fusion protein comprising an IL-2 protein and a CD80 protein, or the fusion protein dimer where the two fusion proteins are attached is as described above.

Route of administration, dose, and frequency of administration of the fusion protein or fusion protein dimer may vary depending on the patient's condition and the presence or absence of side effects, and thus the fusion protein or fusion protein dimer may be administered to a subject in various ways and amounts. The optimal administration method, dose, and frequency of administration can be selected in an appropriate range by those skilled in the art. In addition, the fusion protein or fusion protein dimer may be administered in combination with other drugs or physiologically active substances whose therapeutic effect is known with respect to a disease to be treated, or may be formulated in the form of combination preparations with other drugs.

Due to IL-2 activity, the fusion protein in an embodiment of the present invention can activate immune cells such as natural killer cells. Thus, the fusion protein can be effectively used for cancer and infectious diseases. In particular, it was identified that as compared with the wild type, an IL-2 variant with two to five amino acid substitutions, in particular, an IL-2 variant that contains amino acid substitutions at two, three, four, or five positions among the positions selected from the group consisting of R38A, F42A, Y45A, E61R, and L72G, has low binding ability for the IL-2 receptor alpha chain and thus exhibits improved characteristics with respect to pharmacological side effects of conventional IL-2. Thus, such an IL-2 variant, when used alone or in the form of a fusion protein, can decrease incidence of vascular (or capillary) leakage syndrome (VLS), a problem with IL-2 conventionally known.

Mode for the Invention

Hereinafter, the present invention will be described in more detail by way of the following examples. However, the following examples are only for illustrating the present invention, and the scope of the present invention is not limited thereto.

I. Preparation of Fusion Protein

Preparation Example 1

Preparation of hCD80-Fc-IL-2 Variant (2M): GI101

In order to produce a fusion protein comprising a human CD80 fragment, an Fc domain, and an IL-2 variant, a polynucleotide was synthesized through the Invitrogen GeneArt Gene Synthesis service of ThermoFisher Scientific. Specifically, the polynucleotide contains a nucleotide sequence (SEQ ID NO: 8) which encodes a fusion protein that contains a signal peptide (SEQ ID NO: 1), a CD80 fragment (SEQ ID NO: 2), an Ig hinge (SEQ ID NO: 3), an Fc domain (SEQ ID NO: 4), a linker (SEQ ID NO: 5), and an IL-2 variant (2M) (R38A, F42A) (SEQ ID NO: 6) having two amino acid substitutions, in this order, from the N-terminus. The polynucleotide was inserted into pcDNA3_4 vector. In addition, the vector was introduced into CHO cells (Expi-CHO™) to express the fusion protein of SEQ ID NO: 9. After the vector was introduced, culture was performed for 7 days in an environment of 37° C., 125 RPM, and 8% $CO_2$ concentration. Then, the culture was harvested and the fusion protein was purified therefrom. The purified fusion protein was designated "GI101".

Purification was carried out using chromatography containing MabS elect SuRe protein A resin. The fusion protein was bound thereto under a condition of 25 mM Tris, 25 mM NaCl, pH 7.4. Then, elution was performed with 100 mM NaCl, 100 mM acetic acid, pH 3. 20% 1 M Tris-HCl at pH 9 was placed in a collection tube, and then the fusion protein was collected. For the collected fusion protein, the buffer was exchanged through dialysis with PBS buffer for 16 hours.

Thereafter, absorbance at 280 nm wavelength was measured, over time, with size exclusion chromatography using a TSKgel G3000SWXL column (TOSOH Bioscience), to obtain a highly concentrated fusion protein. Here, the isolated and purified fusion protein was subjected to SDS-PAGE under reduced (R) or non-reduced (NR) condition, and stained with Coomassie Blue to check its purity (FIG. 6). It was identified that the fusion protein was contained at a concentration of 2.78 mg/ml when detected with NanoDrop (FIG. 7). In addition, the results obtained by analysis using size exclusion chromatography are provided in FIG. 8.

Preparation Example 2

Preparation of mCD80-Fc-IL-2 Variant (2M): mGI101

In order to produce a fusion protein comprising a mouse CD80, an Fc domain, and an IL-2 variant, a polynucleotide was synthesized through the Invitrogen GeneArt Gene Synthesis service of ThermoFisher Scientific. Specifically, the polynucleotide contains a nucleotide sequence (SEQ ID NO: 14) which encodes a fusion protein that contains a signal peptide (SEQ ID NO: 1), a mCD80 (SEQ ID NO: 13), an Ig hinge (SEQ ID NO: 3), an Fc domain (SEQ ID NO: 4), a linker (SEQ ID NO: 5), and an IL-2 variant (2M) (R38A, F42A) (SEQ ID NO: 6) with two amino acid substitutions, in this order, from the N-terminus. The polynucleotide was inserted into pcDNA3_4 vector. In addition, the vector was introduced into CHO cells (Expi-CHO™) to express the fusion protein of SEQ ID NO: 15. After the vector was introduced, culture was performed for 7 days in an environment of 37°

C., 125 RPM, and 8% $CO_2$ concentration. Then, the culture was harvested and the fusion protein was purified therefrom. The purified fusion protein was designated "mGI101".

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 9). It was found that the fusion protein was contained at a concentration of 1.95 mg/ml when detected by absorbance at 280 nm using NanoDrop.

Preparation Example 3

Preparation of hCD80-Fc: GI101C1

In order to produce a fusion protein comprising a human CD80 fragment and an Fc domain, a polynucleotide was synthesized through the Invitrogen GeneArt Gene Synthesis service of ThermoFisher Scientific. Specifically, the polynucleotide contains a nucleotide sequence (SEQ ID NO: 16) which encodes a fusion protein that contains a signal peptide (SEQ ID NO: 1), a CD80 fragment (SEQ ID NO: 2), an Ig hinge (SEQ ID NO: 3), and an Fc domain (SEQ ID NO: 4). The polynucleotide was inserted into pcDNA3_4 vector. In addition, the vector was introduced into CHO cells (Expi-CHO™) to express the fusion protein of SEQ ID NO: 17. After the vector was introduced, culture was performed for 7 days in an environment of 37° C., 125 RPM, and 8% $CO_2$ concentration. Then, the culture was harvested and the fusion protein was purified therefrom. The purified fusion protein was designated "GI101C1".

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 10). It was observed that the fusion protein was contained at a concentration of 3.61 mg/ml when detected by absorbance at 280 nm using NanoDrop.

Preparation Example 4

Preparation of Fc-IL-2 Variant (2M): GI101C2

In order to produce a fusion protein comprising an Fc domain and an IL-2 variant, a polynucleotide was synthesized through the Invitrogen GeneArt Gene Synthesis service of ThermoFisher Scientific. Specifically, the polynucleotide contains a nucleotide sequence (SEQ ID NO: 18) which encodes a fusion protein that contains a signal peptide (SEQ ID NO: 1), an Fc domain (SEQ ID NO: 4), a linker (SEQ ID NO: 5), and an IL-2 variant (2M) (R38A, F42A) (SEQ ID NO: 6) with two amino acid substitutions, in this order, from the N-terminus. The polynucleotide was inserted into pcDNA3_4 vector. In addition, the vector was introduced into CHO cells (Expi-CHO™) to express the fusion protein of SEQ ID NO: 19. After the vector was introduced, culture was performed for 7 days in an environment of 37° C., 125 RPM, and 8% $CO_2$ concentration. Then, the culture was harvested and the fusion protein was purified therefrom. The purified fusion protein was designated "GI101C2".

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 11). It was found that the fusion protein was contained at a concentration of 4.79 mg/ml when detected by absorbance at 280 nm using NanoDrop.

Preparation Example 5

Preparation of mCD80-Fc: mGI101C1

In order to produce a fusion protein comprising a mouse CD80 and an Fc domain, a polynucleotide was synthesized through the Invitrogen GeneArt Gene Synthesis service of ThermoFisher Scientific. Specifically, the polynucleotide contains a nucleotide sequence (SEQ ID NO: 20) which encodes a fusion protein that contains a signal peptide (SEQ ID NO: 1), a mCD80 (SEQ ID NO: 13), an Ig hinge (SEQ ID NO: 3), and an Fc domain (SEQ ID NO: 4), in this order, from the N-terminus. The polynucleotide was inserted into pcDNA3_4 vector. In addition, the vector was introduced into CHO cells (Expi-CHO™) to express the fusion protein of SEQ ID NO: 21. After the vector was introduced, culture was performed for 7 days in an environment of 37° C., 125 RPM, and 8% $CO_2$ concentration. Then, the culture was harvested and the fusion protein was purified therefrom. The purified fusion protein was designated "mGI101C1".

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 12). It was observed that the fusion protein was contained at a concentration of 2.49 mg/ml when detected by absorbance at 280 nm using NanoDrop.

The fusion proteins prepared in Preparation Examples 1 to 5 are summarized in Table 1 below.

TABLE 1

| Item | N-terminus | Linker | C-terminus |
|---|---|---|---|
| Preparation Example 1 (GI101) | hCD80 fragment | Fc domain | hIL-2m |
| Preparation Example 2 (mGI101) | mCD80 fragment | Fc domain | hIL-2m |
| Preparation Example 3 (GI101C1) | CD80 fragment | Fc domain | — |
| Preparation Example 4 (GI101C2) | — | Fc domain | IL-2m |
| Preparation Example 5 (mGI101C1) | mCD80 fragment | Fc domain | — |

Preparation Example 6

Preparation of CD80-Fc-IL-2: GI101w

In order to produce a fusion protein comprising a human CD80 fragment, an Fc domain, and a human IL-2, a polynucleotide was synthesized through the Invitrogen GeneArt Gene Synthesis service of ThermoFisher Scientific. Specifically, the polynucleotide contais a nucleotide sequence (SEQ ID NO: 31) which encodes a fusion protein that contains a signal peptide (SEQ ID NO: 1), a CD80 fragment (SEQ ID NO: 2), an Ig hinge (SEQ ID NO: 3), an Fc domain (SEQ ID NO: 4), a linker (SEQ ID NO: 5), and mature human IL-2 (SEQ ID NO: 10), in this order, from the N-terminus. The polynucleotide was inserted into pcDNA3_4 vector. In addition, the vector was introduced into CHO cells (Expi-CHO™) to express the fusion protein of SEQ ID NO: 32. After the vector was introduced, culture was performed for 7 days in an environment of 37° C., 125 RPM, and 8% $CO_2$ concentration. Then, the culture was harvested and the fusion protein was purified therefrom. The purified fusion protein was designated "GI101w". The purification and collection of the fusion protein were carried out in the same manner as in Preparation Example 1.

Preparation Example 7

Preparation of hCD80-Fc-IL-2 Variant (3M): GI102-M45

In order to produce a fusion protein comprising a human CD80 fragment, an Fc domain, and an IL-2 variant (3M) (R38A, F42A, Y45A) (GI102-M45) with three amino acid substitutions, a polynucleotide was synthesized through the Invitrogen GeneArt Gene Synthesis service of ThermoFisher Scientific. Specifically, the polynucleotide contains a nucleotide sequence (SEQ ID NO: 25) which encodes a fusion protein that contains a signal peptide (SEQ ID NO: 1), a CD80 fragment (SEQ ID NO: 2), an Ig hinge (SEQ ID NO: 3), an Fc domain (SEQ ID NO: 4), a linker (SEQ ID NO: 5), and an IL-2 variant (SEQ ID NO: 22), in this order, from the N-terminus. The polynucleotide was inserted into pcDNA3_4 vector. In addition, the vector was introduced into CHO cells (Expi-CHO™) to express the fusion protein of SEQ ID NO: 26. After the vector was introduced, culture was performed for 7 days in an environment of 37° C., 125 RPM, and 8% $CO_2$ concentration. Then, the culture was harvested and the fusion protein was purified therefrom. The purified fusion protein was designated "GI102-M45".

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 13).

Preparation Example 8

Preparation of hCD80-Fc-IL-2 Variant (3M): G1102-M61

In order to produce a fusion protein comprising a human CD80 fragment, an Fc domain, and an IL-2 variant (3M) (R38A, F42A, E61R) (GI102-M61) with three amino acid substitutions, a polynucleotide was synthesized through the Invitrogen GeneArt Gene Synthesis service of ThermoFisher Scientific. Specifically, the polynucleotide contains a nucleotide sequence (SEQ ID NO: 27) which encodes a fusion protein that contains a signal peptide (SEQ ID NO: 1), a CD80 fragment (SEQ ID NO: 2), an Ig hinge (SEQ ID NO: 3), an Fc domain (SEQ ID NO: 4), a linker (SEQ ID NO: 5), and an IL-2 variant (SEQ ID NO: 23), in this order, from the N-terminus. The polynucleotide was inserted into pcDNA3_4 vector. In addition, the vector was introduced into CHO cells (Expi-CHO™) to express the fusion protein of SEQ ID NO: 28. After the vector was introduced, culture was performed for 7 days in an environment of 37° C., 125 RPM, and 8% $CO_2$ concentration. Then, the culture was harvested and the fusion protein was purified therefrom. The purified fusion protein was designated "GI102-M61".

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 14).

Preparation Example 9

Preparation of hCD80-Fc-IL-3M: GI102-M72

In order to produce a fusion protein comprising a human CD80 fragment, an Fc domain, and an IL-2 variant (3M) (R38A, F42A, L72G) (GI102-M72) with three amino acid substitutions, a polynucleotide was synthesized through the Invitrogen GeneArt Gene Synthesis service of ThermoFisher Scientific. Specifically, the polynucleotide contains a nucleotide sequence (SEQ ID NO: 29) which encodes a fusion protein that contains a signal peptide (SEQ ID NO: 1), a CD80 fragment (SEQ ID NO: 2), an Ig hinge (SEQ ID NO: 3), an Fc domain (SEQ ID NO: 4), a linker (SEQ ID NO: 5), and an IL-2 variant (SEQ ID NO: 24), in this order, from the N-terminus. The polynucleotide was inserted into pcDNA3_4 vector. In addition, the vector was introduced into CHO cells (Expi-CHO™) to express the fusion protein of SEQ ID NO: 30. After the vector was introduced, culture was performed for 7 days in an environment of 37° C., 125 RPM, and 8% $CO_2$ concentration. Then, the culture was harvested and the fusion protein was purified therefrom. The purified fusion protein was designated "GI102-M72".

The purification and collection of the fusion protein were carried out in the same manner as in Preparation Example 1. The isolated and purified fusion protein was subjected to SDS-PAGE under reduced (R) or non-reduced (NR) condition and stained with Coomassie Blue to check its purity (FIG. 15).

Preparation Example 10

Preparation of mCD80-Fc-IL-3M: mGI102-M61

In order to produce a fusion protein comprising a mouse CD80 fragment, an Fc domain, and an IL-2 variant (3M) (R38A, F42A, E61R) (GI102-M61) with three amino acid substitutions, a polynucleotide was synthesized through the Invitrogen GeneArt Gene Synthesis service of ThermoFisher Scientific. Specifically, the polynucleotide contains a nucleotide sequence (SEQ ID NO: 33) which encodes a fusion protein that contains a signal peptide (SEQ ID NO: 1), a mCD80 fragment (SEQ ID NO: 13), an Ig hinge (SEQ ID NO: 3), an Fc domain (SEQ ID NO: 4), a linker (SEQ ID NO: 5), and an IL-2 variant (SEQ ID NO: 23), in this order, from the N-terminus. The polynucleotide was inserted into pcDNA3_4 vector. In addition, the vector was introduced into CHO cells (Expi-CHO™) to express the fusion protein of SEQ ID NO: 34. After the vector was introduced, culture was performed for 7 days in an environment of 37° C., 125 RPM, and 8% $CO_2$ concentration. Then, the culture was harvested and the fusion protein was purified therefrom. The purified fusion protein was designated "mGI102-M61".

The purification and collection of the fusion protein were carried out in the same manner as in Preparation Example 1.

II. Identification of Binding Affinity Between Fusion Protein and Its Ligand

In order to identify the binding affinity between the fusion protein and its ligand, the binding affinity was measured using Octet RED 384.

Experimental Example 1

Identification of Binding Affinity Between hCTLA-4 and GI101

AR2G biosensor (Amine Reactive $2^{nd}$ gen, ForteBio, Cat: 18-5092) was previously hydrated with 200 μl of distilled water in a 96-well microplate (GreinerBio-one, Cat: 655209). A ligand (CTLA-4, Human CTLA-4/CD152, His tag, Sino Biological, Cat: 11159-H08H) to be attached to the AR2G biosensor was diluted with 10 mM acetate buffer (pH 5, AR2G reagent Kit, ForteBio, Cat: 18-5095) to a concentration of 5 μg/ml. In addition, GI101 to be attached to the ligand was diluted with 1× AR2G kinetic buffer (AR2G reagent Kit, ForteBio, Cat: 18-5095) to a concentration of 1,000 nM, 500 nM, 250 nM, 125 nM, or 62.5 nM. Activation buffer was prepared by mixing 20 mM EDC and 10 mM s-NHS (AR2G reagent Kit, ForteBio, Cat: 18-5095) in distilled water. 80 μl of each reagent was placed in a 384-well microplate (Greiner Bio-one, Cat: 781209) and the program was set up.

As a result, the binding affinity between hCTLA-4 and GI101 was measured as illustrated in FIG. 16.

Experimental Example 2

Identification of Binding Affinity Between hPD-L1/GI101 and hPD-L1/PD-1

Ni-NTA (Nickel charged Tris-NTA, Ni-NTA Biosensors, ForteBio, 18-5101) was previously hydrated with 200 μl of 1× Ni-NTA kinetic buffer (10× Kinetics buffer, ForteBio, 18-1042) in a 96-well microplate (GreinerBio-one, Cat: 655209). A ligand (Human PD-L1/B7-H1 protein, His-tag, Sino biological, Cat: 10084-H08H) to be attached to the Ni-NTA Biosensors was diluted with 1× Ni-NTA kinetic buffer to a concentration of 5 μg/ml. GI101 to be attached to the ligand was diluted with 1× Ni-NTA kinetic buffer at 1,000 nM, 500 nM, 250 nM, 125 nM, or 62.5 nM. In addition, human PD-1/PDCD1 (Human PD-1/PDCD1, Fc Tag, Sino Biological, Cat: 10377-H02H) to be attached to the ligand was diluted with 1× Ni-NTA kinetic buffer to a concentration of 2,000 nM, 1,000 nM, 500 nM, 250 nM, or 125 nM. Then, 80 μl of each reagent was placed in a 384-well microplate and the program was set up.

As a result, the binding affinity between hPD-L1 and GI101 was measured as illustrated in FIG. 17. In addition, the binding affinity between hPD-L1 and hPD-1 was measured as illustrated in FIG. 18.

Experimental Example 3

Identification of Binding Affinity Between mCTLA-4 and mGI101

The binding affinity between mCTLA-4 and mGI101 was examined in the same manner as in Experimental Example 1. Here, the equipment used is as follows: Biosensor: AR2G, Ligand: mCTLA-4 (Recombinant Mouse CTLA-4 Fc chimera, R&D Systems, Cat: 434-CT-200), Analyte: mGI101 (500 nM, 250 nM, 125 nM, 62.5 nM, 31.3 nM).

As a result, the binding affinity between mCTLA-4 and mGI101 was measured as illustrated in FIG. 19.

Experimental Example 4

Identification of Binding Affinity Between mPD-L1 and mGI101

The binding affinity between mPD-L1 and mGI101 was identified in the same manner as in Experimental Example 1. Here, the equipment used is as follows. Biosensor: AR2G, Ligand: mPD-L1 (Recombinant Mouse B7-H1/PD-L1 Fc chimera, R&D Systems, Cat: 434-CT-200), Analyte: mGI101 (500 nM, 250 nM, 125 nM, 62.5 nM, 31.3 nM).

As a result, the binding affinity between mPD-L1 and mGI101 was measured as illustrated in FIG. 20.

Experimental Example 5

Identification of Binding Ability of GI-101 (hCD8O-Fc-hIL-2v) to CTLA-4 and PD-L1

Binding kinetics measurements were performed using the Octet RED 384 instrument (ForteBio, Pall Life Science) with agitation at 30° C. and 1,000 rpm. The binding ability for CTLA-4 was measured using the Amine Reactive 2 generation (AR2G) biosensor chip, and the binding ability for PD-L1 was measured using the Nickel charged Tris-NTA (Ni-NTA) biosensor chip. The AR2G biosensor chip was activated with a combination of 400 mM EDC and 100 mM sulfo-NHS. Then, Human CTLA-4-His Tag (Sino Biological, Cat: 11159-H08H) was diluted with 10 mM acetate buffer (pH 5) to 5 μg/ml, and loaded on the AR2G biosensor chip for 300 seconds and fixed.

Then, binding of CTLA-4 to GI-101 (hCD80-Fc-hIL-2v), GI-101C1 (hCD80-Fc), Ipilimumab (Bristol-Myers Squibb), and GI-101C2 (Fc-hIL-2v) at various concentrations was measured for 300 seconds and dissociation thereof was also measured for 300 seconds. On the other hand, Human PD-L1-His Tag (Sino biological, Cat: 10084-H08H) was diluted with 1×Ni-NTA kinetic buffer to a concentration of 5 μg/ml, and loaded on the Ni-NTA biosensor chip for 600 seconds and fixed. Then, binding of PD-L1 to GI-101, GI-101C1, hPD-1-Fc (Sino biological, Cat: 10377-H02H), and GI101C2 at various concentrations was measured for 300 seconds and dissociation thereof was also measured for 300 seconds. Binding kinetics analysis was performed using Octet Data Analysis HT software ver. 10 provided by Pall Corporation. The results are illustrated in FIGS. 21 and 22.

Experimental Example 6

Identification of Effect of GI-101 (hCD80-Fc-hIL-2v) on PD-1/PD-L1 Binding

A blocking experiment was performed using the Octet RED 384 instrument (ForteBio, Pall Life Science) with agitation at 30° C. and 1,000 rpm. Human PD-L1-His Tag (Sino biological, Cat: 10084-H08H) was diluted with 1×Ni-NTA kinetic buffer to a concentration of 5 μg/ml, and loaded on the Ni-NTA biosensor chip for 600 seconds and fixed. In order to proceed with the blocking experiment, hPD-L1 fixed on the biosensor chip was allowed to bind to GI-101 at various concentrations (300 nM, 100 nM, 50 nM, 25 nM, 12.5 nM, and 0 nM) for 600 seconds, and then again allowed to bind to the competitor human PD-1 (100 nM) for 600 seconds so as to measure how much more hPD-1 can bind thereto. On the contrary, hPD-L1 was allowed to bind to hPD-1 at various concentrations (300 nM, 100 nM, 50 nM, 25 nM, 12.5 nM, and 0 nM) for 600 seconds, and then again allowed to bind to the competitor GI-101 (100 nM) for 600 seconds so as to measure how much more GI-101 can bind thereto. The blocking experiment was analyzed using the epitope binning menu of Octet Data Analysis HT software ver. 10 provided by Pall Corporation. The results are illustrated in FIG. 23.

Experimental Example 7

Identification of Binding Affinity Between IL-2Rα or IL-2Rβ and GI101

The binding ability for IL-2Rα was measured using the AR2G biosensor, and the binding ability for IL-2Rβ was measured using the Ni-NTA biosensors (Nickel charged Tris-NTA, Ni-NTA Biosensors, ForteBio, 18-5101).

A ligand (IL-2Rα-His Tag, Acro, Cat: ILA-H52H9) to be attached to the AR2G biosensor was diluted with 10 mM acetate buffer (pH 5, AR2G reagent Kit, ForteBio, Cat: 18-5095) to a concentration of 5 μg/ml. The AR2G biosensor was activated with a buffer prepared by mixing 400 mM EDC and 100 mM sulfo-NHS, and then the diluted ligand was loaded on the AR2G biosensor for 300 seconds and fixed.

Meanwhile, a ligand (IL-2Rβ-His Tag, Acro, Cat: CD2-H5221) to be attached to the Ni-NTA biosensor was diluted with 1× Ni-NTA kinetic buffer to a concentration of 5 μg/ml. The diluted ligand was loaded on the Ni-NTA biosensor for 600 seconds and fixed.

Thereafter, GI101, GI101w, or Proleukin (Novartis, hIL-2), at various concentrations, to be attached to the ligand was loaded thereon for 300 seconds. Then, binding thereof was measured and dissociation thereof was also measured for 300 seconds. Binding kinetics analysis was performed using Octet Data Analysis HT software ver. 10 provided by Pall Corporation. The results are illustrated in FIGS. 24 to 26.

As a result, it was identified that GI101 has low binding ability for the IL-2 receptor alpha chain, IL-2Rα, and high binding ability for IL-2Rβ, as compared with GI101w and Proleukin.

Experimental Example 8

Measurement of Binding Affinity Between Fusion Protein and Ligand

In order to identify binding affinity between the fusion protein and its ligand, binding affinity was measured using Octet RED 384.

Experimental Example 8.1

Identification of Binding Affinity Between IL2 Alpha Receptor and GI101-M45, GI101-M61, or GI101-M72

AR2G biosensor (Amine Reactive 2nd gen, ForteBio, Cat: 18-5092) was previously hydrated with 200 μl of distilled water (DW) in a 96-well microplate (GreinerBio-one, Cat: 655209). A ligand (Human IL-2 R alpha protein, His Tag, Acro, ILA-H52H9) to be attached to the biosensor was diluted with 10 mM acetate buffer (pH 5) (AR2G reagent Kit, ForteBio, Cat: 18-5095) to a concentration of 5 μg/ml. An analyte (GI101-M45, GI101-M61, GI101-M72) to be attached to the ligand was diluted with 1× AR2G kinetic buffer (AR2G reagent Kit, ForteBio, Cat: 18-5095) to 500 nM, 250 nM, 125 nM, and 62.5 nM, respectively. Activation buffer was prepared by mixing 20 mM EDC and 10 mM s-NHS (AR2G reagent Kit, ForteBio, Cat: 18-5095) in DW. 80 μl of each reagent was placed in a 384-well microplate (Greiner Bio-one, Cat: 781209) and the program was set up.

As a result, the binding affinity between IL2 alpha receptor and GI101-M45 is illustrated in FIG. 27. In addition, the binding affinity between IL2 alpha receptor and GI101-M61 is illustrated in FIG. 28, and the binding affinity between IL2 alpha receptor and GI101-M72 is illustrated in FIG. 29.

Experimental Example 8.2

Identification of Binding Affinity of GI102-M45, GI102-M61, and GI102-M72 to IL-2Rβ

Ni-NTA Biosensors were previously hydrated with 200 μl of 1× Ni-NTA kinetic buffer (10× Kinetics buffer, ForteBio, 18-1042) in a 96-well microplate. A ligand (Human IL-2 R beta protein, His-Tag, Acro, CD2-H5221) to be attached to the biosensor was diluted with 1× Ni-NTA kinetic buffer to a concentration of 2 μg/ml. GI102-M45, GI102-M61, or GI102-M72 to be attached to the ligand was diluted with 1× Ni-NTA kinetic buffer to a concentration of 500 nM, 250 nM, 125 nM, or 62.5 nM. 80 μl of each reagent was placed in a 384-well microplate and the program was set up.

As a result, the binding affinity between IL-2Rβ and GI102-M45 was measured as illustrated in FIG. 30, and the binding affinity between IL-2Rβ and GI102-M61 was measured as illustrated in FIG. 31. In addition, the binding affinity between IL-2Rβ and GI102-M72 was measured as illustrated in FIG. 32.

III. Identification of Immune Activity of Fusion Protein

Experimental Example 9

Identification of IFN-γ Production Caused by Fusion Protein

Experimental Example 9.1

Culture of CFSE-Labeled PBMCs

Peripheral blood mononuclear cells (PBMCs) isolated from a human were labeled with carboxyfluorescein succinimidyl ester (CF SE) by being reacted with 1 μM CellTrace CFSE dye at 37° C. for 20 minutes. CFSE not bound to the cells was removed by being reacted for 5 minutes with a culture medium having a 5-fold volume of the staining reaction solution and then by being centrifuged at 1,300 rpm for 5 minutes. The CFB-labeled PBMCs were resuspended in the culture medium (RPMI1640 medium containing 10% FBS, 10 mM HEPES, 100 U/ml penicillin/streptomycin, 1 mM sodium pyruvate, 55 μM 2-mercaptoethanol, 1 mM non-essential amino acid, and 2 mM L-glutamine), and then added to a 96-well plate at $1\times10^5$ cells per well. Treatment with 5 μg/ml of PHA (Lactin from Phaseolus Vulgaris, red kidney bean, Sigma-Aldrich, St. Louis, MO, USA, Cat. No. L1668-5MG), and GI101, GI101C1, GI101C2, or IL-2

(Aldesleukin; human recombinant IL-2, Novartis) was performed and incubation was performed in a 5% $CO_2$ incubator at 37° C. for 6 days.

Here, the treatment with GI101, GI101C1, GI101C2, and IL-2 was performed at a concentration of 1 nM, 10 nM, or 100 nM. The cells were analyzed by FACS, and human IFN-γ present in the culture medium was measured using an ELISA kit (Biolegend, San Diego, CA, USA, Cat. No. 430103).

Experimental Example 9.2

FACS Aanalysis

The cell pellets obtained by removing the supernatant were washed with FACS buffer (3% FBS, 10 mM EDTA, 1M HEPES, 100 unit/mL Penicillin Streptomycin, 10 μg/ml, 1 mM sodium pyruvate), and then reacted with Fc blocker (Biolegend, Cat. No. 422302) at 4° C. for 5 minutes. Then, treatment with APC anti-CD3 Ab (Biolegend, Cat. No. 300412) and PE anti-CD8a Ab (Biolegend, Cat. No. 300908) was performed and reaction was allowed to proceed at 4° C. for 20 minutes. Then, the resultant was washed with FACS buffer. The cell pellets were resuspended in FACS buffer and then analyzed using BD LSR Fortessa (BD Biosciences, San Diego, CA, USA) and FlowJo software.

Experimental Example 9.3

Human IFN-γ ELISA

The amount of human IFN-γ secreted into the supernatant of each sample in which the cells had been cultured was measured using a human IFN-γ ELISA kit (Biolegend, Cat. No. 430103). Briefly, anti-human-IFN-γ antibodies were added to an ELISA plate, and reaction was allowed to proceed overnight at 4° C. so that these antibodies were coated thereon. Then, blocking was performed at room temperature for 1 hour with a PBS solution to which 1% BSA had been added. Washing with a washing buffer (0.05% Tween-20 in PBS) was performed, and then a standard solution and each sample were properly diluted and added thereto. Then, reaction was allowed to proceed at room temperature for 2 hours.

After the reaction was completed, the plate was washed and secondary antibodies (detection antibodies) were added thereto. Reaction was allowed to proceed at room temperature for 1 hour. Washing with a washing buffer was performed, and then an Avidin-HRP solution was added thereto. Reaction was allowed to proceed at room temperature for 30 minutes. A substrate solution was added thereto and color development reaction was induced in the dark at room temperature for 20 minutes. Finally, $H_2SO_4$ was added thereto to stop the color development reaction, and the absorbance at 450 nm was measured with Epoch Microplate Spectrophotometer (BioTek Instruments, Inc., Winooski, VT, USA).

As a result, it was found that cells treated with GI101 exhibited a remarkable increase in IFN-γ secretion, as compared with cells treated with GI101C1, GI101C2, or IL-2 (FIGS. 33 and 34).

Experimental Example 10

Identification of Effect of GI101 on Proliferation of CD8+ T Cells

Peripheral blood mononuclear cells (PBMCs) isolated from a human were labeled with CFSE by being reacted with 1 μM CellTrace CFSE dye at 37° C. for 20 minutes. CFSE not bound to the cells was removed by being reacted for 5 minutes with a culture medium having a 5-fold volume of the staining reaction solution and then by being centrifuged at 1,300 rpm for 5 minutes. The CFB-labeled PBMCs were resuspended in the culture medium (RPMI1640 medium containing 10% FBS, 10 mM HEPES, 100 U/ml penicillin/streptomycin, 1 mM sodium pyruvate, 55 μM 2-mercaptoethanol, 1 mM non-essential amino acid, and 2 mM L-glutamine), and then added to a 96-well plate at $1\times10^5$ cells per well.

Thereafter, treatment with 1 μg/ml of anti-CD3ϵ antibody (Biolegend Cat. No. L1668-5MG), and GI101, GI101C1, GI101C2, or Proleukin (Novartis) was performed and incubation was performed in a 5% $CO_2$ incubator at 37° C. for 6 days. Here, the cells were treated with GI101, GI101C1, GI101C2, and IL-2 at a concentration of 100 nM. The incubated cells were examined for their degree of proliferation by measuring, with FACS analysis using APC-TCRαβ and PE-CD8α antibodies, a proportion of CD8+ T cells that had not been labeled with CFSE.

As a result, it was found that GI101 activated proliferation of CD8+ T cells in vitro to a similar extent to the wild-type IL-2 Proleukin (FIGS. 35 and 36).

Experimental Example 11

Identification of Effect of GI101 and GI102 on Proliferation of CD8+ T Cells Human PBMCs were purchased from Allcells (Lot #3014928, USA). 1M CellTrace CFSE dye was used, which was reacted with the human PBMCs under a light-blocking condition at room temperature for 20 minutes. The cells were labeled with CFSE by being reacted with 1 μM CellTrace CFSE dye at 37° C. for 20 minutes. CFSE not bound to the cells was removed by being reacted for 5 minutes with culture medium having a 5-fold volume of the staining reaction solution and then by being centrifuged at 1,300 rpm for 5 minutes. The CFB-labeled PBMCs were resuspended in the culture medium (RPMI1640 medium containing 10% FBS, 10 mM HEPES, 100 U/ml penicillin/streptomycin, 1 mM sodium pyruvate, 55 μM 2-mercaptoethanol, 1 mM non-essential amino acid, and 2 mM L-glutamine), and then added to a 96-well plate at $1\times10^5$ cells per well.

Thereafter, the CFB-labeled PBMCs were subjected to treatment with 1 μg/ml of anti-CD3c antibody (OKT3, eBioscience, USA), and GI101, GI101C1, GI101C2, or Proleukin (Novartis), and incubation was performed in a 5% $CO_2$ incubator at 37° C. for 7 days. Here, the cells were subjected to treatment with GI101, GI101C1, GI101C2, and IL-2 at a concentration of 10 μM.

The incubated cells were examined for their degree of proliferation by measuring, with FACS analysis using anti-human CD4-PE antibody (BioLegend, USA), anti-human CD8-PE/Cy7 antibody (BioLegend, USA), and anti-human FoxP3-APC antibody (BioLegend, USA), a proportion of CD8+ T cells that had not been labeled with CF SE.

As a result, the GI101, GI102_M61, GI101C2, and Proleukin treatment groups exhibited a significant increase in proportion of CD8+ T cells, as compared with the control group (no stimulus), the anti-CD3 antibody alone treatment group, and the GI101C1 treatment group. In addition, as compared with the negative control group (no stimulus) and the anti-CD3 alone treatment group, the GI101, GI101C2, and Proleukin treatment groups exhibited a significant increase in proliferation of CD4+/FoxP3+ Treg cells, whereas the GI102 and GI101C1 treatment groups did not exhibit a significant increase in proliferation of CD4+/FoxP3+ Treg cells (FIG. 37).

Experimental Example 12

Identification of Effect of GI101 or GI101w on Proliferation of CD8+ T Cells and NK Cells 7-week-old C57BL/6 mice purchased from Orient Bio (Busan, Korea) were divided into 3 groups, each group containing 3 mice, and PBS, GI101, or GI101w was injected intraperitoneally thereinto. Here, GI101 and GI101w were respectively prepared to be at 40.5 μs in 200 μl of PBS, and injected intraperitoneally thereinto. Five days after the injection, the spleens were removed from the mice of each group. The cells were isolated therefrom, and the total number of cells was measured using a hematocytometer. Splenocytes were examined for proportions of CD8+ T cells and NK cells therein, with FACS analysis using staining with APC-CD3ϵ antibody (Biolegend; 145-2C11), PE-NK1.1 antibody (Biolegend; PK136), and Pacific blue-CD8α antibody (BD; 53-6.7). As such, the numbers of CD8+ T cells and NK cells present in the spleen were calculated.

As a result, it was identified that GI101 activated proliferation of CD8+ T cells and NK cells in vivo as compared with GI101w (FIGS. 38 and 39).

Experimental Example 13

Identification of Effect of GI101 on Function of T Cells

An experiment was performed using a CTLA-4 blockade bioassay kit (Promega Cat. No. JA4005). The experiment is briefly described as follows. CTLA-4 effector cells kept in liquid nitrogen were thawed in a 37° C. constant temperature water bath for 3 minutes, and 0.8 ml of CTLA-4 effector cells were mixed well with 3.2 ml of pre-warmed assay buffer (90% RPMI+10% FBS). Then, the mixture was added to a 96-well white cell culture plate (SPL, Cat. No. 30196) at 25 μl per well. Then, 25 μl of GI101 at various concentrations was added thereto. For a negative control, 25 μl of assay buffer was added thereto. Then, the white plat cell culture plate was covered and placed at room temperature until aAPC/Raji cells were prepared.

aAPC/Raji cells kept in liquid nitrogen were thawed in a 37° C. constant temperature water bath for 3 minutes, and 0.8 ml of aAPC/Raji cells were mixed well with 3.2 ml of pre-warmed assay buffer. Then, 25 μl of the mixture was added to the plate at per well, and reaction was allowed to proceed in a 5% $CO_2$ incubator at 37° C. for 16 hours. After the reaction was completed, the resultant was allowed to stand at room temperature for 15 minutes, and then the Bio-Glo reagent was added thereto while taking care to avoid bubbles. The Bio-Glo reagent was also added to three of the outermost wells and the wells were used as blanks to correct the background signal. Reaction was allowed to proceed at room temperature for 10 minutes, and then luminescence was measured with Cytation 3 (BioTek Instruments, Inc., Winooski, VT, USA). Final data analysis was performed by calculating RLU (GI101-background)/RLU (no treatment-background).

As a result, it was found that GI101 attached to CTLA-4 expressed on effector T cells, and activated the function of T cells rather than inhibiting the same (FIGS. 40 and 41).

Experimental Example 14

Identification of Effect of mGI101 and mGI102 on Immune Cells 7-week-old C57BL/6 mice purchased from Orient Bio (Korea) were divided into 3 groups, each group containing 3 mice, and PBS, 3 mg/kg, 6 mg/kg, or 12 mg/kg of GI101, or 3 mg/kg, 6 mg/kg, or 12 mg/kg of mGI102 (mGI102-M61) was administered intravenously thereinto. On days 1, 3, 5, 7, and 14 after the injection, the spleens were removed from the mice of each group. Thereafter, for the spleen tissue, the numbers of effector CD8+ T cells, NK cells, and Treg cells were calculated with FACS analysis using respective antibodies, and proportions of effector CD8+ T cells and NK cells with respect to Treg cells were respectively calculated. The information on the antibodies used in each cell assay is as follows:

Effector CD8+ T cells: PB anti-mouse CD3ϵ antibody (Biolegend, #155612; KT3.1.1), FITC anti-mouse CD8α antibody (BD, #553031, 53-6.7), PE/Cy7 anti-mouse CD44 antibody (Biolegend, #103030; IM7), APC anti-mouse CD122 antibody (Biolegend, #123214; TM-I31)

NK cells: PB anti-mouse CD3ϵ antibody (Biolegend, #155612; KT3.1.1), PE anti-mouse NK-1.1 (Biolegend, #108708; PK136)

Treg cells: FITC anti-mouse CD3 antibody (Biolegend, #100204; 17A2), PB anti-mouse CD4 antibody (Biolegend, #100531; RM4-5), PE anti-mouse CD25 antibody (Biolegend, #102008; PC61), APC anti-mouse Foxp3 antibody (Invitrogen, #FJK-16s, 17-5773-82).

As a result, the group having received mGI101 or mGI102 (mGI102-M61) exhibited a significant increase in numbers of CD8+ T cells and NK cells at the time points from 3 days to 14 days after administration, as compared with the PBS administration group. In addition, it was found that the group having received mGI102 exhibited a significant increase in proportions of activated CD8+ T cells/Treg cells and NK cells/Treg cells at the time points from 3 days to 14 days after administration, as compared with the PBS administration group (FIG. 42).

IV. Identification of Anticancer Effect of Fusion Protein

Experimental Example 15

Identification of Effect of GI101 on Cancer Cells Overexpressing PD-L1

NC1-H292 cancer cell line overexpressing PD-L1 was cultured for 3 hours in a culture medium containing 10 μg/ml Mitomycin C (Sigma), and then Mitomycin C was removed by washing with the culture medium. Thereafter, $5\times10^4$ cells of the Mitomycin C-treated NC1-H292 cancer cell line were incubated with $1\times10^5$ cells of human PBMCs in a 96-well plate. Here, treatment with 5 μg/ml of PHA (Sigma) was performed for T cell activity. In addition, GI101C1 and GI101 at a concentration of 50 nM were reacted with IgG1-Fc (Biolegend) or abatacept (=Orencia; Bristol-Myers Squibb) at a concentration of 50 nM for 30 minutes at 4° C., and then the resultant was used to treat the NCl-H292 cancer cells. After 3 days, the supernatant of the cell incubate was collected and the amount of IFN-γ was quantified using an ELISA kit (Biolegend).

As a positive control group, human PBMCs stimulated with PHA in the absence of the Mitomycin C-treated NCl- H292 cancer cell line were used; and as a negative control group, human PBMCs stimulated with PHA in the presence of the Mitomycin C-treated NCl-H292 cancer cell line was used. An experimental method using the IFN-γ ELISA kit was carried out in the same manner as in Experimental Example 9.3.

As a result, GI101 effectively activated the immune response that had been inhibited by the cancer cell line overexpressing PD-L1. In addition, it was discovered that GI101 inhibited signaling of CTLA-4 expressed on effector T cells (FIGS. 43 and 44).

Experimental Example 16

Identification of Anticancer Effect of GI101 in Mouse-Derived Colorectal Cancer Cell-Transplanted Mice $5\times10^6$ cells/0.05 ml of mouse-derived CT-26 cancer cell line was mixed with 0.05 ml Matrigel matrix phenol red-free (BD), and transplantation of 0.1 ml of the mixture was performed by subcutaneous administration in the right dorsal region of 6-week-old female BALB/c mice (Orient Bio). A certain period of time after the cancer cell transplantation, the tumor volume was measured and subjects that reached about 80 $mm^3$ to 120 $mm^3$ were separated. Then, the subjects were intravenously administered with 0.1 ml of GI101. A total of three administrations were given once every three days after the first administration, and PBS was given to a negative control group. The tumor size was measured daily to identify an anticancer effect.

As a result, it was observed that the CT-26 cancer cell line-transplanted mice treated with GI101 exhibited a remarkable decrease in tumor size as compared with the negative control group (FIGS. 45 and 46).

Experimental Example 17

Identification of Anticancer Effect of mGI101 in Mouse-Derived Melanoma-Transplanted Mice C57BL/6 mice (female, 7-week-old) acquired from Orient Bio were subjected to an acclimation period of 7 days. Then, $5\times10^6$ cells of B16F10 cancer cell line (ATCC, USA) were mixed with 0.05 ml of Matrigel matrix phenol red-free (BD), and allotransplantation of the mixture was performed by subcutaneous administration at 0.1 ml in the right dorsal region of the mice. A certain period of time after the cancer cell transplantation, the tumor volume was measured and subjects that reached about 50 $mm^3$ to 120 $mm^3$ were selected, and then the selected mice were grouped evenly based on tumor size and body weight, each group containing 10 mice.

Thereafter, using a disposable syringe (31G, 1 mL), hIgG4 was administered at a dose of 4 mg/kg to a negative control group, and an anti-PD-1 antibody was administered at a dose of 5 mg/kg to a positive control group. For experimental groups, mGI101 at a dose of 1 mg/kg or 4 mg/kg was administered intravenously thereto. Additionally, groups having received mGI101 at a dose of 4 mg/kg and an anti-PD-1 antibody at a dose of 5 mg/kg were also set as experimental groups. A total of three administrations were given once every three days after the first administration. The tumor size was measured daily.

As a result, the initial tumor volume of all groups was 90 $mm^3$, and standard error (S.E.) of each group was 5 $mm^3$ to 6 $mm^3$. In the negative control group, a change in tumor volume was observed during the experimental period, in which the tumor volume increased from 90 $mm^3$ to 1,434 $mm^3$ up to 15 days after the administration.

In the group having received mGI101 at a dose of 1 mg/kg, the tumor volume was observed to increase from 90 $mm^3$ to 885 $mm^3$ during the experimental period which is the same period as the negative control group, and a statistically significant inhibition of tumor growth was observed at some measurement time points (p-value: 0.5 on day 11, p-value <0.01 on day 7, p-value <0.001 on day 3). In the group having received mGI101 at a dose of 4 mg/kg, the tumor volume was observed to increase from 90 $mm^3$ to 748 $mm^3$ during the experimental period which is the same period as the negative control group, and a statistically significant inhibition of tumor growth was observed at some measurement time points (p-value: 0.5 on day 9, p-value <0.01 on days 7 and 11).

In addition, tumor growth inhibition rate was analyzed by using, as a reference, the group having received mIgG at a dose of 4 mg/kg and comparing this group with each of the other groups. In the group having received mGI101 at a dose of 1 mg/kg, growth inhibition rate of 36.5% was observed as compared with the negative control group, and no statistically significant difference (p-value: 0.5) was observed. In the group having received mGI101 at a dose of 4 mg/kg, a statistically significant (p-value: 0.5) tumor growth inhibition rate was observed as compared with the negative control group. A total of two administrations were given once every three days after the first administration. The tumor size was measured daily.

Through this, it was found that in tumor growth inhibitory efficacy test for B16F10, a melanoma allotransplanted into C57BL/6 mice, mGI101 had an effect of inhibiting tumor growth in a dose-dependent manner (FIGS. 47 and 48).

Experimental Example 18

Identification of Anticancer Effect of mGI101 in Mouse-Derived Colorectal Cancer Cell-Transplanted Mice BALB/c mice (female, 7-week-old) acquired from Orient Bio were subjected to an acclimation period of 7 days. Then, $5\times10^6$ cells of CT-26 cancer cell line (ATCC, USA)were mixed with 0.05 ml of Matrigel matrix phenol red-free (BD), and allotransplantation of the mixture was performed by subcutaneous administration at 0.1 ml in the right dorsal region of the mice. A certain period of time after the cancer cell transplantation, the tumor volume was measured and subjects that reached about 28 $mm^3$ were selected, and then the selected mice were grouped evenly based on tumor size and body weight, each group containing 10 mice. Thereafter, using a disposable syringe (31G, 1 mL), hIgG4 was administered at a dose of 6 mg/kg to a negative control group. For experimental groups, mGI101 at a dose of 3 mg/kg, 6 mg/kg, or 12 mg/kg was administered intravenously thereto. A total of three administrations were given once every three days after the first administration. The tumor size was measured daily.

As a result, it was found that the experimental group having received mGI101 at a dose of 6 mg/kg or 12 mg/kg mGI101 exhibited significant inhibition of tumor growth at some measurement time points and at the end of the test, as compared with the negative control group (FIG. 49). In addition, as a result of measuring a survival rate, it was found that the experimental group having received mGI101 at a dose of 6 mg/kg exhibited significant improvement at some measurement time points and at the end of the test, as compared with the negative control group (FIG. 50).

Experimental Example 19

Identification of Anticancer Effect of GI101 in Mice Transplanted with Mouse-Derived Colorectal Cancer Cells Experimental Example 19.1

Identification of Tumor Inhibitory Effect

BALB/c mice (female, 7-week-old) acquired from Orient Bio were subjected to an acclimation period of 7 days. Then, $5\times10^6$ cells of CT-26 cancer cell line (ATCC, USA) were suspended in 0.1 ml PBS, and allotransplantation of the suspension was performed by subcutaneous administration at 0.1 ml in the right dorsal region of the mice. A certain period of time after the cancer cell transplantation, the tumor volume was measured and subjects that reached about 50 $mm^3$ to 200 $mm^3$ were selected, and then the selected mice were grouped evenly based on tumor size and body weight, each group containing 10 mice. Thereafter, using a disposable syringe (31G, 1 mL), no drug was administered to a negative control group, and an anti-PD-1 antibody at a dose of 5 mg/kg, or an anti-PD-1 antibody at a dose of 5 mg/kg and an anti-CTLA-4 antibody at a dose of 5 mg/kg were administered intravenously to positive control groups. For experimental groups, GI101 at a dose of 0.1 mg/kg or 1 mg/kg was administered intravenously thereto. A total of three administrations were given once every three days after the first administration. The tumor size was measured daily.

As a result, in the CT-26 cancer cell line-transplanted mice, all groups having received anti-PD-1 antibody, anti-PD-1 antibody and anti-CTLA-4 antibody, or GI101 at a dose of 0.1 mg/kg or 1 mg/kg exhibited significant inhibition of tumor growth, as compared with the negative control. In particular, the experimental group having received GI101 at a dose of 0.1 mg/kg exhibited a significant tumor inhibitory effect, as compared with the anti-PD-1 antibody treatment group (*$p<0.05$) (FIG. 51).

Experimental Example 19.2

Immune Cell Analysis in Cancer Tissue

The mice of each group in Experimental Example 19.1 were sacrificed when the tumor volume reached an average of 200 $mm^3$, and cancer tissues were collected. Thereafter, the cancer tissues were separated to a single-cell level to analyze immune cells therein, and then FACS analysis was performed on immune cells in the cancer tissues using the following antibodies: Anti-mouse-CD3 (Biolegend, Cat. No. 100320), Anti-mouse-CD4 (Biolegend, Cat. No. 100526), Anti-mouse-CD8 (Biolegend, Cat. No. 100750), Anti-mouse-FoxP3 (eBioscience, Cat. No. 12-5773-82), Anti-mouse-CD25 (Biolegend, Cat. No. 102049), Anti-mouse-CD44 (eBioscience, Cat. No. 61-0441-82), Anti-mouse-PD-1 (Biolegend, Cat. No. 135218), Anti-mouse-IFN-gamma (Biolegend, Cat. No. 505832), Anti-mouse-CD49b (Biolegend, Cat. No. 108906), Anti-mouse-H2 (Invitrogen, Cat. No. A15443), Anti-mouse-CD11c (Biolegend, Cat. No. 117343), Anti-mouse-CD80 (eBioscience, Cat. No. 47-4801-82), Anti-mouse-CD86 (Biolegend, Cat. No. 104729), Anti-mouse-F4/80 (eBioscience, Cat. No. 47-4801-82), and Anti-mouse-CD206 (eBioscience, Cat. No. 17-2061-80).

As a result, the experimental group having received GI101 at a dose of 0.1 mg/kg exhibited a significant increase in CD8+ T cells, as compared with the positive control group having received anti-PD-1 antibody alone at a dose of 5 mg/kg (*$p<0.05$, FIGS. 52 and 53). Furthermore, all experimental groups having received GI101 exhibited a significantly increased level of expression of IFN-γ in T cells, as compared with the negative control group (*$p<0.05$, FIGS. 52 and 53). In addition, the experimental group having received GI101 at a dose of 0.1 mg/kg exhibited an increase in M1 macrophages as compared with the negative control group and the positive control group having received anti-PD-1 antibody alone (FIGS. 54 and 55). In addition, all experimental groups having received GI101 exhibited an increased level of CD86 expression in macrophages and dendritic cells (*$p<0.05$, FIGS. 54 to 57).

Experimental Example 20

Identification of Anticancer Effect of GI101 in Mice Transplanted with Mouse-Derived Lung Cancer Cells Experimental Example 20.1

Identification of Tumor Inhibitory Effect

C57BL/6 mice (female, 7-week-old) acquired from Orient Bio were subjected to an acclimation period of 7 days. Then, $5\times10^6$ cells of LLC2 cancer cell line (ATCC, USA) were suspended in 0.1 ml PBS, and allotransplantation of the suspension was performed by subcutaneous administration at 0.1 ml in the right dorsal region of the mice. A certain period of time after the cancer cell transplantation, the tumor volume was measured and subjects that reached about 50 $mm^3$ to 200 $mm^3$ were selected, and then the selected mice were grouped evenly based on tumor size and body weight, each group containing 10 mice. Thereafter, using a disposable syringe (31G, 1 mL), no drug was administered to a negative control group, and an anti-PD-1 antibody at a dose of 5 mg/kg, or an anti-PD-1 antibody at a dose of 5 mg/kg and an anti-CTLA-4 antibody at a dose of 5 mg/kg were administered intravenously to positive control groups. For experimental groups, GI101 at a dose of 0.1 mg/kg or 1 mg/kg was administered intravenously thereto. A total of three administrations were given once every three days after the first administration. The tumor size was measured daily.

As a result, all experimental groups exhibited a significant tumor inhibitory effect, as compared with the negative control group (*$p<0.05$) (FIG. 58).

Experimental Example 20.2

Immune Cell Analysis in Cancer Tissue

The mice of each group in Experimental Example 20.1 were sacrificed when the tumor volume reached an average of 200 $mm^3$, and cancer tissues were collected. Thereafter, FACS analysis was performed in the same manner as Experimental Example 19.2 to analyze immune cells in the cancer tissues.

As a result, the experimental group having received GI101 at a dose of 0.1 mg/kg exhibited a significant increase in CD8+ T cells, as compared with the positive control group having received anti-PD-1 antibody alone (*$p<0.05$, FIG. 59). Furthermore, all experimental groups having received GI101 exhibited a significantly increased level of expression of IFN-γ, as compared with the negative control group (*$p<0.05$, FIG. 59). In addition, all experimental groups having received GI101 exhibited an increased level of CD86 expression in macrophages and dendritic cells (*$p<0.05$, FIGS. 59 to 61).

Experimental Example 21

Identification of Anticancer Effect of mGI102-M61 in Mice Transplanted with Mouse-Derived Colorectal Cancer Cells BALB/c mice (female, 7-week-old) acquired from Orient Bio were subjected to an acclimation period of 7 days. Then, $5\times10^6$ cells of CT-26 cancer cell line (ATCC, USA) were mixed with 0.05 ml of Matrigel matrix phenol red-free (BD), and allotransplantation of the mixture was performed by subcutaneous administration at 0.1 ml in the right dorsal region of the mice. A certain period of time after the cancer cell transplantation, the tumor volume was measured and subjects that reached about 28 $mm^3$ were selected, and then the selected mice were grouped evenly based on tumor size and body weight, each group containing 10 mice. Thereafter, using a disposable syringe (31G, 1 mL), hIgG4 was administered at a dose of 6 mg/kg to a negative control group. For experimental groups, mGI102-M61 at a dose of 3 mg/kg, 6 mg/kg, or 12 mg/kg was administered intravenously thereto. A total of three administrations were given once every three days after the first administration. The tumor size was measured daily.

As a result, it was identified that the experimental group having received mGI102-M61 at a dose of 12 mg/kg exhibited significant inhibition of tumor growth at some measurement time points and at the end of the test, as compared with the negative control group (FIG. 62). In addition, as a result of measuring a survival rate, it was identified that the experimental group having received mGI102-M61 at a dose of 12 mg/kg exhibited significant improvement at some measurement time points and at the end of the test, as compared with the negative control group (FIG. 63).

Experimental Example 22

Identification of Anticancer Effect of mGI101 in Mice Transplanted with Mouse-Derived Colorectal Cancer Cells BALB/c mice (female, 7-week-old) acquired from Orient Bio were subjected to an acclimation period of 7 days. Then, $5\times10^6$ cells of CT-26 cancer cell line (ATCC, USA) were mixed with 0.05 ml of Matrigel matrix phenol red-free (BD), and allotransplantation of the mixture was performed by subcutaneous administration at 0.1 ml in the right dorsal region of the mice. A certain period of time after the cancer cell transplantation, the tumor volume was measured and subjects that reached about 200 $mm^3$ to 250 $mm^3$ were selected, and then the selected mice were grouped evenly based on tumor size and body weight, each group containing 10 mice.

Thereafter, using a disposable syringe (31G, 1 mL), hIgG4 was administered at a dose of 4 mg/kg to a negative control group. For experimental groups, mGI101 at a dose of 1 mg/kg, 4 mg/kg, or 6 mg/kg was administered intravenously thereto. Additionally, groups having received mCD80 at 4.9 mg/kg or Fc-IL-2v (GI101C2) at 2.8 mg/kg were set as control groups. In addition, a group having simultaneously received mCD80 at 4.9 mg/kg and Fc-IL-2v (GI101C2) at 2.8 mg/kg was set as a control group.

In tumor volume measurement, it was identified that the group having received mGI101 at a dose of 6 mg/kg exhibited significant inhibition at some measurement time points and at the end of the test, as compared with the negative control. An excellent tumor growth inhibition rate was observed as compared with the group having received a combination of mCD80 and Fc-IL-2v (GI101C2) (FIGS. 64 and 65).

In conclusion, in the tumor growth-inhibitory efficacy test on BALB/c mice allotransplanted with CT-26, a BALB/c mouse-derived colorectal cancer cell line, it was demonstrated that the test substance mGI101 had tumor inhibitory efficacy under this test condition as compared with mCD80 and IL-2v single preparations; and it was identified that mGI101 exhibited excellent anticancer efficacy as compared with the group having received a combination of mCD80 and IL-2v (FIGS. 64 and 65). In particular, the group having received mGI101 at a dose of 6 mg/kg exhibited significant inhibition of tumor size, as compared with the negative control group and the group having received a combination of mCD80 and Fc-IL2v (GI101C2).

V. Toxicity Evaluation of Fusion Protein

Experimental Example 23

Toxicity Evaluation of GI101 Using Monkeys

Experimental Example 23.1

Monkey Breeding and Drug Administration

In the present experiment, nine male Philippine monkeys (Cynomolgus monkeys) aged 2 to 3 years were used. The experiment was carried out in accordance with the "Act on Welfare and Management of Animals" in Japan and the "Guidance for Animal Care and Use" of Ina Research Inc. The experimental protocol was reviewed by the Institutional Animal Care and Use Committee (IACUC) of Ina Research Inc, and then approved by AAALAC International (Accredited Unit No. 001107).

The experiment was conducted from one day before drug administration up to 15 days after drug administration. Each monkey was observed around the cage, and the stool status was additionally checked. Body weights were measured using a digital scale (LDS-150H, Shimadzu Corporation) one day before drug administration, and on days 1, 8, and 15 after drug administration. In addition, the remaining amount of food was measured from one day before drug administration up to sacrifice of the monkeys.

Here, a disposable syringe (24G) was filled with the drug GI101, and a total of two administrations were given via an intravenous route, each administration being made at a rate of 0.17 ml/sec. GI101 was given twice, at a week's interval, at a dose of 5 mg/kg/day or 10 mg/kg/day. A control group was administered PBS (pH 7.4) in the same manner.

Experimental Example 23.2

Clinical Observation, Identification of Changes in Body Weight and Food Intake

Clinical observation, and measurement of changes in body weight and food intake were performed from one day before drug administration up to days 1, 8, and 15 after drug administration. As a result, no toxicity was caused by GI101 (FIGS. 66 to 69).

Experimental Example 23.3

Blood Analysis

Blood was collected from the monkeys in Experimental Example 23.1 one day before drug administration, and on days 1, 8, and 15 after drug administration. Here, the blood was collected via the femoral vein with a disposable syringe (22G). The collected blood was subjected to blood analysis using the Automated Hematology System XN-2000 (Sysmex Corporation) and the Automated Blood Coagulation Analyzer CA-510 (Sysmex Corporation) for the items listed in Table 2 below.

TABLE 2

| Parameter | Abbr. | Unit | Method | Equipment |
|---|---|---|---|---|
| Complete blood count | | | | |
| Red blood cell count | RBC | $10^6/\mu L$ | DC sheath-flow detection | XN-2000 |
| Hemoglobin concentration | HGB | g/dL | SLS-hemoglobin | XN-2000 |
| Hematocrit | HCT | % | RBC pulse height detection | XN-2000 |
| Mean corpuscular volume | MCV | fL | HCT/RBC ($\times 10^4/\mu L$) × 1000 | XN-2000 |
| Mean corpuscular hemoglobin | MCH | pg | HGB/RBC ($\times 10^4/\mu L$) × 1000 | XN-2000 |
| Mean corpuscular hemoglobin concentration | MCHC | g/dL | HGB/HCT × 100 | XN-2000 |
| Reticulocytes | RET % | % | Flow cytometry | XN-2000 |
| Ratio Count | RET # | $10^9/L$ | | |
| Platelet count | PLT | $10^3/\mu L$ | Flow cytometry | XN-2000 |
| White blood cell count | WBC | $10^3/\mu L$ | Flow cytometry | XN-2000 |
| Differential white blood cells | Diff WBC % | % | Flow cytometry | XN-2000 |
| [a]Ratio Count | | | | |
| | Diff WBC # | $10^3/\mu L$ | | |
| Coagulation tests | | | | |
| Prothrombin time | PT | s | Light scattering detection | CA-510 |
| Activated partial thromboplastin time | APTT | s | Light scattering detection | CA-510 |

[a]Neutrophils (NEUT), lymphocytes (LYMPH), monocytes (MONO), eosinophils (EO) and basophils (BASO)

As a result, the group having received G1101 at a dose of 5 mg/kg/day or 10 mg/kg/day exhibited an increase in numbers of reticulocytes, leukocytes, and lymphocytes on day 15 (FIGS. 70 to 72).

Experimental Example 23.4

Clinical and Chemical Analysis

Blood was collected from the monkeys in Experimental Example 23.1 one day before drug administration, and on days 1, 8, and 15 after drug administration. Here, the blood was collected in the same manner as in Experimental Example 23.3. The collected blood was subjected to clinical and chemical analysis using the Clinical Analyzer Model 7180 (Hitachi High-Technologies Corporation) for the items listed in Table 3 below.

TABLE 3

| Parameter | Abbr. | Unit | Method |
|---|---|---|---|
| Aspartate aminotransferase | AST | U/L | JSCC traceable method |
| Alanine aminotransferase | ALT | U/L | JSCC traceable method |
| Alkaline phosphatase | ALP | U/L | JSCC traceable method |
| Lactate dehydrogenase | LD | U/L | JSCC traceable method |
| Creatine kinase | CK | U/L | JSCC traceable method |
| Glucose | GLU | mg/dL | Enzymatic (Gluc-DH) |
| Total bilirubin | BIL | mg/dL | Enzymatic (BOD) |
| Urea nitrogen | UN | mg/dL | Enzymatic (urease-LEDH) |
| Creatinine | CRE | mg/dL | Enzymatic |
| Total cholesterol | CHO | mg/dL | Enzymatic (cholesterol oxidase) |
| Triglycerides | TG | mg/dL | Enzymatic (GK-GPO with free glycerol elimination) |
| Phospholipids | PL | mg/dL | Enzymatic (choline oxidase) |
| Inorganic phosphorus | IP | mg/dL | Enzymatic (maltose phosphorylase) |
| Calcium | CA | mg/dL | OCPC |
| Sodium | NA | mEq/L | Ion-selective electrode |
| Potassium | K | mEq/L | Ion-selective electrode |
| Chloride | CL | mEq/L | Ion-selective electrode |
| Total protein | TP | g/dL | Biuret |
| Albumin | ALB | g/dL | BCG |
| Albumin-globulin ratio | A/G | — | Calculated |

JSCC: Japan Society of Clinical Chemistry

As a result, no toxicity caused by GI101 was detected in the clinical and chemical analysis (FIGS. 73 to 79).

Experimental Example 21.5

Cytokine Analysis

Blood was collected from the monkeys in Experimental Example 23.1 one day before drug administration, and on days 1, 8, and 15 after drug administration. Here, the blood was collected in the same manner as in Experimental Example 23.3. Using the Bio-Plex 200 (Bio-Rad Laboratories, Inc.) instrument and the Non-Human Primate Cytokine Magnetic Bead Panel (EMD Millipore) Assay Kit, the collected blood was analyzed for TNF-α, IFN-γ IL-1β, IL-2, IL-4, IL-6, IL-8, IL-10, and IL-12. As a result, no toxicity caused by GI101 was detected with respect to the cytokine analysis (FIGS. 80 and 81).

Experimental Example 23.6

Immune Cell Analysis

Blood was collected from the monkeys in Experimental Example 23.1 one day before drug administration, and on days 1, 8, and 15 after drug administration. Here, the blood was collected in the same manner as in Experimental Example 23.3. Using a flow cytometer (LSRFortessa X-20, Becton, Dickinson and Company), the collected blood was analyzed for the following items:

1) Ki67+CD4: CD45+/CD3+/CD4+/Ki67+
2) Ki67+CD8: CD45+/CD3+/CD8+/Ki67+
3) Ki67+Treg: CD45+/CD3+/FoxP3+/Ki67+
4) Ki67+ICOS +Treg: CD45+/CD3+/FoxP3+/Ki67+/CD278+
5) ICOS+Treg: CD45+/CD3+/FoxP3+/CD278+
6) Ki67+NK cell: CD45+/CD16+and CD56+/Ki67+.

As a result, in the immune cell analysis, all groups having received GI101 exhibited, on day 15, an increase in numbers of T cells, CD4+ T cells, CD8+ T cells, regulatory T cells, NK cells and Ki67+ T cells, Ki67+ CD4+ T cells, Ki67+

CD8+ T cells, Ki67+ regulatory T cells, Ki67+ ICOS+ regulatory T cells, Ki67+ NK cells, ICOS+ regulatory T cells.

Specifically, in lymphocytes, proportions of T cells, CD4+ T cells, regulatory T cells increased and a proportion of NK cells decreased, while a proportion of CD8+ T cells did not change. A proportion of regulatory T cells increased on day 3 and decreased on days 8 and 15. However, the proportion was still higher than the control group.

In addition, regarding proportions of immune cells, which are Ki67+, in the respective immune cells, proportions of Ki67+ T cells, Ki67+ CD4+ T cells, Ki67+ CD8+ T cells, Ki67+ regulatory T cells, Ki67+ ICOS+ regulatory T cells, Ki67+ NK cells, and ICOS+ regulatory T cells increased.

Furthermore, proportions of Ki67+ T cells, Ki67+ CD8+ T cells, and Ki67+ NK cells increased on days 3, 8, and 15; proportions of Ki67+ CD4+ T cells and Ki67+ regulatory T cells increased on days 3 and 8; and proportions of Ki67+ ICOS+ regulatory T cells and ICOS+ regulatory T cells increased only on day 8 (FIGS. 82 to 87).

Experimental Example 23.7

Pathological Analysis

On day 16, the monkeys in Experimental Example 23.1 were sacrificed and all organs and tissues were fixed using 10% formalin. However, the testes were fixed using a formalin-sucrose-acetic acid (FSA) solution, and the eyes and optic nerve were fixed using 1% formaldehyde-2.5% glutaraldehyde in phosphate buffer. Hematoxylin-eosin staining was performed on the organs and tissues in the items listed in Table 4 below, and observations were made under an optical microscope.

TABLE 4

| | Specimen preparation | | | |
|---|---|---|---|---|
| Organ/tissue | Fixation | Organ weight | HE-stained | Note |
| Heart | O | O | — | Left ventricular papillary muscle, right ventricular wall and areas including the coronary artery and aortic valve |
| Aorta (thoracic) | O | — | | |
| Sternum | O | — | | Decalcified |
| Sternal bone marrow | | — | | |
| Femurs | O (R&L) | — | | Distal articular cartilage and shaft; decalcified |
| Femoral bone marrow | O (R) | — | | Decalcified |
| Thymus | O | O | O | |
| Spleen | O | O | O | |
| Submandibular lymph nodes | O | — | O | |
| Mesenteric lymph nodes | O | — | O | |
| Trachea | O | — | | Decalcified |
| Bronchi Lungs | O (R&L) | O (R&L separated) | — | Left anterior and right posterior lobes |
| Tongue | O | — | | |
| Submandibular glands | O (R&L) | O (R&L combined) | | |
| Parotid glands | O (R&L) | — | | |

TABLE 4-continued

| | Specimen preparation | | | |
|---|---|---|---|---|
| Organ/tissue | Fixation | Organ weight | HE-stained | Note |
| Esophagus | O | — | | |
| Stomach | O | — | | Cardia, body and pylorus |
| Duodenum | O | — | | |
| Jejunum | O | — | | |
| Ileum Peyer's patches | O | — | | |
| Cecum | O | — | | |
| Colon | O | — | | |
| Rectum | O | — | | |
| Liver Gallbladder | O | O (with bile-drained gallbladder) | O O | Left lateral lobe and right medial lobe including the gallbladder |
| Pancreas | O | O | — | |
| Kidneys | O (R&L) | O (R&L separated) | O (R&L) | |
| Urinary bladder | O | — | | |
| Pituitary | O | O | | |
| Thyroids Parathyroids | O (R&L) | O (R&L separated) | | |
| Adrenals | O (R&L) | O (R&L separated) | | |
| Testes | O (R&L) | O (R&L separated) | | |
| Epididymides | O (R&L) | O (R&L separated) | | |
| Prostate | O | O | | |
| Seminal vesicles | O | O | — | |
| Brain | O | O | — | Cerebrum (frontal, parietal (including basal ganglia and hippocampus) and occipital lobes); cerebellum; pons; and medulla oblongata |
| Spinal cord (thoracic) | O | — | | |
| Sciatic nerve | O (L) | — | | |
| Eyes | O (R&L) | — | | |
| Optic nerves | O (R&L) | — | | |
| Lacrimal glands | O (R&L) | — | | |
| Skeletal muscle (biceps femoris) | O (L) | — | | |
| Skin (thoracic) | O | — | | |
| Injection site (tail vein) | O | — | | Decalcified |
| Skin of the thoracic or medial femoral region with ID No. | O | — | — | |

O: conducted
—: Not conducted
R&L: Both the right and left organs/tissues were conducted.
L: Either the right or left organ/tissue (usually the left) was conducted.
R: Either the right or left organ/tissue (usually the right) was conducted As a result, the group treated with GI101 at a dose of 5 mg/kg/day or 10 mg/kg/day exhibited an increase in spleen weight (FIG. 88). No significant changes were observed in the other tissues. In conclusion, in the groups having received GI101, some changes were observed but no toxicity was observed.

VI. Experimental Example 24 for Identifying Anticancer Efect of GI102

Identification of Anticancer Effect of GI102-M45

Experimental Example 24.1

Identification of Anticancer Effect of GI102-M45 in Mice Transplanted with Mouse-Derived Colorectal Cancer Cells $5\times10^6$ cells/0.05 ml of mouse-derived CT-26 cancer cell line were mixed with 0.05 ml Matrigel matrix phenol red-free (BD), and transplantation of the mixture was performed by subcutaneous administration at 0.1 ml in the right dorsal region of 6-week-old female BALB/c mice (Orient Bio). A certain period of time after the cancer cell transplantation, the tumor volume was measured and subjects that reached about 80 $mm^3$ to 120 mm3 were separated. Then, the subjects were intravenously administered 0.1 ml of GI102-M45. A total of three administrations were given once every three days after the first administration, and PBS was given for a negative control. The tumor size was measured daily to identify an anticancer effect. Activity of GI102-M45 was identified in the same manner as in Experimental Example 16.

Experimental Example 24.2

Identification of Anticancer Effect of GI102-M45 in Mice Transplanted with Mouse-Derived Lung Cells C57BL/6 mice (female, 7-week-old) acquired from Orient Bio were subjected to an acclimation period of 7 days. Then, $5\times10^6$ cells of LLC2 cancer cell line (ATCC, USA) were suspended in 0.1 ml PBS, and allotransplantation of the suspension was performed by subcutaneous administration at 0.1 ml in the right dorsal region of the mice. A certain period of time after the cancer cell transplantation, the tumor volume was measured and subjects that reached about 50 $mm^3$ to 200 $mm^3$ were selected, and then the selected mice were grouped evenly based on tumor size and body weight, each group containing 10 mice. Thereafter, using a disposable syringe (31G, 1 mL), no drug was administered to a negative control group, and an anti-PD-1 antibody at a dose of 5 mg/kg, or an anti-PD-1 antibody at a dose of 5 mg/kg and an anti-CTLA-4 antibody at a dose of 5 mg/kg were administered intravenously to positive control groups. For experimental groups, GI102-M45 at a dose of 0.1 mg/kg or 1 mg/kg was administered intravenously thereto. A total of three administrations were given once every three days after the first administration. The tumor size was measured daily. Activity of GI102-M45 was identified in the same manner as in Experimental Example 20.1.

Experimental Example 25

Identification of Anticancer Effect of GI102-M61

Experimental Example 25.1

Identification of Anticancer Effect of GI102-M61 in Mice Transplanted with Mouse-Derived Colorectal Cancer Cells $5\times10^6$ cells/0.05 ml of mouse-derived CT-26 cancer cell line were mixed with 0.05 ml Matrigel matrix phenol red-free (BD), and transplantation of the mixture was performed by subcutaneous administration at 0.1 ml in the right dorsal region of 6-week-old female BALB/c mice (Orient Bio). A certain period of time after the cancer cell transplantation, the tumor volume was measured and subjects that reached about 80 $mm^3$ to 120 $mm^3$ were separated. Then, the subjects were intravenously administered 0.1 ml of GI102-M61. A total of three administrations were given once every three days after the first administration, and PBS was given to a negative control. The tumor size was measured daily to identify an anticancer effect. Activity of GI102-M61 was identified in the same manner as in Experimental Example 16.

Experimental Example 25.2

Identification of Antitumor Effect of GI102-M61 in Mice Transplanted with Mouse-Derived Lung Cancer Cells C57BL/6 mice (female, 7-week-old) acquired from Orient Bio were subjected to an acclimation period of 7 days. Then, $5\times10^6$ cells of LLC2 cancer cell line (ATCC, USA) were suspended in 0.1 ml PBS, and allotransplantation of the suspension was performed by subcutaneous administration at 0.1 ml in the right dorsal region of the mice. A certain period of time after the cancer cell transplantation, the tumor volume was measured and subjects that reached about 50 $mm^3$ to 200 $mm^3$ were selected, and then the selected mice were grouped evenly based on tumor size and body weight, each group containing 10 mice. Thereafter, using a disposable syringe (31G, 1 mL), no drug was administered to a negative control group, and an anti-PD-1 antibody at a dose of 5 mg/kg, or an anti-PD-1 antibody at a dose of 5 mg/kg and an anti-CTLA-4 antibody at a dose of 5 mg/kg were administered intravenously to positive control groups. For experimental groups, GI102-M61 at a dose of 0.1 mg/kg or 1 mg/kg was administered intravenously thereto. A total of three administrations were given once every three days after the first administration. The tumor size was measured daily. Activity of GI102-M61 was identified in the same manner as in Experimental Example 20.1.

Experimental Example 26

Identification of Anticancer Effect of GI102-M72

Experimental Example 26.1

Identification of Antitumor Effect of GI102-M72 in Mice Transplanted with Mouse-Derived Colorectal Cancer Cells $5\times10^6$ cells/0.05 ml of mouse-derived CT-26 cancer cell line were mixed with 0.05 ml Matrigel matrix phenol red-free (BD), and transplantation of the mixture was performed by subcutaneous administration at 0.1 ml in the right dorsal region of 6-week-old female BALB/c mice (Orient Bio). A certain period of time after the cancer cell transplantation, the tumor volume was measured and subjects that reached about 80 $mm^3$ to 120 $mm^3$ were separated. Then, the subjects were intravenously administered 0.1 ml of GI102-M72. A total of three administrations were given once every three days after the first administration, and PBS was given to a negative control. The tumor size was measured daily to identify an anticancer effect. Activity of GI102-M72 was identified in the same manner as in Experimental Example 16.

Experimental Example 26.2

Identification of Anticancer Effect of GI102-M72 in Mice Transplanted with Mouse-Lung Cancer Cells C57BL/6 mice (female, 7-week-old) acquired from Orient Bio were subjected to an acclimation period of 7 days. Then, $5\times10^6$ cells of LLC2 cancer cell line (ATCC, USA) were suspended in 0.1 ml PBS, and allotransplantation of the suspension was performed by subcutaneous administration at 0.1 ml in the right dorsal region of the mice. A certain period of time after the cancer cell transplantation, the tumor volume was measured and subjects that reached about 50 $mm^3$ to 200 $mm^3$ were selected, and then the selected mice were grouped evenly based on tumor size and body weight, each group containing 10 mice. Thereafter, using a disposable syringe (31G, 1 mL), no drug was administered to a negative control group, and an anti-PD-1 antibody at a dose of 5 mg/kg, or an anti-PD-1 antibody at a dose of 5 mg/kg and an anti-CTLA-4 antibody at a dose of 5 mg/kg were administered intravenously to positive control groups. For experimental groups, GI102-M72 at a dose of 0.1 mg/kg or 1 mg/kg was administered intravenously thereto. A total of three administrations were given once every three days after the first administration. The tumor size was measured daily. Activity of GI102-M72 was identified in the same manner as in Experimental Example 20.1.

The invention claimed is:

1. A polynucleotide encoding a fusion protein of the following structural formula (I) or (II):

N'-X-[linker (1)]$_n$-Fc domain-[linker (2)]$_m$-Y—C' (I)

N'-Y-[linker (1)]$_n$-Fc domain-[linker (2)]$_m$-X—C' (II)

in the structural formulas (I) and (II),

N' is the N-terminus of the fusion protein,

C' is the C-terminus of the fusion protein,

X is a CD80 protein,

Y is an IL-2 protein, the linkers (1) and (2) are peptide linkers, and n and m are each independently 0 or 1.

2. The polynucleotide of claim 1, wherein n and m are each independently 1.

3. The polynucleotide of claim 1, wherein the IL-2 protein comprises the amino acid sequence of SEQ ID NO: 10.

4. The polynucleotide of claim 1, wherein the IL-2 protein is an IL-2 variant.

5. The polynucleotide of claim 4, wherein the IL-2 variant is obtained by substitution of at least one selected from the 38th, 42nd, 45th, 61st, and 72nd amino acids in the amino acid sequence of SEQ ID NO: 10.

6. The polynucleotide of claim 4, wherein the IL-2 variant comprises at least one substitution selected from the group consisting of R38A, F42A, Y45A, E61R, and L72G in the amino acid sequence of SEQ ID NO: 10.

7. The polynucleotide of claim 4, wherein the IL-2 variant comprises any one selected from the following substitution combinations (a) to (d) in the amino acid sequence of SEQ ID NO: 10:

(a) R38A/F42A (b) R38A/F42A/Y45A (c) R38A/F42A/E61R (d) R38A/F42A/L72G.

8. The polynucleotide of claim 4, wherein the IL-2 variant comprises the amino acid sequence of SEQ ID NO: 6, 22, 23, or 24.

9. The polynucleotide of claim 1, wherein the CD80 protein comprises the amino acid sequence of SEQ ID NO: 11.

10. The polynucleotide of claim 1, wherein the CD80 protein is a CD80 fragment.

11. The polynucleotide of claim 10, wherein the CD80 fragment consists of the 35th amino acid to 242nd amino acid in the amino acid sequence of SEQ ID NO: 11.

12. The polynucleotide of claim 1, wherein the Fc domain is a wild type or variant.

13. The polynucleotide of claim 1, wherein the Fc domain comprises the amino acid sequence of SEQ ID NO: 4.

14. The polynucleotide of claim 13, wherein the variant of the Fc domain comprises the amino acid sequence of SEQ ID NO: 12.

15. The polynucleotide of claim 1, wherein the linker (1) is a peptide linker consisting of the amino acid sequence of SEQ ID NO: 3.

16. The polynucleotide of claim 1, wherein the linker (2) is a peptide linker consisting of the amino acid sequence of SEQ ID NO: 5.

17. The polynucleotide of claim 1, wherein the fusion protein comprises a sequence identity of 90% or higher to the amino acid sequence of SEQ ID NO: 9, 26, 28, or 30.

18. The polynucleotide of claim 1, wherein the polynucleotide has a sequence identity of 85% or higher to the nucleotide sequence of SEQ ID NO: 8, 25, 27, or 29.

19. A vector comprising the polynucleotide of claim 1.

20. A transformed cell comprising the vector of claim 19.

* * * * *

SEQUENCE LISTING

```
Sequence total quantity: 37
SEQ ID NO: 1            moltype = AA  length = 25
FEATURE                 Location/Qualifiers
REGION                  1..25
                        note = signal peptide (TPA)
source                  1..25
                        mol_type = protein
                        organism = synthetic construct
SEQUENCE: 1
MDAMLRGLCC VLLLCGAVFV SPSHA                                          25

SEQ ID NO: 2            moltype = AA  length = 208
FEATURE                 Location/Qualifiers
REGION                  1..208
                        note = hB7-1:35-242
source                  1..208
                        mol_type = protein
                        organism = synthetic construct
SEQUENCE: 2
VIHVTKEVKE VATLSCGHNV SVEELAQTRI YWQKEKKMVL TMMSGDMNIW PEYKNRTIFD  60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                       208

SEQ ID NO: 3            moltype = AA  length = 30
FEATURE                 Location/Qualifiers
REGION                  1..30
                        note = hinge
source                  1..30
                        mol_type = protein
                        organism = synthetic construct
SEQUENCE: 3
GSGGGGSGGG GSGGGGSAES KYGPPCPPCP                                     30

SEQ ID NO: 4            moltype = AA  length = 216
FEATURE                 Location/Qualifiers
REGION                  1..216
                        note = immunoglobulin fc
source                  1..216
                        mol_type = protein
                        organism = synthetic construct
SEQUENCE: 4
APEAAGGPSV FLFPPKPKDQ LMISRTPEVT CVVVDVSQED PEVQFNWYVD GVEVHNAKTK  60
PREEQFNSTY RVVSVLTVLH QDWLNGKEYK CKVSNKGLPS SIEKTISKAK GQPREPQVYT  120
LPPSQEEMTK NQVSLTCLVK GFYPSDIAVE WESNGQPENN YKTTPPVLDS DGSFFLYSRL  180
TVDKSRWQEG NVFSCSVLHE ALHNHYTQKS LSLSLG                              216

SEQ ID NO: 5            moltype = AA  length = 5
FEATURE                 Location/Qualifiers
REGION                  1..5
                        note = linker
source                  1..5
                        mol_type = protein
                        organism = synthetic construct
SEQUENCE: 5
GGGGS                                                                5
```

-continued

```
SEQ ID NO: 6            moltype = AA  length = 133
FEATURE                 Location/Qualifiers
REGION                  1..133
                        note = hIL-2M
source                  1..133
                        mol_type = protein
                        organism = synthetic construct
SEQUENCE: 6
APTSSSTKKT QLQLEHLLLD LQMILNGINN YKNPKLTAML TAKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                    133

SEQ ID NO: 7            moltype = AA  length = 617
FEATURE                 Location/Qualifiers
REGION                  1..617
                        note = fusion protein comprising variants of IL-2 and
                         fragments of CD80
source                  1..617
                        mol_type = protein
                        organism = synthetic construct
SEQUENCE: 7
MDAMLRGLCC VLLLCGAVFV SPSHAVIHVT KEVKEVATLS CGHNVSVEEL AQTRIYWQKE  60
KKMVLTMMSG DMNIWPEYKN RTIFDITNNL SIVILALRPS DEGTYECVVL KYEKDAFKRE  120
HLAEVTLSVK ADFPTPSISD FEIPTSNIRR IICSTSGGFP EPHLSWLENG EELNAINTTV  180
SQDPETELYA VSSKLDFNMT TNHSFMCLIK YGHLRVNQTF NWNTTKQEHF PDNGSGGGGS  240
GGGGSGGGGS AESKYGPPCP PCPAPEAAGG PSVFLFPPKP KDQLMISRTP EVTCVVVDVS  300
QEDPEVQFNW YVDGVEVHNA KTKPREEQFN STYRVVSVLT VLHQDWLNGK EYKCKVSNKG  360
LPSSIEKTIS KAKGQPREPQ VYTLPPSQEE MTKNQVSLTC LVKGFYPSDI AVEWESNGQP  420
ENNYKTTPPV LDSDGSFFLY SRLTVDKSRW QEGNVFSCSV LHEALHNHYT QKSLSLSLGG  480
GGGSAPTSSS TKKTQLQLEH LLLDLQMILN GINNYKNPKL TAMLTAKFYM PKKATELKHL  540
QCLEEELKPL EEVLNLAQSK NFHLRPRDLI SNINVIVLEL KGSETTFMCE YADETATIVE  600
FLNRWITFCQ SIISTLT                                                617

SEQ ID NO: 8            moltype = DNA  length = 1857
FEATURE                 Location/Qualifiers
misc_feature            1..1857
                        note = nucleotiedes coding fusion protein (GI101)
source                  1..1857
                        mol_type = other DNA
                        organism = synthetic construct
SEQUENCE: 8
atggatgcta tgctgagagg cctgtgttgc gtgctgctgc tgtgtggcgc tgtgttcgtg  60
tctccttctc acgctgtgat ccacgtgacc aaagaagtga aagaggtcgc cacactgtcc  120
tgcggccaca acgtttcagt ggaagaactg gcccagacca ggatctactg gcagaaagaa  180
aagaaaatgg tgctgaccat gatgtccggc gacatgaaca tctggcctga gtacaagaac  240
cggaccatct tcgacatcac caacaacctg tccatcgtga ttctggccct gaggccttct  300
gatgagggca cctatgagtg cgtggtgctg aagtacgaga aggacgcctt caagcgcgag  360
cacctggctg aagtgacact gtccgtgaag gccgactttc ccacaccttc catctccgac  420
ttcgagatcc ctacctccaa catccggcgg atcatctgtt ctacctctgg cggctttcct  480
gagcctcacc tgtcttggct ggaaaacggc gaggaactga acgccatcaa caccaccgtg  540
tctcaggacc ccgaaaccga gctgtacgct gtgtcctcca agctggactt caacatgacc  600
accaaccaca gcttcatgtg cctgattaag tacggccacc tgagagtgaa ccagaccttc  660
aactggaaca ccaccaagca agagcacttc cctgacaatg gatctggcgg cggaggttct  720
ggcggaggtg gaagcggagg cggaggatct gctgagtcta agtatggccc tccttgtcct  780
ccatgtcctg ctccagaagc tgctggcgga ccctctgtgt tcctgtttcc tccaaagcct  840
aaggaccagc tcatgatctc tcggacaccc gaagtgacct gcgtggtggt ggatgtgtct  900
caagaggacc ctgaggtgca gttcaattgg tacgtggacg gcgtggaagt gcacaacgcc  960
aagaccaagc ctagagagga acagttcaac tccacctaca gagtggtgtc cgtgctgacc  1020
gtgctgcacc aggattggct gaacggcaaa gagtacaagt gcaaggtgtc caacaagggc  1080
ctgccttcca gcatcgaaaa gaccatctcc aaggctaagg gccagcctag ggaaccccag  1140
gtttacaccc tgcctccaag ccaagaggaa atgaccaaga accaggtgtc cctgacctgc  1200
ctggtcaagg gcttctaccc ttccgacatt gccgtggaat gggagtccaa tggccagcct  1260
gagaacaact acaagaccac acctcctgtg ctggactccg acggctcctt ctttctgtac  1320
tctcgcctga ccgtggacaa gtctagatgg caagagggca acgtgttctc ctgctctgtg  1380
ctgcacgagg ccctgcacaa tcactacacc cagaagtccc tgtctctgtc tcttggaggt  1440
ggtggcggtt ctgcccctac cagctcctct accaagaaaa cccagctcca gttggagcat  1500
ctgctgctgg acctccagat gattctgaac gggatcaaca actataagaa ccccaagctg  1560
accgccatgc tgaccgctaa gttctacatg cccaagaagg ccaccgagct gaagcacctc  1620
cagtgcctgg aagaagaact gaagcccctg gaagaggtgc tgaatctggc ccagtccaag  1680
aacttccacc tgaggccacg ggacctgatc agcaacatca acgtgatcgt gctggaactg  1740
aagggctccg agacaacctt tatgtgcgag tacgccgacg agacagccac catcgtggaa  1800
tttctgaacc ggtggatcac cttctgccag agcatcatct ccacactgac ctgatga     1857

SEQ ID NO: 9            moltype = AA  length = 592
FEATURE                 Location/Qualifiers
REGION                  1..592
                        note = fusion protein (GI101)
source                  1..592
                        mol_type = protein
```

-continued

```
                         organism = synthetic construct
SEQUENCE: 9
VIHVTKEVKE VATLSCGHNV SVEELAQTRI YWQKEKKMVL TMMSGDMNIW PEYKNRTIFD  60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDNGS GGGGSGGGGS GGGGSAESKY GPPCPPCPAP  240
EAAGGPSVFL FPPKPKDQLM ISRTPEVTCV VVDVSQEDPE VQFNWYVDGV EVHNAKTKPR  300
EEQFNSTYRV VSVLTVLHQD WLNGKEYKCK VSNKGLPSSI EKTISKAKGQ PREPQVYTLP  360
PSQEEMTKNQ VSLTCLVKGF YPSDIAVEWE SNGQPENNYK TTPPVLDSDG SFFLYSRLTV  420
DKSRWQEGNV FSCSVLHEAL HNHYTQKSLS LSLGGGGGSA PTSSSTKKTQ LQLEHLLLDL  480
QMILNGINNY KNPKLTAMLT AKFYMPKKAT ELKHLQCLEE ELKPLEEVLN LAQSKNFHLR  540
PRDLISNINV IVLELKGSET TFMCEYADET ATIVEFLNRW ITFCQSIIST LT          592

SEQ ID NO: 10            moltype = AA  length = 133
FEATURE                  Location/Qualifiers
REGION                   1..133
                         note = hIL-2
source                   1..133
                         mol_type = protein
                         organism = synthetic construct
SEQUENCE: 10
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                    133

SEQ ID NO: 11            moltype = AA  length = 288
FEATURE                  Location/Qualifiers
REGION                   1..288
                         note = CD80
source                   1..288
                         mol_type = protein
                         organism = synthetic construct
SEQUENCE: 11
MGHTRRQGTS PSKCPYLNFF QLLVLAGLSH FCSGVIHVTK EVKEVATLSC GHNVSVEELA  60
QTRIYWQKEK KMVLTMMSGD MNIWPEYKNR TIFDITNNLS IVILALRPSD EGTYECVVLK  120
YEKDAFKREH LAEVTLSVKA DFPTPSISDF EIPTSNIRRI ICSTSGGFPE PHLSWLENGE  180
ELNAINTTVS QDPETELYAV SSKLDFNMTT NHSFMCLIKY GHLRVNQTFN WNTTKQEHFP  240
DNLLPSWAIT LISVNGIFVI CCLTYCFAPR CRERRRNERL RRESVRPV                288

SEQ ID NO: 12            moltype = AA  length = 215
FEATURE                  Location/Qualifiers
REGION                   1..215
                         note = modified Fc
source                   1..215
                         mol_type = protein
                         organism = synthetic construct
SEQUENCE: 12
SHTQPLGVFL FPPKPKDTLM ISRTPEVTCV VVDVSQEDPE VQFNWYVDGV EVHNAKTKPR  60
EEQFNSTYRV VSVLTVLHQD WLNGKEYKCK VSNKGLPSSI EKTISKAKGQ PREPQVYTLP  120
PSQEEMTKNQ VSLTCLVKGF YPSDIAVEWE SNGQPENNYK TTPPVLDSDG SFFLYSRLTV  180
DKSRWQEGNV FSCSVMHEAL HNHYTQKSLS LSLGK                              215

SEQ ID NO: 13            moltype = AA  length = 306
FEATURE                  Location/Qualifiers
REGION                   1..306
                         note = mCD80
source                   1..306
                         mol_type = protein
                         organism = synthetic construct
SEQUENCE: 13
MACNCQLMQD TPLLKFPCPR LILLFVLLIR LSQVSSDVDE QLSKSVKDKV LLPCRYNSPH  60
EDESEDRIYW QKHDKVVLSV IAGKLKVWPE YKNRTLYDNT TYSLIILGLV LSDRGTYSCV  120
VQKKERGTYE VKHLALVKLS IKADFSTPNI TESGNPSADT KRITCFASGG FPKPRFSWLE  180
NGRELPGINT TISQDPESEL YTISSQLDFN TTRNHTIKCL IKYGDAHVSE DFTWEKPPED  240
PPDSKNTLVL FGAGFGAVIT VVVIVVIIKC FCKHRSCFRR NEASRETNNS LTFGPEEALA  300
EQTVFL                                                            306

SEQ ID NO: 14            moltype = DNA  length = 1848
FEATURE                  Location/Qualifiers
misc_feature             1..1848
                         note = nucleotiedes coding fusion protein (mGI101)
source                   1..1848
                         mol_type = other DNA
                         organism = synthetic construct
SEQUENCE: 14
atggatgcta tgctgagagg cctgtgttgc gtgctgctgc tgtgtggcgc tgtgttcgtg  60
tctccttctc acgctgtgga cgagcagctc tccaagtccg tgaaggataa ggtcctgctg  120
ccttgccggt acaactctcc tcacgaggac gagtctgagg accggatcta ctggcagaaa  180
cacgacaagg tggtgctgtc cgtgatcgcc ggaaagctga aagtgtggcc tgagtacaag  240
```

-continued

```
aacaggaccc tgtacgacaa caccacctac agcctgatca tcctgggcct cgtgctgagc  300
gatagaggca cctattcttg cgtggtgcag aagaaagagc ggggcaccta cgaagtgaag  360
cacctggctc tggtcaagct gtccatcaag gccgacttca gcacccctaa catcaccgag  420
tctggcaacc cttccgccga caccaagaga atcacctgtt tcgcctctgg cggcttccct  480
aagcctcggt tctcttggct ggaaaacggc agagagctgc ccggcatcaa taccaccatt  540
tctcaggacc cagagtccga gctgtacacc atctccagcc agctcgactt taacaccacc  600
agaaaccaca ccatcaagtg cctgattaag tacggcgacg cccacgtgtc cgaggacttt  660
acttgggaga aacctcctga ggaccctcct gactctggat ctggcggcgg aggttctggc  720
ggaggtggaa gcggaggcgg aggatctgct gagtctaagt atggccctcc ttgtcctcca  780
tgtcctgctc cagaagctgc tggcggaccc tctgtgttcc tgtttcctcc aaagcctaag  840
gaccagctca tgatctctcg gacccctgaa gtgacctgcg tggtggtgga tgtgtctcaa  900
gaggaccctg aggtgcagtt caattggtac gtggacggcg tggaagtgca caacgccaag  960
accaagccta gagaggaaca gttcaactcc acctatagag tggtgtccgt gctgaccgtg  1020
ctgcaccagg attggctgaa cggcaaagag tacaagtgca aggtgtccaa caagggcctg  1080
ccttccagca tcgaaaagac catcagcaag gctaagggcc agcctaggga accccaggtt  1140
tacaccctgc ctccaagcca agaggaaatg accaagaacc aggtgtccct gacctgcctg  1200
gtcaagggct tctacccttc cgacattgcc gtggaatggg agtccaatgg ccagcctgag  1260
aacaactaca agaccacacc tcctgtgctg gactccgacg gctccttctt tctgtactct  1320
cgcctgaccg tggacaagtc taggtggcaa gagggcaacg tgttctcctg ctctgtgctg  1380
cacgaggctc tgcacaacca ctacacccag aagtccctgt ctctgtctct tggaggtggt  1440
ggcggttctg cccctacctc cagctctacc aagaaaaccc agctccagtt ggagcatctg  1500
ctgctggacc tccagatgat cctgaatggc atcaacaatt acaagaaccc caagctgacc  1560
gccatgctga ccgctaagtt ctacatgccc aagaaggcca ccgagctgaa gcacttgcag  1620
tgcctggaag aggaactgaa gcccctggaa gaagtgctga atctggccca gtccaagaac  1680
ttccacctga ggcctaggga cctgatctcc aacatcaacg tgatcgtgct ggaactgaaa  1740
ggctccgaga caaccttcat gtgcgagtac gccgacgaga cagccaccat cgtggaattt  1800
ctgaaccggt ggatcacctt ctgccagagc atcatctcca cactgacc              1848

SEQ ID NO: 15          moltype = AA  length = 616
FEATURE                Location/Qualifiers
REGION                 1..616
                       note = fusion protein (mGI101)
source                 1..616
                       mol_type = protein
                       organism = synthetic construct
SEQUENCE: 15
MDAMLRGLCC VLLLCGAVFV SPSHAVDEQL SKSVKDKVLL PCRYNSPHED ESEDRIYWQK  60
HDKVVLSVIA GKLKVWPEYK NRTLYDNTTY SLIILGLVLS DRGTYSCVVQ KKERGTYEVK  120
HLALVKLSIK ADFSTPNITE SGNPSADTKR ITCFASGGFP KPRFSWLENG RELPGINTTI  180
SQDPESELYT ISSQLDFNTT RNHTIKCLIK YGDAHVSEDF TWEKPPEDPP DSGSGGGGSG  240
GGGSGGGGSA ESKYGPPCPP CPAPEAAGGP SVFLFPPKPK DQLMISRTPE VTCVVVDVSQ  300
EDPEVQFNWY VDGVEVHNAK TKPREEQFNS TYRVVSVLTV LHQDWLNGKE YKCKVSNKGL  360
PSSIEKTISK AKGQPREPQV YTLPPSQEEM TKNQVSLTCL VKGFYPSDIA VEWESNGQPE  420
NNYKTTPPVL DSDGSFFLYS RLTVDKSRWQ EGNVFSCSVL HEALHNHYTQ KSLSLSLGGG  480
GGSAPTSSST KKTQLQLEHL LLDLQMILNG INNYKNPKLT AMLTAKFYMP KKATELKHLQ  540
CLEEELKPLE EVLNLAQSKN FHLRPRDLIS NINVIVLELK GSETTFMCEY ADETATIVEF  600
LNRWITFCQS IISTLT                                                 616

SEQ ID NO: 16          moltype = DNA  length = 1437
FEATURE                Location/Qualifiers
misc_feature           1..1437
                       note = nucleotiedes coding fusion protein (GI101C1)
source                 1..1437
                       mol_type = other DNA
                       organism = synthetic construct
SEQUENCE: 16
atggatgcta tgctgagagg cctgtgttgc gtgctgctgc tgtgtggcgc tgtgttcgtg  60
tctccttctc acgctgtgat ccacgtgacc aaagaagtga aagaggtcgc cacactgtcc  120
tgcggccaca acgtttcagt ggaagaactg gcccagacca ggatctactg gcagaaagaa  180
aagaaaatgg tgctgaccat gatgtccggc gacatgaaca tctggcctga gtacaagaac  240
cggaccatct tcgacatcac caacaacctg tccatcgtga ttctggccct gaggccttct  300
gatgagggca cctatgagtg cgtggtgctg aagtacgaga aggacgcctt caagcgcgag  360
cacctggctg aagtgacact gtccgtgaag gccgactttc ccacaccttc catctccgac  420
ttcgagatcc ctacctccaa catccggcgg atcatctgtt ctacctctgg cggctttcct  480
gagcctcacc tgtcttggct ggaaaacggc gaggaactga acgccatcaa caccaccgtg  540
tctcaggacc ccgaaaccga gctgtacgct gtgtcctcca agctggactt caacatgacc  600
accaaccaca gcttcatgtg cctgattaag tacggccacc tgagagtgaa ccagaccttc  660
aactggaaca ccaccaagca agagcacttc cctgacaatg gatctggcgg cggaggttct  720
ggcggaggtg gaagcggagg cggaggatct gctgagtcta agtatggccc tccttgtcct  780
ccatgtcctg ctccagaagc tgctggcgga ccctctgtgt tcctgtttcc tccaaagcct  840
aaggaccagc tcatgatctc tcggacaccc gaagtgacct gcgtggtggt ggatgtgtct  900
caagaggacc ctgaggtgca gttcaattgg tacgtggacg gcgtggaagt gcacaacgcc  960
aagaccaagc ctagagagga acagttcaac tccacctaca gagtggtgtc cgtgctgacc  1020
gtgctgcacc aggattggct gaacggcaaa gagtacaagt gcaaggtgtc caacaagggc  1080
ctgccttcca gcatcgaaaa gaccatctcc aaggctaagg gccagcctag ggaaccccag  1140
gtttacaccc tgcctccaag ccaagaggaa atgaccaaga accaggtgtc cctgacctgc  1200
ctggtcaagg gcttctaccc ttccgacatt gccgtggaat gggagtccaa tggccagcct  1260
gagaacaact acaagaccac acctcctgtg ctggactccg acggctcctt ctttctgtac  1320
tctcgcctga ccgtggacaa gtctaggtgg caagagggca acgtgttctc ctgctctgtg  1380
```

-continued

```
ctgcacgagg ccctgcacaa tcactacacc cagaagtccc tgtctctgtc cctgggc     1437

SEQ ID NO: 17          moltype = AA  length = 454
FEATURE                Location/Qualifiers
REGION                 1..454
                       note = fusion protein (GI101C1)
source                 1..454
                       mol_type = protein
                       organism = synthetic construct
SEQUENCE: 17
VIHVTKEVKE VATLSCGHNV SVEELAQTRI YWQKEKKMVL TMMSGDMNIW PEYKNRTIFD  60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDNGS GGGGSGGGGS GGGGSAESKY GPPCPPCPAP  240
EAAGGPSVFL FPPKPKDQLM ISRTPEVTCV VVDVSQEDPE VQFNWYVDGV EVHNAKTKPR  300
EEQFNSTYRV VSVLTVLHQD WLNGKEYKCK VSNKGLPSSI EKTISKAKGQ PREPQVYTLP  360
PSQEEMTKNQ VSLTCLVKGF YPSDIAVEWE SNGQPENNYK TTPPVLDSDG SFFLYSRLTV  420
DKSRWQEGNV FSCSVLHEAL HNHYTQKSLS LSLG                              454

SEQ ID NO: 18          moltype = DNA  length = 1176
FEATURE                Location/Qualifiers
misc_feature           1..1176
                       note = nucleotiedes coding fusion protein (GI101C2)
source                 1..1176
                       mol_type = other DNA
                       organism = synthetic construct
SEQUENCE: 18
atggatgcta tgctgagagg cctgtgttgc gtgctgctgc tgtgtggcgc tgtgttcgtg  60
tctccatctc acgccgctga gtctaagtac ggccctcctt gtcctccatg tcctgctcca  120
gaagctgctg gcggaccctc tgtgttcctg tttcctccaa agcctaagga ccagctcatg  180
atctctcgga cccctgaagt gacctgcgtg gtggtggatg tgtctcaaga ggaccctgag  240
gtgcagttca attggtacgt ggacggcgtg gaagtgcaca acgccaagac caagcctaga  300
gaggaacagt tcaactccac ctacagagtg gtgtccgtgc tgaccgtgct gcaccaggat  360
tggctgaacg gcaaagagta caagtgcaag gtgtccaaca agggcctgcc ttccagcatc  420
gaaaagacca tctccaaggc taagggccag cctagggaac cccaggttta caccctgcct  480
ccaagccaag aggaaatgac caagaaccag gtgtccctga cctgcctggt caagggcttc  540
taccccttccg acattgccgt ggaatgggag tccaatggcc agcctgagaa caactacaag  600
accacacctc ctgtgctgga ctccgacggc tccttcttc tgtactctcg cctgaccgtg  660
gacaagtcta ggtggcaaga gggcaacgtg ttctcctgct ctgtgctgca cgaggccctg  720
cacaatcact acacccagaa gtccctgtct ctgtctcttg gcggaggcgg aggatctgct  780
cctacctcca gctccaccaa gaaaacccag ctccagttgg agcatctgct gctggacctc  840
cagatgatcc tgaatggcat caacaattac aagaacccca agctgaccgc catgctgacc  900
gctaagttct acatgcccaa gaaggccacc gagctgaagc acctccagtg cctggaagag  960
gaactgaagc ccctggaaga agtgctgaat ctggcccagt ccaagaactt ccacctgagg  1020
cctagggacc tgatctccaa catcaacgtg atcgtgctgg aactgaaagg ctccgagaca  1080
accttcatgt gcgagtacgc cgacgagaca gccaccatcg tggaatttct gaaccggtgg  1140
atcaccttct gccagtccat catctccaca ctgacc                            1176

SEQ ID NO: 19          moltype = AA  length = 367
FEATURE                Location/Qualifiers
REGION                 1..367
                       note = fusion protein (GI101C2)
source                 1..367
                       mol_type = protein
                       organism = synthetic construct
SEQUENCE: 19
AESKYGPPCP PCPAPEAAGG PSVFLFPPKP KDQLMISRTP EVTCVVVDVS QEDPEVQFNW  60
YVDGVEVHNA KTKPREEQFN STYRVVSVLT VLHQDWLNGK EYKCKVSNKG LPSSIEKTIS  120
KAKGQPREPQ VYTLPPSQEE MTKNQVSLTC LVKGFYPSDI AVEWESNGQP ENNYKTTPPV  180
LDSDGSFFLY SRLTVDKSRW QEGNVFSCSV LHEALHNHYT QKSLSLSLGG GGGSAPTSSS  240
TKKTQLQLEH LLLDLQMILN GINNYKNPKL TAMLTAKFYM PKKATELKHL QCLEEELKPL  300
EEVLNLAQSK NFHLRPRDLI SNINVIVLEL KGSETTFMCE YADETATIVE FLNRWITFCQ  360
SIISTLT                                                            367

SEQ ID NO: 20          moltype = DNA  length = 1434
FEATURE                Location/Qualifiers
misc_feature           1..1434
                       note = nucleotiedes coding fusion protein (mGI101C1)
source                 1..1434
                       mol_type = other DNA
                       organism = synthetic construct
SEQUENCE: 20
atggatgcta tgctgagagg cctgtgttgc gtgctgctgc tgtgtggcgc tgtgttcgtg  60
tctccttctc acgctgtgga cgagcagctc tccaagtccg tgaaggataa ggtcctgctg  120
ccttgccggt acaactctcc tcacgaggac gagtctgagg accggatcta ctggcagaaa  180
cacgacaagg tggtgctgtc cgtgatcgcc ggaaagctga aagtgtggcc tgagtacaag  240
aacaggaccc tgtacgacaa caccacctac agcctgatca tcctgggcct cgtgctgagc  300
gatagaggca cctattcttg cgtggtgcag aagaaagagc ggggcaccta cgaagtgaag  360
cacctggctc tggtcaagct gtccatcaag gccgacttca gcacccctaa catcaccgag  420
```

```
tctggcaacc cttccgccga caccaagaga atcacctgtt tcgcctctgg cggcttccct  480
aagcctcggt tctcttggct ggaaaacggc agagagctgc ccggcatcaa taccaccatt  540
tctcaggacc cagagtccga gctgtacacc atctccagcc agctcgactt taacaccacc  600
agaaaccaca ccatcaagtg cctgattaag tacggcgacg cccacgtgtc cgaggacttt  660
acttgggaga aacctcctga ggaccctcct gactctggat ctggcggcgg aggttctggc  720
ggaggtggaa gcggaggcgg aggatctgct gagtctaagt atggccctcc ttgtcctcca  780
tgtcctgctc cagaagctgc tggcggaccc tctgtgttcc tgtttcctcc aaagcctaag  840
gaccagctca tgatctctcg gacccctgaa gtgacctgcg tggtggtgga tgtgtctcaa  900
gaggaccctg aggtgcagtt caattggtac gtggacggcg tggaagtgca caacgccaag  960
accaagccta gagaggaaca gttcaactcc acctatagag tggtgtccgt gctgaccgtg  1020
ctgcaccagg attggctgaa cggcaaagag tacaagtgca aggtgtccaa caagggcctg  1080
ccttccagca tcgaaaagac catcagcaag gctaagggcc agcctaggga accccaggtt  1140
tacaccctgc ctccaagcca agaggaaatg accaagaacc aggtgtccct gacctgcctg  1200
gtcaagggct tctacccttc cgacattgcc gtggaatggg agtccaatgg ccagcctgag  1260
aacaactaca agaccacacc tcctgtgctg gactccgacg gctccttctt tctgtactct  1320
cgcctgaccg tggacaagtc taggtggcaa gagggcaacg tgttctcctg ctctgtgctg  1380
cacgaggctc tgcacaacca ctacacccag aagtccctgt ctctgtccct gggc        1434

SEQ ID NO: 21          moltype = AA  length = 478
FEATURE                Location/Qualifiers
REGION                 1..478
                       note = fusion protein (mGI101C1)
source                 1..478
                       mol_type = protein
                       organism = synthetic construct
SEQUENCE: 21
MDAMLRGLCC VLLLCGAVFV SPSHAVDEQL SKSVKDKVLL PCRYNSPHED ESEDRIYWQK  60
HDKVVLSVIA GKLKVWPEYK NRTLYDNTTY SLIILGLVLS DRGTYSCVVQ KKERGTYEVK  120
HLALVKLSIK ADFSTPNITE SGNPSADTKR ITCFASGGFP KPRFSWLENG RELPGINTTI  180
SQDPESELYT ISSQLDFNTT RNHTIKCLIK YGDAHVSEDF TWEKPPEDPP DSGSGGGGSG  240
GGGSGGGGSA ESKYGPPCPP CPAPEAAGGP SVFLFPPKPK DQLMISRTPE VTCVVVDVSQ  300
EDPEVQFNWY VDGVEVHNAK TKPREEQFNS TYRVVSVLTV LHQDWLNGKE YKCKVSNKGL  360
PSSIEKTISK AKGQPREPQV YTLPPSQEEM TKNQVSLTCL VKGFYPSDIA VEWESNGQPE  420
NNYKTTPPVL DSDGSFFLYS RLTVDKSRWQ EGNVFSCSVL HEALHNHYTQ KSLSLSLG    478

SEQ ID NO: 22          moltype = AA  length = 133
FEATURE                Location/Qualifiers
REGION                 1..133
                       note = variants of IL-2 (3M, M45)
source                 1..133
                       mol_type = protein
                       organism = synthetic construct
SEQUENCE: 22
APTSSSTKKT QLQLEHLLLD LQMILNGINN YKNPKLTAML TAKFAMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                    133

SEQ ID NO: 23          moltype = AA  length = 133
FEATURE                Location/Qualifiers
REGION                 1..133
                       note = variants of IL-2 (3M, M61)
source                 1..133
                       mol_type = protein
                       organism = synthetic construct
SEQUENCE: 23
APTSSSTKKT QLQLEHLLLD LQMILNGINN YKNPKLTAML TAKFYMPKKA TELKHLQCLE  60
RELKPLEEVL NLAQSKNFHL RPRDLISNIN VIVLELKGSE TTFMCEYADE TATIVEFLNR  120
WITFCQSIIS TLT                                                    133

SEQ ID NO: 24          moltype = AA  length = 133
FEATURE                Location/Qualifiers
REGION                 1..133
                       note = variants of IL-2 (3M, M72)
source                 1..133
                       mol_type = protein
                       organism = synthetic construct
SEQUENCE: 24
APTSSSTKKT QLQLEHLLLD LQMILNGINN YKNPKLTAML TAKFYMPKKA TELKHLQCLE  60
EELKPLEEVL NGAQSKNFHL RPRDLISNIN VIVLELKGSE TTFMCEYADE TATIVEFLNR  120
WITFCQSIIS TLT                                                    133

SEQ ID NO: 25          moltype = DNA  length = 1851
FEATURE                Location/Qualifiers
misc_feature           1..1851
                       note = nucleotiedes coding fusion protein (GI102-M45)
source                 1..1851
                       mol_type = other DNA
                       organism = synthetic construct
SEQUENCE: 25
```

-continued

```
atggatgcta tgctgagagg cctgtgttgc gtgctgctgc tgtgtggcgc tgtgttcgtg  60
tctccttctc acgctgtgat ccacgtgacc aaagaagtga aagaggtcgc cacactgtcc  120
tgcggccaca acgtttcagt ggaagaactg gcccagacca ggatctactg gcagaaagaa  180
aagaaaatgg tgctgaccat gatgtccggc gacatgaaca tctggcctga gtacaagaac  240
cggaccatct tcgacatcac caacaacctg tccatcgtga ttctggccct gaggccttct  300
gatgagggca cctatgagtg cgtggtgctg aagtacgaga aggacgcctt caagcgcgag  360
cacctggctg aagtgacact gtccgtgaag gccgactttc ccacaccttc catctccgac  420
ttcgagatcc ctacctccaa catccggcgg atcatctgtt ctacctctgg cggctttcct  480
gagcctcacc tgtcttggct ggaaaacggc gaggaactga acgccatcaa caccaccgtg  540
tctcaggacc ccgaaaccga gctgtacgct gtgtcctcca agctggactt caacatgacc  600
accaaccaca gcttcatgtg cctgattaag tacggccacc tgagagtgaa ccagaccttc  660
aactggaaca ccaccaagca agagcacttc cctgacaatg gatctggcgg cggaggttct  720
ggcggaggtg gaagcggagg cggaggatct gctgagtcta agtatggccc tccttgtcct  780
ccatgtcctg ctccagaagc tgctggcgga ccctctgtgt tcctgtttcc tccaaagcct  840
aaggaccagc tcatgatctc tcggacaccc gaagtgacct gcgtggtggt ggatgtgtct  900
caagaggacc ctgaggtgca gttcaattgg tacgtggacg gcgtggaagt gcacaacgcc  960
aagaccaagc ctagagagga acagttcaac tccacctaca gagtggtgtc cgtgctgacc  1020
gtgctgcacc aggattggct gaacggcaaa gagtacaagt gcaaggtgtc caacaagggc  1080
ctgccttcca gcatcgaaaa gaccatctcc aaggctaagg gccagcctag ggaaccccag  1140
gtttacaccc tgcctccaag ccaagaggaa atgaccaaga accaggtgtc cctgacctgc  1200
ctggtcaagg gcttctaccc ttccgacatt gccgtggaat gggagtccaa tggccagcct  1260
gagaacaact acaagaccac acctcctgtg ctggactccg acggctcctt ctttctgtac  1320
tctcgcctga ccgtggacaa gtctagatgg caagagggca acgtgttctc ctgctctgtg  1380
ctgcacgagg ccctgcacaa tcactacacc cagaagtccc tgtctctgtc tcttggaggt  1440
ggtggcggtt ctgcccctac cagctcctct accaagaaaa cccagctcca gttggagcat  1500
ctgctgctgg acctccagat gattctgaac gggatcaaca actataagaa ccccaagctg  1560
accgccatgc tgaccgctaa gttcgccatg cccaagaagg ccaccgagct gaagcacctc  1620
cagtgcctgg aagaagaact gaagcccctg gaagaggtgc tgaatctggc ccagtccaag  1680
aacttccacc tgaggccacg ggacctgatc agcaacatca acgtgatcgt gctggaactg  1740
aagggctccg agacaacctt tatgtgcgag tacgccgacg agacagccac catcgtggaa  1800
tttctgaacc ggtggatcac cttctgccag agcatcatct ccacactgac c           1851
```

```
SEQ ID NO: 26          moltype = AA  length = 592
FEATURE                Location/Qualifiers
REGION                 1..592
                       note = fusion protein (GI102-M45)
source                 1..592
                       mol_type = protein
                       organism = synthetic construct
SEQUENCE: 26
VIHVTKEVKE VATLSCGHNV SVEELAQTRI YWQKEKKMVL TMMSGDMNIW PEYKNRTIFD  60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDNGS GGGGSGGGGS GGGGSAESKY GPPCPPCPAP  240
EAAGGPSVFL FPPKPKDQLM ISRTPEVTCV VVDVSQEDPE VQFNWYVDGV EVHNAKTKPR  300
EEQFNSTYRV VSVLTVLHQD WLNGKEYKCK VSNKGLPSSI EKTISKAKGQ PREPQVYTLP  360
PSQEEMTKNQ VSLTCLVKGF YPSDIAVEWE SNGQPENNYK TTPPVLDSDG SFFLYSRLTV  420
DKSRWQEGNV FSCSVLHEAL HNHYTQKSLS LSLGGGGGSA PTSSSTKKTQ LQLEHLLLDL  480
QMILNGINNY KNPKLTAMLT AKFAMPKKAT ELKHLQCLEE ELKPLEEVLN LAQSKNFHLR  540
PRDLISNINV IVLELKGSET TFMCEYADET ATIVEFLNRW ITFCQSIIST LT          592
```

```
SEQ ID NO: 27          moltype = DNA  length = 1851
FEATURE                Location/Qualifiers
misc_feature           1..1851
                       note = nucleotiedes coding fusion protein (GI102-M61)
source                 1..1851
                       mol_type = other DNA
                       organism = synthetic construct
SEQUENCE: 27
atggatgcta tgctgagagg cctgtgttgc gtgctgctgc tgtgtggcgc tgtgttcgtg  60
tctccttctc acgctgtgat ccacgtgacc aaagaagtga aagaggtcgc cacactgtcc  120
tgcggccaca acgtttcagt ggaagaactg gcccagacca ggatctactg gcagaaagaa  180
aagaaaatgg tgctgaccat gatgtccggc gacatgaaca tctggcctga gtacaagaac  240
cggaccatct tcgacatcac caacaacctg tccatcgtga ttctggccct gaggccttct  300
gatgagggca cctatgagtg cgtggtgctg aagtacgaga aggacgcctt caagcgcgag  360
cacctggctg aagtgacact gtccgtgaag gccgactttc ccacaccttc catctccgac  420
ttcgagatcc ctacctccaa catccggcgg atcatctgtt ctacctctgg cggctttcct  480
gagcctcacc tgtcttggct ggaaaacggc gaggaactga acgccatcaa caccaccgtg  540
tctcaggacc ccgaaaccga gctgtacgct gtgtcctcca agctggactt caacatgacc  600
accaaccaca gcttcatgtg cctgattaag tacggccacc tgagagtgaa ccagaccttc  660
aactggaaca ccaccaagca agagcacttc cctgacaatg gatctggcgg cggaggttct  720
ggcggaggtg gaagcggagg cggaggatct gctgagtcta agtatggccc tccttgtcct  780
ccatgtcctg ctccagaagc tgctggcgga ccctctgtgt tcctgtttcc tccaaagcct  840
aaggaccagc tcatgatctc tcggacaccc gaagtgacct gcgtggtggt ggatgtgtct  900
caagaggacc ctgaggtgca gttcaattgg tacgtggacg gcgtggaagt gcacaacgcc  960
aagaccaagc ctagagagga acagttcaac tccacctaca gagtggtgtc cgtgctgacc  1020
gtgctgcacc aggattggct gaacggcaaa gagtacaagt gcaaggtgtc caacaagggc  1080
ctgccttcca gcatcgaaaa gaccatctcc aaggctaagg gccagcctag ggaaccccag  1140
gtttacaccc tgcctccaag ccaagaggaa atgaccaaga accaggtgtc cctgacctgc  1200
```

```
ctggtcaagg gcttctaccc ttccgacatt gccgtggaat gggagtccaa tggccagcct  1260
gagaacaact acaagaccac acctcctgtg ctggactccg acggctcctt ctttctgtac  1320
tctcgcctga ccgtggacaa gtctagatgg caagagggca acgtgttctc ctgctctgtg  1380
ctgcacgagg ccctgcacaa tcactacacc cagaagtccc tgtctctgtc tcttggaggt  1440
ggtggcggtt ctgcccctac cagctcctct accaagaaaa cccagctcca gttggagcat  1500
ctgctgctgg acctccagat gattctgaac gggatcaaca actataagaa ccccaagctg  1560
accgccatgc tgaccgctaa gttctacatg cccaagaagg ccaccgagct gaagcacctc  1620
cagtgcctgg aaagggaact gaagcccctg gaagaggtgc tgaatctggc ccagtccaag  1680
aacttccacc tgaggccacg ggacctgatc agcaacatca acgtgatcgt gctggaactg  1740
aagggctccg agacaacctt tatgtgcgag tacgccgacg agacagccac catcgtggaa  1800
tttctgaacc ggtggatcac cttctgccag agcatcatct ccacactgac c           1851
```

```
SEQ ID NO: 28          moltype = AA  length = 592
FEATURE                Location/Qualifiers
REGION                 1..592
                       note = fusion protein (GI102-M61)
source                 1..592
                       mol_type = protein
                       organism = synthetic construct
SEQUENCE: 28
VIHVTKEVKE VATLSCGHNV SVEELAQTRI YWQKEKKMVL TMMSGDMNIW PEYKNRTIFD  60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDNGS GGGGSGGGGS GGGGSAESKY GPPCPPCPAP  240
EAAGGPSVFL FPPKPKDQLM ISRTPEVTCV VVDVSQEDPE VQFNWYVDGV EVHNAKTKPR  300
EEQFNSTYRV VSVLTVLHQD WLNGKEYKCK VSNKGLPSSI EKTISKAKGQ PREPQVYTLP  360
PSQEEMTKNQ VSLTCLVKGF YPSDIAVEWE SNGQPENNYK TTPPVLDSDG SFFLYSRLTV  420
DKSRWQEGNV FSCSVLHEAL HNHYTQKSLS LSLGGGGGSA PTSSSTKKTQ LQLEHLLLDL  480
QMILNGINNY KNPKLTAMLT AKFYMPKKAT ELKHLQCLER ELKPLEEVLN LAQSKNFHLR  540
PRDLISNINV IVLELKGSET TFMCEYADET ATIVEFLNRW ITFCQSIIST LT          592
```

```
SEQ ID NO: 29          moltype = DNA  length = 1857
FEATURE                Location/Qualifiers
misc_feature           1..1857
                       note = nucleotiedes coding fusion protein (GI102-M72)
source                 1..1857
                       mol_type = other DNA
                       organism = synthetic construct
SEQUENCE: 29
atggatgcta tgctgagagg cctgtgttgc gtgctgctgc tgtgtggcgc tgtgttcgtg  60
tctccttctc acgctgtgat ccacgtgacc aaagaagtga aagaggtcgc cacactgtcc  120
tgcggccaca acgtttcagt ggaagaactg gcccagacca ggatctactg gcagaaagaa  180
aagaaaatgg tgctgaccat gatgtccggc gacatgaaca tctggcctga gtacaagaac  240
cggaccatct tcgacatcac caacaacctg tccatcgtga ttctggccct gaggccttct  300
gatgagggca cctatgagtg cgtggtgctg aagtacgaga aggacgcctt caagcgcgag  360
cacctggctg aagtgacact gtccgtgaag gccgactttc ccacaccttc catctccgac  420
ttcgagatcc ctacctccaa catccggcgg atcatctgtt ctacctctgg cggctttcct  480
gagcctcacc tgtcttggct ggaaaacggc gaggaactga acgccatcaa caccaccgtg  540
tctcaggacc ccgaaaccga gctgtacgct gtgtcctcca agctggactt caacatgacc  600
accaaccaca gcttcatgtg cctgattaag tacggccacc tgagagtgaa ccagaccttc  660
aactggaaca ccaccaagca agagcacttc cctgacaatg gatctggcgg cggaggttct  720
ggcggaggtg gaagcggagg cggaggatct gctgagtcta agtatggccc tccttgtcct  780
ccatgtcctg ctccagaagc tgctggcgga ccctctgtgt tcctgtttcc tccaaagcct  840
aaggaccagc tcatgatctc tcggacaccc gaagtgacct gcgtggtggt ggatgtgtct  900
caagaggacc ctgaggtgca gttcaattgg tacgtggacg gcgtggaagt gcacaacgcc  960
aagaccaagc ctagagagga acagttcaac tccacctaca gagtggtgtc cgtgctgacc  1020
gtgctgcacc aggattggct gaacggcaaa gagtacaagt gcaaggtgtc caacaagggc  1080
ctgccttcca gcatcgaaaa gaccatctcc aaggctaagg gccagcctag ggaaccccag  1140
gtttacaccc tgcctccaag ccaagaggaa atgaccaaga accaggtgtc cctgacctgc  1200
ctggtcaagg gcttctaccc ttccgacatt gccgtggaat gggagtccaa tggccagcct  1260
gagaacaact acaagaccac acctcctgtg ctggactccg acggctcctt ctttctgtac  1320
tctcgcctga ccgtggacaa gtctagatgg caagagggca acgtgttctc ctgctctgtg  1380
ctgcacgagg ccctgcacaa tcactacacc cagaagtccc tgtctctgtc tcttggaggt  1440
ggtggcggtt ctgcccctac cagctcctct accaagaaaa cccagctcca gttggagcat  1500
ctgctgctgg acctccagat gattctgaac gggatcaaca actataagaa ccccaagctg  1560
accgccatgc tgaccgctaa gttctacatg cccaagaagg ccaccgagct gaagcacctc  1620
cagtgcctgg aagaagaact gaagcccctg gaagaggtgc tgaatggggc ccagtccaag  1680
aacttccacc tgaggccacg ggacctgatc agcaacatca acgtgatcgt gctggaactg  1740
aagggctccg agacaacctt tatgtgcgag tacgccgacg agacagccac catcgtggaa  1800
tttctgaacc ggtggatcac cttctgccag agcatcatct ccacactgac ctgatga     1857
```

```
SEQ ID NO: 30          moltype = AA  length = 592
FEATURE                Location/Qualifiers
REGION                 1..592
                       note = fusion protein (GI102-M72)
source                 1..592
                       mol_type = protein
                       organism = synthetic construct
SEQUENCE: 30
```

-continued

```
VIHVTKEVKE VATLSCGHNV SVEELAQTRI YWQKEKKMVL TMMSGDMNIW PEYKNRTIFD  60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDNGS GGGGSGGGGS GGGGSAESKY GPPCPPCPAP  240
EAAGGPSVFL FPPKPKDQLM ISRTPEVTCV VVDVSQEDPE VQFNWYVDGV EVHNAKTKPR  300
EEQFNSTYRV VSVLTVLHQD WLNGKEYKCK VSNKGLPSSI EKTISKAKGQ PREPQVYTLP  360
PSQEEMTKNQ VSLTCLVKGF YPSDIAVEWE SNGQPENNYK TTPPVLDSDG SFFLYSRLTV  420
DKSRWQEGNV FSCSVLHEAL HNHYTQKSLS LSLGGGGGSA PTSSSTKKTQ LQLEHLLLDL  480
QMILNGINNY KNPKLTAMLT AKFYMPKKAT ELKHLQCLEE ELKPLEEVLN GAQSKNFHLR  540
PRDLISNINV IVLELKGSET TFMCEYADET ATIVEFLNRW ITFCQSIIST LT          592

SEQ ID NO: 31          moltype = DNA  length = 1851
FEATURE                Location/Qualifiers
misc_feature           1..1851
                       note = nucleotiedes coding fusion protein (GI101w)
source                 1..1851
                       mol_type = other DNA
                       organism = synthetic construct
SEQUENCE: 31
atggatgcta tgctgagagg cctgtgttgc gtgctgctgc tgtgtggcgc tgtgttcgtg  60
tctccttctc acgctgtgat ccacgtgacc aaagaagtga aagaggtcgc cacactgtcc  120
tgcggccaca acgtttcagt ggaagaactg gcccagacca ggatctactg gcagaaagaa  180
aagaaaatgg tgctgaccat gatgtccggc gacatgaaca tctggcctga gtacaagaac  240
cggaccatct tcgacatcac caacaacctg tccatcgtga ttctggccct gaggccttct  300
gatgagggca cctatgagtg cgtggtgctg aagtacgaga aggacgcctt caagcgcgag  360
cacctggctg aagtgacact gtccgtgaag gccgactttc ccacaccttc catctccgac  420
ttcgagatcc ctacctccaa catccggcgg atcatctgtt ctacctctgg cggctttcct  480
gagcctcacc tgtcttggct ggaaaacggc gaggaactga acgccatcaa caccaccgtg  540
tctcaggacc ccgaaaccga gctgtacgct gtgtcctcca agctggactt caacatgacc  600
accaaccaca gcttcatgtg cctgattaag tacggccacc tgagagtgaa ccagaccttc  660
aactggaaca ccaccaagca agagcacttc cctgacaatg gatctggcgg cggaggttct  720
ggcggaggtg gaagcggagg cggaggatct gctgagtcta agtatggccc tccttgtcct  780
ccatgtcctg ctccagaagc tgctggcgga ccctctgtgt tcctgtttcc tccaaagcct  840
aaggaccagc tcatgatctc tcggacaccc gaagtgacct gcgtggtggt ggatgtgtct  900
caagaggacc ctgaggtgca gttcaattgg tacgtggacg gcgtggaagt gcacaacgcc  960
aagaccaagc ctagagagga acagttcaac tccacctaca gagtggtgtc cgtgctgacc  1020
gtgctgcacc aggattggct gaacggcaaa gagtacaagt gcaaggtgtc caacaagggc  1080
ctgccttcca gcatcgaaaa gaccatctcc aaggctaagg gccagcctag ggaaccccag  1140
gtttacaccc tgcctccaag ccaagaggaa atgaccaaga accaggtgtc cctgacctgc  1200
ctggtcaagg gcttctaccc ttccgacatt gccgtggaat gggagtccaa tggccagcct  1260
gagaacaact acaagaccac acctcctgtg ctggactccg acggctcctt ctttctgtac  1320
tctcgcctga ccgtggacaa gtctagatgg caagagggca acgtgttctc ctgctctgtg  1380
ctgcacgagg ccctgcacaa tcactacacc cagaagtccc tgtctctgtc tcttggaggt  1440
ggtggcggtt ctgcccctac cagctcctct accaagaaaa cccagctcca gttggagcat  1500
ctgctgctgg acctccagat gattctgaac gggatcaaca actataagaa ccccaagctg  1560
acccgcatgc tgacctttaa gttctacatg cccaagaagg ccaccgagct gaagcacctc  1620
cagtgcctgg aagaagaact gaagcccctg gaagaggtgc tgaatctggc ccagtccaag  1680
aacttccacc tgaggccacg ggacctgatc agcaacatca acgtgatcgt gctggaactg  1740
aagggctccg agacaacctt tatgtgcgag tacgccgacg agacagccac catcgtggaa  1800
tttctgaacc ggtggatcac cttctgccag agcatcatct ccacactgac c           1851

SEQ ID NO: 32          moltype = AA  length = 592
FEATURE                Location/Qualifiers
REGION                 1..592
                       note = fusion protein (GI101w)
source                 1..592
                       mol_type = protein
                       organism = synthetic construct
SEQUENCE: 32
VIHVTKEVKE VATLSCGHNV SVEELAQTRI YWQKEKKMVL TMMSGDMNIW PEYKNRTIFD  60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDNGS GGGGSGGGGS GGGGSAESKY GPPCPPCPAP  240
EAAGGPSVFL FPPKPKDQLM ISRTPEVTCV VVDVSQEDPE VQFNWYVDGV EVHNAKTKPR  300
EEQFNSTYRV VSVLTVLHQD WLNGKEYKCK VSNKGLPSSI EKTISKAKGQ PREPQVYTLP  360
PSQEEMTKNQ VSLTCLVKGF YPSDIAVEWE SNGQPENNYK TTPPVLDSDG SFFLYSRLTV  420
DKSRWQEGNV FSCSVLHEAL HNHYTQKSLS LSLGGGGGSA PTSSSTKKTQ LQLEHLLLDL  480
QMILNGINNY KNPKLTRMLT FKFYMPKKAT ELKHLQCLEE ELKPLEEVLN LAQSKNFHLR  540
PRDLISNINV IVLELKGSET TFMCEYADET ATIVEFLNRW ITFCQSIIST LT          592

SEQ ID NO: 33          moltype = DNA  length = 1848
FEATURE                Location/Qualifiers
misc_feature           1..1848
                       note = nucleotiedes coding fusion protein (mGI102-M61)
source                 1..1848
                       mol_type = other DNA
                       organism = synthetic construct
SEQUENCE: 33
atggatgcta tgctgagagg cctgtgttgc gtgctgctgc tgtgtggcgc tgtgttcgtg  60
```

-continued

```
tctccttctc acgctgtgga cgagcagctc tccaagtccg tgaaggataa ggtcctgctg  120
ccttgccggt acaactctcc tcacgaggac gagtctgagg accggatcta ctggcagaaa  180
cacgacaagg tggtgctgtc cgtgatcgcc ggaaagctga aagtgtggcc tgagtacaag  240
aacaggaccc tgtacgacaa caccacctac agcctgatca tcctgggcct cgtgctgagc  300
gatagaggca cctattcttg cgtggtgcag aagaaagagc ggggcaccta cgaagtgaag  360
cacctggctc tggtcaagct gtccatcaag gccgacttca gcacccctaa catcaccgag  420
tctggcaacc cttccgccga caccaagaga atcacctgtt tcgcctctgg cggcttccct  480
aagcctcggt tctcttggct ggaaaacggc agagagctgc ccggcatcaa taccaccatt  540
tctcaggacc cagagtccga gctgtacacc atctccagcc agctcgactt taacaccacc  600
agaaaccaca ccatcaagtg cctgattaag tacggcgacg cccacgtgtc cgaggacttt  660
acttgggaga aacctcctga ggaccctcct gactctggat ctggcggcgg aggttctggc  720
ggaggtggaa gcggaggcgg aggatctgct gagtctaagt atggccctcc ttgtcctcca  780
tgtcctgctc cagaagctgc tggcggaccc tctgtgttcc tgtttcctcc aaagcctaag  840
gaccagctca tgatctctcg gacccctgaa gtgacctgcg tggtggtgga tgtgtctcaa  900
gaggaccctg aggtgcagtt caattggtac gtggacggcg tggaagtgca caacgccaag  960
accaagccta gagaggaaca gttcaactcc acctatagag tggtgtccgt gctgaccgtg  1020
ctgcaccagg attggctgaa cggcaaagag tacaagtgca aggtgtccaa caagggcctg  1080
ccttccagca tcgaaaagac catcagcaag gctaagggcc agcctaggga accccaggtt  1140
tacaccctgc ctccaagcca agaggaaatg accaagaacc aggtgtccct gacctgcctg  1200
gtcaagggct tctacccttc cgacattgcc gtggaatggg agtccaatgg ccagcctgag  1260
aacaactaca agaccacacc tcctgtgctg gactccgacg gctccttctt tctgtactct  1320
cgcctgaccg tggacaagtc taggtggcaa gagggcaacg tgttctcctg ctctgtgctg  1380
cacgaggctc tgcacaacca ctacacccag aagtccctgt ctctgtctct tggaggtggt  1440
ggcggttctg cccctacctc cagctctacc aagaaaaccc agctccagtt ggagcatctg  1500
ctgctggacc tccagatgat cctgaatggc atcaacaatt acaagaaccc caagctgacc  1560
gccatgctga ccgctaagtt ctacatgccc aagaaggcca ccgagctgaa gcacttgcag  1620
tgcctggaaa gggaactgaa gcccctggaa gaagtgctga atctggccca gtccaagaac  1680
ttccacctga ggcctaggga cctgatctcc aacatcaacg tgatcgtgct ggaactgaaa  1740
ggctccgaga caaccttcat gtgcgagtac gccgacgaga cagccaccat cgtggaattt  1800
ctgaaccggt ggatcacctt ctgccagagc atcatctcca cactgacc              1848
```

```
SEQ ID NO: 34          moltype = AA  length = 616
FEATURE                Location/Qualifiers
REGION                 1..616
                       note = fusion protein (mGI102-M61)
source                 1..616
                       mol_type = protein
                       organism = synthetic construct
SEQUENCE: 34
MDAMLRGLCC VLLLCGAVFV SPSHAVDEQL SKSVKDKVLL PCRYNSPHED ESEDRIYWQK  60
HDKVVLSVIA GKLKVWPEYK NRTLYDNTTY SLIILGLVLS DRGTYSCVVQ KKERGTYEVK  120
HLALVKLSIK ADFSTPNITE SGNPSADTKR ITCFASGGFP KPRFSWLENG RELPGINTTI  180
SQDPESELYT ISSQLDFNTT RNHTIKCLIK YGDAHVSEDF TWEKPPEDPP DSGSGGGGSG  240
GGGSGGGGSA ESKYGPPCPP CPAPEAAGGP SVFLFPPKPK DQLMISRTPE VTCVVVDVSQ  300
EDPEVQFNWY VDGVEVHNAK TKPREEQFNS TYRVVSVLTV LHQDWLNGKE YKCKVSNKGL  360
PSSIEKTISK AKGQPREPQV YTLPPSQEEM TKNQVSLTCL VKGFYPSDIA VEWESNGQPE  420
NNYKTTPPVL DSDGSFFLYS RLTVDKSRWQ EGNVFSCSVL HEALHNHYTQ KSLSLSLGGG  480
GGSAPTSSST KKTQLQLEHL LLDLQMILNG INNYKNPKLT AMLTAKFYMP KKATELKHLQ  540
CLERELKPLE EVLNLAQSKN FHLRPRDLIS NINVIVLELK GSETTFMCEY ADETATIVEF  600
LNRWITFCQS IISTLT                                                 616
```

```
SEQ ID NO: 35          moltype = AA  length = 153
FEATURE                Location/Qualifiers
REGION                 1..153
                       note = wild type hIL-2
source                 1..153
                       mol_type = protein
                       organism = synthetic construct
SEQUENCE: 35
MYRMQLLSCI ALSLALVTNS APTSSSTKKT QLQLEHLLLD LQMILNGINN YKNPKLTRML  60
TFKFYMPKKA TELKHLQCLE EELKPLEEVL NLAQSKNFHL RPRDLISNIN VIVLELKGSE  120
TTFMCEYADE TATIVEFLNR WITFCQSIIS TLT                              153
```

```
SEQ ID NO: 36          moltype = AA  length = 158
FEATURE                Location/Qualifiers
REGION                 1..158
                       note = IL-2 with signal sequence
source                 1..158
                       mol_type = protein
                       organism = synthetic construct
SEQUENCE: 36
MDAMLRGLCC VLLLCGAVFV SPSHAAPTSS STKKTQLQLE HLLLDLQMIL NGINNYKNPK  60
LTRMLTFKFY MPKKATELKH LQCLEEELKP LEEVLNLAQS KNFHLRPRDL ISNINVIVLE  120
LKGSETTFMC EYADETATIV EFLNRWITFC QSIISTLT                         158
```

```
SEQ ID NO: 37          moltype = DNA  length = 474
FEATURE                Location/Qualifiers
misc_feature           1..474
                       note = nucleotide sequence coding IL-2 with signal sequence
```

-continued

```
source                1..474
                      mol_type = other DNA
                      organism = synthetic construct
SEQUENCE: 37
atggatgcta tgctgagagg cctgtgttgc gtgctgctgc tgtgtggcgc tgtgttcgtg  60
tctccttctc acgctgcccc taccagctcc tctaccaaga aaacccagct ccagttggag  120
catctgctgc tggacctcca gatgattctg aacgggatca acaactataa gaaccccaag  180
ctgacccgca tgctgacctt taagttctac atgcccaaga aggccaccga gctgaagcac  240
ctccagtgcc tggaagaaga actgaagccc ctggaagagg tgctgaatct ggcccagtcc  300
aagaacttcc acctgaggcc acgggacctg atcagcaaca tcaacgtgat cgtgctggaa  360
ctgaagggct ccgagacaac ctttatgtgc gagtacgccg acgagacagc caccatcgtg  420
gaatttctga accggtggat caccttctgc cagagcatca tctccacact gacc        474
```